US012584105B2

(12) United States Patent
    Kim

(10) Patent No.: US 12,584,105 B2
(45) Date of Patent: Mar. 24, 2026

---

(54) AUTOLOGOUS CELL REPLACEMENT THERAPY FOR PARKINSON'S DISEASE

(71) Applicant: The McLean Hospital Corporation, Belmont, MA (US)

(72) Inventor: Kwang-Soo Kim, Lexington, MA (US)

(73) Assignee: The McLean Hospital Corporation, Belmont, MA (US)

( * ) Notice: Subject to any disclaimer, the term of this patent is extended or adjusted under 35 U.S.C. 154(b) by 1005 days.

(21) Appl. No.: 17/613,586

(22) PCT Filed: May 21, 2020

(86) PCT No.: PCT/US2020/034098
    § 371 (c)(1),
    (2) Date: Nov. 23, 2021

(87) PCT Pub. No.: WO2020/237104
    PCT Pub. Date: Nov. 26, 2020

(65) Prior Publication Data
    US 2022/0243174 A1     Aug. 4, 2022

Related U.S. Application Data

(60) Provisional application No. 62/949,906, filed on Dec. 18, 2019, provisional application No. 62/852,008, filed on May 23, 2019.

(51) Int. Cl.
    *C12N 5/0793*       (2010.01)
    *A61K 35/30*        (2015.01)
        (Continued)

(52) U.S. Cl.
    CPC ............ *C12N 5/0619* (2013.01); *A61K 35/30* (2013.01); *A61P 25/16* (2018.01); *C12N 15/85* (2013.01);
        (Continued)

(58) Field of Classification Search
    CPC .. C12N 5/0619; C12N 15/85; C12N 2501/01; C12N 2501/119; C12N 2501/13;
        (Continued)

(56) References Cited

U.S. PATENT DOCUMENTS 9,657,273 B2     5/2017   Cha et al.
9,750,768 B2     9/2017   Kim et al.
        (Continued)

FOREIGN PATENT DOCUMENTS

CN       107988261       5/2018
JP       2017-511153     4/2017
        (Continued)

OTHER PUBLICATIONS

Eguchi, Takanori, and Takuo Kuboki. "Cellular reprogramming using defined factors and microRNAs." Stem cells international Jan. 2016 (2016) (Year: 2016).*
        (Continued)

*Primary Examiner* — Tracy Vivlemore
*Assistant Examiner* — Thomas R. Amick
(74) *Attorney, Agent, or Firm* — Fish & Richardson P.C.

(57)                ABSTRACT

Methods for generating midbrain dopamine (mDA) neuronal progenitor cells useful for autologous cell therapy in Parkinson's Disease, compositions comprising the cells, and methods of use thereof.

20 Claims, 62 Drawing Sheets

Specification includes a Sequence Listing.

(51) Int. Cl.
　　*A61P 25/16*　　　　(2006.01)
　　*C12N 15/85*　　　　(2006.01)
(52) U.S. Cl.
　　CPC .... *C12N 2501/01* (2013.01); *C12N 2501/119*
　　　　　(2013.01); *C12N 2501/13* (2013.01); *C12N*
　　　　*2501/15* (2013.01); *C12N 2506/45* (2013.01);
　　　　　　　　　　　　*C12N 2800/108* (2013.01)
(58) Field of Classification Search
　　CPC ............ C12N 2501/15; C12N 2506/45; C12N
　　　　　　　　2800/108; C12N 2501/60; C12N
　　　　　　2501/999; C12N 5/0618; C12N 15/113;
　　　　　　　C12N 2310/141; A61K 35/30; A61P
　　　　　　　　25/16; A61P 25/28; C12M 23/10
　　See application file for complete search history.

(56) References Cited

U.S. PATENT DOCUMENTS

| | | | |
|---|---|---|---|
| 2009/0226401 | A1 | 9/2009 | Kim et al. |
| 2012/0064596 | A1* | 3/2012 | Marquette ................ C12N 5/00 |
| | | | 435/174 |
| 2012/0128655 | A1 | 5/2012 | Kim et al. |
| 2013/0052268 | A1 | 2/2013 | Chung et al. |
| 2014/0199274 | A1 | 7/2014 | Kim et al. |
| 2015/0265652 | A1 | 9/2015 | George et al. |
| 2016/0002604 | A1 | 1/2016 | Cha et al. |
| 2018/0051248 | A1* | 2/2018 | McMahon ........... A61K 38/185 |
| 2018/0094242 | A1 | 4/2018 | Studer et al. |
| 2018/0195033 | A1 | 7/2018 | Quartier Latin et al. |
| 2018/0371422 | A1 | 12/2018 | Wang et al. |

FOREIGN PATENT DOCUMENTS

| | | | | |
|---|---|---|---|---|
| WO | WO-2009149233 | A1 * | 12/2009 | ........... C07K 14/005 |
| WO | WO 2018/035214 | | 2/2018 | |

OTHER PUBLICATIONS

Thermo Fisher Webpage, "Live-Cell Staining of Pluripotent Stem Cells" (Year: 2025).*
Szymczak, A. L., & Vignali, D. A. (2005). Development of 2A peptide-based strategies in the design of multicistronic vectors. Expert Opinion on Biological Therapy, 5(5), 627-638 (Year: 2005).*
Office Action in Chinese Appln. No. 202080052998.3, mailed on Nov. 29, 2024, 20 pages (with English translation).
Arenas et al., "How to make a midbrain dopaminergic neuron," Development, Jun. 2015, 142:1918-1936.
Banyard et al., "Regulation of epithelial plasticity by miR-424 and miR-200 in a new prostate cancer metastasis model," Sci Rep., Nov. 2013, 3(3151), 12 pages.
Barker et al., "Human Trials of Stem Cell-Derived Dopamine Neurons for Parkinson's Disease: Dawn of a New Era," Cell Stem Cell, Nov. 2017, 21(5):569-573.
Barker et al., "Cell-based therapies for Parkinson disease-past insights and future potential," Nat Rev Neurol., Sep. 2015, 11(9):492-503.
Beck et al., "An inventory for measuring clinical anxiety: psychometric properties," J Consult Clin Psychol., Dec. 1988, 56(6):893-897.
Bell et al., "Differentiation of Human Induced Pluripotent Stem Cells (iPSCs) into an Effective Model of Forebrain Neural Progenitor Cells and Mature Neurons," Bio-protocol, Mar. 2019, 9(5)e3188, 18 pages.
Bianchi et al., "Rapid and efficient differentiation of functional motor neurons from human iPSC for neural injury modelling," Stem Cell Research, Oct. 2018, 32:126-134.
Bjorklund et al., "Cell therapy for Parkinson's disease: what next?," Mov Disord., Jan. 2013, 28(1):110-115.

Blandini et al., "Animal models of Parkinson's disease," FEBS J., Apr. 2012, 279(7):1156-1166.
Cha et al., "Metabolic control of primed human pluripotent stem cell fate and function by the miR-200c-SIRT2 axis," Nat Cell Biol., May 2017, 19(5):445-456.
Chambers et al., "Highly efficient neural conversion of human ES and iPS cells by dual inhibition of SMAD signaling," Nat Biotechnol., Mar. 2009, 27(3):275-280.
Chan et al., "Live cell imaging distinguishes bona fide human iPS cells from partially reprogrammed cells," Nat Biotechnol., Oct. 2009, 27:1033-1037.
Chaudhuri et al., "The metric properties of a novel non-motor symptoms scale for Parkinson's disease: Results from an international pilot study," Mov Disord., Oct. 2007, 22(13):1901-1911.
Chung et al., "Wnt1-1mx1a forms a novel autoregulatory loop and controls midbrain dopaminergic differentiation synergistically with the SHH-FoxA2 pathway," Cell Stem Cell, Dec. 2009, 5(6):646-658.
Cummings et al., "Measurement of cell death in mammalian cells," Curr Protoc Pharmacol., 2001, Unit 12.8, 24 pages.
D' Aiuto et al., "Large-scale generation of human iPSC-derived neural stem cells/early neural progenitor cells and their neuronal differentiation," Organogenesis, 2014, 10(4):365-377.
Darband et al., "Quercetin: A functional dietary flavonoid with potential chemo-preventive properties in colorectal cancer," J Cell Physiol., Sep. 2018, 233(9):6544-6560.
De Lau et al., "Epidemiology of Parkinson's disease," Lancet Neurol., Jun. 2006, 5(6):525-535.
Doi et al., "Isolation of human induced pluripotent stem cell-derived dopaminergic progenitors by cell sorting for successful transplantation," Stem Cell Reports, Mar. 2014, 2(3):337-350.
Dowd et al., "The Corridor Task: a simple test of lateralised response selection sensitive to unilateral dopamine deafferentation and graft-derived dopamine replacement in the striatum," Brain Res Bull., Dec. 2005, 68(1-2):24-30.
Effenberg et al., "Striatal Transplantation of Human Dopaminergic Neurons Differentiated From Induced Pluripotent Stem Cells Derived From Umbilical Cord Blood Using Lentiviral Reprogramming," Cell Transplant, 2015, 24(10):2099-2112.
Fernandes et al., "Fibroblast sources: Where can we get them?," Cytotechnology, Mar. 2016, 68(2):223-228.
Garitaonandia et al., "Novel Approach to Stem Cell Therapy in Parkinson's Disease," Stem Cells Dev., Jul. 2018, 27(14):951-957.
Goetz et al., "Movement Disorder Society-sponsored revision of the Unified Parkinson's Disease Rating Scale (MDS-UPDRS): scale presentation and clinimetric testing results," Mov Disord., Nov. 2008, 23(15):2129-2170.
Grealish et al., "Human ESC-derived dopamine neurons show similar preclinical efficacy and potency to fetal neurons when grafted in a rat model of Parkinson's disease," Cell Stem Cell, Nov. 2014, 15(5):653-665.
Gunhnlar et al., "A simplified protocol for differentiation of electrophysiologically mature neuronal networks from human induced pluripotent stem cells," Molecular Psychiatry, 2018, 23:1336-1344.
Guzman et al., "Robust Pacemaking in Substantia Nigra Dopaminergic Neurons," J Neurosci., Sep. 2009, 29:11011-11019.
Hargus et al., "Differentiated Parkinson patient-derived induced pluripotent stem cells grow in the adult rodent brain and reduce motor asymmetry in Parkinsonian rats," PNAS, Sep. 2007, 107(36):15921-15926.
International Preliminary Report on Patentability in International Application No. PCT/US2020/034098, mailed on Dec. 2, 2021, 8 pages.
International Search Report and Written Opinion in International Application No. PCT/US2020/034098, mailed on Oct. 15, 2020, 12 pages.
Invitation to Pay Additional Fees in International Application No. PCT/US2020/034098, mailed on Aug. 18, 2020, 2 pages.
Jiang et al., "Essential role for survivin in early brain development," J Neurosci., Jul. 2005, 25(30):6962-6970.
Joksimovic et al., "Spatiotemporally separable Shh domains in the midbrain define distinct dopaminergic progenitor pools," PNAS, Nov. 2009, 106(45):19185-19190.

(56)        References Cited

OTHER PUBLICATIONS

Joksimovic et al., "Wnt antagonism of Shh facilitates midbrain floor plate neurogenesis," Nat Neurosci., Jan. 2009, 12:125-131.

Kandoth et al., "Mutational landscape and significance across 12 major cancer types," Nature, Oct. 2012, 502(7471):333-339.

Kang et al., "Management of tardive dyskinesia," Ration Drug Ther., Aug. 1988, 22(8):1-7.

Katsukawa et al., "Fail-Safe Therapy by Gamma-Ray Irradiation Against Tumor Formation by Human-Induced Pluripotent Stem Cell-Derived Neural Progenitors," Stem Cells Dev., Jun. 2016, 25(11):815-825, 45 pages.

Kefalopoulou et al., "Long-term clinical outcome of fetal cell transplantation for Parkinson disease: two case reports," JAMA Neurol., Jan. 2014, 71(1):83-87.

Kikuchi et al., "Human iPS cell-derived dopaminergic neurons function in a primate Parkinson's disease model," Nature, Aug. 2017, 548(7669):592-596.

Kikuchi et al., "Idiopathic Parkinson's disease patient-derived induced pluripotent stem cells function as midbrain dopaminergic neurons in rodent brains," J Neurosci Res., Feb. 2017, 95(9):1829-1837.

Kilpinen et al., "Common genetic variation drives molecular heterogeneity in human iPSCs," Nature, Jun. 2017, 546(7658):370-375.

Kirkeby et al., "Predictive Markers Guide Differentiation to Improve Graft Outcome in Clinical Translation of hESC-Based Therapy for Parkinson's Disease," Cell Stem Cell, Jan. 2017, 20(1):135-148.

Korpal et al., "The miR-200 family inhibits epithelial-mesenchymal transition and cancer cell migration by direct targeting of E-cadherin transcriptional repressors ZEB1 and ZEB2," J Biol Chem., May 2008, 283(22):14910-14914.

Kriks et al., "Dopamine neurons derived from human ES cells efficiently engraft in animal models of Parkinson's disease," Nature, Nov. 2011, 480(7378):547-551.

Lee et al., "Inhibition of pluripotent stem cell-derived teratoma formation by small molecules," PNAS, Aug. 2013, 110(35):E3281-E3290.

Lehnen et al., "IAP-Based Cell Sorting Results in Homogeneous Transplantable Dopaminergic Precursor Cells Derived from Human Pluripotent Stem Cells," Stem Cell Reports, Oct. 2017, 9:1207-1220.

Lindvall, "Clinical translation of stem cell transplantation in Parkinson's disease," J Intern Med., Jan. 2016, 279(1):30-40.

Lundblad et al., "Pharmacological validation of behavioural measures of akinesia and dyskinesia in a rat model of Parkinson's disease," Eur J Neurosci., Jan. 2002, 15(1):120-132.

Malik et al., "A review of the methods for human iPSC derivation," Methods Mol Biol., 2013, 997:23-33.

Mandai et al., "Autologous Induced Stem-Cell-Derived Retinal Cells for Macular Degeneration," N Engl J Med., Mar. 2017, 377(8):792-793.

Martincorena et al., "Somatic mutation in cancer and normal cells," Science, Sep. 2015, 349(6255):1483-1489.

Marton et al., "A Comprehensive Analysis of Protocols for Deriving Dopaminergic Neurons from Human Pluripotent Stem Cells," Stem Cells Translational Medicine, Apr. 2019, 8(4):366-374.

Merkle et al., "Human pluripotent stem cells recurrently acquire and expand dominant negative P53 mutations," Nature, May 2017, 545(7653):229-233.

Miura et al., "Variation in the safety of induced pluripotent stem cell lines," Nat Biotechnol., 2009, 27:743-745.

Morizane et al., "MHC matching improves engraftment of iPSC-derived neurons in non-human primates," Nature Communications, Aug. 2017, 8(385), 12 pages.

Nakagawa et al., "Promotion of direct reprogramming by transformation-deficient Myc," PNAS, Aug. 2010, 107(32):14152-14157.

Nasreddine et al., "The Montreal Cognitive Assessment, MoCA: a brief screening tool for mild cognitive impairment," J Am Geriatr Soc., Apr. 2005, 53(4):695-699.

Ohnishi et al., "Premature termination of reprogramming in vivo leads to cancer development through altered epigenetic regulation," Cell, Feb. 2013, 156(4):663-677.

Olsson et al., "Forelimb akinesia in the rat Parkinson model: differential effects of dopamine agonists and nigral transplants as assessed by a new stepping test," J Neurosci., May 1995, 15(5):3863-3875.

Ostrom et al., "The epidemiology of glioma in adults: a "state of the science" review," Neuro Oncol., Jul. 2014, 16(7):896-913.

Park et al., "Reprogramming of human somatic cells to pluripotency with defined factors," Nature, Jan. 2008, 451(7175):141-146.

Pennartz et al., "Purification of neuronal precursors from the adult mouse brain: comprehensive gene expression analysis provides new insights into the control of cell migration, differentiation, and homeostasis," Mol Cell Neurosci., Apr. 2004, 25(4):692-706.

Peto et al., "The development and validation of a short measure of functioning and well-being for individuals with Parkinson's disease," Qual Life Res., Jun. 1995, 4(3):241-8.

Pieters et al., "Role of cell-cell adhesion complexes in embryonic stem cell biology," J Cell Sci., Jun. 2014, 127(12):2603-2613.

Porter et al., "Emerging roles of caspase-3 in apoptosis," Cell Death Differ., Feb. 1999, 6(2):99-104.

Raab et al., "A Comparative View on Human Somatic Cell Sources for iPSC Generation," Stem Cells Int., Nov. 2014, 2014:768391, 13 pages.

Rhee et al., "Protein-based human iPS cells efficiently generate functional dopamine neurons and can treat a rat model of Parkinson disease," J Clin Invest., May 2011, 121(6):2326-2335.

Salimi et al., "Comparison of different protocols for neural differentiation of human induced pluripotent stem cells," Mol Biol Rep., Mar. 2014, 41(3):1713-1721.

Samata et al., "Purification of functional human ES and iPSC-derived midbrain dopaminergic progenitors using LRTM1," Nat Commun., Oct. 2016, 7:13097, 11 pages.

Samata et al., "X-linked severe combined immunodeficiency (X-SCID) rats for xeno-transplantation and behavioral evaluation," J Neurosci Methods, Mar. 2015, 243:68-77.

Schweitzer et al., "Columnar Injection for Intracerebral Cell Therapy," Oper Neurosurg (Hagerstown), Mar. 2019, 18:321-328.

Schweitzer et al., "Personalized iPSC-Derived Dopamine Progenitor Cells for Parkinson's Disease Supplementary Appendix," N Engl J Med., 2020, 1926-1932, 84 pages.

Schweitzer et al., "Personalized iPSC-Derived Dopamine Progenitor Cells for Parkinson's Disease," N Engl J Med., May 2020, 1926-1932.

Schweitzer et al., "Protocol for: Personalized iPSC-derived Dopamine Progenitor Cells for Parkinson's Disease," N Engl J Med, 2020, 382, 322 pages.

Scudellari, "How iPS cells changed the world," Nature, Jun. 2016, 534(7607):310-312.

Sonntag et al., "Pluripotent Stem Cell-based therapy for Parkinson's Disease: current status and future prospects," Prog Neurobiol., Sep. 2010, 168:1-20, 88 pages.

Statnews.com [online], "A secret experiment revealed: In a medical first, doctors treat Parkinson's with a novel brain cell transplant," May 12, 2020, retrieved on Sep. 30, 2022, retrieved from URL <https://www.statnews.com/2020/05/12/medical-first-parkinsons-brain-cell-transplant-stem-cells/>, 19 pages.

Streckfuss-Bömeke et al., "Comparative study of human-induced pluripotent stem cells derived from bone marrow cells, hair keratinocytes, and skin fibroblasts," Eur Heart J., Sep. 2013, 34(33):2618-29.

Swistowski et al., "Efficient generation of functional dopaminergic neurons from human induced pluripotent stem cells under defined conditions," Stem Cells, Oct. 2010, 28:1893-1904.

Takahashi et al., "A decade of transcription factor-mediated reprogramming to pluripotency," Nat Rev Mol Cell Biol., Mar. 2016, 17:183-193.

Takahashi et al., "Induction of pluripotent stem cells from adult human fibroblasts by defined factors," Cell, 2007, 131:861-872.

Takahashi et al., "Induction of pluripotent stem cells from mouse embryonic and adult fibroblast cultures by defined factors," Cell, Aug. 2006, 126:663-676.

(56) References Cited

OTHER PUBLICATIONS

Takahashi, "Preclinical evaluation of patient-derived cells show promise for Parkinson's disease," J Clin Invest., 2020, 4 pages.

Tanabe et al., "Maturation, not initiation, is the major roadblock during reprogramming toward pluripotency from human fibroblasts," PNAS, Jul. 2013, 110(30):12172-12179.

Tao et al., "Neural Subtype Specification from Human Pluripotent Stem Cells," Cell Stem Cell, Nov. 2016, 19(5):573-586.

Tapia et al., "Molecular Obstacles to Clinical Translation of iPSCs," Cell Stem Cell, Sep. 2016, 19(3):298-309.

Tieu, "A guide to neurotoxic animal models of Parkinson's disease," Cold Spring Harb Perspect Med., Sep. 2011, 1(1):a009316, 20 pages.

Trilck et al., "Generation and Neuronal Differentiation of Patient-Specific Induced Pluripotent Stem Cells Derived from Niemann-Pick Type C1 Fibroblasts," Methods Mol Biol., 2016, 1353:233-59.

Ungerstedt et al., "Quantitative recording of rotational behavior in rats after 6-hydroxy-dopamine lesions of the nigrostriatal dopamine system," Brain Res., Dec. 1970, 24(3):485-493.

Valastyan et al., "Roles for microRNAs in the regulation of cell adhesion molecules," J Cell Sci., Apr. 2011, 124(7):999-1006.

Wakeman et al., "Cryopreservation Maintains Functionality of Human iPSC Dopamine Neurons and Rescues Parkinsonian Phenotypes In Vivo," Stem Cell Reports, Jun. 2017, 9:149-161.

Weintraub et al., "Questionnaire for Impulsive-Compulsive Disorders in Parkinson's Disease-Rating Scale," Mov Disord., Feb. 2012, 27(2):242-247.

Yu et al., "Induced pluripotent stem cell lines derived from human somatic cells," Science, Dec. 2007, 318:1917-1920.

Zhang et al., "Highly efficient methods to obtain homogeneous dorsal neural progenitor cells from human and mouse embryonic stem cells and induced pluripotent stem cells," Stem Cell Res Ther., Mar. 2018, 9(1):67, 13 pages.

Balzano et al., "MiR200 and miR302: Two Big Families Influencing Stem Cell Behavior," Molecules, Jan. 2018, 23(2):282, 19 pages.

Genetic Engineering, 4th Edition, Jan. 31, 2017, Zhang Huizhan, East China University of Science and Technology Publishing House, p. 392, 9 pages (with English translation).

Office Action in Chinese Appln. No. 202080052998.3, dated Apr. 12, 2024, 28 pages (with English translation).

The New Techniques and Methods in Pharmacological Research, 1st edition, Mar. 31, 2014, Chen Xiaoguang, China Union Medical University University Press, pp. 302-303, 10 pages (with English translation).

Zhang et al., "Research progress on methods of delivering reprogramming factors into cells in the process of inducing pluripotent stem cells," Heilongjiang Animal Science and Veterinary Medicine, Oct. 31, 2018, 19:36-40, 1 page (English abstract only).

Office Action in Japanese Appln. No. 2021-569378, dated Jul. 30, 2024, 14 pages (with English translation).

Extended European Search Report in European Appln. No. 20809434.2, dated May 9, 2023, 10 pages.

Liu et al., "Looking into the Future: Toward Advanced 3D Biomaterials for Stem-Cell-Based Regenerative Medicine," Adv Mater., Apr. 2018, 30(17):e1705388, 20 pages.

Office Action in Canadian Appln. No. 3141716, dated Aug. 23, 2023, 5 pages.

Office Action Korean Appln. No. 10-2021-7041610, mailed Aug. 8, 2025, 28 pages (with English translation).

Office Action in Canadian Appln. No. 3141716, mailed on Mar. 4, 2025, 4 pages.

Office Action in Chinese Appln. No. 2020800529983, mailed on Mar. 12, 2025, 20 pages (with English translation).

Office Action in Japanese Appln. No. 2021-569378, mailed on May 13, 2025, 6 pages (with English Translation).

* cited by examiner

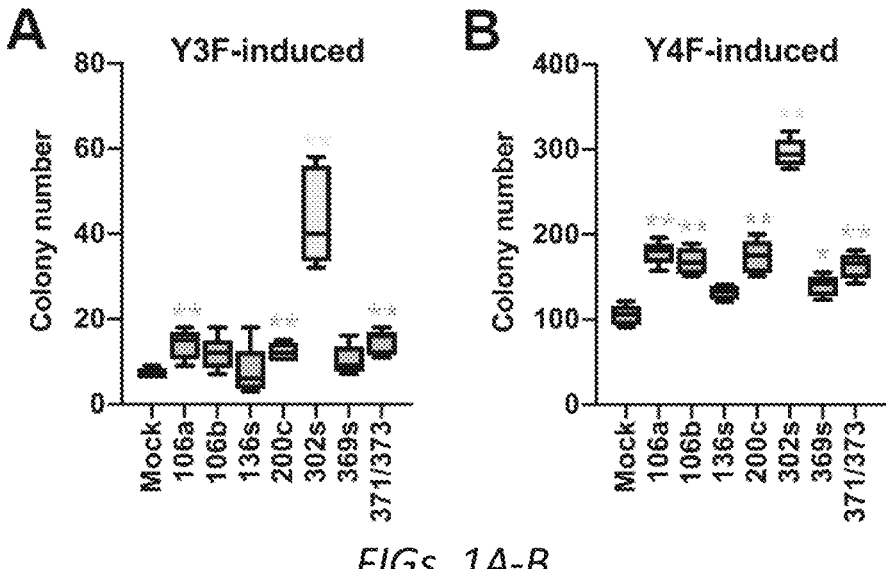
FIGs. 1A-B
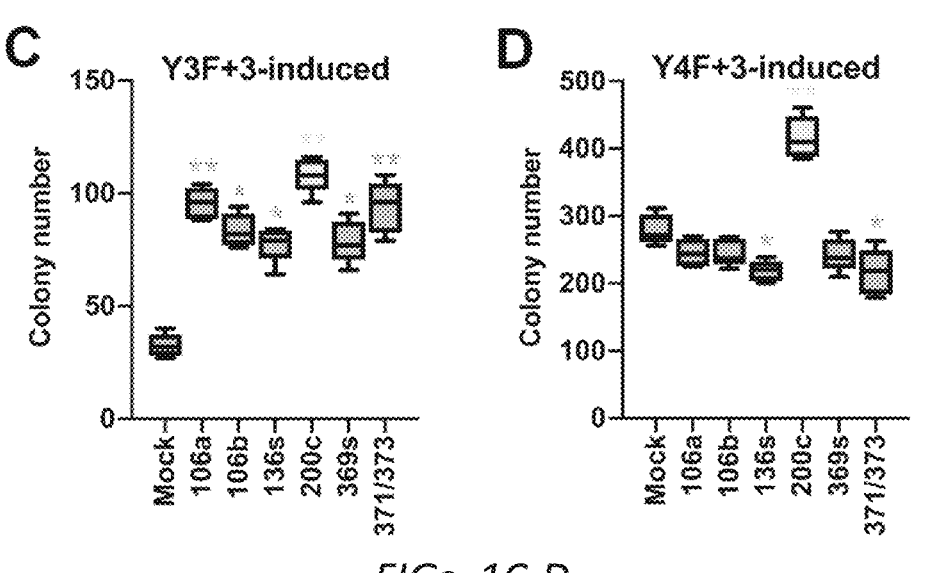
FIGs. 1C-D

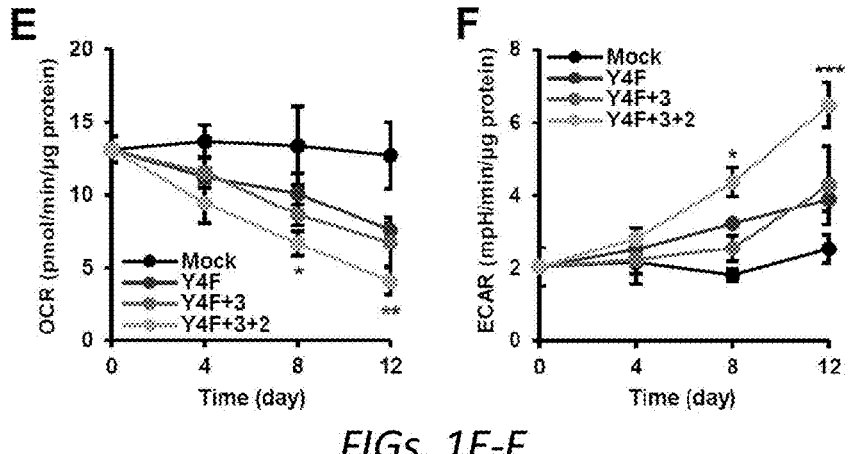
FIGs. 1E-F
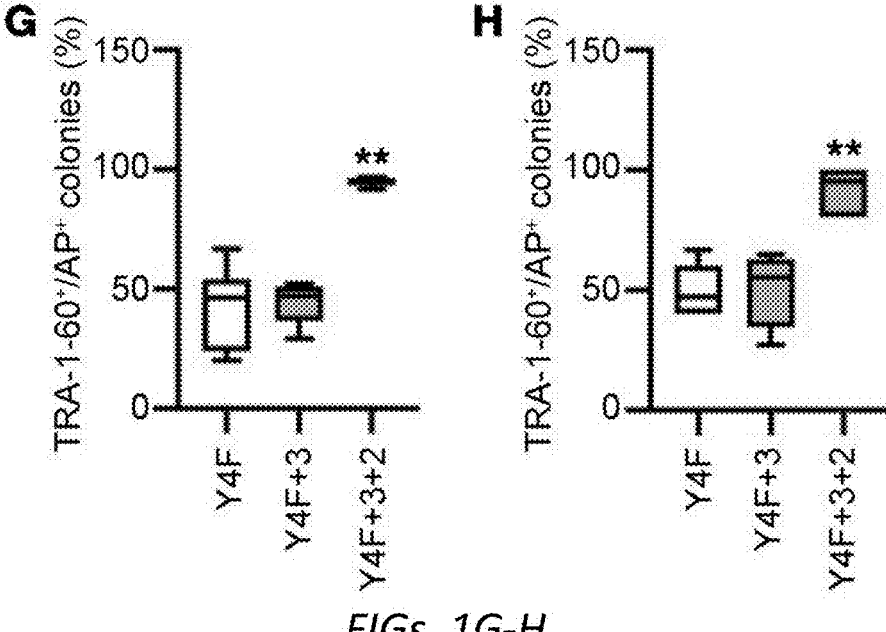
FIGs. 1G-H

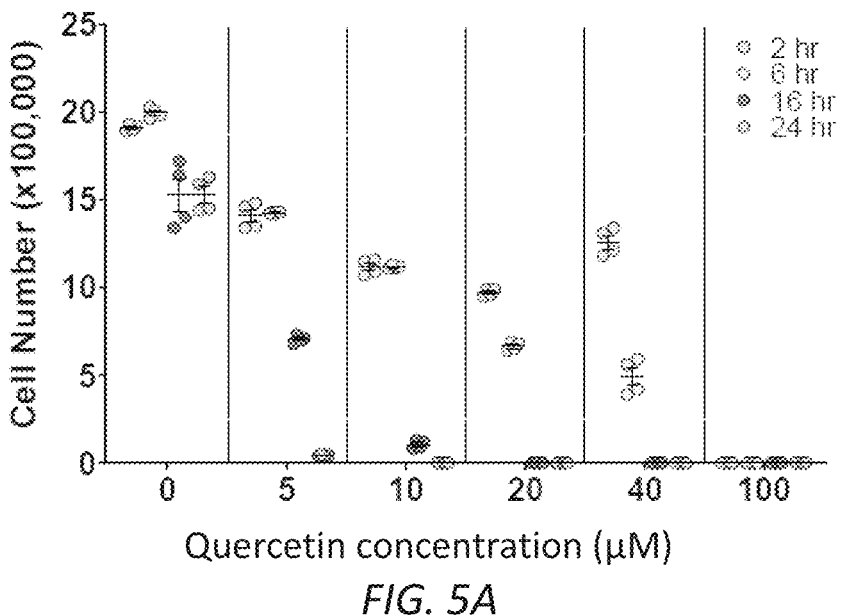
*FIG. 5A*
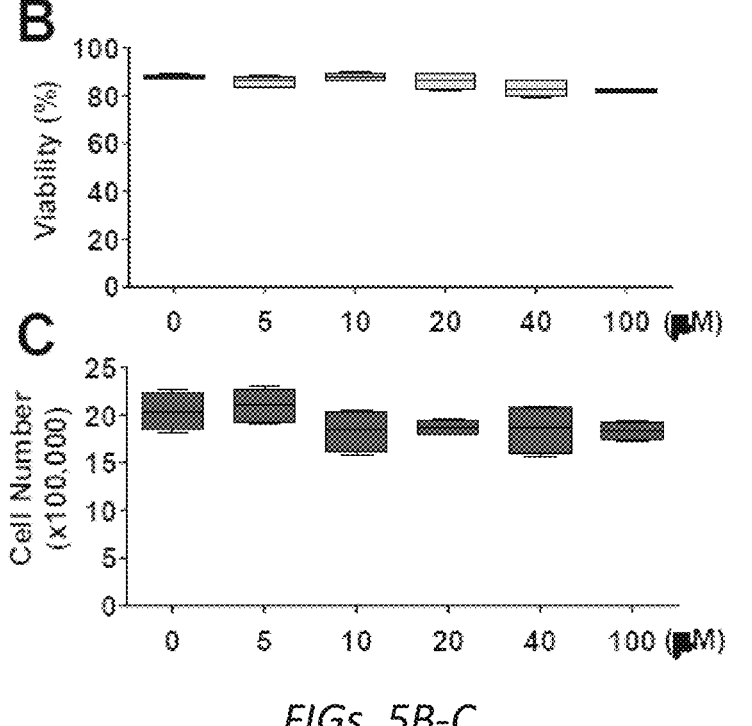
*FIGs. 5B-C* hiPSCs input cell numbers per $10^5$ fibroblasts

| Input | 100,000 | 10,000 | 1,000 | 100 | 10 | 1 |
|---|---|---|---|---|---|---|
| Counted | n.c. | 928 | 110 | 7 | 1 | 0 |

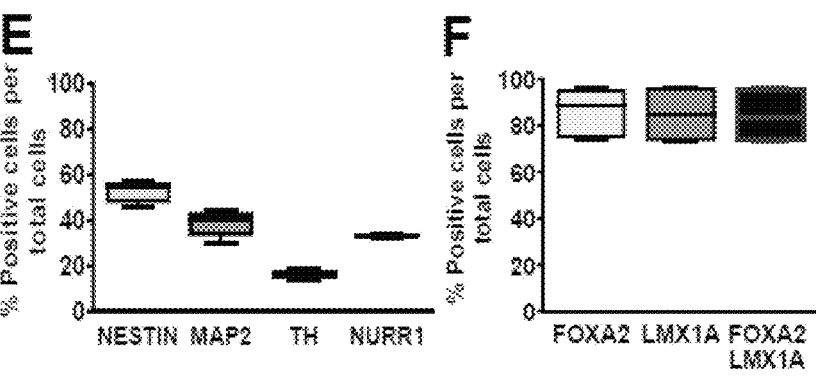
FIGs. 6E-F
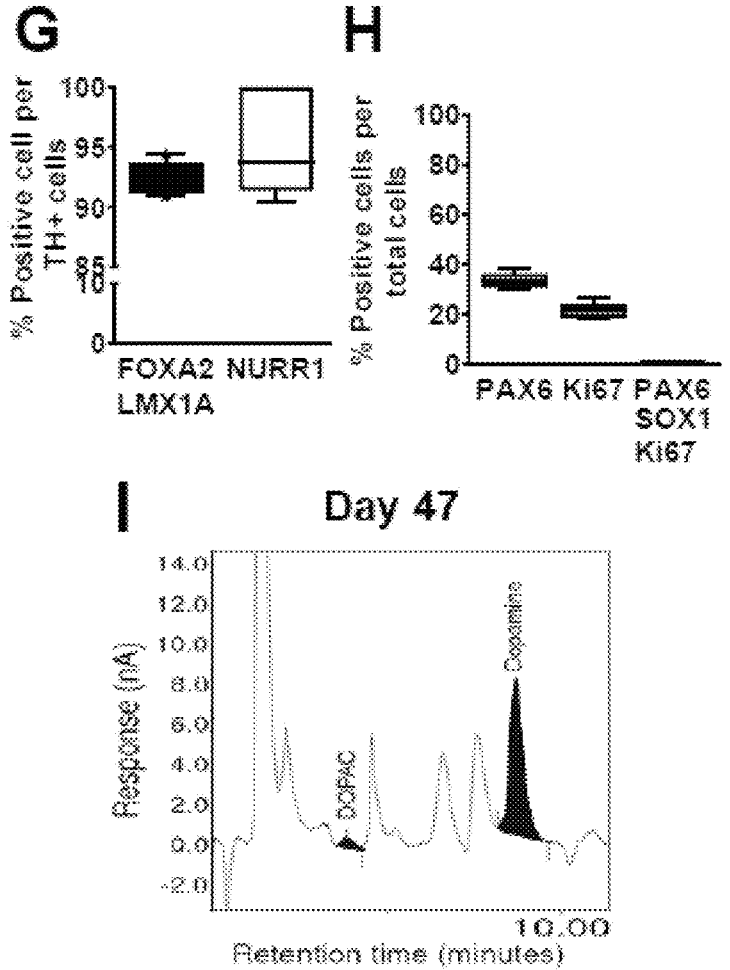
FIG. 6G-I

*FIGs. 7B-C*

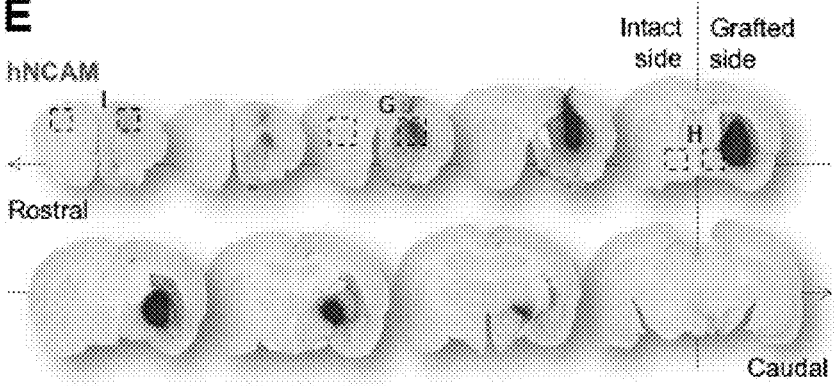
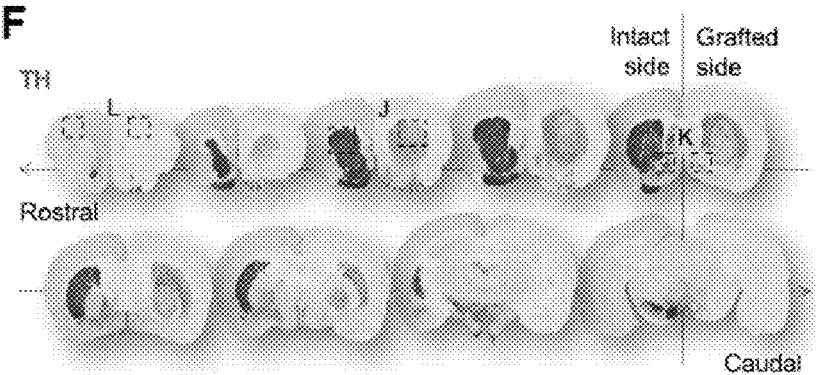
FIG. 8E-F

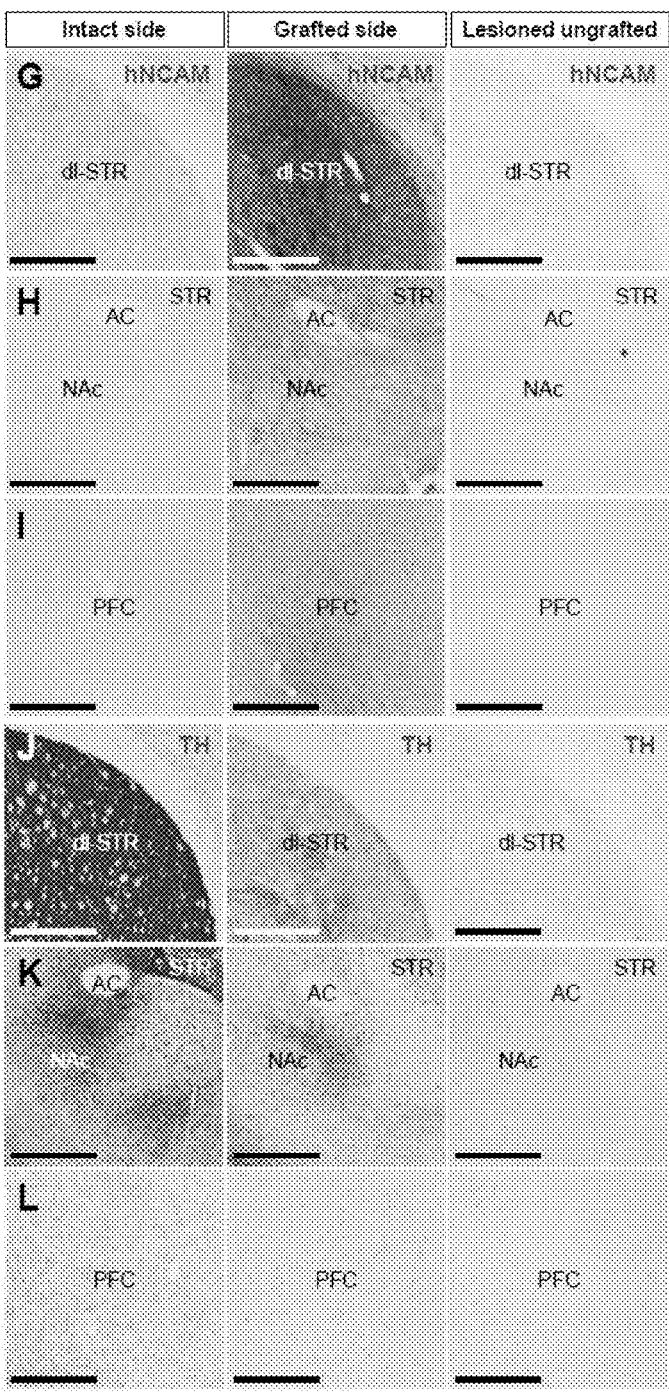
*FIGs. 8G-L*

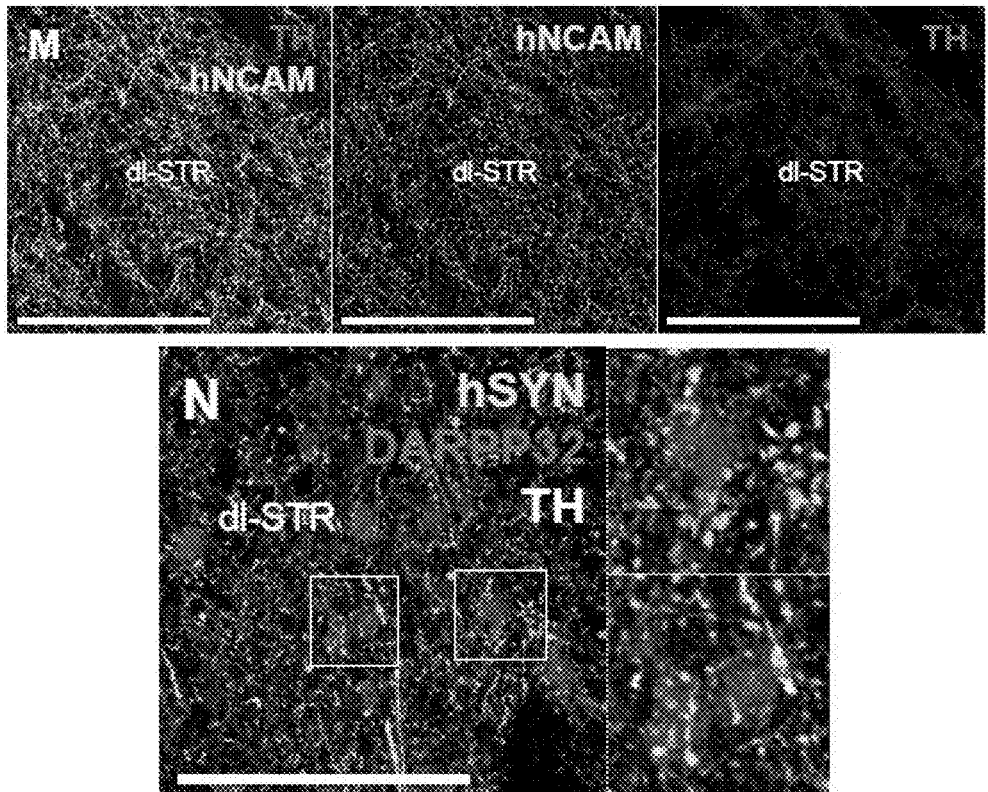
*FIGs. 8M-N*

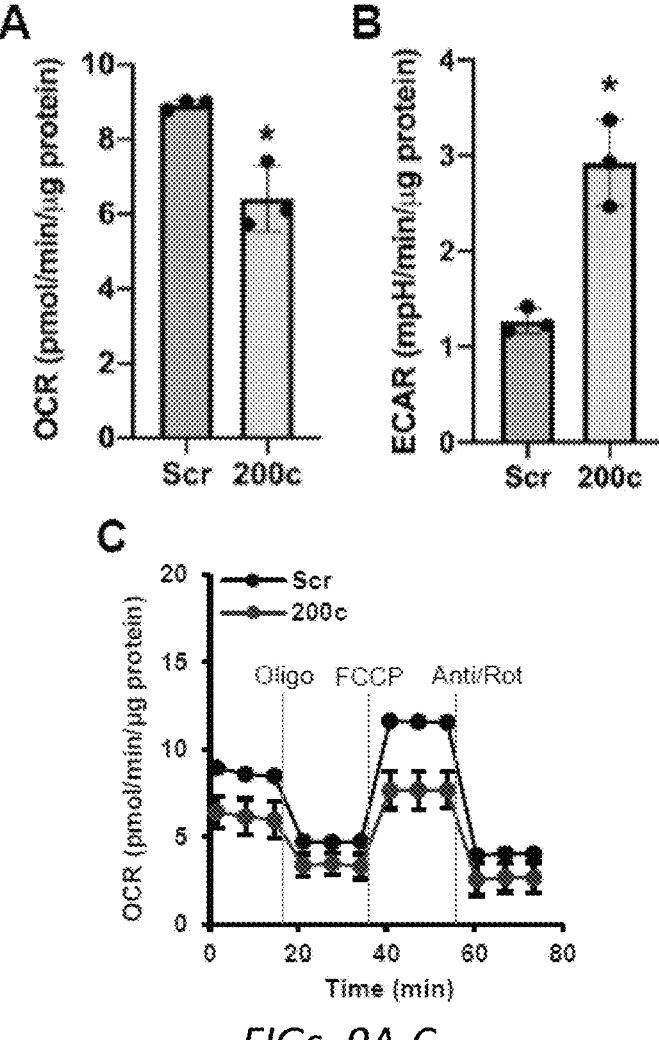
FIGs. 9A-C

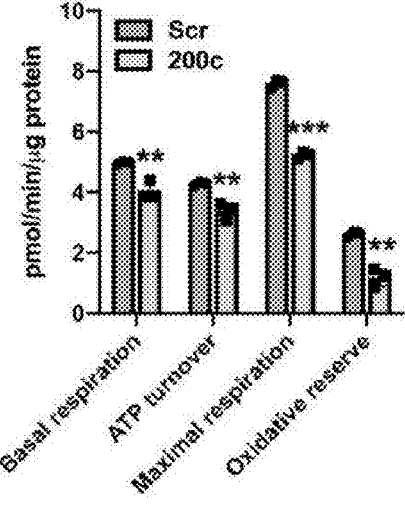
FIG. 9D
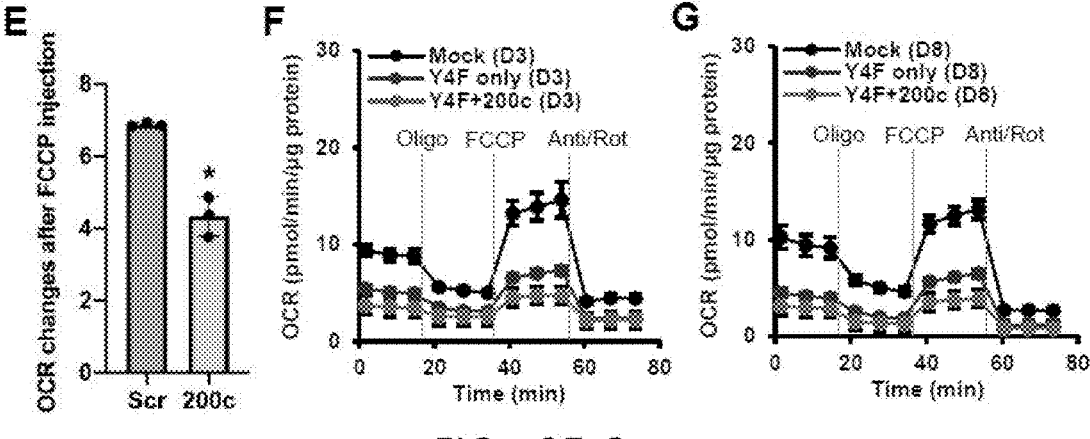
FIGs. 9E-G

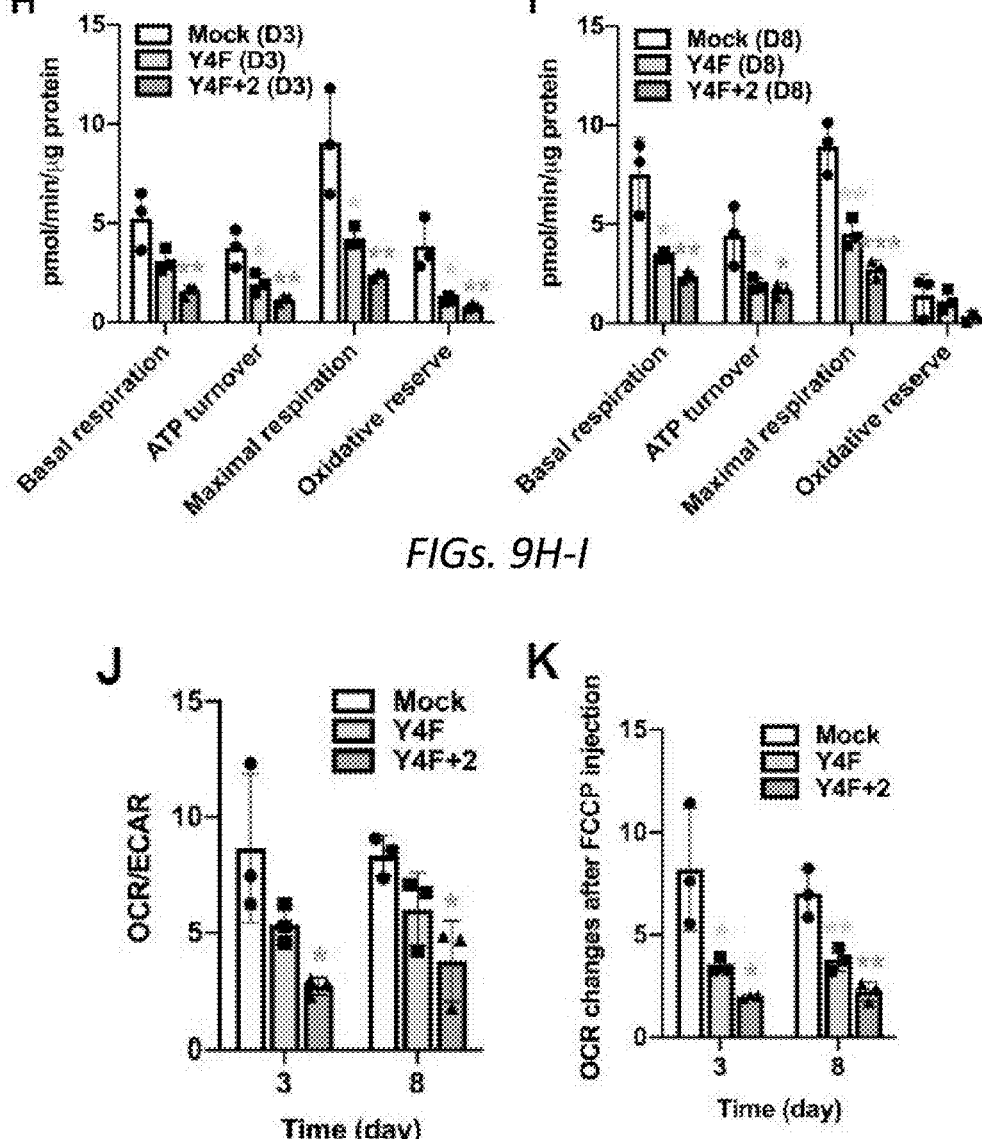
FIGs. 9H-I
FIGs. 9J-K

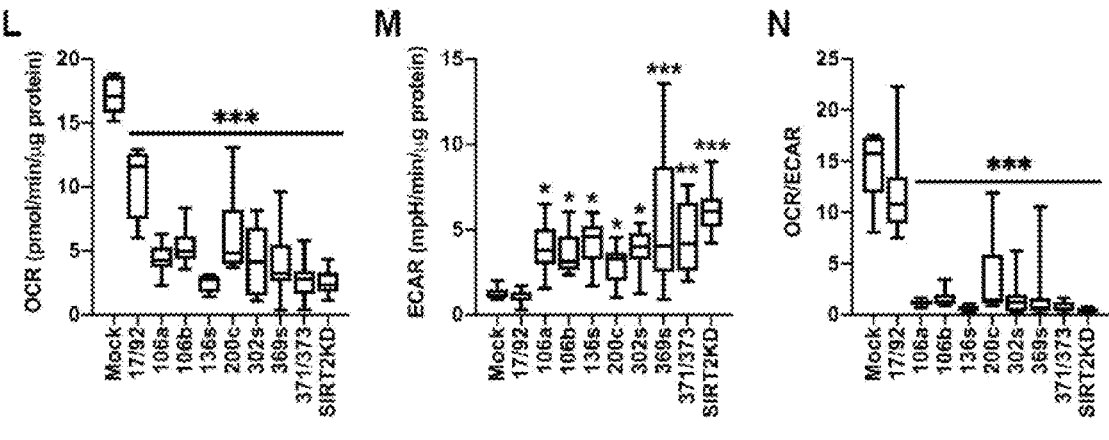
FIGs. 9L-N
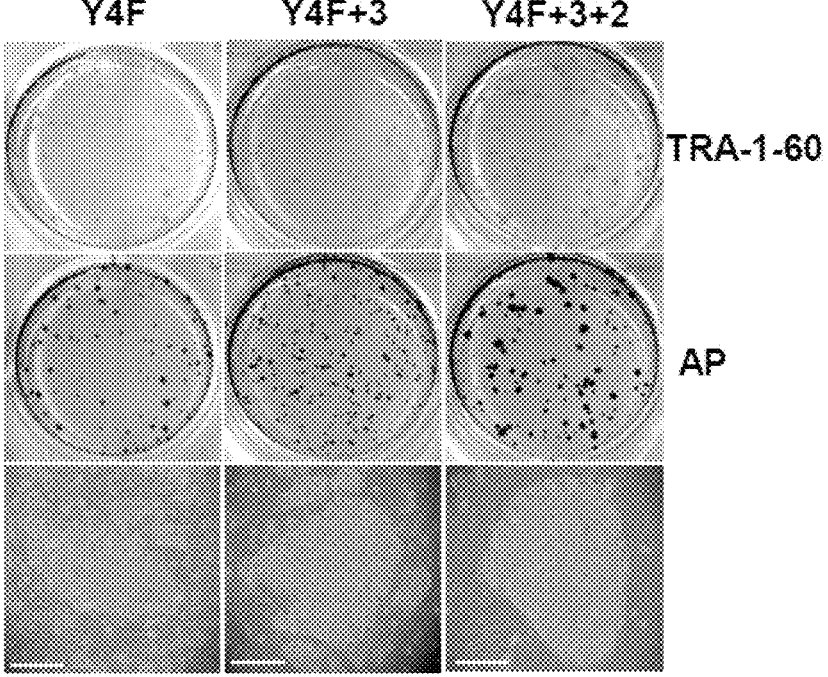
FIG. 10A

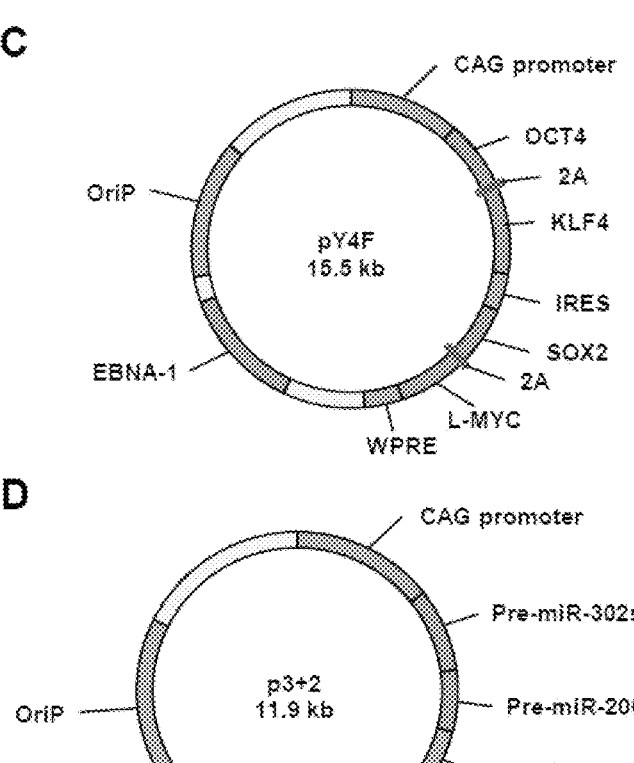
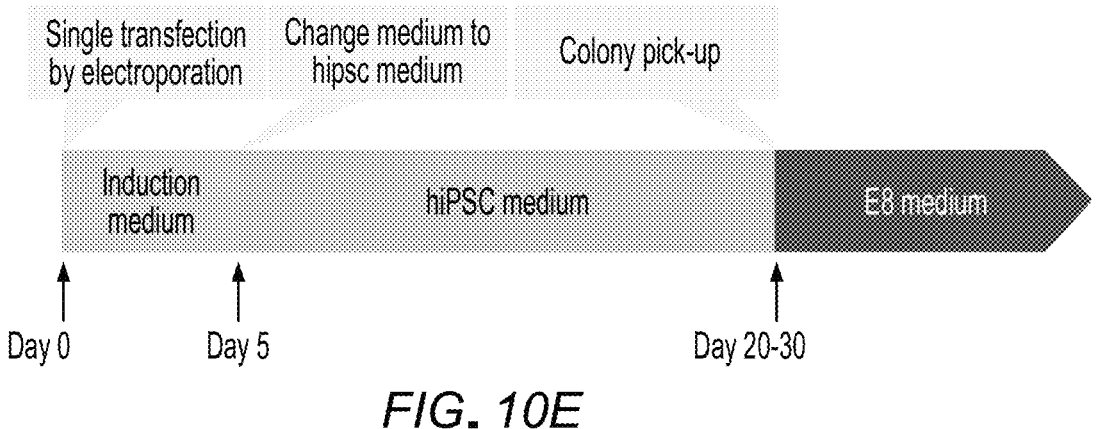
FIG. 10C-D
FIG. 10E

B
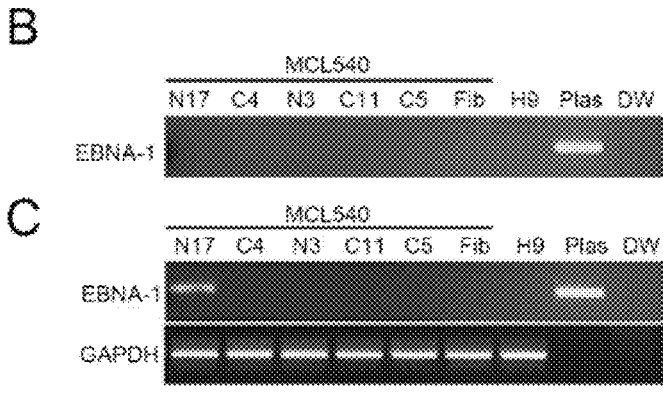
C
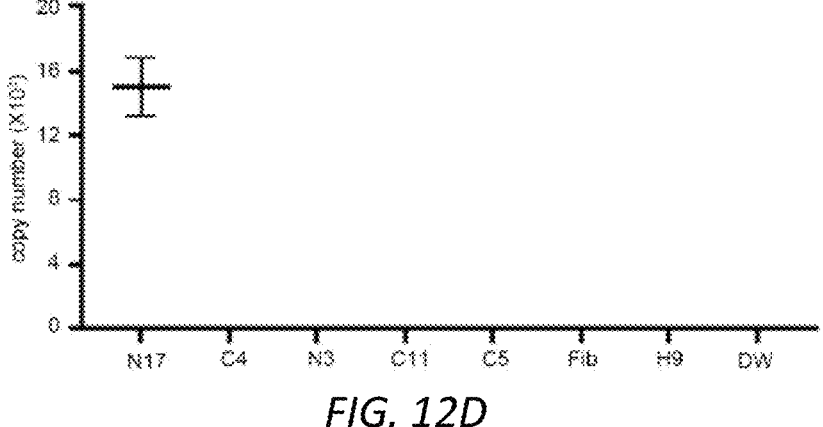
*FIGs. 12B-C*
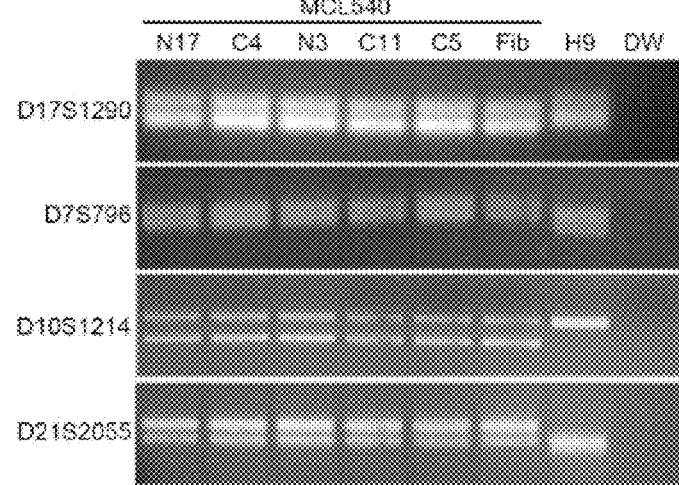
*FIG. 12D*
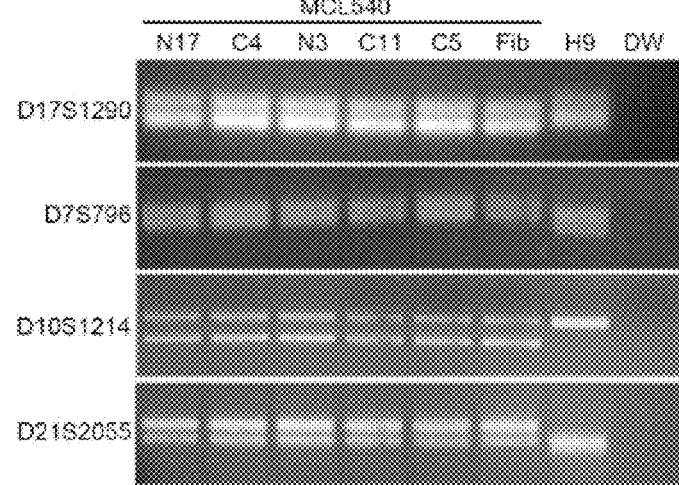
*FIG. 12E*

6 cm dish

10 cm dish

Day 70

20mV

100ms

30pA

-10pA

Control TTX TTX-sensitive
Na⁺-current 0.5nA 0.5nA 0.5nA
20ms 20ms 20ms

20pA
100ms

-60 mV 20 mV 1 s

NEUROBIOTIN        TH        NEUROBIOTIN/TH

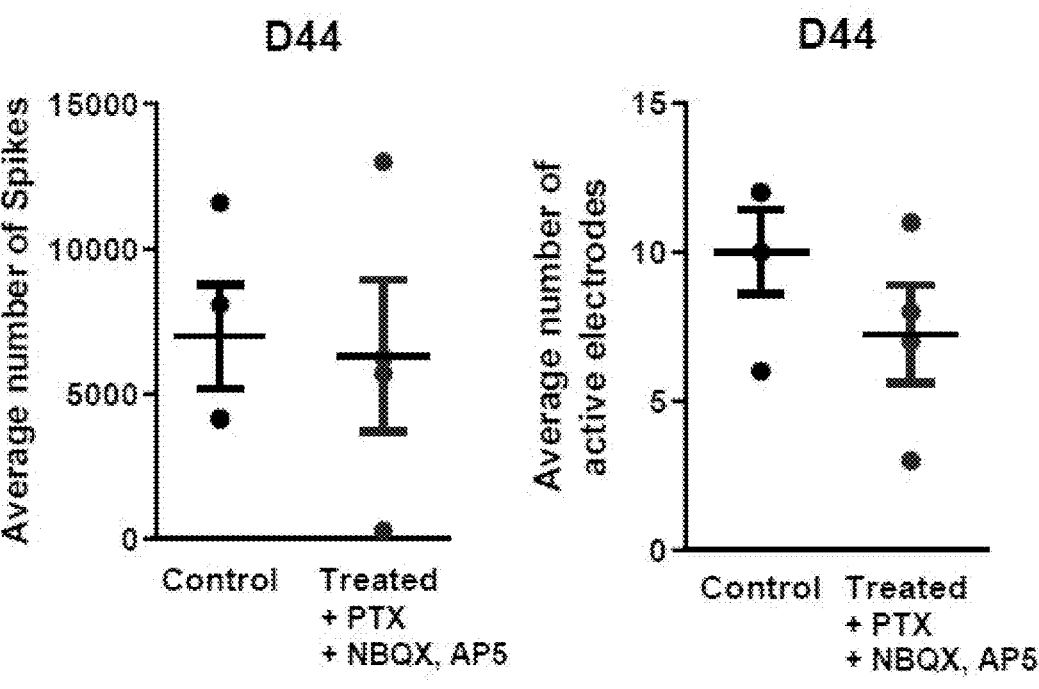
*FIG. 18G-H*
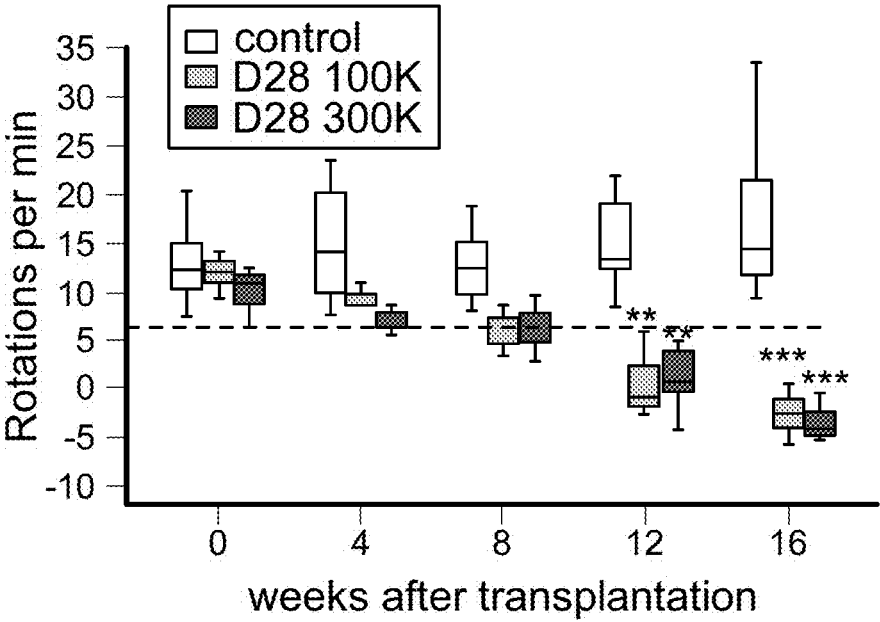
*FIG. 19A*

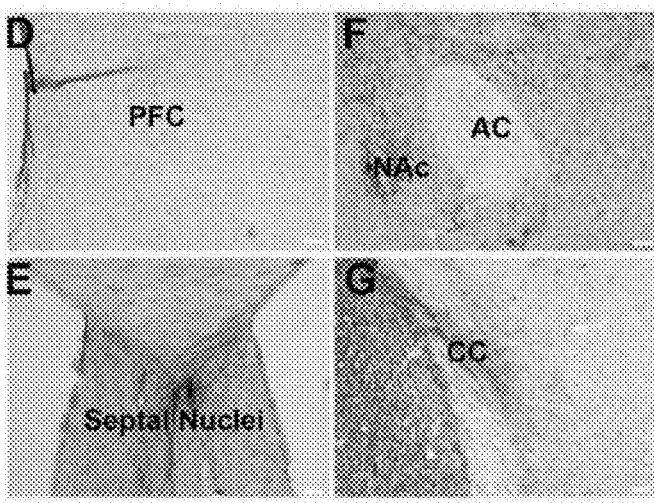
*FIGs. 19D-G*
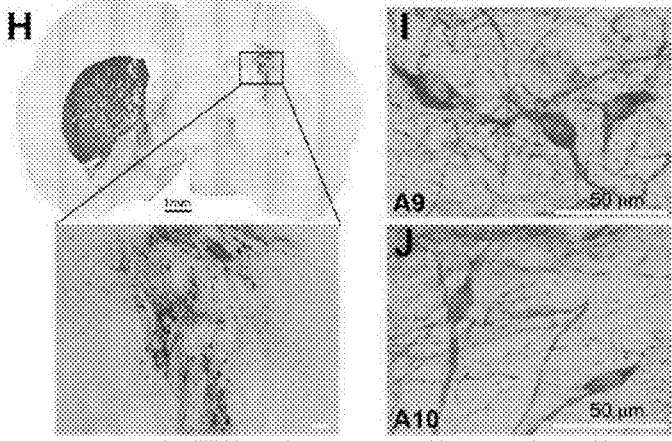
*FIGs. 19H-J*
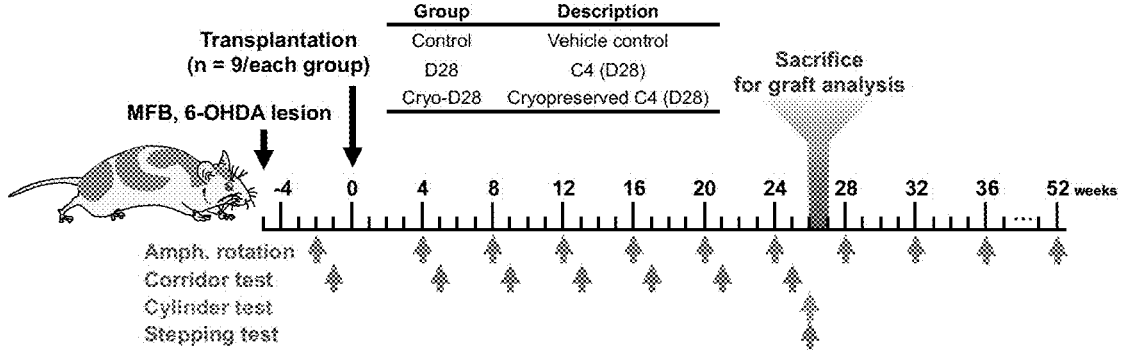
*FIG. 19K*

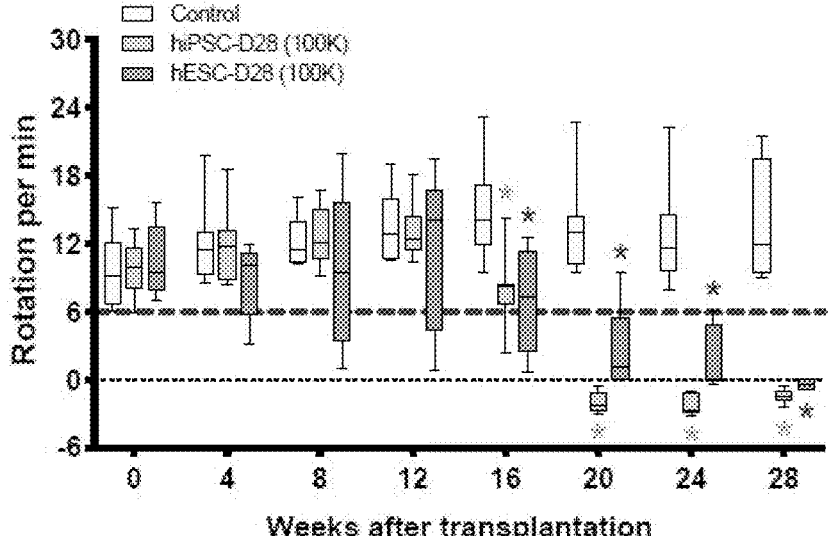
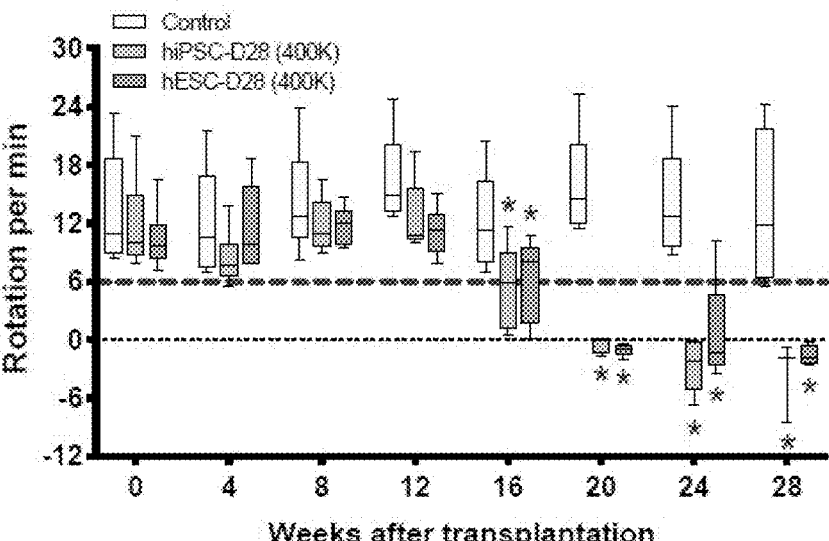
*FIG. 20A*

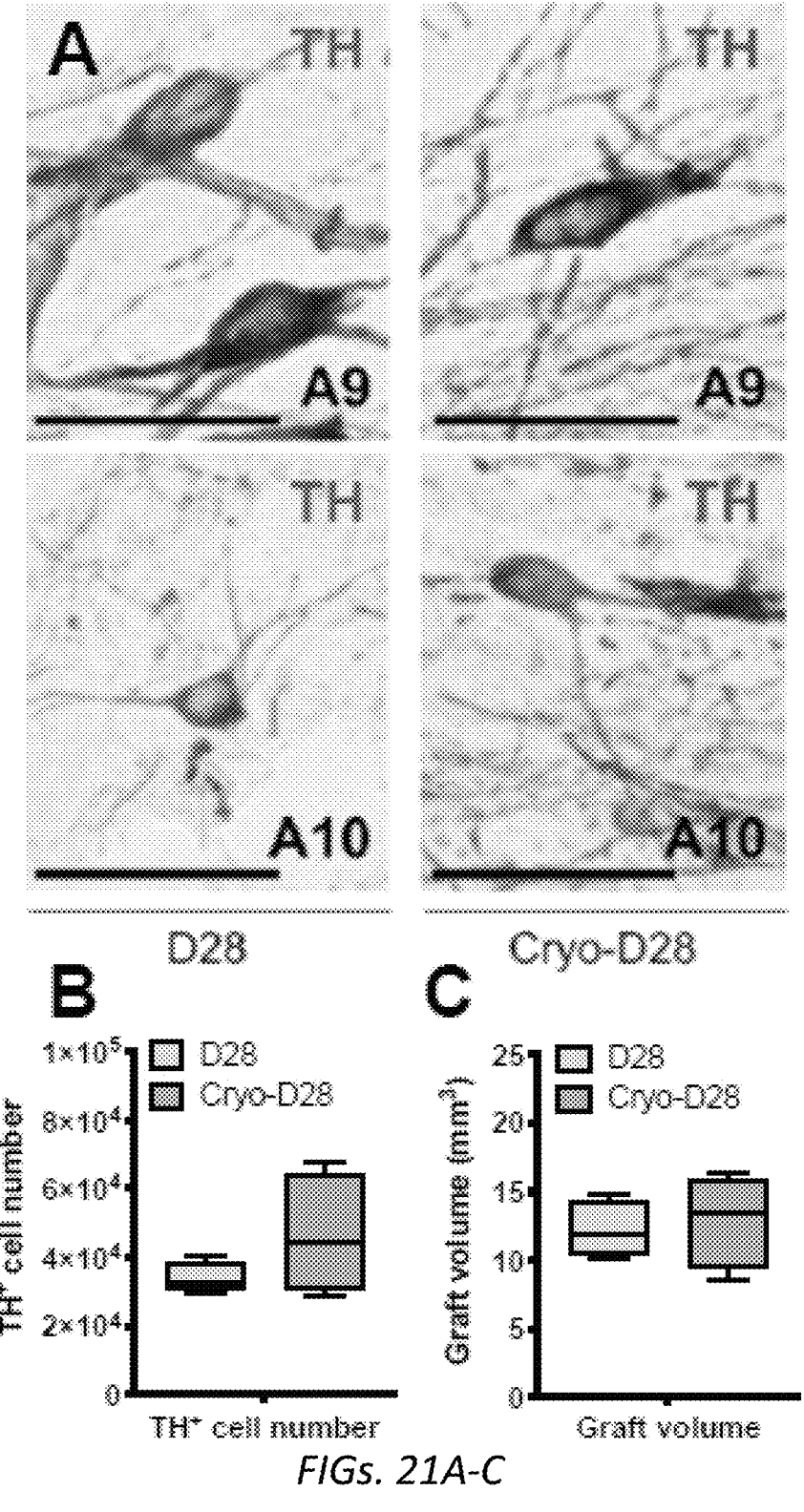
FIGs. 21A-C

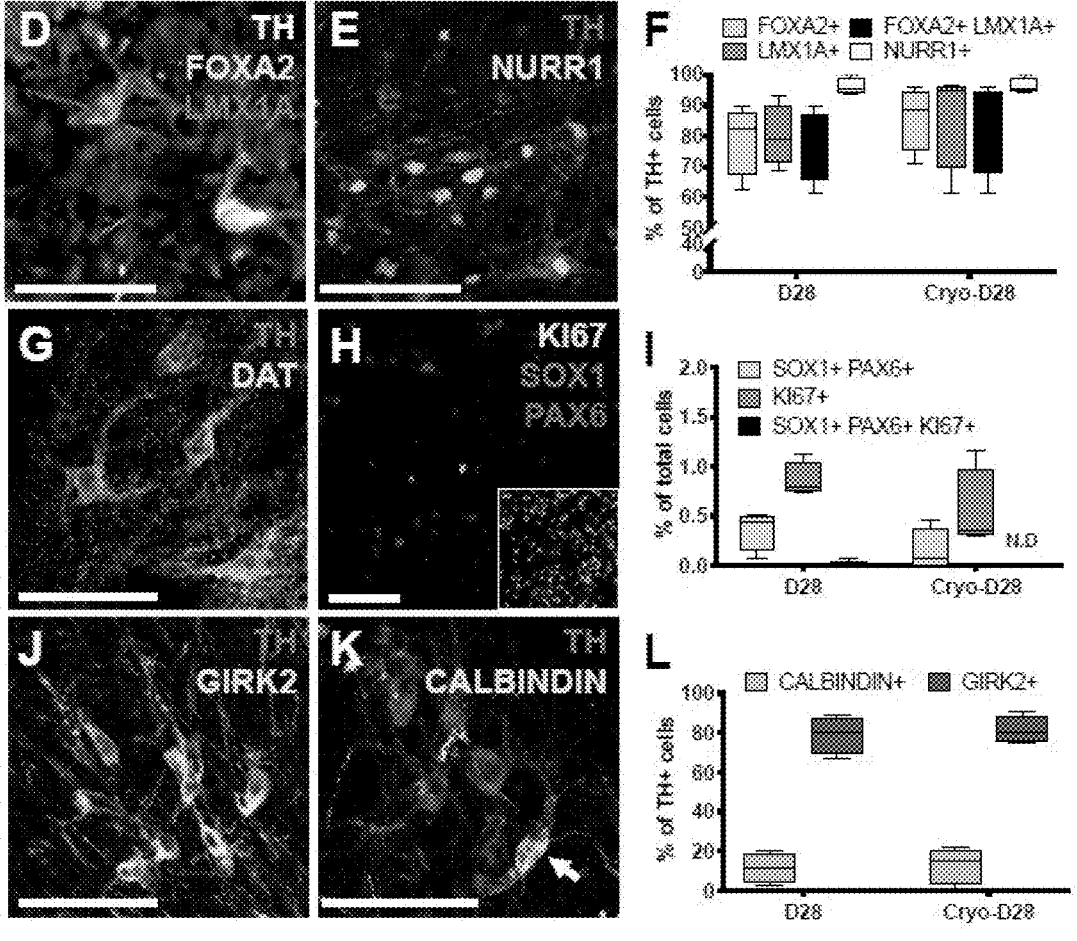
*FIGs. 21D-L*

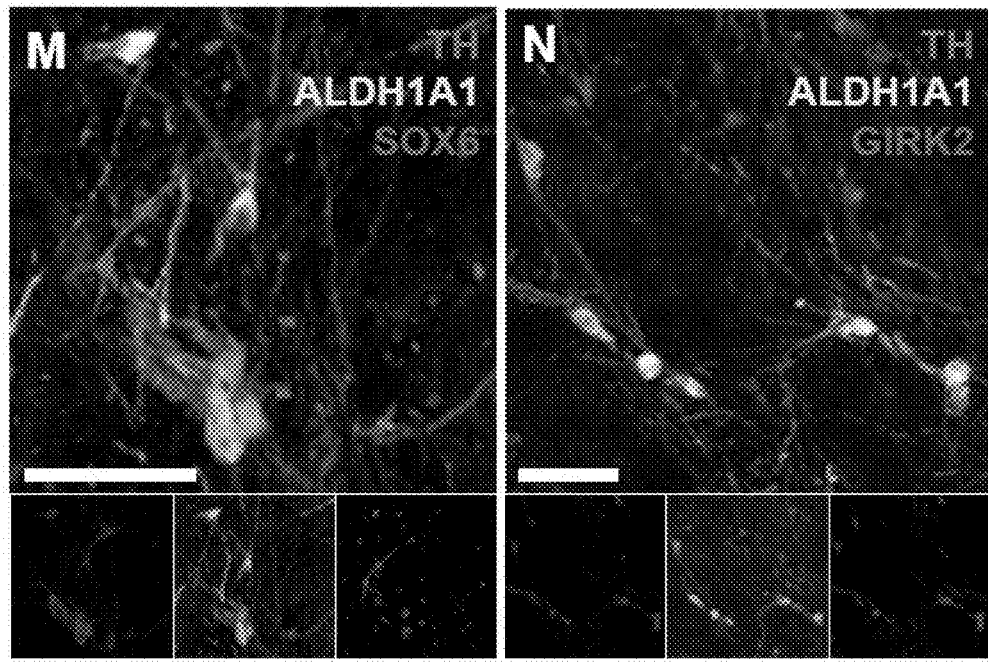
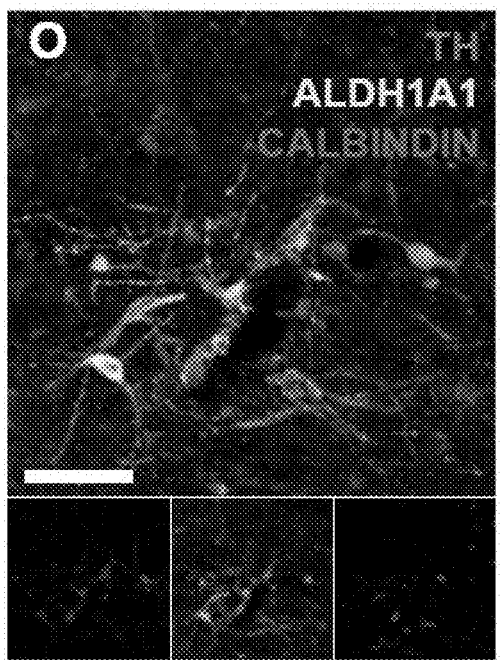
*FIGs. 21M-O*

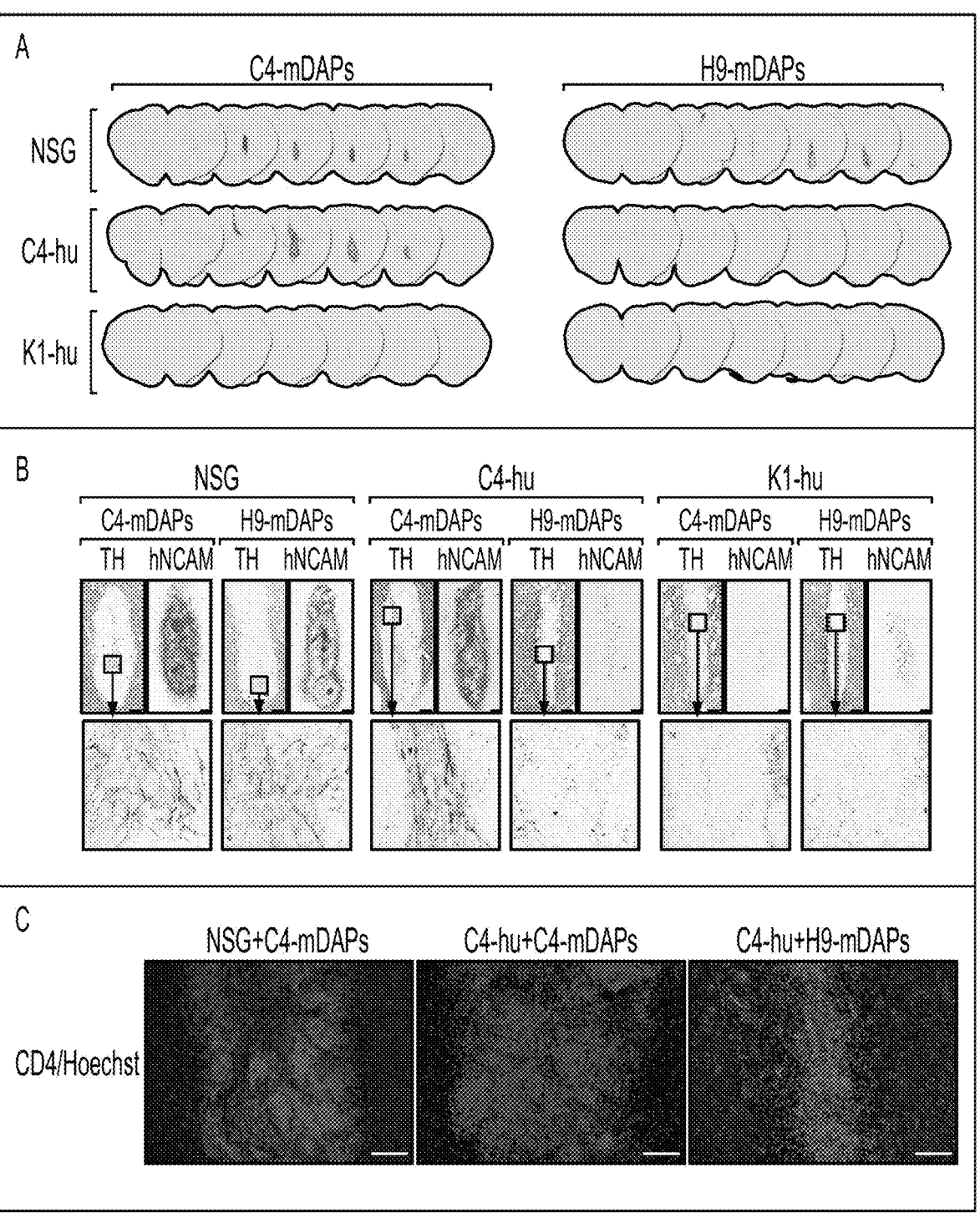
*FIGs. 23A-C*

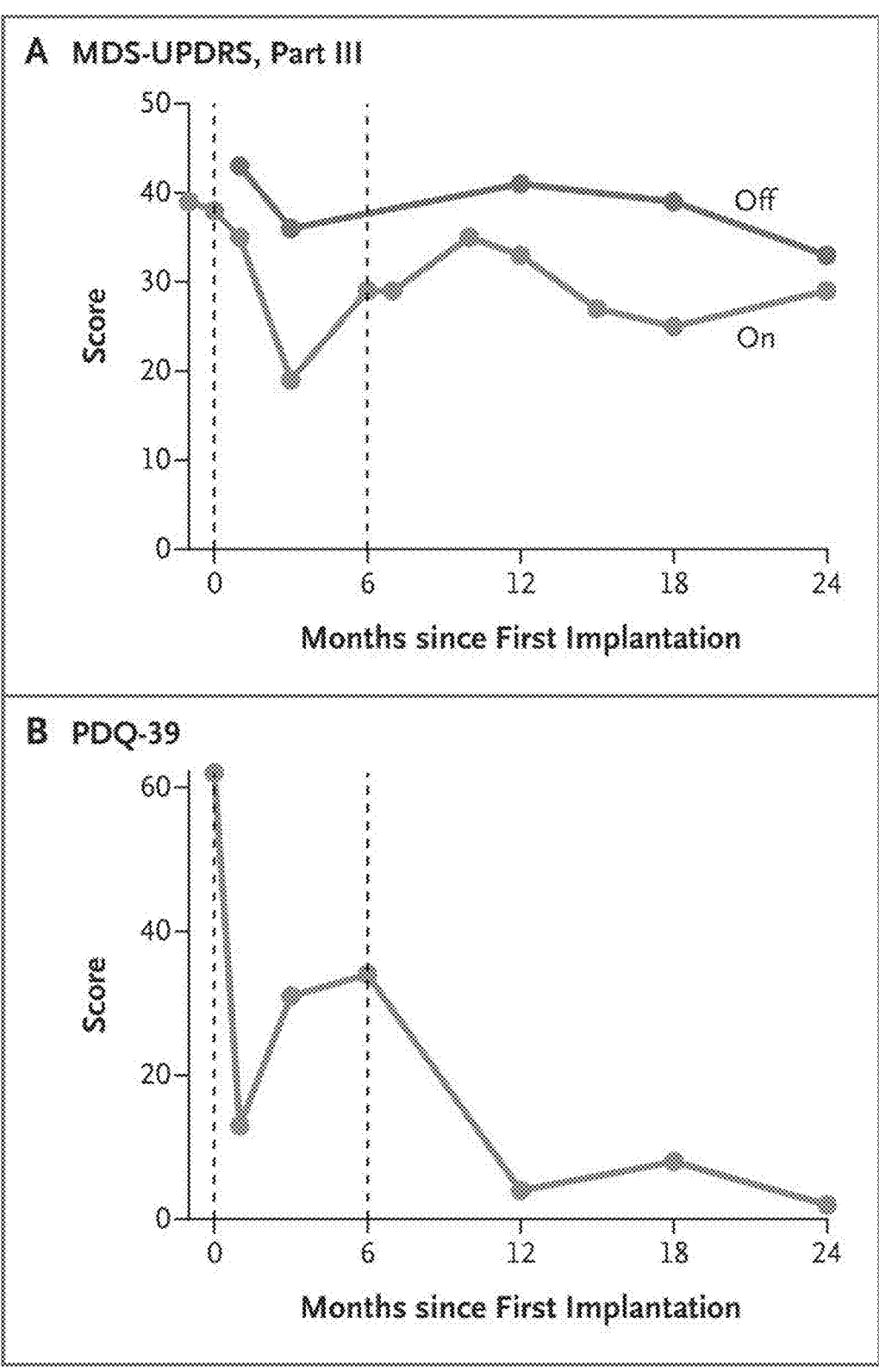
*FIG. 25A-B*

SEQUENCE LISTING

<160> NUMBER OF SEQ ID NOS: 109

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic

```
         peptide
<220> FEATURE:
<221> NAME/KEY: MOD_RES
<222> LOCATION: (5)..(5)
<223> OTHER INFORMATION: Any amino acid

<400> SEQUENCE: 1

Gly Asp Val Glu Xaa Asn Pro Gly Pro
1               5

<210> SEQ ID NO 2
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcgccagtaa agcagacatt aaactttgat ttctgaaact tgcaggtgat gtagagtcaa        60
atccaggtcc a                                                             71

<210> SEQ ID NO 3
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcagcggaa aacagctgtt gaattttgac cttctcaagt tggcgggaga cgtggagtcc        60
aacccagggc cc                                                            72

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gccactaact tctccctgtt gaaacaagca ggggatgtcg aagagaatcc cgggcca           57

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
caatgtacta actacgcttt gttgaaactc gctggcgatg ttgaaagtaa ccccggtcct        60

<210> SEQ ID NO 6
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggcggcgggt ccggaggaga gggcagagga agtcttctaa catgcggtga cgtggaggag        60
```

-continued

```
aatcctggcc ca                                                            72

<210> SEQ ID NO 7
<211> LENGTH: 81
<212> TYPE: RNA
<213> ORGANISM: Homo sapiens

<400> SEQUENCE: 7
ccuuggccau guaaaagugc uuacagugca gguagcuuuu ugagaucuac ugcaauguaa        60
gcacuucuua cauuaccaug g                                                  81

<210> SEQ ID NO 8
<211> LENGTH: 82
<212> TYPE: RNA
<213> ORGANISM: Homo sapiens

<400> SEQUENCE: 8
ccugccgggg cuaaagugcu gacagugcag auaguggucc ucuccgugcu accgcacugu        60
ggguacuugc ugcuccagca gg                                                 82

<210> SEQ ID NO 9
<211> LENGTH: 82
<212> TYPE: RNA
<213> ORGANISM: Homo sapiens

<400> SEQUENCE: 9
ugagcccucg gaggacucca uuuguuuuga ugauggauuc uuaugcucca ucaucgucuc        60
aaaugagucu ucagaggguu cu                                                 82

<210> SEQ ID NO 10
<211> LENGTH: 68
<212> TYPE: RNA
<213> ORGANISM: Homo sapiens

<400> SEQUENCE: 10
cccucgucuu acccagcagu guuugggugc gguuggagu cucuaauacu gccggguaau         60
gauggagg                                                                 68

<210> SEQ ID NO 11
<211> LENGTH: 69
<212> TYPE: RNA
<213> ORGANISM: Homo sapiens

<400> SEQUENCE: 11
ccaccacuua aacguggaug uacuugcuuu gaaacuaaag aaguaagugc uuccauguuu        60
uggugaugg                                                                69

<210> SEQ ID NO 12
<211> LENGTH: 73
<212> TYPE: RNA
<213> ORGANISM: Homo sapiens

<400> SEQUENCE: 12
gcucccuuca acuuuaacau ggaagugcuu ucgugacuu uaaaaguaag ugcuuccaug         60
uuuuaguagg agu                                                           73

<210> SEQ ID NO 13
<211> LENGTH: 68
<212> TYPE: RNA
```

<213> ORGANISM: Homo sapiens

<400> SEQUENCE: 13
ccuuugcuuu aacauggggg uaccugcugu gugaaacaaa aguaagugcu uccauguuuc      60
aguggagg      68

<210> SEQ ID NO 14
<211> LENGTH: 68
<212> TYPE: RNA
<213> ORGANISM: Homo sapiens

<400> SEQUENCE: 14
ccucuacuuu aacauggagg cacuugcugu gacaugacaa aaauaagugc uuccauguuu      60
gagugugg      68

<210> SEQ ID NO 15
<211> LENGTH: 68
<212> TYPE: RNA
<213> ORGANISM: Homo sapiens

<400> SEQUENCE: 15
ccauuacugu ugcuaauaug caacucuguu gaauauaaau uggaauugca cuuuagcaau      60
ggugaugg      68

<210> SEQ ID NO 16
<211> LENGTH: 70
<212> TYPE: RNA
<213> ORGANISM: Homo sapiens

<400> SEQUENCE: 16
uugaagggag aucgaccgug uuauauucgc uuuauugacu ucgaauaaua caugguugau      60
cuuuucucag      70

<210> SEQ ID NO 17
<211> LENGTH: 67
<212> TYPE: RNA
<213> ORGANISM: Homo sapiens

<400> SEQUENCE: 17
guggcacuca aacuguggggg gcacuuucug cucucuggug aaagugccgc caucuuuga      60 guguuac      67

<210> SEQ ID NO 18
<211> LENGTH: 66
<212> TYPE: RNA
<213> ORGANISM: Homo sapiens

<400> SEQUENCE: 18
gguaacacuc aaaagauggc ggcacuuuca ccagagagca gaaagugccc ccacaguuug      60
agugcc      66

<210> SEQ ID NO 19
<211> LENGTH: 67
<212> TYPE: RNA
<213> ORGANISM: Homo sapiens

<400> SEQUENCE: 19
gugggccuca aauguggagc acauucuga uguccaagug gaaagugcug cgacauuuga      60
gcgucac      67

```
<210> SEQ ID NO 20
<211> LENGTH: 69
<212> TYPE: RNA
<213> ORGANISM: Homo sapiens

<400> SEQUENCE: 20
gggauacuca aaauggggggc gcuuuccuuu uugucuguac ugggaagugc uucgauuuug      60
gggugucc                                                              69

<210> SEQ ID NO 21
<211> LENGTH: 23
<212> TYPE: RNA
<213> ORGANISM: Homo sapiens

<400> SEQUENCE: 21
uaauacugcc ggguaaugau gga                                             23

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 22
gagaaaagag gcccaggagt                                                 20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 23
cccctacagg gtggaaaaat                                                 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 24
ggcagtggac ctcaaagaag                                                 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 25
ctatgtcttg gccctgatcc                                                 20

<210> SEQ ID NO 26
<211> LENGTH: 21
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 26
gggtgataac catggacgag g                                                  21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
acttggacgt ttttggggtc                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ataaccatgg acgaggacgg                                                    20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcagccaatg caacttggac                                                    20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gggtagagga cgtgaaagag c                                                  21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggagacccgg atgatgatga c                                                  21

<210> SEQ ID NO 32
<211> LENGTH: 18
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 32
caacagagca agactgtc                                                        18

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggaaacagtt aaatggccaa                                                      20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttttggtatt ggccatccta                                                      20

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaaaggaaca gagagacagg g                                                    21

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
attgccccaa aacttttttg                                                      20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttgaagacca gtctgggaag                                                      20

<210> SEQ ID NO 38
<211> LENGTH: 24
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 38
aacagaacca ataggctatc tatc                                                24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tacagtaaat cacttggtag gaga                                                24

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
catgtacgtt gctatccagg c                                                   21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctccttaatg tcacgcacga t                                                   21

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aatgggagtg aacctttggt ca                                                  22

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gtcgggatgt gcagtagaca                                                     20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
tcatgaaaca cgaagcctac                                                    20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cacccttctc tcctttgaag                                                    20

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cctggaaggg ctgaccgacg agatcaa                                            27

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cttcccagcc aggctctgca gctcc                                              25

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
acagagggga ggtgcgccag ttcacg                                             26

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acggggtgga cctcgctgca cagatc                                             26

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 50
cgaaggtagt tcgccttgag                                                    20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cggtgatagt cagccaggtt                                                    20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cgtggcttac tccccattta                                                    20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tctcgctgtc tctccctctc                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tgtcaagcca tgatggaaaa                                                    20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggtgagccag agatgctttc                                                    20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 56
ggtgctttgg ctgacttttt                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gttgctcacg gaggagtagc                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
accacagtcc atgccatcac                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tccaccaccc tgttgctgta                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ggtgcaggtg aaaatctggt                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gctgctgatg ctgacttctg                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
```

-continued aaatgtttgt gttgcggtca                                                      20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tctggcacag gtgtcttcag                                                      20

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gacctgaagt ggagattcaa cc                                                   22

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tgtatgcgat caaccaccag a                                                    21

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gggtgccgga agtcatactc                                                      20

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gctaggatct gtatagcgtt tgg                                                  23

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

-continued acggcctaaa gatggaggag 20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cggtagaagc aggtggtctc 20

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
caggtggcgg acgtgtgaaa attgagagtg 30

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cacgctggat ctgcctgggg actgtg 26

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cgagaggacc ccgtggatgc agag 24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ggcggccatc ttcagcttct ccag 24

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74 gggcccatc aacttcaccg tcttcc 26

```
<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tgtagtcgat gttccccgcc aggtcc                                                26

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
caaaggcaaa caacccactt                                                       20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tctgctggag gctgaggtat                                                       20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ttgcctgcta cccttgagac                                                       20

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gggctctgat ctctgcatct ac                                                    22

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ctcgctcatt tgttggcga                                                        19
```

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ggagtcgtgt gctttggact                                                          20

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ccgggccgag aaaggtatg                                                           19

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ctgtaggcag aaaagggaa                                                           19

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cactcttcgg gagaatacag                                                          20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
catttggtac aagcaaggtg                                                          20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gaaggatgtg gtccgagtgt                                                          20

```
<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gtgaagtgag ggctcccata                                                 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
acaagtggcc aattcactcc                                                 20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gaggtggaca agggatctga                                                 20

<210> SEQ ID NO 90
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
acccattatc cagatgtgtt tgcccgag                                        28

<210> SEQ ID NO 91
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
atggtgaagc tgggcatagg cggcag                                          26

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ggaaccgcta ccccgacatg ag                                              22

<210> SEQ ID NO 93
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tgaaggcgaa tggaaaggtc t                                             21

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggcggaaata gaacctgtca                                               20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cttccaggat gggttgagaa                                               20

<210> SEQ ID NO 96
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
cctccgtcca tcctctg                                                  17

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
aagcatcaaa caacctcaag                                               20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
aaccccaaga tgcacaactc                                               20

<210> SEQ ID NO 99
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cggggccggt atttataatc                                                           20

<210> SEQ ID NO 100
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cgctttcatg gtgtgggcta aggacg                                                    26

<210> SEQ ID NO 101
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tagttggggt ggtcctgcat gtgctg                                                    26

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
cgggcttctc ggaccaggtg ta                                                        22

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ctcctcggcg gtgtactcca ca                                                        22

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cggtggtgga gccctacaac                                                           20

<210> SEQ ID NO 105
<211> LENGTH: 19
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 105
aggtggtgac tccgctcat                                             19

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
attgccccaa aacttttttg                                            20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ccacatctcc ctccagaaaa                                            20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
agggtctggg ccatagaact                                            20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ttgaagacca gtctgggaag                                            20
```

AUTOLOGOUS CELL REPLACEMENT THERAPY FOR PARKINSON'S DISEASE

CLAIM OF PRIORITY

This application is the national stage entry of International Patent Application No. PCT/US2020/034098, filed on May 21, 2020, and claims the benefit of U.S. Provisional Patent Application Ser. No. 62/852,008, filed on May 23, 2019, and 62/949,906, filed on Dec. 18, 2019. The entire contents of the foregoing are hereby incorporated by reference.

FEDERALLY SPONSORED RESEARCH OR DEVELOPMENT

This invention was made with Government support under Grant No. NS070577 awarded by the National Institutes of Health. The Government has certain rights in the invention.

TECHNICAL FIELD

Described herein are methods for generating midbrain dopamine (mDA) neuronal progenitor cells useful for autologous cell therapy in Parkinson's Disease (PD), compositions comprising the cells, and methods of use thereof.

BACKGROUND

Parkinson's Disease (PD), characterized by both motor and non-motor system pathology, is the second most common neurodegenerative disorder after Alzheimer's disease. Affecting about 1% of the population over age 60, its prevalence presents an increasing social burden as the population ages with over 14 million people worldwide expected to have PD by 2030 (1). Since its introduction in the 1960's, dopamine (DA)-replacement therapy (e.g., L-DOPA and DA agonists) has remained the gold standard pharmacological treatment. While significantly improving PD patients' quality of life, prolonged usage of these medications usually (>80%) results in undesirable side effects such as dyskinesias and motor fluctuations (2).

SUMMARY

Parkinson's disease (PD) is a common neurodegenerative disorder associated with loss of striatal dopamine secondary to degeneration of midbrain dopamine (mDA) neurons in the substantia nigra, rendering cell transplantation a promising therapeutic strategy. To establish human induced pluripotent stem cell (hiPSC)-based autologous cell therapy for PD, we developed a platform of core techniques for the production of mDA progenitors as a safe and effective therapeutic product. First, by combining metabolism-regulating microRNAs with reprogramming factors, we developed a method to more efficiently generate clinical grade iPSCs, as evidenced by genomic integrity and unbiased pluripotent potential. Second, we established a "spotting"-based in vitro differentiation methodology to generate functional and healthy mDA cells in a scalable manner, with significantly less cell loss. Third, we developed a chemical method that safely eliminates undifferentiated cells with neoplastic potential from the final product with great efficiency. Dopaminergic cells produced in this manner express high levels of characteristic mDA markers, produce and secrete dopamine, and exhibit electrophysiological features typical of mDA cells. Furthermore, transplantation of these cells into rodent models of PD robustly restored motor dysfunction with prominent reinnervation to the host brain, while showing no evidence of tumor formation or redistribution of the implanted cells. In addition, implantation of cells derived using this method into a human suffering from PD appears to have arrested and perhaps reversed the disease process (see Example 10). Thus, this platform is suitable for the successful implementation of personalized, autologous, cell replacement therapy for PD.

Thus provided herein are methods of generating a population of differentiated cells, e.g., neurons, e.g., midbrain dopaminergic progenitor cells (mDAPs). The methods include providing a population of induced pluripotent stem cells (iPSCs), preferably human iPSCs; plating the population of cells in discrete, individual, preferably substantially circular, areas ("spots") with sufficient distance between the areas to maintain isolation between areas, in a biomatrix hydrogel support, with a density of about 5,000-20,000, e.g., about 10,000, cells per area; and maintaining the cells under conditions sufficient for the iPSCs to differentiate, e.g., into neurons, e.g., mDAPs.

In some embodiments, the biomatrix hydrogel support is a basement membrane extract or synthetic matrix.

In some embodiments, the cells are suspended in the gel, e.g., in about 10 µl of the gel, before plating.

In some embodiments, the areas are about 2-10 mm, e.g., about 5 mm, in diameter.

In some embodiments, the distance between the areas is 1-3 cm.

In some embodiments, the iPSC express alkaline phosphatase (AP) and TRA-1-60.

In some embodiments, the mDAPs express one, two, or more markers comprising FOXA2, OTX2, LMX1A, and/or EN1, preferably at least FOXA2 and LMX1A; optionally wherein the mDAPS are TH+ cells that co-express FOXA2, LMX1A and NURR1.

In some embodiments, the iPSC are generated by a method comprising: obtaining a population of primary cells from a subject, preferably wherein the primary cells are fibroblasts, hair keratinocytes, blood cells, or bone marrow mesenchymal stem cells (MSCs); inducing expression of at least OCT4, KLF4, and SOX2, and/or L-MYC, and/or C-MYC in the cells; and maintaining the cells under conditions sufficient for the primary cells to become iPSCs.

In some embodiments, inducing expression of at least OCT4, KLF4, and SOX2, and/or L-MYC, and/or C-MYC comprises transfecting the primary cells with a polycistronic episomal vector that comprises human Oct4 linked with 2A sequence of foot-and-mouth disease virus (OCT4-F2A), KLF4, and SOX2 linked with 2A sequence of porcine teschovirus (SOX2-P2A), and/or L-MYC coding sequences, and/or C-MYC coding sequences.

In some embodiments, the iPSC are generated by a method comprising expressing in the cells one or more exogenous microRNAs (miRNAs) selected from the group consisting of miR-106a, -106b, -136s, -200c, -302s, -369s, and -371/373. miR-302s indicates the miR-302 cluster, which encompasses five miRNAs including 302a, 302b, 302c, 302d, and 367.

In some embodiments, the miRNAs comprise one or both of miR-302s and miR-200c.

In some embodiments, the methods include introducing into the cells an episomal vector that comprises sequences coding for miR-302s and miR-200c.

In some embodiments, the iPSC are generated by a method comprising expressing in the primary cells all of OCT4, KLF4, SOX2, miR-302s and miR-200c; or OCT4, KLF4, SOX2, L-MYC/C-MYC, miR-302s and miR-200c.

In some embodiments, the methods include introducing into the cells any one or more of (i) a viral vector (e.g., lentiviral, adenoviral, or AAV vector) or polycistronic episomal vector that comprises human Oct4 linked with 2A sequence of foot-and-mouth disease virus (OCT4-F2A), KLF4, SOX2 linked with 2A sequence of porcine teschovirus (SOX2-P2A), L-MYC coding sequences, and C-MYC coding sequences, or mature RNAs of any one or more of Oct4, KLF4, SOX2, L-MYC/C-MYC, or corresponding proteins, and (ii) a viral vectors or episomal vector that comprises sequences coding for miR-302s and miR-200c, or mature miR-302s and miR-200c.

In some embodiments, the cells are human cells. In some embodiments, C-MYC is used in place of L-MYC, and/or vice-versa.

In some embodiments, a method described herein comprises reduction of undifferentiated iPSCs, preferably by inhibiting the BIRC5 gene.

Also provided herein are populations of cells comprising mDAPs made by a method described herein, and compositions comprising the cells. In some embodiments, the cells have one or more somatic mutations not present in the primary cells, and/or have no somatic mutations currently known to be causally implicated in cancer.

Further, provided herein are methods of using the cells for treating a subject who has or is at risk of developing Parkinson's Disease (PD). The methods can include obtaining primary somatic cells, preferably from the subject who has or is at risk of developing PD or an autologous subject, and generating iPSCs from the primary cells; preferably treating the iPSCs with quercetin for a time sufficient to reduce numbers of SOX1 positive, KI67 positive, SOX1/K167 double positive, SOX1/PAX6 double positive, and SOX1/PAX6/K167 triple positive cells; generating a population of cells comprising mDAPs by a method described herein; and administering the population of cells to the subject. In some embodiments, the cells are administered by being implanted directly into or near the affected area of the subject's brain, preferably bilaterally into one or more of the caudate nucleus, putamen, and substantia nigra, optionally using magnetic resonance imaging-guided stereotactic surgery.

In some embodiments, the cells are administered via injection, preferably with a device that creates columns spanning the sagittal extent of the putamen (e.g., as described in Schweitzer et al., Oper Neurosurg (Hagerstown) 2019), preferably with three tracks, preferably with a single high parasagittal cortical entry point. In some embodiments, a dose of about 1 million, 2 million, 3 million, 4 million, 5 million, 6 million, 7 million, or 8 million cells, preferably wherein the cells are divided equally among the three tracks. In some embodiments, the cells are administered in a single treatment. In some embodiments, the cells are administered in two or more treatments.

In some embodiments, both hemispheres of the brain are treated, and the cells are administered to a first hemisphere in a first treatment, and the other hemisphere in a second treatment. In some embodiments, the time between the first and second treatments is about 2 weeks, 1 month, 2 months, 3 months, 4 months, 5 months, 6 months, 7 months, 8 months, 9 months, 10 months, 11 months, 12 months, 18 months, 24 months, 30 months, 36 months, 48 months, 54 months, or 60 months.

In some embodiments, at least one antibiotic is administered preoperatively, perioperatively, and/or postoperatively.

Also provided herein are culture dishes for culturing cells, e.g., for use in a method described herein, wherein an underside of the dishes is inscribed with a grid with a distance between the lines of 1.5-2.5 cm, e.g., about 2 cm, e.g., a 2×2 cm grid. In some embodiments, the grid is formed as part of the dish, printed or etched on the underside. In some embodiments, the dishes comprise polystyrene, polyethylene, polypropylene, polycarbonate, and polyvinyl thermoplastic resins. In some embodiments, the dishes comprise a layer of biomatrix hydrogel support, preferably a basement membrane extract or synthetic matrix, disposed therein.

Appendices 1 and 2, and all publications, patent applications, patents, sequences, database entries, and other references mentioned therein, are hereby incorporated by reference in their entirety for any and all purposes.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-H. An improved reprogramming method combining Y4F and metabolism-regulating miRNAs. (A-D) Screening of miRNAs that enhance the generation hiPSC-like colonies by Y3F (A), by Y4F (B), by Y3F+3 (C), or Y4F+3 (D) from hDFs, relative to an empty vector (Mock) control. Mean±s.d., n=5, *$p<0.05$; **$p<0.01$, one-way ANOVA with Tukey's post-test. (E-F) Time course of OCR (E) and ECAR (F) in hDFs infected with Y4F, miR-302s, and/or miR-200c. Mean±s.d., n=3, *$p<0.05$; $p<0.01$; *$p<0.005$, two-way ANOVA with Tukey's post-test. (G) Percentage of TRA-1-60$^+$ colonies among AP$^+$ colonies following lentiviral infection encoding Y4F, Y4F+3, or Y4F+3+2. Mean±s.d., n=6, *$p<0.005$, two-way ANOVA with Tukey's post-test. (H) Percentage of TRA-1-60$^+$ colonies among AP$^+$ colonies following transfection with episomal vectors encoding Y4F, Y4F+3, or Y4F+3+2. Mean±s.d., n=4, $p<0.01$, two-way ANOVA with Tukey's post-test.

FIGS. 5A-G Effects of quercetin treatment on undifferentiated and differentiated cells. (A) Screening to determine optimal quercetin treatment conditions. Surviving hiPSCs were counted using a hemocytometer after treatment with different quercetin concentrations and durations. (B-C) Viability (B) and total cell number (C) of dopaminergic cells at D11 after quercetin treatment on D9. Cultures were treated for 16 hours at 5, 10, 20, 40 and 100 μM. Mean±s.d., n=4, one-way ANOVA. (D) Colony formation by hiPSCs serially diluted by factors of 10 from $10^5$ to 1 together with a constant number of fibroblasts ($10^5$). Cells were treated with 40 μM quercetin (QC) for 16 hours or left untreated, and then cultured for 6 days, followed by staining for alkaline phosphatase activity. Representative results from two separate experiments. (E) Plotting of final colony number counted against original input hiPSC number. (F) Generation of standard curve for OCT4 copy number against input hiPSC number by qRT-PCR. OCT4 copy number was measured by qRT-PCR and calculated from 10-fold serially diluted hiPSCs, from $10^5$ to $10^2$ cells. (G) Measurement using OCT4 qRT-PCR of OCT4-positive cell numbers among mDA cells differentiated from hiPSCs at various time points with or without QC treatment. Mean±s.d., n=2, ***p<0.005, two-way ANOVA.

FIGS. 6A-I. Molecular, cellular, and physiological characterization of in vitro differentiated C4 hiPSCs. (A) Schematic overview of mDA differentiation method based on spotting protocol. Numbers represent concentrations in ng/ml and those in parentheses represent in μM. AA, Ascorbic acid; β-mer, beta-mercaptoethanol; BDNF, Brain-derived neurotrophic factor; CHIR, CHIR99021; dbcAMP, dibutyryl cyclic adenosine monophosphate; FGF-8, Fibroblast growth factor 8; GDNF, Glial cell line-derived neurotrophic factor; KSR, knockout serum replacement; LDN, LDN193189; L-Glu, L-glutamine; NEAA, Non-essential amino acid; PMN, Purmorphamine; QC, Quercetin; SB, SB431542; SHH, Sonic Hedgehog; TGF-β3, transforming growth factor beta 3. (B) Heatmap of gene expression of stage-specific neural markers in mDA differentiated cells. (C) Gradual increase in FOXA2, LMX1A, NURR1 and TH gene expression during differentiation. (D) Immunofluorescence staining of neural precursor marker (NESTIN), mDAP markers (FOXA2/LMX1A/TH), mDAN markers (MAP2, NURR1/TH), and proliferating markers PAX6/SOX1/KI67 cells in differentiated D28 cells. Scale bar; 100 μm. (E) Percentages of NESTIN⁺, MAP2⁺, TH⁺, and NURR1⁺ cells among total D28 cells (n=6). (F) Percentages of FOXA2⁺, LMXA1⁺, and FOXA2⁺/LMX1A⁺ cells among total D28 cells (n=6). (G) Percentages of FOXA2⁺/LMX1A⁺ and NURR1⁺ cells among the TH⁺ D28 cells (n=6). (H) Percentages of PAX6⁺, SOX1⁺, and PAX6⁺/SOX1⁺/KI67⁺ cells among total D28 cells (n=6). N.D, not detected. (I) HPLC analysis of KCl-induced release of dopamine and dopamine metabolites (DOPAC) on D47. Data are presented as mean±SEM.

FIGS. 7A-H. In-vivo safety of C4-derived mDA cells in NOD-SCID mice. (A) H&E staining of NOD-SCID mouse brain after striatal transplantation of C4 iPS cells (D0, left), or of C4-derived mDA progenitors at D14 (middle) or D28 (right). The white circle in the D14 group identifies rosette-like structures. (B) Quantification of teratoma formation percentage at D0 (n=4) and D14 without quercetin (n=4), and at D14 (n=19) and D28 (n=23) with quercetin treatment groups. QC=quercetin. (C) Quantification of rosette formation at D14 of differentiation without quercetin, and at D14 and D28 with quercetin treatment. (D) Immunohistochemistry of Vimentin in D14 and D28 groups. (E-F) Immunofluorescence staining of SOX1, PAX6 and KI67 in D14 (E) and D28 groups (F). (G) Quantification of SOX1⁺, KI67⁺, SOX1⁺/KI67⁺, SOX1⁺/PAX6⁺, SOX1⁺/PAX6⁺/KI67⁺ populations in D14 and D28 groups. Data are presented as mean±SEM, n=4, ***p<0.001, Student's t-test. (H) Biodistribution assay. RT-PCR of human or mouse specific gene expression in "brain mix" (mixture of olfactory bulb and cerebellum), spinal cord, lung, heart, spleen, kidney and liver of the NOD SCID mice that had received intrastriatal hiPSC-derived D28 dopaminergic progenitor grafts 6 months previously. hiPSC serves as a positive control. The human specific gene is located on chromosome 10 at 29125650 to 29125967. The mouse specific gene is part of mouse TNFα. N.D, not detected. All scale bars indicate 100 μm unless otherwise specified.

FIGS. 9A-N. Identification of microRNAs regulating metabolic reprogramming and improved reprogramming method based on their combination with Y4F. (A-B) Oxygen consumption rate (OCR) (A) and extracellular acidification rate (ECAR) (B) of hDFs transfected with microRNA mimics for control (Scr) or miR-200c (200c) at 3 days after transfection, were assessed using the XFp analyzer. Mean±s.d., n=3, *$p<0.05$, two-tailed unpaired t-test. (C) OXPHOS capacity of hDFs transfected with Scr or miR-200c 3 days after transfection. Mean±s.d., n=3. (D-E) Basal respiration, ATP turnover, maximum respiration, oxidative reserve (D) or relative OCR changes after FCCP injection (E). Mean±s.d., n=3, *$p<0.05$, two-tailed unpaired t-test. (F-G) OCR were shown for hDFs infected with lentiviruses expressing Y4F and/or miR-200c (200c) at 3 (F) or 8 (G) days following transduction. Mean±s.d., n=3. (H-I) Basal respiration, ATP turnover, maximum respiration, and oxidative reserve in hDFs at 3 (H) or 8 (I) days following transduction, as shown in F-G. Mean±s.d., n=3, * $p<0.05$;  $p<0.01$; * $p<0.005$, one-way ANOVA with Tukey's post-test. (J-K) OCR/ECAR ratio (J) or relative OCR changes after FCCP injection (K) in hDFs following transduction, as shown in F-G. Mean±s.d., n=3, * $p<0.05$; ** $p<0.01$, two-way ANOVA with Tukey's post-test. (L-M) OCR (L) and ECAR (M) in hDFs transduced with lentivirus expressing individual miRNAs at 3 days after transduction. Mean±s.d., n=9, *$p<0.05$; $p<0.01$; * $p<0.005$, one-way ANOVA with Tukey's post-test. (N) OCR/ECAR ratio, as shown in L-M. Mean±s.d., n=9, *** $p<0.005$, one-way ANOVA with Tukey's post-test.

FIGS. 10A-E. Identification of Y4F+3+2 reprogramming protocol. (A) Representative pictures of TRA-1-60 (upper) or AP (lower)-positive colonies at 14 days post-transduction. (B) Percentage of TRA-1-60+ colonies among AP+ colonies following lentiviral transduction of Y4F, Y4F+3, or Y4F+3+2 in human adult fibroblasts (GM03529). Mean±s.d., n=6, **$p<0.01$, two-way ANOVA with Tukey's post-test. (C-D) Plasmid maps encoding pY4F (OCT4, SOX2, KLF4, and L-MYC) (C) and miR-302s and -200c (p3+2) (D). (E) Schematic diagram of our established episomal system-based reprogramming method using single transfection with pY4F and pY3+2.

FIGS. 12A-G. Characterization of hiPSC lines generated by our improved reprogramming method. (A) Standard curve of qRT-PCR detection of EBNA-1 specific sequence (EB-01). (B) No residual plasmid DNA was detected in cytoplasm of any hiPSC line. Samples from the original fibroblasts (Fib), a human ESC line (H9), and negative control (distilled water: DW) were also tested. Plasmid-specific primers based on EBNA sequence (EB-01) were used for qRT-PCR analyses. (C) Detection of integrated plasmid DNAs in the host genome. One line (N17) was found to have integrated plasmid DNA sequences in the host chromosomal DNAs. (D) qRT-PCR analysis of integrated plasmid sequences. Mean±s.d., n=3, ***$p<0.005$, one-way ANOVA. (E) Chromosomal genotyping of hiPSC lines derived from the skin biopsy of a sporadic PD patient (MCL540). Patterns were compared with samples from the original fibroblasts (Fib) and the hESC line (H9) as positive and negative controls, respectively. DW, distilled water. (F) Representative images of C4 and N3 normal karyotype. (G) Representative images of teratoma formation and the three germ layer tissues from the 19-9-11T hiPSC line from WiCell (upper), C4 (middle) and N3 (lower). Scale bar: 100 μm.

FIGS. 18A-H. Electrophysiological features of in vitro differentiated C4 hiPSC. (A) Representative voltage traces of action potentials induced by depolarizing current injection (500 ms) on D70. (B) Representative current traces evoked by voltage pulses in voltage-clamp mode. Left: transient inward and sustained outward currents induced by voltage pulses from −70 mV to +40 mV in 10 mV increments (100 ms duration). Middle: inward currents were completely blocked by TTX (1 μM). Right: traces recorded in the presence of TTX were subtracted from the traces recorded under control conditions to isolate voltage-gated Na+ currents at different membrane potentials. (C) Spontaneous postsynaptic currents recorded at −70 mV in voltage-clamp mode. (D) Spontaneous firing of differentiated cells in current-clamp mode at the resting membrane potential. (E) Immunofluorescence staining of individual recorded cells. Neurobiotin-filled cell (red) shows TH positivity (green). Scale bar: 100 μm. (F) Cumulative activity map and spiking activity of in vitro differentiated C4 hiPSC at D30, D37 and D44 using the multielectrode array. (G-H) The average spikes number (G) and the active electrodes numbers (H) of D44 differentiated C4 hiPSC with or without treatment with a combination of glutamate receptor antagonists, NBQX+ AP5, and a GABAA receptor antagonist, Picrotoxin. Data are presented as mean±SEM, n=4.

FIGS. 19A-M. Analyses of in vivo transplantation outcomes in athymic rat models of PD. (A) 6-OHDA lesioned Taconic rats Amphetamine induced rotation test before and after transplantation with C4-derived D28 DA progenitors (100,000 or 300,000 cells) at 4, 8, 12 and 16 weeks. Data are presented as mean±SEM.  means p<0.01, * means p<0.001. (B) H&E staining of athymic rat brains 6 months following transplantation with Day 28 cells. (C) Immunohistochemistry of hNCAM reveals extensive fiber outgrowth into multiple areas throughout the host brain in successive coronal sections. (D-G) Higher magnification of hNCAM staining illustrates outgrowth patterns from the graft into prefrontal cortex (D), septal nuclei (E), nucleus accumbens (F), and corpus callosum (G). (H-J) Histological analysis at 6 months post transplantation, of TH+ dopaminergic neurons in the grafts produced by D28 DA progenitors. Note A9-like neuronal morphology with large, angular cell somata (I) as well as smaller spherical A10-like neurons (J). (K) Schematic diagram of in vivo Charles River athymic rat experiments. (L) Comparison of cell viability and FOXA2, LMX1A and TH positive cell numbers between freshly prepared D28 cells and Cryo-D28 cells thawed after 1 week in liquid nitrogen (n=3-4). (M) Amphetamine-induced rotation test from 24 to 52 weeks after D28 cells and Cryo-D28 cells transplantation (n=3-4). Data are presented as mean±SEM. *p<0.05, p<0.01, *p<0.001, Student's t-test. AC, anterior commissure; cc, corpus callosum; NAc, nucleus accumbens; PFC, prefrontal cortex. All scale bars indicate 100 μm unless specified description.

FIGS. 20A-C. Function and innervation analyses of in vivo transplantation. (A) Amphetamine-induced rotation test following transplantation of H9 hESC- and C4 hiPSC-derived D28 cells (n=5-8). (B) Representative images of 6-OHDA lesioned brains from each group. (C) High magnification image of graft innervation into STR and NAc. Data are presented as mean±SEM. *p<0.05, p<0.01, *p<0.001, Student's t-test. STR, striatum; NAc, nucleus accumbens.

FIGS. 21A-O. Graft analyses after transplantation of C4-derived mDA cells. (A) Immunostaining of TH+ neurons (both A9- and A10-like) in D28 and Cryo-D28 grafts. (B) Estimation of number of surviving TH+ neurons in D28 and Cryo-grafts (n=4). (C) Estimation of graft volume in D28 and Cryo-D28 grafts (n=4). (D-F) Immunofluorescence containing for FOXA2, LMX1A (D) and NURR1 (E) and TH in D28 grafts (n=4). (F) Quantification of TH+ neurons that co-express FOXA2, LMX1A, both makers, or NURR1 in D28 and Cryo-D28 grafts (n=4). (G) Immunofluorescence co-staining for DAT and TH. (H) Immunofluorescence staining for PAX6, SOX1 and Ki67 in grafted neurons. (I) Quantification of PAX6+, SOX1+ and Ki67+ cells in D28 and Cryo-D28 grafts (n=4). (J-L) Immunofluorescence co-staining of GIRK2+(J) and calbindin+(K) neurons for TH in D28 and Cryo-D28 grafts (n=4). (L) Quantification of calbindin+ and GIRK2+ neurons in D28 and Cryo-D28 grafts. (M-O) Immunofluorescence co-staining of TH+, ALDH1A1+ and SOX6+(M), TH+, ALDH1A1+ and GIRK2+(N), TH+, ALDH1A1+ and CALBINDIN+(O) in D28 grafts. All graft analysis data of Taconic rats were obtained 18 weeks after transplantation. All graft analysis data of Charles River rats were obtained 26 weeks after transplantation. AC, anterior commissure; cc, corpus callosum; NAc, nucleus accumbens; PFC, prefrontal cortex; SNpc, substantia nigra pars compacta; STR, striatum; T, transplant; VTA, ventral tegmental area. Scale bars: 50 μm (A); 100 μm (D-O).

FIGS. 23A-C. Immunogenicity of mDA progenitor cells in humanized mice. A and B show mouse brain sections stained with antibodies against hNCAM (A) and TH/hNCAM (B) at 2 weeks post transplantation of autologous and allogenic mDAPs, to detect the presence and dopaminergic differentiation of surviving grafts. (C), staining with anti-CD4, demonstrating major cell loss and T cell infiltration only in the allogeneic grafts placed in the patient-humanized animals. All scale bars indicate 100 μm. NSG; NOD/SCID/IL2γnull mouse; C4− hu, NSG mouse humanized with patient-derived PBMCs; Kl-hu, NSG mouse humanized with volunteer-derived PBMCs. C4-mDAP, patient-derived mDAP; H9-mDAP, a human embryonic cell line-derived mDAP.

FIGS. 25A-B. Longitudinal clinical assessments of Parkinson's related motor function, non-motor function and quality of life. Time of the first (left) and second (right) hemisphere implants are denoted by vertical, dotted lines. (A) MDS-UPDRS part III motor scores after overnight withdrawal of levodopa ("Off") and at peak dose of levodopa ("On"). (B) time course of the PDQ rating scale indicated; lower numbers indicate lower symptom severity.

DETAILED DESCRIPTION

Figure 2A:
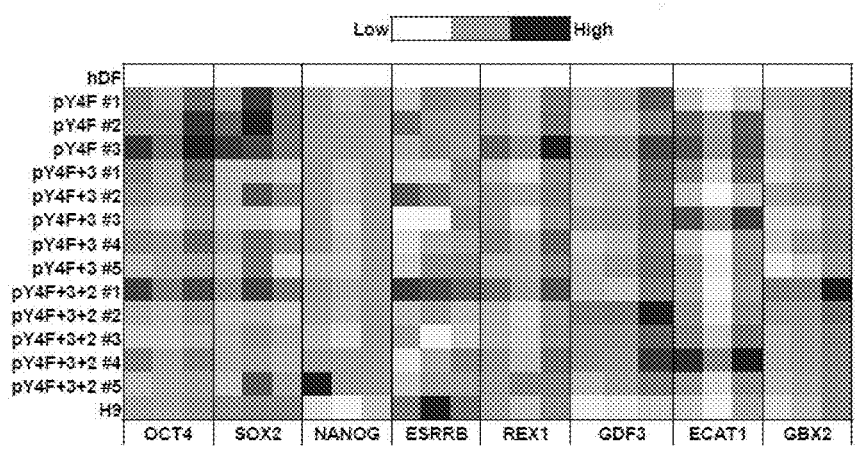
FIGS. 2A-D. Higher quality hiPSC lines generated from our improved reprogramming method. (A) Heatmaps depicting gene expression levels of pluripotency markers among established hiPSC lines compared to the original hDFs and an hESC line (H9). n=3. (B) Immunostaining of hiPSC lines generated by different combinations with specific antibodies against pluripotency markers (e.g., OCT4, NANOG, TRA-1-60, and SOX2) along with Hoechst 33342 nuclear staining (inlet). Scale bar: 100 μm. (C) Immunostaining for lineage-specific markers for ectoderm (OTX2), mesoderm (BRACHYURY), and endoderm (SOX17) following spontaneous differentiation for 7 days. Scale bar: 100 μm. (D) Heatmaps depicting gene expression levels of early-differentiation markers of ectoderm (PAX6, and MAP2), endoderm (FOXA2, SOX17, and CK8), and mesoderm markers (MSX1, MYL2A, and COL6A2) in hiPSC lines generated by pY4F, pY4F+3 or pY4F+3+2. n=2.
Figure 2B:
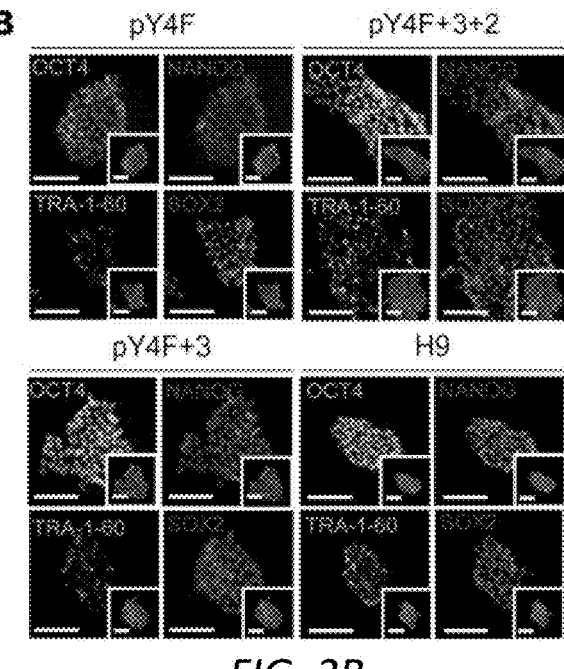
Figure 2C:
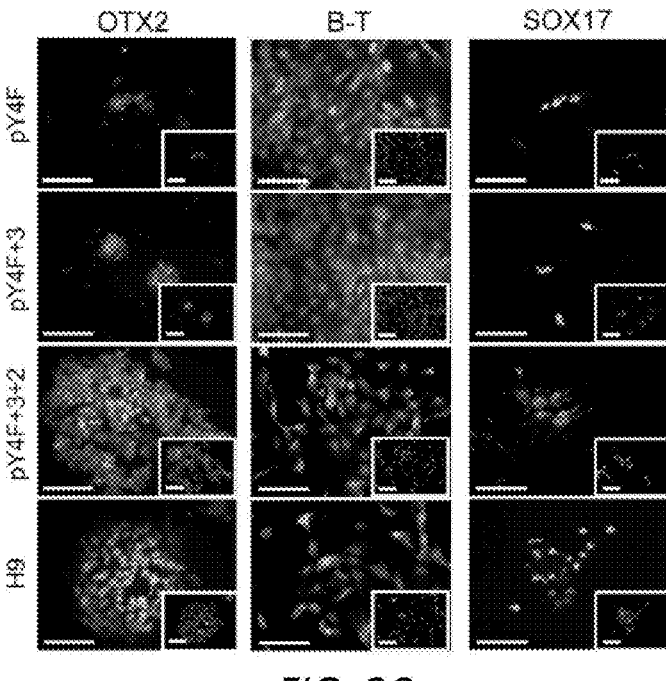
Figure 2D:
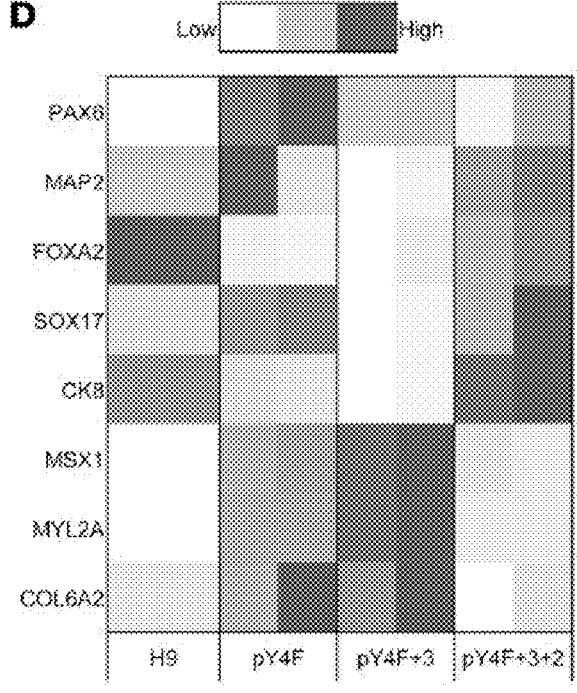

Since the selective degeneration of A9 mDA neurons (mDANs) in the substantia nigra (SN) is a key pathological feature of Parkinson's Disease and is directly associated with the cardinal motor symptoms of the disease, dopaminergic cell transplantation has been proposed as a potential therapeutic strategy (3). In support of this, previous interventions using fetal cell transplantation provided "proof of concept" in which many grafts successfully re-innervated target areas with varying degrees of restoration of function, including some patients who showed significant recovery lasting two decades or more (4-7). Despite these promising results, tissue derived from aborted human fetuses has fundamental ethical, practical, and medical limitations as a viable cell source for treatment of PD.

In 2006, Yamanaka and colleagues published a groundbreaking study showing that mammalian fibroblasts can be converted into embryonic stem cell (ESC)-like induced pluripotent stem cells (iPSCs) by introducing four transcription factors, i.e., Oct4, Sox2, Klf4, and c-Myc (hereafter denoted as Y4F (Yamanaka 4 factors)) (8). Yamanaka's and two other groups subsequently accomplished this feat with human somatic cells, reprograming them into human iPSCs (hiPSCs) (9-11), offering the possibility of generating patient-specific stem cells. Despite initial excitement, it remains uncertain whether this hiPSC technology can readily be used for autologous cell therapy. Indeed, the major goals of most hiPSC research have moved from personalized cell therapy toward mechanistic studies of human disease and development (12). There are several major barriers to implementation of hiPSC-based cell therapy for PD. First, probably due to our limited understanding of the reprogramming process, wide variability exists between the differentiation potential of individual hiPSC lines (13, 14). Second, the safety of hiPSC-based cell therapy has yet to be fully established. In particular, since any hiPSCs that remain undifferentiated or bear sub-clonal tumorigenic mutations have neoplastic potential (15, 16), it is critical to eliminate completely such cells from a therapeutic product. As illustrated by one of two patients in the first hiPSC-based human trial (17), safe clinical use requires that genomic integrity of hiPSCs be confirmed by whole-genome/exome-sequencing (WGS/WES). Third, despite numerous studies by multiple laboratories, in vitro differentiation protocols of hiPSCs into functional mDANs remain suboptimal, adding to end product variability (7, 18). Finally, long term cost-efficacy and reproducibility will be necessary to benefit as many patients as possible.

The present disclosure addresses these challenges, making hiPSC-based personalized cell therapy a viable option for the treatment of PD. First, we identified multiple microRNAs (miRNAs) directly regulating metabolic changes during the reprogramming process and showed that an optimal combination of these miRNAs (miR-302s and miR-200c) with the canonical reprogramming factors can efficiently and reliably generate high quality iPSCs. This new episomal reprogramming method has been applied successfully to generate multiple hiPSCs using adult human fibroblasts from 13 different sources. Whole exome sequencing (WES) and karyotyping analyses of the resulting hiPSCs created using fibroblasts from the skin biopsy of a single sporadic PD patient showed stable chromosomal and genomic integrity without any known cancer-causing mutations. Second, we established a chemical (quercetin) method that can efficiently and reliably eliminate undifferentiated hiPSCs, avoiding tumor formation post transplantation. See, e.g., US20160002604. Third, we established an efficient in vitro differentiation protocol based on a novel "spotting" method, resulting in dramatic reduction of cell loss and higher yield of healthier cells, compared to conventional monolayer methods. Fourth, transplantation of mDA cells generated by this in vitro differentiation protocol provided robust correction of motor dysfunction in athymic rat models of PD, and showed prominent reinnervation into host brain, whether fresh or cryopreserved cells were utilized. Finally, we successfully implemented our platform in a good manufacturing practice (GMP) facility, producing large quantities of high quality mDA cells. Thus, the core techniques described here offer a protocol suitable for the successful implementation of personalized, autologous, cell replacement therapy for PD.

PD is a particularly promising target for cell replacement therapy because selective degeneration of a well-characterized cell type—A9-type mDANs—is the major cause of motor dysfunction associated with the condition. Numerous researchers have extensively investigated cell therapy for PD using diverse cell sources including fetal tissues, autologous adult stem cells, and allogeneic mDA cells (5-7, 54). We have focused instead on hiPSC-derived autologous cell replacement because of its unique advantages in mitigating ethical, practical, and medical issues. To help realize the potential of personalized autologous cell therapy for PD, we sought to address current technical and scientific barriers to the implementation of this therapeutic strategy.

Figure 10B:
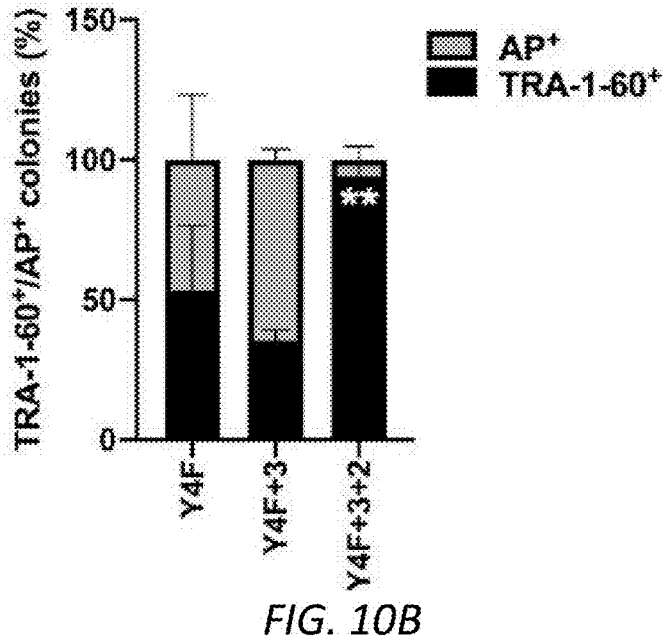
Figure 11A:
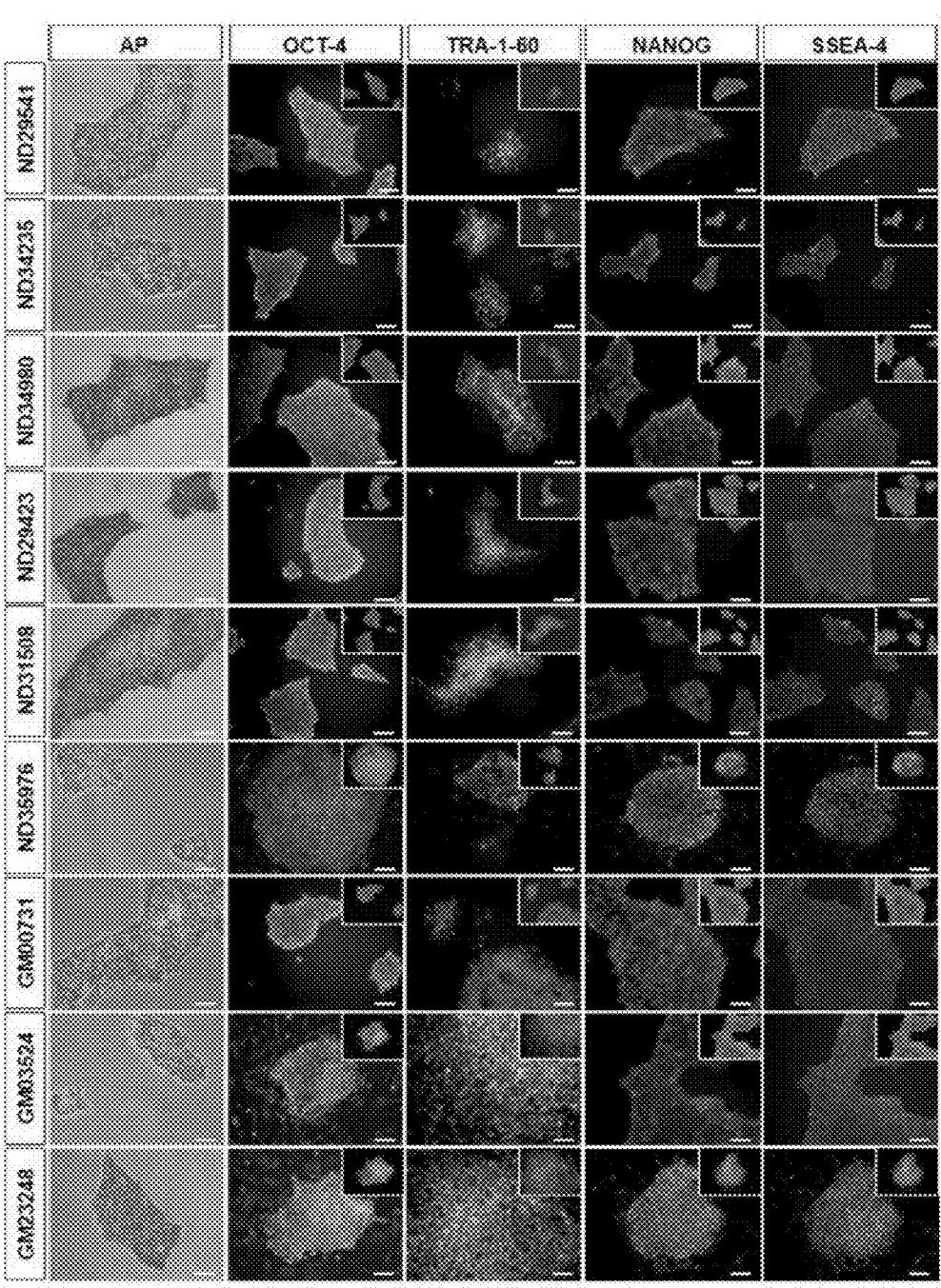
FIGS. 11A-B. Immunocytochemical staining of hiPSC lines generated by our improved reprogramming method. Immunocytochemical staining of human iPSCs generated by our episomal method from various human adult fibroblasts from multiple sources, including 9 fibroblast lines from the Coriell Institute (3 familial PD, 3 sporadic PD, and 3 healthy subjects, A) and 4 samples from new skin biopsies (3 healthy subjects and 1 sporadic PD patient, B).
Figure 11B:
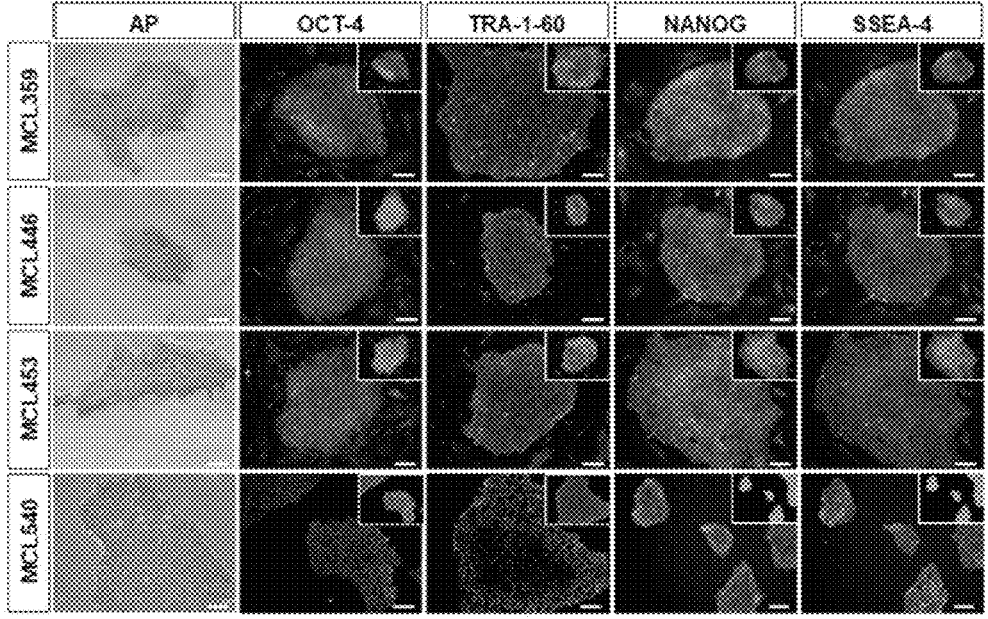

Because personalized cell therapy would require generation of clinical grade hiPSCs from each patient treated, it is critical to establish reprogramming technology allowing efficient and reliable generation of such lines. We found that a combination of two metabolism-modulating miRNAs (miR-302s and miR-200c) with the canonical Yamanaka factors (Y4F) facilitated the generation of hiPSCs meeting stringent quality criteria: First, our hiPSC lines showed expression levels of authentic pluripotency markers including OCT4, SOX2, NANOG, ESRRB, REX1, GDF3, ECAT1, GBX2, and TRA-1-60 similar to those of H9 (FIGS. 2, A and B). Second, H9 hESC and hiPSC lines generated by Y4F+3+2 (our final method), but not by Y4F or Y4F+3, differentiated equally well to all three germ layer lineages, as determined by immunostaining and gene expression of three germ layer-specific markers (FIGS. 2, C and D). Third, our hiPSC lines derived from multiple hDFs showed typical hESC-like compact colony morphology with well-defined borders (FIGS. 10A and 11A). The robustness of this method was validated by successful generation of multiple hiPSC lines from 13 different adult hDF sources. How this same combination would perform using alternative delivery methods (e.g., mature RNA/miRNA or Sendai virus) and in other cell types (e.g., blood and urine cells) warrants further investigation.

The genomic integrity of hiPSCs should be established before they are used for therapy. For example, Merkle and colleagues reported that several hESC lines, including H9, develop mutations in the TP53 gene encoding the tumor suppressor P53, which are mutations commonly seen in human cancers (28). Notably, in the first hiPSC-based human trial, hiPSCs derived from one of two patients were found to have a minor cancer-causing mutation, resulting in cancellation of this second patient's cell treatment (17). To confirm genomic integrity, we analyzed 5 independent hiPSC lines derived from a sporadic PD patient (MCL540 in Table B) by karyotyping, qRT-PCR, and WES analyses and found that 4 clones (C4, N3, C11, C5) out of 5 were free of integrated plasmid DNAs and contain no somatic mutations causally implicated in cancer, showing that our reprogramming method can reliably generate clinically viable hiPSC lines (Table 2). These 4 hiPSC clones contained significantly fewer variants per line, compared to 140 hESC lines studied by Merkle and colleagues (28). In particular, they contained significantly fewer coding variants in genes reported in the COSMIC database (FIG. 3). Another critical safety issue facing hiPSC-based therapy is the need to eliminate the neoplastic potential of residual undifferentiated cells. In this study, we established a chemical method using quercetin, targeting hPSC-specific BIRC5 (40), that eliminated undifferentiated PSCs with >99.99% efficiency (FIG. 5). A theoretical calculation based on qRT-PCR analysis of OCT4 expression predicts 0.0017 undifferentiated cells per 10 million D28 cells after quercetin treatment. Given that the spontaneous incidence rates for all types of glioma range from 4.67 to 5.73 per 100,000 (55), the risk of tumor formation would thus compare favorably to the spontaneous incidence of gliomas. The present methods are simple, effective, require no additional handling such as cell sorting or gamma-ray irradiation (45, 56), and thus can readily meet GMP standards. However, quercetin treatment does not directly eliminate neural overgrowth from rosette-forming epithelial cells, highlighting the importance of combining quercetin treatment with sufficient in vitro differentiation (e.g., 28 days) (FIG. 7).

The present methods provide an efficient in vitro differentiation protocol based on a "spotting" method, in which a smaller number of initial cells are grown and differentiated using physical separation into spots of high cell density, resulting in significantly decreased cell loss and in production of healthier mDA cells, with markedly fewer dead or dying cells (FIG. 4) compared to traditional confluent monolayers. Importantly, the monolayer culture medium, but not that of the spotting cultures, becomes significantly more acidic regardless of frequency of media change (FIG. 14B), probably contributing to poor cell health in the monolayer cultures. When such D28 cells were further differentiated in vitro, they matured and prominently released dopamine (3.1 ng/ml) on D47 and exhibited characteristic mDAN electrophysiological properties by D70. These data show that cultures on D28 of this differentiation protocol consist mostly of authentic mDAPs and represent a promising source for transplantation. We successfully scaled up this protocol at a GMP facility to produce clinically relevant quantities of high quality mDAPs (FIG. 22A-F).

Although numerous studies have demonstrated highly efficient differentiation of hESCs/hiPSCs into the mDA phenotype, their in vivo efficacy has been variable at best and often has correlated poorly with in vitro data (7). In some previous clinical trials, transplantation of DA-producing cells not first subjected to extensive functional validation in appropriate animal models failed to produce clinical benefit (5, 6). The efficacy of the cell grafts described herein has been confirmed, e.g., by several criteria using in vivo animal models of PD: (1) sufficient mDANs differentiate and survive long term in the graft; (2) these mDANs extensively reinnervate target areas in the host striatum; and (3) motor dysfunction is substantially improved in multiple appropriate behavioral tests. When D28 C4 cells were transplanted into unilaterally 6-OHDA lesioned Taconic or Charless River athymic rats, DA yields were high and grafts displayed extensive and appropriate reinnervation of host structures. Grafting resulted in complete recovery of pharmacologically induced rotation behavior. The DA yield (ratio of surviving DA neurons to number of transplanted cells) and the degree of behavioral recovery in this study were markedly higher than in comparable hiPSC-based studies (Table 4) (44, 45, 57-64). Notably, recovery of rotation behavior was sustained up to 52 weeks (FIG. 19M) and significant recovery was observed in several tests including corridor, cylinder and stepping tests (FIG. 8) that, because they are spontaneous and not pharmacologically stimulated, may be closer analogs of clinical PD symptomatology.

To establish the clinical validity of hiPSC-based personalized cell therapy, it is important to compare the therapeutic product to an established "gold standard". In the stem cell field, H9 hESCs have represented this standard for human pluripotent stem cells, and human fetal VM cells have been the gold standard as a transplantable cell source for PD. Parmar and colleagues elegantly compared the efficacy of H9-derived mDA cells with human fetal VM cells for in vivo efficacy in restoration of motor function, demonstrating H9-derived dopamine cells to be as effective as human fetal VM cells (53). The present animal transplantation study confirmed an identical degree and time course of recovery of rotational behavior whether H9 (hESC) or C4 (hiPSC) was the source (FIG. 20A). By inference, these data strongly suggest that dopamine cells generated by our protocol from patient-derived hiPSCs are functionally as effective as fetal VM cells. A recent study by Takahashi et al. elegantly showed that hiPSC-derived DA cells can survive and ameliorate motor behaviors in MPTP-lesioned monkey models (65), but direct comparison of those results with our study is hindered by the different species platform used. We found that fresh and cryopreserved C4 D28 cells resulted in similar yields of surviving DA neurons and behavioral improvement in all tests, suggesting that mDAPs derived from hiPSCs can be cryopreserved, stored, and shipped to the surgical location for transplantation. The importance of this to developing a practical and cost-effective clinical therapy cannot be overstated.

Thus, the present methods provide clinically applicable personalized autologous cell therapy for PD.

See also US 20180371422; US20120128655; US20130052268; US20160002604; US 20140199274; and US 20090226401, as well as U.S. Pat. Nos. 9,657,273 and 9,750,768.

Generation of Autologous Cells for Cell Therapy

The methods described herein can include the use of induced pluripotent stem cells (hiPSCs), e.g., similar to neurogenic floor plate cells, which can be generated using methods known in the art or described herein. In some embodiments, the methods for generating hiPSC can include obtaining a population of primary somatic cells from a subject, e.g., a subject who is afflicted with PD and in need of treatment for PD. Preferably the subject is a mammal, e.g., a human. In some embodiments, the somatic cells are fibroblasts. Fibroblasts can be obtained from connective tissue in the mammalian body, e.g., from the skin, e.g., skin from the eyelid, back of the ear, a scar (e.g., an abdominal cesarean scar), or the groin (see, e.g., Fernandes et al., Cytotechnology. 2016 March; 68(2): 223-228), e.g., using known biopsy methods. Other sources of somatic cells for hiPSC include hair keratinocytes (Raab et al., Stem Cells Int. 2014; 2014:768391), blood cells, or bone marrow mesenchymal stem cells (MSCs) (Streckfuss-Bömeke et al., Eur Heart J. 2013 September; 34(33):2618-29).

According to the present methods, the cells (e.g., fibroblasts) are exposed to factors to induce reprogramming to iPSC. Although other protocols for programming can be used (e.g., as known in the art or described herein), in preferred embodiments the methods include introducing four transcription factors, i.e., Oct4, Sox2, Klf4, and L-Myc. Is some embodiments, the methods comprise transfecting the cells with an OCT4, KLF4, SOX2, and L-MYC-expressing polycistronic episomal vector, e.g., comprising intervening sequences encoding 'self-cleaving' 2A peptides between the coding sequences. 2A peptides are 18-22 amino-acid-long viral peptides that mediate cleavage of polypeptides during translation in eukaryotic cells. 2A peptides include F2A (foot-and-mouth disease virus), E2A (equine rhinitis A virus), P2A (porcine teschovirus-1 2A), and T2A (thosea asigna virus 2A), and generally comprise the sequence GDVEXNPGP (SEQ ID NO:1) at the C-terminus. See, e.g., Liu et al., Sci Rep. 2017; 7: 2193. The following table provides exemplary 2A sequences.

In some embodiments, the methods comprise transfecting the cells with polycistronic episomal vector that comprises human Oct4 linked with 2A sequence of foot-and-mouth disease virus (OCT4-F2A), KLF4, SOX2 linked with 2A sequence of porcine teschovirus (SOX2-P2A), and L-MYC coding sequences, for expression of OCT4, KLF4, SOX2, and L-MYC.

References to exemplary sequences for OCT4, KLF4, SOX2, and L-MYC are provided in the following table.

| Gene | Nucleic acid → protein | |
|---|---|---|
| OCT4 | NM_002701.6 → NP_002692.2 | Isoform 1 |
| (POU class 5 | NM_001173531.2 → NP_001167002.1 | Isoform 2 |
| homeobox 1 | NM_001285987.1 → NP_001272916.1 | Isoform 3 |
| (POU5F1)) | NM_001285986.1 → NP_001272915.1 | Isoform 4 |
| KLF4 | NM_001314052.1 → NP_001300981.1 | Isoform 1 |
| (Kruppel like | NM_004235.6 → NP_004226.3 | Isoform 2 |
| factor 4) | | |
| SOX2 | NM_003106.4 → NP_003097.1 | |
| (SRY-box 2) | | |
| L-MYC | NM_001033081.3 → NP_001028253.1 | Isoform 1 |
| (MYCL | NM_005376.4 → NP_005367.2 | Isoform 2 |
| proto- | NM_001033082.2 → NP_001028254.2 | Isoform 3 |
| oncogene, | | |
| bHLH | | |
| transcription | | |
| factor) | | |

In some embodiments, the methods also or alternatively include expressing in the cells one or more exogenous microRNAs, e.g., one or more of miR-106a, -106b, -136s, -200c, -302s, -369s, and -371/373. miR-302s indicates the miR-302 cluster which encompasses five miRNAs including 302a, 302b, 302c, 302d, and 367; any one or more of them can be used. In preferred embodiments, the methods include expressing in the cells miR-302s and miR-200c, e.g., from a single episomal vector. In some embodiments, the methods comprise introducing into the cells an episomal vector that comprises sequences coding for miR-302s and miR-200c.

Exemplary sequences for miRNAs are provided in the following table. The sequences in bold represent mature miRNAs.

| 2A | Coding Sequence | SEQ ID NO: | Source |
|---|---|---|---|
| F2A: | GCGCCAGTAAAGCAGACATTAAACTTT GATTTCTGAAACTTGCAGGTGATGTAG AGTCAAATCCAGGTCCA | 2 | STEMCCA (PMID: 20715179 |
| F2A: | GGCAGCGGAAAACAGCTGTTGAATTTTG ACCTTCTCAAGTTGGCGGGAGACGTGGA GTCCAACCCAGGGCCC | 3 | pEB-C5 (PMID: 25772473) |
| P2A: | GCCACTAACTTCTCCCTGTTGAAACAAG CAGGGGATGTCGAAGAGAATCCCGGGCCA | 4 | STEMCCA (PMID: 20715179) |
| E2A: | CAATGTACTAACTACGCTTTGTTGAAAC TCGCTGGCGATGTTGAAAGTAACCCCGG TCCT | 5 | STEMCCA (PMID: 20715179) |
| T2A: | GGCGGCGGGTCCGGAGGAGAGGGCAGAG GAAGTCTTCTAACATGCGGTGACGTGGA GGAGAATCCTGGCCCA | 6 | pEB-C5 (PMID: 25772473) |

| miRNA precursor | Sequence | SEQ ID NO: |
|---|---|---|
| hsa-miR-106a | CCUUGGCCAUGUAAAAGUGCUUACAGUGCAGGUAGCUUUUU GAGAUCUACUGCAAUGUAAGCACUUCUUACAUUACCAUGG | 7 |
| hsa-miR-106b | CCUGCCGGGGCUAAAGUGCUGACAGUGCAGAUAGUGGUCCU CUCCGUGCUACCGCACUGUGGGGUACUUGCUGCUCCAGCAGG | 8 |
| hsa-miR-136s | UGAGCCCUCGGAGGACUCCAUUUGUUUUGAUGAUGGAUUCU UAUGCUCCAUCAUCGUCUCAAAUGAGUCUUCAGAGGGUUCU | 9 |
| hsa-miR-200c | CCCUCGUCUUACCCAGCAGUGUUUGGGUGCGGUUGGGAGUCU CUAAUACUGCCGGGUAAUGAUGGAGG | 10 |
| hsa-miR-302a | CCACCACUUAAACGUGGAUGUACUUGCUUUGAAACUAAAGAA GUAAGUGCUUCCAUGUUUUGGUGAUGG | 11 |
| hsa-miR-302b | GCUCCCUUCAACUUUAACAUGGAAGUGCUUUCUGUGACUUU AAAAGUAAGUGCUUCCAUGUUUUAGUAGGAGU | 12 |
| hsa-miR-302c | CCUUUGCUUUAACAUGGGGGUACCUGCUGUGUGAAACAAAA GUAAGUGCUUCCAUGUUUCAGUGGAGG | 13 |
| hsa-miR-302d | CCUCUACUUUAACAUGGAGGCACUUGCUGUGACAUGACAAA AAUAAGUGCUUCCAUGUUUGAGUGUGG | 14 |
| hsa-miR-367 | CCAUUACUGUUGCUAAUAUGCAACUCUGUUGAAUAUAAAUU GGAAUUGCACUUUAGCAAUGGUGAUGG | 15 |
| hsa-miR-369 | UUGAAGGGAGAUCGACCGUGUUAUAUUCGCUUUAUUGACUU CGAAUAAUACAUGGUUGAUCUUUUCUCAG | 16 |
| hsa-miR-371a | GUGGCACUCAAACUGUGGGGGCACUUUCUGCUCUCUGGUGA AAGUGCCGCCAUCUUUUGAGUGUUAC | 17 |
| hsa-miR-371b | GGUAACACUCAAAAGAUGGCGGCACUUUCACCAGAGAGCA GAAAGUGCCCCCACAGUUUGAGUGCC | 18 |
| hsa-miR-372 | GUGGGCCUCAAAUGUGGAGCACUAUUCUGAUGUCCAAGUG GAAAGUGCUGCGACAUUUGAGCGUCAC | 19 |
| hsa-miR-373 | GGGAUACUCAAAAUGGGGGCGCUUUCCUUUUUGUCUGUACU GGGAAGUGCUUCGAUUUUGGGGUGUCCC | 20 |

The sequences used can be at least 80, 85, 90, 95, or 100% identical to the exemplary (reference) sequences provided herein, but should retain the desired activity of the exemplary (reference) sequence. Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 60% (e.g., at least 70%, 80%, 90% or 100%) of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

In some embodiments, the methods comprise expressing in the cells all of OCT4, KLF4, SOX2, L-MYC, miR-302s and miR-200c. In some embodiments the methods comprising introducing into the cells a lentiviral vector or polycistronic episomal vector that comprises human Oct4 linked with 2A sequence of foot-and-mouth disease virus (OCT4-F2A), KLF4, SOX2 linked with 2A sequence of porcine teschovirus (SOX2-P2A), and L-MYC coding sequences, and a vector, e.g., lentiviral vector or episomal vector, that comprises sequences coding for miR-302s (e.g., as shown above) and miR-200c (e.g., a sequence as shown above or uaauacugccggguaaugaugga (SEQ ID NO:21)).

The primary somatic cells can be transfected directly, or they can be cultured first, removed from the culture plate and resuspended before transfection is carried out. The cells are combined with exogenous nucleic acid sequence to, e.g., stably integrate into their genomes, and treated in order to accomplish transfection. As used herein, the term "transfection" includes a variety of techniques for introducing an exogenous nucleic acid into a cell including calcium phosphate or calcium chloride precipitation, microinjection, DEAE-dextrin-mediated transfection, lipofection, or electroporation, all of which are known in the art). Where the vectors are viral vectors, transfection can include transducing the cells with viral particles.

After introducing these factors into the cells, the cells are maintained in conditions and for a time sufficient for expression of the factors and induction of reprogramming to iPS cells, e.g., cells that express alkaline phosphatase (AP) as well as the more stringent pluripotency marker, TRA-1-60 (Chan et al., 2009; Tanabe et al., 2013). A number of methods are known in the art; see, e.g., Malik and Rao, Methods Mol Biol. 2013; 997:23-33. In some embodiments, the conditions comprise maintaining the cells in media, e.g., media comprising DMEM/F-12, L-glutamine (e.g., 2 mM), serum, e.g., fetal bovine serum (FBS) (e.g., 10%), Non-essential amino acid (NEAA, e.g., 1×), Nicotinamide (NAM, e.g., 1 mM), Sodium butyrate (NaB) (e.g., 25 mM), and Ascorbic acid (AA, e.g., 50 µg/ml); alternatively, DMEM media with knockout serum replacement (KSR, a defined, FBS-free medium), glutamine, and β-mercapto-ethanol can be used. One of skill in the art will appreciate that other concentrations can be used. For example, the cells are incubated for 4-6, e.g., 5-6 days.

In preferred embodiments, the cells can be plated onto plates in discrete, individual, preferably substantially circu-lar or oval, areas (also referred to herein as "spots") of 2-10 mm, e.g., about 5 mm, diameter using an a biomatrix hydrogel support, e.g., a basement membrane extract such as MATRIGEL, PATHCLEAR Grade Basement Membrane Extract (Amsbio), or other synthetic alternatives, e.g., as described in Nguyen et al., Nat Biomed Eng. 2017; 1. pii: 0096, e.g., about 10 µl of the gel. The spots can be made, e.g., by placing droplets of the appropriate volume onto the plate with about 1-3 cm in between, e.g., on cross points of a 2×2 cm grid, to maintain isolation between spots (so that the spots do not touch each other) (FIG. 11C). For example, about 10 µl of the gel can be placed on the intersections of a grid on a gridded culture plate to make a spot of about 2-10 mm, e.g., about 5 mm, in diameter. After incubation for a sufficient time, e.g., 10-60 minutes, e.g., 25-45 minutes, e.g., about 30 minutes, the gel is partially aspirated from the spot (stopping before it is completely dry), leaving a layer of gel in the spot. Plates prepared in this manner (e.g., having gel spots as described herein) are also provided herein. After the plates are prepared, then the cells are plated, e.g., with a density of about 5,000-20,000, e.g., about 10,000, cells per spot, e.g., about 10 µl of the cell suspension with a density of 10,000 per µl.

Following reprogramming to iPSC, the cells can be main-tained in an hiPSC medium, e.g., comprising DMEM/F-12, L-glutamine (e.g., 2 mM), KSR (e.g., 20%), NEAA, NAM, NaB, and bFGF, until formation of ES-like colonies, e.g., which can optionally be identified by (1) staining with antibodies against the three germ layer markers (OTX2, an ectodermal marker; SOX17, an endodermal marker; and BRACHYURY, a mesodermal marker) and (2) gene expres-sion of lineage-specific markers (e.g., PAX6 and MAP2 for ectoderm, FOXA2, SOX17 and CK8 for endoderm, and MSX1, MYL2A and COL6A2 for mesoderm). In some embodiments, the iPSC cells are maintained in ESSENTIAL 8 medium or an equivalent thereof, i.e., comprising or consisting essentially of DMEM F-12, L-scorbic acid, Sele-nium, Transferrin, NaHCO3, Insulin, FGF2, and TGFβ1. See, e.g., Chen et al., Nat Methods 8(5):424-429.

Once iPS cells are generated, they can be maintained as an iPS cell line. In some embodiments, for each patient, multiple iPSC lines are generated and characterized and then the best lines (e.g., the best 1, 2, 3 or more lines) are chosen.

Also provided herein are cells produced by a method described herein, e.g., an iPS cell line, and compositions comprising the cells.

Viral Vectors

Viral vectors for use in the present methods and compo-sitions include recombinant retroviruses, adenovirus, adeno-associated virus, and lentivirus.

A preferred viral vector system useful for delivery of nucleic acids to the inner ear in the present methods is the adeno-associated virus (AAV). AAV is a tiny non-enveloped virus having a 25 nm capsid. No disease is known or has been shown to be associated with the wild type virus. AAV has a single-stranded DNA (ssDNA) genome. AAV has been shown to exhibit long-term episomal transgene expression, and AAV has demonstrated excellent transgene expression in the brain, particularly in neurons. Vectors containing as little as 300 base pairs of AAV can be packaged and can integrate. Space for exogenous DNA is limited to about 4.7 kb. An AAV vector such as that described in Tratschin et al., Mol. Cell. Biol. 5:3251-3260 (1985) can be used to intro-duce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993). There are numerous alternative AAV variants (over 100 have been cloned), and AAV variants have been identified based on desirable characteristics. For example, AAV9 has been shown to efficiently cross the blood-brain barrier. Moreover, the AAV capsid can be genetically engineered to increase transduction efficient and selectivity, e.g., biotinylated AAV vectors, directed molecular evolution, self-complementary AAV genomes and so on. In some embodiments, AAV1 is used.

Alternatively, retrovirus vectors and adeno-associated virus vectors can be used as a recombinant gene delivery system for the transfer of exogenous genes in vivo, particu-larly into humans. These vectors provide efficient delivery of genes into cells, and the transferred nucleic acids are stably integrated into the chromosomal DNA of the host. The development of specialized cell lines (termed "packaging cells") which produce only replication-defective retrovi-ruses has increased the utility of retroviruses for gene therapy, and defective retroviruses are characterized for use in gene transfer for gene therapy purposes (for a review see Miller, Blood 76:271 (1990)). A replication defective retro-virus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., Current Protocols in Molecular Biology, Greene Publishing Associ-ates, (1989), Sections 9.10-9.14, and other standard labora-tory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992)

Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980, 286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 d1324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Differentiation to mDAP/mDAN

In some embodiments, the methods are used to produce mDAP or mDAN as follows. For floor plate induction, after transfection the cells are maintained for about 6 days (D1-D6) in DMEM media with 15% KSR, glutamine, β-mercaptoethanol. For days 6-12 (D6-D12), the neural precursor induction stage, the cells are maintained in DMEM media with 11.5% KSR, 0.25% N2 (D6-8), 7.5% KSR, 0.5% N2 (D8-10), 3.75% KSR, 0.75% N2 (D10-12) including L-glutamine, β-mercaptoethanol and non-essential amino acid (NEAA). Dual Smad inhibitors, 0.2 μM LDN193189 and 10 μM SB431542 can be added, e.g., from D1-D12, and D1-D8, respectively. One or more SHH agonists (e.g., 2 μM Purmorphamine and 100 ng/ml Shh) with 100 ng/ml FGF8 can be added, e.g., from D2 to D10. A Wnt signaling activator, e.g., CHIR99021 (1 μM), can be included, e.g., from D4 to D12. At D9, cells can be treated with quercetin, e.g., 40 μM, e.g., for 6-24 or 12-18 hours, e.g., for 16 hours.

For the DA progenitor induction and maturation stage (D12+), the cells can be maintained in DMEM:F12 media supplemented with N2, BDNF (e.g., 20 ng/ml), GDNF (e.g., 20 ng/ml), dbcAMP (e.g., 500 μM), ascorbic acid (e.g., 200 μM), TGF-β3 (e.g., 10 ng/ml), along with a gamma secretase inhibitor (e.g., DAPT, e.g., 10 μM) and a Wnt agonist (e.g., CHIR99021, e.g., 1 μM) for about D12-15.

At about D15, the cells in the spots can be harvested and dissociated, e.g., chemically, enzymatically, or mechanically, e.g., using EDTA, and a single cell suspension replated, e.g., in Poly-L-ornithine/Fibronectin/Laminin-coated (PLO/FN/L-coated) dishes. From D15, media can be applied, e.g., DMEM:F12 with growth factors including N2, BDNF (e.g., 20 ng/ml), GDNF (e.g., 20 ng/ml), dbcAMP (e.g., 500 μM), ascorbic acid (e.g., 200 μM), and TGF-β3

(e.g., 10 ng/ml). A ROCK inhibitor, e.g., Y-27632 (e.g., 10 μM) can be added for the day of dissociation, and then removed. The cells can then be maintained in culture until induction of mDA progenitor (mDAP) and/or mDA neurons (mDANs), e.g., at least 21-28 days, sufficient for expression of mDAP markers (e.g., OTX2, LMX1A, and EN1) and/or expression of mDAN markers (e.g., TH, DAT, and PITX3).

One of skill in the art will appreciate that other reagents and concentrations can be used. For example, SHH agonists include Purmorphamine, oxysterols, and Smoothened Agonist (SAG); a number of Wnt agonists are provided in Table A.

TABLE A

| Wnt Agonists | |
| --- | --- |
| Compound | Target |
| CHIR-98023 | GSK-3β |
| CHIR-99021 | GSK-3β |
| CHIR-99030 | GSK-3β |
| Hymenialdisine | GSK-3β |
| debromohymeialdisine | GSK-3β |
| dibromocantherelline | GSK-3β |
| Meridianine A | GSK-3β |
| alsterpaullone | GSK-3β |
| cazapaullone | GSK-3β |
| Aloisine A | GSK-3β |
| NSC 693868 (1H-Pyrazolo[3,4-b]quinoxalin-3-amine) | GSK-3β |
| Indirubin-3'-oxime (Indirubin-3'-monoxime; 3-[1,3-Dihydro-3-(hydroxyimino)-2H-indol-2-ylidene]-1,3-dihydro-2H-indol-2-one) | GSK-3β |
| A 1070722 (1-(7-Methoxyquinolin-4-yl)-3-[6-(trifluoromethyl)pyridin-2-yl]urea) | GSK-3β |
| L803 | GSK-3β |
| L803-mts | GSK-3β |
| TDZD8 | GSK-3β |
| NP00111 | GSK-3β |
| HMK-32 | GSK-3β |
| Manzamine A | GSK-3β |
| Palinurin | GSK-3β |
| Tricantin | GSK-3β |
| IM-12 (3-(4-Fluorophenylethylamino)-1-methyl-4-(2-methyl-1H-indol-3-yl)-1H-pyrrole-2,5-dione) | GSK-3β |
| NP031112 | GSK-3β |
| NP00111 | GSK-3β |
| NP031115 | GSK-3β |
| VP 2.51 | GSK-3β |
| VP2.54 | GSK-3β |
| VP 3.16 | GSK-3β |
| VP 3.35 | GSK-3β |
| HLY78 (4-Ethyl-5,6-Dihydro-5-methyl-[1,3]dioxolo[4,5-j]phenanthridine, 4-Ethyl-5-methyl-5,6-dihydro-[l,3]dioxolo[4,5-j]phenanthridine) | Axin |
| WAY-262611 ((1-(4-(Naphthalen-2-yl)pyrimidin-2-yl)piperidin-4-yl)methanamine)) | Dickkopf-1 (DKK1) |
| BHQ880 | DKK1 |
| NCI8642 | DKK1 |
| gallocyanine dyes | DKK1 |
| Compounds 3-8 (Moore et al., J. Med. Chem., 2009; 52:105) | secreted frizzled-related protein 1 (sFRP-1) |
| WAY-316606 | sFRP-1 |

Other gamma secretase inhibitors include those selected from the group consisting of R04929097; DAPT (N-[(3,5-Difluorophenyl)acetyl]-L-alanyl-2-phenyl]glycine-1,1-dimethylethyl ester); L-685458 ((5S)-(t-Butoxycarbonylamino)-6-phenyl-(4R)hydroxy-(2R)benzylhexanoyl)-L-leu-L-phe-amide); BMS-708163 (Avagacestat); BMS-299897 (24(1R)-1-[[(4-Chlorophenyl)sulfonyl](2,5-difluorophenyl)amino] ethyl-5-fluorobenzenebutanoic acid); MK-0752; YO-01027; MDL28170 (Sigma); LY411575 (N-2-((2S)-2-(3,5-difluoro-phenyl)-2-hydroxyethanoyl)-N1-((7S)-5-methyl-6-oxo-6,7-dihydro-5H-dibenzo[b,d]azepin-7-yl)-1-alaninamide, see U.S. Pat. No. 6,541,466); ELN-46719 (2-hydroxy-valeric acid amide analog of LY411575 (where LY411575 is the 3,5-difluoro-mandelic acid amide) (U.S. Pat. No. 6,541,466)); PF-03084014 ((S)-2-((S)-5,7-difluoro-1,2,3,4-tetra-hydronaphthalen-3-ylamino)-N-(1-(2-methyl-1-(neopenty-lamino)propan-2-yl)-1H-imidazol-4-yl)pentanamide, Samon et al., Mol Cancer Ther 2012; 11:1565-1575); Com-pound E ((2S)-2-{[(3,5-Diflurophenyl)acetyl]amino}-N-[(3S)-1-methyl-2-oxo-5-phenyl-2,3-dihydro-1H-1,4-benzo-diazepin-3-yl]propanamide; see WO 98/28268 and Samon et al., Mol Cancer Ther 2012; 11:1565-1575); and Sema-gacestat (LY450139; (2S)-2-hydroxy-3-methyl-N-((1S)-1-methyl-2-{[(1S)-3-methyl-2-oxo-2,3,4,5-tetrahydro-1H-3-benzazepin-1-yl]amino}-2-oxoethyl)butanamide), or pharmaceutically acceptable salts thereof.

Also provided herein are cells produced by a method described herein, e.g., mDAP or mDAN cells, and compo-sitions comprising the cells.

Although the present methods exemplify differentiation of the iPSC into dopaminergic neurons, the spotting methods can be used in differentiation protocols for other cell types, including other neuronal types. A number of neuronal dif-ferentiation protocols are known in the art; see, e.g., Salimi et al., Mol Biol Rep. 2014 March; 41(3):1713-21; Gunhnlar et al., Molecular Psychiatry 23:1336-1344 (2018); Trilck et al., Methods Mol Biol. 2016; 1353:233-59; Zhang et al., Stem Cell Res Ther. 2018 Mar. 15; 9(1):67; D'Aiuto et al., Organogenesis. 2014; 10(4):365-77; Marton and Ioannidis, Stem Cells Translational Medicine 2019; 8:366-374; Bell et al. Bio-protocol 9(5): e3188 (2019). DOI: 10.21769/BioPro-toc.3188; Bianchi et al., Stem Cell Research 32:126-134 (2018).

Methods of Treatment mDAPs and mDANs generated using a method described herein can be used, e.g., as a cell model and to treat subjects who have (or are at risk of developing) Parkinson's Disease (PD). Such subjects can be identified by skilled healthcare providers using methods known in the art. The methods can include obtaining primary somatic cells; generating a popu-lation of cells comprising mDAPs, and administered the cells. Preferably the primary somatic cells are obtained from the subject to be treated who has (or is at risk of developing) PD, but in some embodiments the cells are obtained from a different subject, preferably of the same species as the subject who is to be treated (i.e., autologous cells), prefer-ably an immunologically matched subject. Preferably the mDAPs are generated by a method as described herein sufficient to generate a population comprising cells that express one, two, or more mDAP markers (e.g., FOXA2, OTX2, LMX1A, and EN1, e.g., FOXA2 and LMX1A; optionally TH+ cells that co-express FOXA2, LMX1A and NURR1), and optionally comprising cells that express one, two, or more mDAN markers (e.g., TH, DAT, and PITX3), but not comprising cells that express SOX1, PAX6, and KI67.

The cells can be administered using methods known in the art. In some embodiments, the cells are administered by being implanted directly into or near the affected area of the subject's brain, e.g., bilaterally into one or more of the caudate nucleus, putamen, and substantia nigra, e.g., using magnetic resonance imaging-guided stereotactic surgery. See, e.g., Garitaonandia et al., Stem Cells Dev. 2018 Jul. 15; 27(14):951-957; Kikuchi et al., Nature 548: 592-596 (31 Aug. 2017); MOrizane et al., Nature Communications 8:385 (2017); Sonntag et al., Prog Neurobiol. 2018 September; 168:1-20.

Culture Dishes

Also provided herein are culture dishes for use in a method described herein. The dishes have on the bottom a grid with a distance between the lines of 1.5-2.5 cm, e.g., about 2 cm, e.g., a 2×2 cm grid. The grid can be, e.g., formed as part of the dish, printed or etched on the bottom. The culture dishes can be made using methods known in the art and any acceptable material for culture dishes, e.g., poly-styrene, polyethylene, polypropylene, polycarbonate, and polyvinyl thermoplastic resins, e.g., using conventional injection-molding or thermoforming methods. Another suit-able material is glass. In some embodiments, the dishes have substantially flat bottoms; alternatively, there can be circular or ovoid dips or depressions at the intersection of the grid lines, e.g., of about 2-10 mm, e.g., about 3-7 mm, e.g., about 5 mm diameter. The depressions can be, e.g., 0.01-0.2 mm deep. In some embodiments, the dishes have a biomatrix hydrogel support, i.e, a basement membrane extract or synthetic matrix.

In some embodiments, the culture dishes having a grid are a 10 or 6 cm round culture dish with 12 or 6 intersections, respectively, for plating the cells. The distance between the cell placement areas (center of the spot to center of the adjacent spot) is 2 cm and the diameter of the cell spot is 0.5 cm. The circumference is about 1.57 cm, and the area is about 0.2 cm². Thus for a 6 cm dish there are only 6 possible spots, and for the 10 cm dish there are 12 possible spots at intersecting grid lines.

EXAMPLES

The invention is further described in the following examples, which do not limit the scope of the invention described in the claims.

Materials and Methods

The following materials and methods were used in the Examples below.

Antibodies and reagents used are shown in Table B.

TABLE B

| Reagent information | | |
| --- | --- | --- |
| REAGENT or RESOURCE | SOURCE | Cat# |
| Antibodies | | |
| Rabbit anti-5-HT | Sigma-Aldrich | Cat.# S5545 |
| Rabbit anti-Calbindin | Millipore | Cat.# AB1778 |
| Rabbit anti-cleaved Caspase-3 | Cell Signaling | Cat.# 9661 |

TABLE B-continued

| Reagent information | | |
| --- | --- | --- |
| REAGENT or RESOURCE | SOURCE | Cat# |
| Rabbit anti-DARPP32 | Novus | Cat.# NB100-92027 |
| Rabbit anti-DAT | Millipore | Cat.# AB5802 |
| Mouse anti-FOXA2 | Abnova | Cat.# H00003170-M10 |
| Mouse anti- Dopamine β Hydroxylase | Millipore | Cat.# MAB308 |
| Rabbit anti-GABA | Sigma-Aldrich | Cat.#A2052 |
| Rabbit anti-GIRK2 (Kir3.2) | Alomone Labs | Cat.# APC-006 |
| Mouse anti-NCAM(ERIC1) | Santa Cruz | Cat.# sc-106 |
| Mouse anti-Synaptophysin | Thermo Fisher | Cat.# 14-6525-80 |
| Rabbit anti-KI67 | Abcam | Cat.# ab16667 |
| Rabbit anti-LMX1A | Millipore | Cat.# AB10533 |
| Rabbit anti-MAP2 | Millipore | Cat.# AB5622 |
| Mouse anti-NESTIN | Millipore | Cat.# MAB5326 |
| Rabbit anti-NURR1 | Sigma-Aldrich | Cat.#ABN1675 |
| Mouse anti-PAX6 | DSHB | Cat.# PAX6 |
| Goat anti-SOX1 | R&D System | Cat.#AF3369 |
| Mouse anti-hNuc (STEM101) | Clontech | Cat.# Y40400 |
| Rabbit anti-TH | Pel-Freez | Cat.# P40101-0 |
| Sheep anti-TH | Millipore | Cat.# AB1542 |
| Mouse anti-Tuj1 | Biolegend | Cat.# MMS-435P |
| Rabbit anti-TPH2 | Novus Biologicals | Cat.# NB100-74555 |
| Mouse anti-TRA-1-60 | Santa Cruz | Cat.# sc-21705 |
| Rabbit anti-NANOG | Santa Cruz | Cat.# sc-33759 |
| Mouse anti-SSEA-4 | Millipore | Cat.# MAB4304 |
| Mouse anti-OCT-4 | Santa Cruz | Cat.# sc-5279 |
| Rabbit anti-SOX2 | Thermo Fisher | Cat.# 48-1400 |
| Rabbit anti-OCT-4 | Cell Signaling | Cat.# 2750 |
| Goat anti-OTX2 | R&D System | AF1979 |
| Goat anti-BRACHYURY | R&D System | AF2085 |
| Goat anti-SOX17 | R&D System | AF1924 |
| Mouse anti-Vimentin | Dako | Cat.# M0725 |
| PE mouse anti-SSEA-4 | BD | Cat.# 560128 |
| PE mouse anti-TRA-1-60 | BD | Cat.# 560193 |
| Donkey F(ab')2 Anti-rabbit IgG H&L (Alexa Flour 488) | Abcam | Cat.# Ab181346 |
| Donkey F(ab')2 Anti-rabbit IgG H&L (Alexa Flour 568) | Abcam | Cat.# Ab175694 |
| Donkey F(ab')2 Anti-rabbit IgG H&L (Alexa Flour 647) | Abcam | Cat.# Ab181347 |
| Donkey F(ab')2 Anti-mouse IgG H&L (Alexa Flour 488) | Abcam | Cat.# Ab150101 |
| Donkey anti-mouse IgG H&L; Alexa Fluor 568 | Abcam | Cat.# Ab175699 |
| Donkey F(ab')2 Anti-mouse IgG H&L (Alexa Flour 647) | Abcam | Cat.# Ab150103 |
| Donkey Anti-Sheep IgG H&L (Alexa Fluor 568) | Abcam | Cat.# Ab175712 |
| Donkey F(ab')2 Anti-goat IgG H&L (Alexa Flour 568) | Abcam | Cat.# Ab175705 |
| Chemicals, Peptides, and Recombinant Proteins | | |
| DMEM | Thermo Fisher | Cat.# 11965092 |
| DMEM/F-12 | Thermo Fisher | Cat.# 11320033 |
| mTeSR ™-1 | STEMCELL Technologies | Cat.# 85870 |
| Essential 8 medium | Thermo Fisher | Cat.# A1517001 |
| Fetal bovine serum (FBS) | Thermo Fisher | Cat.# 26140079 |
| Knockout serum replacement (KSR) | Thermo Fisher | Cat.# 10828010 |
| L-Glutamine | Thermo Fisher | Cat.# 25030081 |
| Non-essential amino acids (NEAA) | Thermo Fisher | Cat.# 11140050 |
| Sodium butyrate (NaB) | Sigma-Aldrich | Cat.# 303410 |
| Nicotinamide (NAM) | Sigma-Aldrich | Cat.# N0636 |
| 0.5M EDTA solution | Thermo Fisher | Cat.# 15575020 |
| Accutase | Millipore | Cat.# SCR005 |
| TrypLE | Thermo Fisher | Cat.# 12605010 |
| β-mercapthethanol | Thermo Fisher | Cat.# 21985-023 |
| N2 supplement | Thermo Fisher | Cat.# 17502048 |
| CryoStor ® CS10 | BioLife Solutions | Cat.# 210102 |
| SB431542 | Cayman Chem | Cat.# 13031 |
| LDN193189 | Stemgent | Cat.# 04-0074 |
| Purmorphamine | StemRD | Cat.# PUR-25 |
| CHIR99021 | Cayman Chem | Cat.# 13122 |
| DAPT | Cayman Chem | Cat.# 13197 |
| Boc-D-FMK | Cayman Chem | Cat.# 16118 |
| Quercetin | Sigma-Aldrich | Cat.# Q4951 |

TABLE B-continued

Reagent information

| REAGENT or RESOURCE | SOURCE | Cat# |
|---|---|---|
| Y-27632 | Selleckchem | Cat.# S1049 |
| Ascorbic acid (AA) | Sigma-Aldrich | Cat.# A4403 |
| dbcAMP | Sigma-Aldrich | Cat.# D0627 |
| SHH | PeproTech | Cat.# 100-45 |
| BDNF | PeproTech | Cat.# 450-02 |
| GDNF | PeproTech | Cat.# 450-10 |
| TGF-β3 | R&D System | Cat.# 243B3010 |
| FGF-8 | PeproTech | Cat.# 100-25 |
| Recombinant human FGF2 (bFGF) | Thermo Fisher | PHG0023 |
| Poly-L-ornithine solution | Sigma-Aldrich | Cat.# P4957 |
| Fibronectin | Sigma-Aldrich | Cat.# F0895 |
| Laminin | Sigma-Aldrich | Cat.# L2020 |
| Matrigel matrix | Corning | Cat.# 354277 |
| 6-OHDA | Sigma-Aldrich | Cat.# H116 |
| Desipramine | Sigma-Aldrich | Cat.# D3900 |
| D-Amphetamine | Sigma-Aldrich | Cat.# A5880 |
| Hoechst 33342 | Thermo Fisher | Cat.# H3570 |
| Trizol | Thermo Fisher | Cat.# 15596026 |
| Superscript ® II Reverse Transcriptase | Thermo Fisher | Cat.# 18064-014 |
| SsoAdv Univer SYBR SMX 5000 | Bio-Rad | Cat.# 1725275 |
| Tetrodotoxin | Tocris | Cat.# 1078 |
| PolyJet transfection reagent | SignaGen laboratories | Cat.# SL100688 |
| Picrotoxin | Millipore | Cat.# 528105 |
| NBQX | Tocris | Cat.# 1044 |
| D-AP5 | Tocris | Cat.# 0106 |
| Critical Commercial Assays | | |
| Venor GeM Mycoplasma Detection Kit | Sigma-Aldrich | Cat.# MP0025 |
| Neon transfection system | Thermo Fisher | Cat.# MPK1096 |
| Bradford protein assay | Bio-Rad | Cat.# 5000201 |
| GeneJET Plasmid Miniprep Kit | Thermo Fisher | Cat.# K0503 |
| DNeasy Blood & Tissue Kit | QIAGEN | Cat.# 69504 |
| QIAamp DNA FFPE Tissue Kit | QIAGEN | Cat.# 56404 |
| Vectastain Elite ABC Kit | Vector Laboratories | Cat.# PK-6100 |
| DAB peroxidase substrate Kit | Vector Laboratories | Cat.# SK-4100 |
| Cell Mito Stress Test Kit | Agilent Technologies | Cat.# 103010-100 |
| Cell Energy Phenotype Test Kit | Agilent Technologies | Cat.# 103275-100 |
| Experimental Models: Organisms/Strains | | |
| Human BJ dermal fibroblasts | ATCC | CRL-2522 |
| WA09 hESC cell line | WiCell Institute | Lot. # WB66593 |
| H7 hESC cell line | WiCell Institute | |
| iPS-DF19-9-11T | WiCell Institute | |
| Human adult fibroblasts | Coriell Institute | Cat.# GM03529 |
| HEK293T cells | ATCC | CRL-11268 |
| Recombinant DNA | | |
| pGEM-T Easy vector | Promega | Cat.# A1360 |
| pCXLE-EGFP episomal vector | Addgene | Cat.# 27082 |
| FUW-tetO-MCS vector | Addgene | Cat.# 84008 |
| FUW-tetO-hMYC | Addgene | Cat.# 20723 |
| FUW-tetO- SOX2 | Addgene | Cat.# 20724 |
| FUW-tetO- KLF4 | Addgene | Cat.# 20725 |
| FUW-tetO- OCT4 | Addgene | Cat.# 20726 |
| STEMCCA lentiviral vector | Mostoslavsky's lab | |
| psPAX2 | Addgene | Cat.# 12260 |
| pMD2.G | Addgene | Cat.# 12259 |
| Software and Algorithms | | |
| Image J | National Institutes of Health | Version 2.0 |
| Stereo Investigator | MBF Biosciences | Version 2017 |
| Axion BioSystems's Neural Metric Tool | Axion Biosystems | Version 2.2 |
| Axis Navigator software | Axion Biosystems | Version 1.5.1 |
| C6 software | BD Biosciences | |
| BWA-MEM | bio-bwa.sourceforge.net/ | Version 0.7.15 |
| SAM tools | samtools.github.io/ | Version 1.3.1 |
| Picard tools | broadinstitute.github.io/picard/ | Version 2.5.0 |
| Genome Analysis Toolkit MuTect2 | software.broadinstitute.org/gatk | Version 3.6.0 |
| Variant Effect Predictor | ensembl.org/vep | Version GRCh38.89 (annotation cache version 89) |

TABLE B-continued

| Reagent information | | |
|---|---|---|
| REAGENT or RESOURCE | SOURCE | Cat# |
| ngCGH | github.com/seandavi/ngCGH | Version 0.4.4 |
| Integrated Genome Viewer | software.broadinstitute.org/software/igv/ | Version 2.3.79 |
| Personalis Cancer Exome pipeline | Personalis, Inc., CA, USA | ACE3 |
| R | The R foundation | Version 3.4 |

Biopsy

Skin biopsies from three healthy subjects and one sporadic PD patient (Table C) were taken under an IRB approved protocol (Partners IRB #2010P001100).

Human iPSC Generation

For lentivirus-based hiPSC generation, cells were transduced with lentiviral particles from individual lentiviral vectors or polycistronic STEMCCA vectors containing Y4

TABLE C

| | | | | | | | | | | |
|---|---|---|---|---|---|---|---|---|---|---|
| Summary of episomal plasmid-based hiPSC generation | | | | | | | | | | |
| source | subtype | cell ID | Age (years) | gender | race | starting Cell No. | # iPS-like colony | efficiency (/initial) | initial P/U | # final iPS lines |
| Coriell | Familial PD | ND29541 | 65 | Male | Caucasian | 5.0E+04 | 130 | 0.260% | 12 | 5 |
| Coriell | Familial PD | ND34235 | 71 | Male | Caucasian | 5.0E+04 | 67 | 0.134% | 6 | 3 |
| Coriell | Familial PD | ND34980 | 58 | Male | Caucasian | 5.0E+04 | 131 | 0.262% | 12 | 4 |
| Coriell | Sporadic PD | ND29423 | 73 | Male | Caucasian | 5.0E+04 | 187 | 0.374% | 24 | 6 |
| Coriell | Sporadic PD | ND31508 | 71 | Male | Caucasian | 5.0E+04 | 92 | 0.184% | 12 | 4 |
| Coriell | Sporadic PD | ND35976 | 63 | Male | Caucasian | 5.0E+04 | 118 | 0.236% | 24 | 10 |
| Coriell | Healthy | GM00731 | 96 | Male | Caucasian | 5.0E+04 | 181 | 0.362% | 24 | 5 |
| Coriell | Healthy | GM03524 | 67 | Female | Black | 5.0E+04 | 153 | 0.306% | 24 | 7 |
| Coriell | Healthy | GM23248 | 55 | Male | Caucasian | 5.0E+04 | 84 | 0.168% | 12 | 7 |
| Biopsy | Healthy | MCL359 | 25 | Male | N/A | 2.0E+04 | 32 | 0.160% | 12 | 4 |
| Biopsy | Healthy | MCL446 | 20 | Male | N/A | 2.0E+04 | 37 | 0.185% | 12 | 5 |
| Biopsy | Healthy | MCL453 | 22 | Female | N/A | 2.0E+04 | 20 | 0.100% | 6 | 3 |
| Biopsy | Sporadic PD | MCL540 | 68 | Male | Hispanic | 2.0E+04 | 62 | 0.340% | 36 | 11 |

Experimental Animals

Strain details and number of animals in each group are as follows:

6-OHDA lesioned athymic rats (NTac:NIH-Foxn1$^{mu}$, Taconic Biosciences), males, 12-14 weeks old. Athymic rats (Crl:NIH-Foxn1$^{mu}$, Charles River, Strain Code #316), males, 12-14 weeks old. NOD-SCID (NOD.CB17-Prkdc$^{scid}$/NCrCrl, Charles River Strain Code #394), males or females, 8-10 weeks old. All animals were housed in ventilated cages, under a 12 hours light/dark cycle with ad libitum access to sterile food and water.

Cell Culture

Human BJ dermal fibroblasts (hDF) and HEK293T cells were purchased from ATCC and grown according to previously published protocols (19). For hiPSC induction, infected cells were maintained in Induction medium containing DMEM/F-12, 2 mM L-glutamine, 10% FBS, 1× NEAA, 1 mM NAM, 25 mM NaB, and 50 µg/ml AA for 5 days post-transfection, then maintained in hiPSC medium containing DMEM/F-12, 2 mM L-glutamine, 20% KSR, 1× NEAA, 1 mM NAM, 25 mM NaB, and 10 ng/ml bFGF. H9 hESC line was obtained from WiCell Institute. All hiPSC lines were maintained in Essential 8 medium using Matrigel matrix and passaged using 0.5 mM EDTA solution for gentle dissociation. All hESC lines were maintained in mTeSR™ 1 medium using Matrigel matrix. No cell lines used in this study were found in the database of commonly misidentified cell lines that is maintained by ICLAC and NCBI Biosample. All cell lines were authenticated by Interspecies Determination (Isoenzyme Analysis and STR analysis) by the providing company and routinely tested for mycoplasma detection.

factors (OCT4, SOX2, KLF4, and C-MYC; generously provided by Dr. Gustavo Mostoslaysky) and/or miRNAs overnight. Next day, the medium was exchanged with induction medium and cells incubated for 5 days. On day 6, cells were fed with hiPSC medium and kept in that medium until formation of ES-like colonies. The observed ESC-like colonies were handpicked and transferred onto Matrigel-coated tissue culture plates in Essential 8 medium to generate hiPSC lines.

For episomal system-based hiPSC generation, cells were electroporated with reprogramming factors-expressing pCXLE vector using the Neon transfection system, then plated onto a Matrigel-coated, 6 well plate in hDF medium supplemented with 10 µM Y-27632. Next day, cells were fed with Induction medium for additional 5 days.

Plasmid Construction and Lentivirus Production

Coding sequences for individual miRNAs for miR-17/92, -106a, -106b, -200c, -302s, -369s and -371/373 were PCR-amplified from H9 hESCs, cloned into the pGEM-T Easy vector and their identify confirmed by sequencing. Subsequently, they were introduced into the EcoRI site of the FUW-tetO vector. For the OCT4, KLF4, SOX2, and L-MYC-expressing polycistronic episomal vector, human Oct4 linked with 2A sequence of foot-and-mouth disease virus (OCT4-F2A), KLF4, SOX2 linked with 2A sequence of porcine teschovirus (SOX2-P2A), and L-MYC coding sequences were PCR-amplified from H9 hESCs, then introduced sequentially into a modified pCXLE episomal vector freed of EGFP sequences. For miR-302s and/or miR-200c expressing episomal vector, human miR-302s or -200c coding sequences were introduced into the modified pCXLE vector.

Lentivirus production was performed as described previously with slight modifications (Cha et al., 2017. Nat Cell Biol 19:445-456). Briefly, lentiviral vectors were co-transfected with packaging plasmids including pMD2.G, and psPAX2 into 293T cells, maintained in DMEM supplemented with 10% FBS, using PolyJet transfection reagent according to the manufacturer's instruction. Supernatants containing lentiviruses were collected 48 h post-transfection and filtered through 0.45 μm Millex-HV (Millipore) filters to remove cell debris.

hiPSC Formation Assay

For TRA-1-60 staining, cells were fixed with 4% formaldehyde for 5 min, washed with PBS and then incubated with anti-TRA-1-60 antibody (1:500) at 4° C. overnight. After three washes with PBS cells were incubated for 1 h with horseradish peroxidase (HRP)-conjugated goat anti-mouse IgG (1:500). After washing three times with 0.1% Triton X-100 in PBS, cells were stained with 3,3'-diaminobenzidine (DAB) following the manufacturer's instructions. For AP staining, fixed cells were washed with PBS and then stained with a solution of the alkaline phosphatase substrate NBT/BCIP followed by three washes with PBS to stop the reaction.

Live Cell Metabolic Analysis

Oxygen consumption rate (OCR) and extracellular acidification rate (ECAR) were measured using the XFp analyzer (Agilent Technologies) according to the manufacturer's instruction. Briefly, cells were plated onto wells of an XF mini-plate and incubated at 37° C. in a $CO_2$ incubator overnight. The assay was performed after cells were equilibrated for 1 h in XF assay medium supplemented with 10 mM glucose, 5 mM sodium pyruvate, and 2 mM L-glutamine in a non-$CO_2$ incubator. hDFs' mitochondrial activity was monitored through sequential injections of 1 μM oligomycin (Oligo), 2 μM FCCP, and 0.5 μM antimycin A/rotenone (Anti/Rot) to calculate basal respiration (=baseline OCR–Anti/Rot OCR), ATP turnover (=basal respiration–Oligo OCR), maximum respiration (=FCCP OCR–Anti/Rot OCR), and oxidative reserve (=maximum respiration–basal respiration). Each plotted value was normalized to total protein quantified using the Bradford protein assay.

Quantitative RT-PCR

To extract total RNA, cells were lysed with Trizol and RNA was separated according to the manufacturer's recommendations. RNA concentration was measured using a Nanodrop ND-1000 spectrophotometer (NanoDrop Technologies). RNAs were reverse transcribed with oligo dT primer using Superscript II. For real time quantitative RT-PCR we used SsoAdvanced Universal SYBR Green Supermix and reactions were performed on a CFX Connect Real-Time System (Bio-Rad). PCR amplification was generated using gene-specific primers (Table D). Target gene expression was determined by normalization to endogenous actin by the comparative Ct method.

TABLE D

| List of primer sequences used in this study | | | |
| --- | --- | --- | --- |
| Gene | Full gene name | Sequences(fwd/rev) | SEQ ID NO: |
| EBNA #1 (EB-01) | Epstein-Barr virus-encoded nuclear antigen | 5'-GAGAAAAGAGGCCCAGGAGT-3' 5'-CCCCTACAGGGTGGAAAAAT-3' | 22. 23. |
| EBNA #2 (EB-02) | | 5'-GGCAGTGGACCTCAAAGAAG-3' 5'-CTATGTCTTGGCCCTGATCC-3' | 24. 25. |
| EBNA #3 (EB-03) | | 5'-GGGTGATAACCATGGACGAGG-3' 5'-ACTTGGACGTTTTTGGGGTC-3' | 26. 27. |
| EBNA #4 (EB-04) | | 5'-ATAACCATGGACGAGGACGG-3' 5'-GCAGCCAATGCAACTTGGAC-3' | 28. 29. |
| EBNA #5 (EB-05) | | 5'-GGGTAGAGGACGTGAAAGAGC-3' 5'-GGAGACCCGGATGATGATGAC-3' | 30. 31. |
| D17S1290 | | 5' CAACAGAGCAAGACTGTC 3' 5' GGAAACAGTTAAATGGCCAA 3' | 32. 33. |
| D7S796 | | 5' TTTTGGTATTGGCCATCCTA 3' 5' GAAAGGAACAGAGAGACAGGG 3' | 34. 35. |
| D10S1214 | | 5' ATTGCCCCAAAACTTTTTTG 3' 5' TTGAAGACCAGTCTGGGAAG 3' | 36. 37. |
| D21S2055 | | 5'AACAGAACCAATAGGCTATCTATC 3' 5' TACAGTAAATCACTTGGTAGGAGA 3' | 38. 39. |
| ACTIN | Actin beta (ACTB) | 5' CATGTACGTTGCTATCCAGGC 3' 5' CTCCTTAATGTCACGCACGAT 3' | 40. 41. |
| CORIN | Serine peptidase (CORIN) | 5'-AATGGGAGTGAACCTTTGGTCA-3 5'-GTCGGGATGTGCAGTAGACA-3' | 42. 43. |
| COL6A2 | Collagen type VI alpha 2 chain | 5'-TCATGAAACACGAAGCCTAC-3' 5'-CACCCTTCTCTCCTTTGAAG-3' | 44. 45. |
| CK8 | Keratin 8 (KRT8) | 5'-CCTGGAAGGGCTGACCGACGAGATCAA-3' 5'-CTTCCCAGCCAGGCTCTGCAGCTCC-3' | 46. 47. |

TABLE D-continued

<u>List of primer sequences used in this study</u>

| Gene | Full gene name | Sequences(fwd/rev) | SEQ ID NO: |
|------|----------------|--------------------|------------|
| DAT | Solute carrier family 6 member 3 | 5'-ACAGAGGGGAGGTGCGCCAGTTCACG-3'<br>5'-ACGGGGTGGACCTCGCTGCACAGATC-3' | 48.<br>49. |
| ECAT1 | KH domain containing 3 like, subcortical maternal complex member (KHDC3L) | 5'-CGAAGGTAGTTCGCCTTGAG-3'<br>5'-CGGTGATAGTCAGCCAGGTT-3' | 50.<br>51. |
| EN1 | Engrailed-1 | 5'-CGTGGCTTACTCCCCATTTA-3'<br>5'-TCTCGCTGTCTCTCCCTCTC-3' | 52.<br>53. |
| ESRRB | Estrogen related receptor beta | 5'-TGTCAAGCCATGATGGAAAA-3'<br>5'-GGTGAGCCAGAGATGCTTTC-3' | 54.<br>55. |
| FOXA2 | Forkhead box A2 | 5'-GGTGCTTTGGCTGACTTTTT-3'<br>5'-GTTGCTCACGGAGGAGTAGC-3' | 56.<br>57. |
| GAPDH | Glyceraldehyde 3-phosphate dehydrogenase | 5' ACCACAGTCCATGCCATCAC 3'<br>5' TCCACCACCCTGTTGCTGTA 3' | 58.<br>59. |
| GBX2 | Gastrulation brain homeobox 2 | 5'-GGTGCAGGTGAAAATCTGGT-3<br>5'-GCTGCTGATGCTGACTTCTG-3' | 60.<br>61. |
| GDF3 | Growth differentiation factor 3 | 5'-AAATGTTTGTGTTGCGGTCA-3'<br>5'-TCTGGCACAGGTGTCTTCAG-3' | 62.<br>63. |
| GIRK2 | Potassium voltage-gated channel subfamily J member 6 | 5'-GACCTGAAGTGGAGATTCAACC-3'<br>5'-TGTATGCGATCAACCACCAGA-3' | 64.<br>65. |
| GLI1 | GLI family zinc finger 1 | 5'-GGGTGCCGGAAGTCATACTC-3'<br>5'-GCTAGGATCTGTATAGCGTTTGG-3' | 66.<br>67. |
| LMX1a | LIM homeobox transcription factor 1, alpha | 5'-ACGGCCTAAAGATGGAGGAG-3'<br>5'-CGGTAGAAGCAGGTGGTCTC-3' | 68.<br>69. |
| MAP2 | Microtubule associated protein 2 | 5'-CAGGTGGCGGACGTGTGAAAATTGAGAGTG-3'<br>5'-CACGCTGGATCTGCCTGGGGACTGTG-3' | 70.<br>71. |
| MSX1 | MSH homeobox 1 | 5'-CGAGAGGACCCCGTGGATGCAGAG-3'<br>5'-GGCGGCCATCTTCAGCTTCTCCAG-3' | 72.<br>73. |
| MYL2A | Myosin light chain 7 (MYL7) | 5'-GGGCCCCATCAACTTCACCGTCTTCC-3'<br>5'-TGTAGTCGATGTTCCCCGCCAGGTCC-3' | 74.<br>75. |
| NANOG | Nanog homeobox | 5'-CAAAGGCAAACAACCCACTT-3'<br>5'-TCTGCTGGAGGCTGAGGTAT-3' | 76.<br>77. |
| NESTIN | Nestin | 5'-TTGCCTGCTACCCTTGAGAC-3'<br>5'-GGGCTCTGATCTCTGCATCTAC-3' | 78.<br>79. |
| NKX2.1 | NK2 homeobox 1 | 5'-CTCGCTCATTTGTTGGCGA-3'<br>5'-GGAGTCGTGTGCTTTGGACT-3' | 80.<br>81. |
| NKX2.2 | NK2 homeobox 2 | 5'-CCGGGCCGAGAAAGGTATG-3'<br>5'-CTGTAGGCAGAAAAGGGAA-3' | 82.<br>83. |
| NURR1 | Nuclear receptor subfamily 4, group A, member 2 | 5'-CACTCTTCGGGAGAATACAG-3'<br>5'-CATTTGGTACAAGCAAGGTG-3' | 84.<br>85. |
| OCT4 | POU class 5 homeobox 1 | 5' GAAGGATGTGGTCCGAGTGT 3'<br>5' GTGAAGTGAGGGCTCCCATA 3' | 86.<br>87. |
| OTX2 | Orthodenticle homeobox 2 | 5'-ACAAGTGGCCAATTCACTCC-3'<br>5'-GAGGTGGACAAGGGATCTGA-3' | 88.<br>89. |

TABLE D-continued

| Gene | Full gene name | Sequences(fwd/rev) | SEQ ID NO: |
|------|----------------|--------------------|------------|
| PAX6 | Paired box 6 | 5'-ACCCATTATCCAGATGTGTTTGCCCGAG-3' | 90. |
| | | 5'-ATGGTGAAGCTGGGCATAGGCGGCAG-3' | 91. |
| PITX3 | Paired like homeodomain 3 | 5'-GGAACCGCTACCCCGACATGAG-3' | 92. |
| | | 5'-TGAAGGCGAATGGAAAGGTCT-3' | 93. |
| REX1 | ZFP42 zinc finger protein | 5'-GGCGGAAATAGAACCTGTCA-3' | 94. |
| | | 5'-CTTCCAGGATGGGTTGAGAA-3' | 95. |
| SOX1 | SRY-box 1 | 5'-CCTCCGTCCATCCTCTG-3' | 96. |
| | | 5'-AAGCATCAAACAACCTCAAG-3' | 97. |
| SOX2 | SRY-box 2 | 5'-AACCCCAAGATGCACAACTC-3 | 98. |
| | | 5'-CGGGGCCGGTATTTATAATC-3' | 99. |
| SOX17 | SRY-box 17 | 5'-CGCTTTCATGGTGTGGGCTAAGGACG-3' | 100. |
| | | 5'-TAGTTGGGGTGGTCCTGCATGTGCTG-3' | 101. |
| TH | Tyrosine hydroxylase | 5'-CGGGCTTCTCGGACCAGGTGTA-3' | 102. |
| | | 5'-CTCCTCGGCGGTGTACTCCACA-3' | 103. |
| TUJ1 | Tubulin beta 3 class III | 5'-CGGTGGTGGAGCCCTACAAC-3' | 104. |
| | | 5'-AGGTGGTGACTCCGCTCAT-3' | 105. |

Karyotype Analysis

To evaluate the number and structure of the human iPS cells chromosome, the human iPS cells were sent to Cell Line Genetics, Inc (Madison, Wis.) for standard G-banded karyotype analysis.

Episomal Plasmid Detection

Cytosolic plasmid was separated with Thermo Scientific GeneJET Plasmid Miniprep Kit to detect the presence of residual non-integrated vector. Each 2 µl from 20 µl extract was used for conventional PCR amplification of 95° C. 30 sec, 55° C. 30 sec and 72° C. 30 sec in 30 cycles with EBNA-1 specific primers. Genomic DNA was prepared with Qiagen's DNeasy Blood & Tissue Kit. For the detection of plasmid derived sequence, we used same PCR condition and EBNA-1 primer. GAPDH primers were used as input control. EBNA-1 and GAPDH primer sequences are presented in Table D.

DNA Fingerprinting

Genomic DNA was extracted from cells using the QIAamp DNA FFPE Tissue Kit and PCR were performed using standard buffer conditions, 0.2 µg of DNA and GoTaq DNA polymerase employed 35 cycles with denaturing at 95° C. for 30 sec, annealing at 55° C. for 30 sec, and extension at 72° C. for 1 min in a total volume of 20 µl. Primers used in this study are listed in Table D.

Whole Exome Sequencing

To identify somatic mutations resulting from fibroblasts reprogramming and passaging of reprogrammed iPSCs, we performed WES of fibroblast and of four iPSC lines using the Personalis ACE WES service providing augmented coverage of >8,000 medically implicated genes, including >1,400 cancer-related genes (Patwardhan et al. 2015. Genome Med 7:71). Mean depth of coverage for target regions was over 75× across all samples. For the four iPSC lines, we performed paired analysis of fibroblast and each iPSC line to detect somatic mutations using MuTect2 (Cibulskis et al., 2013. Nat Biotechnol 31:213-219).

Sequencing reads were aligned to GRCh38 reference genome including alternative contigs and decoys using the BWA-MEM program (version 0.7.15) (Li and Durbin, 2010. Bioinformatics 26:589-595). The mapped reads were further processed with SAMtools (version 1.3.1) (Li et al., 2009. Bioinformatics 25:2078-2079), Picard tools (broadinstitute-.github.io/picard, version 2.5.0) and Genome Analysis Tool Kit (GATK) software (version 3.6) (DePristo et al. 2011. Nat Genet 43:491-498) to generate analysis-ready BAM files. Each iPSC line was analyzed for somatic mutations compared to fibroblasts using the MuTect2 module in GATK (Cibulskis et al., supra). Identified somatic mutations were annotated using the Ensembl Variant Effect Predictor (version GRCh38.89) (McLaren et al., 2016. Genome Biol 17:122) to investigate their consequences on gene transcription and protein product. To reduce false positive somatic mutation calls, we only considered those discovered in well covered regions with 20 or more effective high-quality aligned reads across all samples. Among the candidates, we excluded mutations with maximum minor allele frequency >0.01% in the Exome Aggregation Consortium (ExAC) database (Lek et al. 2016. Nature 536:285-291) to filter out potential germline variants. For the remaining somatic mutation candidates, we queried the Catalogue Of Somatic Mutations In Cancer (COSMIC) (cancer.sanger.ac.uk, version 80) (Forbes et al. 2017. Nucleic Acids Res 45:D777-D783) and Cancer Gene Census (CGC) databases (Futreal et al. 2004. Nat Rev Cancer 4:177-183) to identify frequently reported mutations and genes in cancer. We investigated chromosomal aberrations and other regional changes in copy number using ngCGH (github.com/seandavi/ngCGH, version 0.4.4) and copy number variation (CNV) analysis results from the Personalis ACE Cancer Exome pipeline (Personalis, Inc., CA). We visually inspected all CNV candidates for read alignments in Integrated Genome Viewer (version 2.3.79).

Quercetin Treatment

To test the effect of Quercetin on human iPSC removal, human iPSCs were plated on 6 well plates. Cells were treated with each concentration of Quercetin (5, 10, 20, 40, and 100 µM) for 2, 6, 16, and 24 hours. After each time point, Quercetin containing medium was replaced with fresh medium and cells cultured for 48 hours from the initial Quercetin treatment time. Cells were dissociated using TrypLE and cell viability was measured using Trypan blue exclusion and hemocytometer.

Flow Cytometry

All the FACS analysis were performed using BD Accuri C6 system (BD Bioscience) and data analyses were carried out according to manufacturer's instructions. Human iPS Cells were dissociated using TrypLE or Accutase, respectively, and filtered through a 70 μm cell strainer. Single cell suspensions were first fixed with 4% formaldehyde for 10 mins and suspended in permeabilization buffer for 15 min on ice. After blocking for 30 min, cells were incubated with primary labeled antibodies (PE conjugated anti SSEA-4, TRA-1-60) for 1 hour on ice in the dark. After washing with PBS with 1% FBS, FACS analysis was performed. Fluorochrome matched isotype controls were used and subtracted during analysis.

For cell loss/cell harvest analysis, the supernatant from monolayer- or spotting-based culture dish were harvested and run FACS. The particle numbers in 100 μl of supernatant were calculated and the total cell numbers were obtained based on the ratio of 100 μl to total supernatant volume.

Detecting the Presence of Undifferentiated Cells

Mixtures of undifferentiated C4 cells were serially diluted among hDFs by successive factors of 10 ($10^5$, $10^4$, $10^3$, $10^2$, $10^1$ and $10^0$) in a total of 100,000 cells to detect residual C4 cells using 3 different methods. For colony forming assay, each cell dilution was cultured for 6 days in E8 medium and pluripotent colonies were identified by AP staining. For the quercetin removal of undifferentiated cells, cells were treated with 40 μM quercetin for 16 hours and cultured in fresh E8 medium. For fluorescence activated cell sorting (FACS), C4 cells were dissociated using TrypLE and filtered through a 70 μm cell strainer. Single cell suspensions were first fixed with 4% formaldehyde for 10 mins and suspended in permeabilization buffer for 15 min on ice. After blocking for 30 min, cells were incubated with primary labeled antibodies (PE conjugated anti SSEA-4, TRA-1-60) for 1 hour on ice in the dark. After washing with PBS with 1% FBS, FACS analysis was performed using a BD Accuri C6 system (BD Bioscience) and data analyses were carried out according to manufacturer's instructions. Fluorochrome matched isotype controls were used and subtracted during analysis. For qRT-PCR assay, total RNA from all dilutions was extracted and subjected to qRT-PCR to determine OCT4 cycle times (Ct) value. OCT4 copy numbers were calculated from the equation curve that was generated from qRT-PCR of purified OCT4 partial sequence. Then, OCT4 copy numbers were plotted against PSC numbers.

Spotted Dish Preparation

Figure 13A:
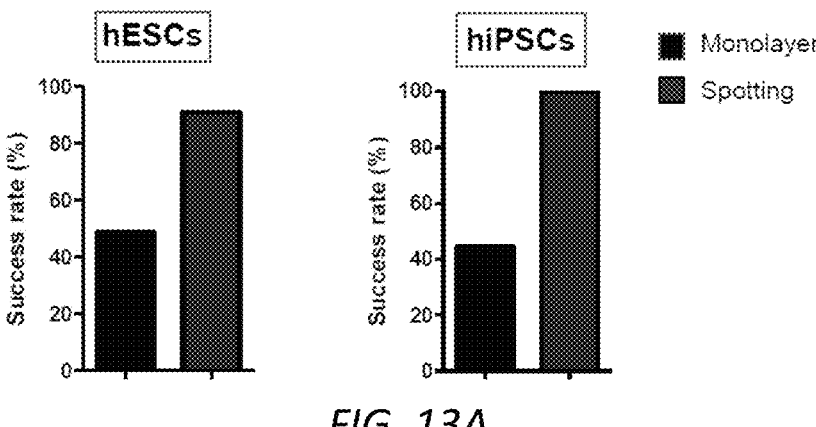
FIGS. 13A-C. Schematic diagram of spotting-based differentiation protocol. (A) The differentiation success rate of hESCs and hiPSCs using monolayer-based or spotting-based methods (n=76 for hESCs and n=48 for hiPSCs). In vitro differentiation was considered to be a success when 1) cells could survive with >50% confluence at D15 and 2) cells could be harvested and plated on the cover glass for further characterization by ICC. (B-C) Schematic diagram of spotting for the 6-cm culture plate with 6 spots and for the 10-cm culture plate with 12 spots.
Figure 13B:
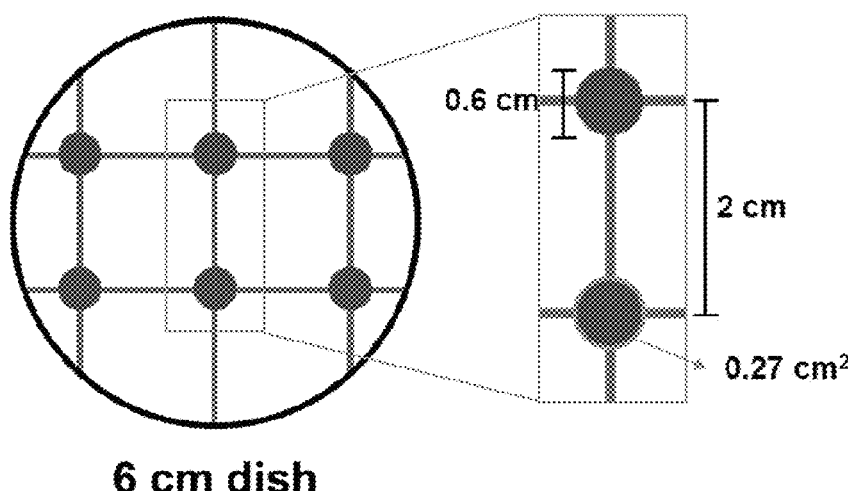
Figure 13C:
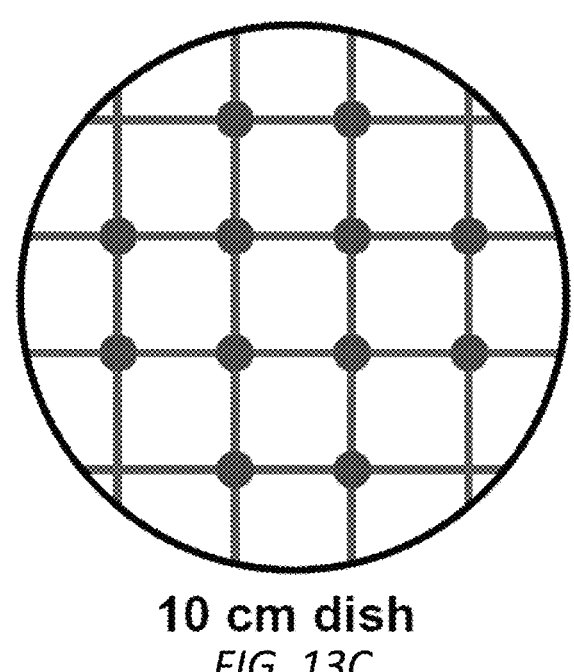

As shown in FIG. 13B, a grid consisting of 2 horizontal and 3 vertical lines was drawn at the bottom of 6-cm dishes yielding 6 junctions. 10 μl of cold Matrigel was loaded at each junction to make a limited spot-coated area. The spotted dishes were incubated at 37° C. for at least 30 min and the Matrigel was aspirated just before cell plating. Homogenously suspended cells were plated at a density of 730K/dish in 60 mm cell culture dish (regular plating conditions) while the spotted dishes received either 40K/10 μl spot, 10K/10 μl spot, 2.5K/10 μl spot (spotting conditions).

mDA Progenitor Differentiation

Differentiation media conditions and all the morphogen factors are shown in FIG. 5A. Through the entire differentiation procedure, no antibiotics were used. For the floor plate induction stage (D1-6), we used DMEM media with 15% KSR, glutamine, □-mercaptoethanol. For the neural precursor induction stage (D6-12), we used DMEM media with 11.5% KSR, 0.25% N2 (D6-8), 7.5% KSR, 0.5% N2 (D8-10), 3.75 KSR, 0.75% N2 (D10-12) including L-glutamine, β-mercaptoethanol and non-essential amino acid (NEAA). Dual Smad inhibitors, 0.2 μM LDN193189 and 10 μM SB431542 were added from D1-D12, and D1-D8, respectively. From D2 to D10, cells were treated with SHH agonist (2 μM Purmorphamine and 100 ng/ml Shh) with 100 ng/ml FGF8. The Wnt signaling activator, CHIR99021 (1 μM), was included from D4 to D12. At D9, cells were treated with 40 μM quercetin for 16 hours. For the DA progenitor induction and maturation stage (D12+), DMEM:F12 media was supplemented with $N_2$ supplement, 20 ng/ml BDNF, 20 ng/ml GDNF, 500 μM dbcAMP, 200 μM ascorbic acid, 10 ng/ml TGF-□3, along with 10 μM DAPT and 1 μM CHIR (D12-15). At D15, the cells were dissociated by 0.5 mM EDTA and the single cell suspension were re-plated in Poly-L-ornithine/Fibronectin/Laminin-coated dishes at approximately 2.5 millions/dish. From D15 onward, DMEM:F12 media was applied with $N_2$ supplement, 20 ng/ml BDNF, 20 ng/ml GDNF, 500 μM dbcAMP, 200 μM ascorbic acid, 10 ng/ml TGF-□3. At harvest, 10 μM Y-27632 was added to the medium.

Immunocytochemistry hiPSC derived dopaminergic neurons were washed with phosphate-buffered saline (PBS) (with $Ca^{2+}$ and $Mg^{2+}$) and fixed with 4% formaldehyde in PBS (pH 7.4) for 10 mins. Cells were incubated for 1 hr in blocking solution (0.3% Triton X-100 and 1% horse serum in PBS) at room temperature. Cells were incubated with primary antibodies in PBS containing 0.3% Triton X-100 and 1% horse serum overnight. Cells were then incubated with the proper fluorescence-conjugated secondary antibodies with Hoechst 33342 for nuclei staining at room temperature for 1 hr. Cell images were obtained by confocal microscopy (KEYENCE, Osaka, Japan). Data regarding specific cell populations were determined from microscopic images using ImageJ software (11). To measure apoptotic cells, cells were stained for cleaved caspase 3, an apoptotic marker, and Hoechst 33342, a DNA-binding nuclear dye. After staining with Hoechst 33342, compacted chromatin is brighter than in normal cells, and the condensed nuclei were counted by fluorescence microscopy. Data regarding specific cell populations were determined from microscopic images by ImageJ software.

High-Performance Liquid Chromatography (HPLC) Analysis

On day 47 of differentiation, supernatants were collected and centrifuged at 300×g for 5 min to remove cell debris. Samples were immediately stored at −80° C. and shipped to Emory University's HPLC Bioanalytical Core for reverse phase HPLC with electrochemical detection to determine the levels of DA and DOPAC. In brief, the supernatants were transferred into fresh 0.22 μM PVDF microcentrifuge filtered tubes. Any remaining particulate matter was eliminated by filtration through the spin filter at 5000 rpm for 5 min at 4° C. Monoamine concentrations were determined by reverse phase HPLC with electrochemical detection. For HPLC, an ESA 5600A CoulArray detection system, equipped with an ESA Model 584 pump and an ESA 542 refrigerated autosampler was used. Separations were performed at 25° C. using an MD-150×3.2 mm C18 column equipped with a C18 column guard cartridge. The mobile phase consisted of 1.5 mM 1-octanesulfonic acid sodium, 75 mM Na H2PO4, 0.025% triethylamine, and 8% acetonitrile at pH 2.95. Sample volumes of 25 μl were injected. Samples were eluted isocratically at 0.4 mL/min and detected using a 6210 electrochemical cell (ESA, Bedford, Mass.) equipped with a 5020 guard cell. The Guard cell potential was set at 500 mV, while analytical cell potentials were −175, 200, 350 and 425 mV. The analytes were identified by the matching criteria of retention time to known standards (Sigma Chemical Co., St. Louis Mo.). Compounds were quantified by comparing peak areas to those of standards on the dominant sensor.

Electrophysiology

For electrophysiological recordings, day 70 dopaminergic cells were placed in the recording chamber and continuously perfused at the rate of 1.2 ml/min with artificial cerebrospinal fluid consisting of 130 mM NaCl, 2.5 mM KCl, 2.5 mM $CaCl_2$, 1 mM $MgSO_4$, 1.25 mM $Na_2HPO4$, 26 mM $NaHCO_3$, 10 mM glucose, which was continuously bubbled with 95% $O_2$ and 5% $CO_2$. Whole-cell patch-clamp recordings were performed at room temperature (22±1.0° C.) using a EPC9 amplifier and Pulse v8.80 software (HEKA Elektronik). The recording electrodes (5-6 MΩ resistance) were filled with pipette solution containing 150 mM K-gluconate, 5 mM NaCl, 1 mM $MgCl_2$, 0.2 mM EGTA, 10 mM HEPES, 2 mM Mg-ATP, 0.5 mM Na-GTP (292 mOsm, adjusted to pH 7.3 with KOH). The liquid junction potential of 15.1 mV was corrected for using K-gluconate-based pipette solution. In current clamping mode, action potential firing was recorded at the resting membrane potential. Series (access) resistance was not compensated but continuously monitored. Spontaneous synaptic events were analyzed offline using Mini Analysis v6.0.7 (Synaptosoft) and Clampfit 8.2 (Molecular Devices) programs. Voltage-gated sodium channels were blocked with 1 μM Tetrodotoxin (TTX). Neurobiotin (0.2%) was included in intrapipette solution and recorded cells were fixed in 4% formaldehyde at 4° C. and co-stained with TH antibody.

Multi-Electrode Array (MEA) Recording 24-well microelectrode array (MEA) plate from Axion Biosystems were precoated with Poly L-ornithine (0.0015%), Fibronectin (1 μg/ml) and Laminin (1 μg/ml) for one night each at 37° C. in a $CO_2$ incubator. Next day, C4 derived D28 cells were plated at 20,000/well on the precoated MEA plate and generated according to the same schedule as described above. D28 cells were maintained in a humidified incubator at 37° C. with 5% $CO_2$ for 2 days to allow for proper attachment before electrophysiological recordings were initiated. A 60% medium change was performed every other day. Extracellular recordings of spontaneous action potentials were performed in culture medium at 37° C. using a Maestro MEA system and AxIS software (Axion Biosystems before and after treatment with compounds. This MEA platform is configured with 324 channels, and when using 24-well plates, is formatted to have 16 electrodes per well in a 4×4 grid. Approximately 20,000 cells were plated in each well dotted on the electrode grid. The baseline and post treatment raw data files (*.raw) were converted to spike files (*.spk) and excel files (*.csv) using AxIS Navigator 1.5.1 software. The conversion to these file formats allows for further processing and analysis of the data. For mDA neurons, the measurement for neural spikes within the AxIS software was set with a high pass=200 Hz and a low pass=3,000 Hz. The threshold for spike detection was set to 6 times the rolling standard deviation of the filtered field potential on each electrode. Five-minute recordings were used to calculate the average spike rate and the number of active electrodes in each well ("Active Electrodes"). An active electrode was defined as an electrode with a spike rate ≥5 spks/min.

Axion BioSystems' Neural Metric Tool was used to inspect the spike train raster plots to verify both the robustness of the activity and the quality and consistency of the well activity. These raster plot visualizations were also used to assist in the interpretation of the post treatment data. Wells with no spike activity, sparse spike activity, or little or no bursting or network synchrony are excluded from the experiment. Plates were equilibrated on the system for at least 2 min before the recording commences. In order to isolate dopaminergic neurons spontaneous activity, cells were treated with a combination of picrotoxin, a GABAergic antagonist; NBQX, an AMPA receptor antagonist; and AP5 NMDAR antagonist, all at a concentration of 10 μM in 500 μl of media per well. After adding the blocker, both the average number of spikes and the average number of electrodes was calculated. Recordings and analysis were done as mentioned above. A t-test was used to compare the average number of spikes and the average number of active electrodes between the control and treated groups.

Cell Preparation for Transplantation and Cryopreservation

C4-derived D28 cells were rinsed twice with DPBS and then treated with Accutase for 5 min at 37° C. Cells were harvested using DMEM:F12 medium with $N_2$ supplement, 20 ng/ml BDNF, 20 ng/ml GDNF, 500 μM dbcAMP, 200 μM ascorbic acid, 10 ng/ml TGF-β3, and 10 μM Y-27632). After centrifugation at 300×g for 3 mins, cell pellets were suspended with transplantation medium (DMEM/F-12 (without phenol red), 20 ng/ml BDNF, 20 ng/ml GDNF, 10 μM Y-27632, 20 mM Boc-D-FMK). Cell suspensions were passed through a 70 μm strainer to remove big clumps. Cell concentrations were calculated by Trypan blue exclusion using a hemocytometer. The final cell product consisted of 50,000 or 100,000 cells/μl in transplantation medium. For cryopreservation, cell pellets were suspended in CryoStor® CS10 cryopreservation medium. Cells in cryovials were placed into a Mr. Frosty™ Freezing Container (Nalgene) for controlled freezing at −80° C. Frozen cells were then transferred to liquid nitrogen. After one week, frozen cells were thawed for transplantation.

Surgical Procedure

Animals were anesthetized with isoflurane using a SomnoSuite Anesthesia System (Kent Scientific Corporation, Torrington, Conn.). Stereotaxic surgeries were performed on a stereotaxic frame (David KOPF Instruments, Tujunga, Calif.) equipped with a Micro4 controller (World Precision Instruments, Sarasota, Fla.).

For Charles River athymic rats, unilateral lesions of the nigrostriatal pathway were established by stereotaxic injection of 6-OHDA into the medial forebrain bundle. Desipramine (10 mg/kg) was injected into the rats to protect noradrenergic projections 15 min prior to anesthesia. Two microliters of 6-OHDA (7.5 mg/ml in 0.2% ascorbic acid and 0.9% saline) were injected using a 2.5 μl Hamilton syringe (Hamilton Company, Reno, Nev.). The coordinates were calculated with reference to bregma: antero-posterior (AP), −4.0; medio-lateral (ML), −1.3; and dorsoventral (DV), −7.0 (Torres et al., 2011. J Neurosci Methods 200: 29-35). For intra-striatal transplantation of H9 or C4-derived D28 cells, one deposit of 2 μl (50,000 cells/μl) was placed at the following coordinates: AP, +0.8; ML, −3.0; and DV, −5.5. Cells were injected through a 10 μl Hamilton syringe fitted with a blunt 26G, 0.75-inch needle at a speed of 0.4 μl/min. For Taconic athymic rats, C4 D28 cells were suspended at a concentration of 100,000 cells/μl. One microliter of cells was injected into AP, +0.8; ML, −3.0; and DV, −5.5 for the 100,000 cell group. For the 300,000 cell group, two deposits of 1.5 μl were placed at the following coordinates: AP, +0.8; ML, −3.0; and DV, −5.0 and DV, −6.0. Control rats only received transplantation medium injections. For NOD SCID mouse striatal injections, one deposit of 2 μl (50,000 cells/μl) of C4 D0, D14 or D28 cells were injected in the striatum, according to the following co-ordinates relative to bregma (in mm): AP+0.5; ML −/+1.8; DV −3.2 bilaterally.

After injection, the needle was kept in the brain for 5 min. and then the needle was withdrawn slowly over a period of 5 min. After surgery, the incised skin was sealed with Autoclip® Surgical Suture (Fine science tools, Foster City, Calif.) and animals were monitored on a warm pad until recovery. All animals were injected with Ketoprofen (5 mg/kg; Ketofen, Santa Cruz, SC-363115Rx) subcutaneously to reduce pain and 1 ml 0.9% sodium chloride intraperitoneally to prevent dehydration.

For NOD SCID mouse testis injection, a 1 cm longitudinal incision was made through the skin and peritoneum, and the testes placed on sterile gauze. 10 μl (5,000/μl) of C4 iPSC were slowly injected into the center of the testis capsule away from any major blood vessels. The needle was removed slowly to avoid reflux of the cells. The testes and fatty tissue were replaced back to their original position in the abdomen.

D-Amphetamine-Induced Rotation Test

D-Amphetamine, a presynaptic (indirect) DA agonist, was administrated intraperitoneally (4 mg/kg) to induce rotational behavior in rats that have been successfully lesioned with 6-OHDA. Rotational bias was recorded using an automated system (SD Instruments, San Diego, Calif.). Rats were recorded for 90 min (9 intervals; 10 min/interval). Only full body turns were counted and then expressed as net turns per minute, with rotations toward the side of the lesion given a positive value. Only animals showing more than 6 ipsilateral turns per minute were considered successfully lesioned (Kirkeby et al. 2012. Cell Rep 1:703-714).

Corridor Test

To measure non-pharmacological behavior improvement, we used the corridor test (Dowd et al. 2005. Brain Res Bull 68:24-30). First, to reduce exploratory behavior during testing, rats were habituated to the corridor with scattered sugar pellets for 10 min for 2 days. The next day, rats were placed at the end of a corridor with 10 adjacent pairs of cups filled with 5-10 sugar pellets consistently distanced along the floor of the corridor. Animals were allowed to explore the corridor freely. An investigator blinded to the group identity directly counted retrievals. A 'retrieval' was defined as each time the rat poked its nose into a unique cup. All rats were tested until 20 retrievals were made or the test duration reached 5 minutes. Before testing, all rats were located in an empty corridor for 5 minutes to reduce environment novelty. Rats were food restricted the day prior and during the 4 days of testing. Results were calculated as an average of the contralateral retrievals (right) and presented as percentage of total retrievals. Tests were performed every 4 weeks until 24 weeks after transplantation.

Cylinder Test

To measure forelimb asymmetry in exploratory behavior, rats were assessed using the cylinder task (Bjorklund et al. 2010. Brain 133:496-511), where the rat is placed in a glass cylinder (20 cm in diameter) and a maximum of 30 paw touches to the walls are recorded. An investigator blinded to the group identity made the evaluation. Results were calculated as an average of touches using the right-side paw (contralateral) and presented as percentage of average of total touches. Tests were performed 24 weeks after transplantation.

Stepping Test

To measure forelimb akinesia, rats were assessed using the side-stepping test (Olsson et al. 1995. J Neurosci 15:3863-3875), where forelimb adjusting steps are quantified over a total length of 90 cm. Steps were counted by an investigator blinded to the group identity. Results were calculated as an average of the number of right forelimb steps (contralateral) and presented as percentage of average of the left forelimb steps. Tests were performed 24 weeks after transplantation.

Bio-Distribution Analysis

To verify the existence of transplanted human cells we used RT-PCR method specific for amplification of human specific genes. First DNA was extracted from each 15 mg mouse tissue (olfactory bulb and cerebellum mixture, spinal cord, lung, heart, liver, kidney, and spleen) with QIAamp DNA FFPE Tissue Kit according to the manufacturer's instruction. The concentration of extracted DNA was measured on a Nanodrop ND-1000 spectrophotometer and 100 ng of DNA was used for real time RT-PCR reaction. Human specific primer sequences are as follows; forward 5'-ATTGCCCCAAAACTTTTTTG-3' (SEQ ID NO:106) and reverse 5'-TTGAAGACCAGTCTGGGAAG-3'. Endogenous mouse gene was detected using the following primers: forward: 5'-CCACATCTCCCTCCAGAAAA-3' (SEQ ID NO:107) and reverse 5'-AGGGTCTGGGCCATAGAACT-3' (SEQ ID NO:108).

Brain Sectioning and Immunohistochemistry

Deep anesthesia was induced with an intraperitoneal injection of Ketamine (75 mg/kg)/Xylazine (7.5 mg/kg), followed by intracardial perfusion with ice-cold phosphate buffered saline (PBS; 0.01M, pH 7.4) for 8 min, followed by perfusion with 4% formaldehyde for 20 min, at a flow rate of 10 ml/min. Brains were removed and post-fixed overnight in 4% formaldehyde at 4° C. and then cryopreserved by successive incubations in 20% and 30% sucrose. Brains were embedded in OCT and coronal sections (30 μm) covering the entire striatum were serially collected (Leica CM1950, Buffalo Grove, Ill.). Brain slices were incubated with PBS containing 30% $H_2O_2$ for 30 min and then were incubated with rabbit anti-TH antibody (1:5000), mouse anti-hNCAM antibody (1:1000) and mouse anti-hNuc (1:1000) overnight. After rinsing, the samples were stained with biotinylated secondary antibody (Vector Labs) for 1h. Finally, sections were visualized with the Vectastain Elite ABC kit and the DAB peroxidase substrate kit following the manufacturer's protocol. To count TH$^+$ neurons in the grafts, the optical fractionator probe of the Stereo Investigator (MBF Bioscience, Williston, Vt.) was used under 63X oil lens with counting frame 50×50 μm and grid size 200×200 μm. Final counts were corrected for series number (1:6) to get an estimate of the total number of TH positive neurons per animal brain.

Vimentin immunohistochemistry was performed by the Rodent Histopathology Core at Harvard Medical School, Boston, Mass.

Brain Sections Immunofluorescence

Free-floating coronal sections of the entire midbrain were pre-incubated in blocking solution containing 5% normal donkey serum, 3% BSA and 0.3% Triton X-100 in PBS at room temperature for 1 h. Primary antibodies were diluted in 3% BSA and 0.3% Triton X-100 in PBS and were applied overnight at 4° C. After three washes with PBS containing 0.3% Tween 20, the sections were incubated with Alexa 488-, Alexa 568- or Alexa 647-conjugated secondary antibodies diluted in the same buffer as the primary antibodies for 1 hr at room temperature. All sections were counterstained with Hoechst 33342. Following three additional washes, a cover slip was applied over the sections with mounting media and visualized with a fluorescence microscope (KEYENCE, Osaka, Japan). Sections stained with secondary antibodies alone were processed and photographed under the same conditions and used as negative controls.

Hematoxylin and Eosin Staining

For pathological analysis of NOD SCID mouse testes, each mouse was anesthetized by Ketamine/Xylazine and testes were removed and stored temporarily in 4% formaldehyde. For NOD SCID mouse brain tissue pathological analysis, every sixth coronal sections covering the entire striatum were mounted on a glass slide. Glass slides of testes and brain tissues were sent to the Rodent Histopathology Core at Harvard Medical School, Boston, Mass. for Hematoxylin and Eosin staining.

Quantification and Statistical Analysis

All experiments were performed in biological triplicate unless otherwise indicated. The "n" for each experiment can be found in the figure legends and represents independently generated samples for all experiments. Statistical analyses were performed using the GraphPad Prism v7 software. A value of $p<0.05$ was considered to be statistically significant. Throughout the figures, asterisks indicate the significance of the p value: $*p<0.05$; $p<0.01$; $*p<0.001$. For the test of mutations present in fraction of cells within each iPSC line, p-values were generated by two-sided binomial test and adjusted by Bonferroni correction. The mutation data were analyzed and visualized using R.

Example 1. Identification of microRNAs (miRNAs) that Regulate Metabolic Reprogramming We recently showed that SIRT2, directly targeted by miR-200c, is critical for metabolic reprogramming and hiPSCs generation (19). To validate a functional link between miR-200c and reprogramming, we tested whether forced expression of miR-200c would induce a metabolic change. Indeed, miR-200c overexpression (OE) in human dermal fibroblasts (hDFs) resulted in significant metabolic changes, including decreased oxygen consumption rate (OCR) and increased extracellular acidification rate (ECAR) (FIGS. 9A and B). Compared to empty-vector control lines, miR-200c OE cells showed significantly decreased oxidative phosphorylation (OXPHOS) capacity, with decreases in basal respiration, ATP turnover, maximum respiration, and oxidative reserve, as well as OCR changes after carbonyl cyanide-p-trifluoromethoxyphenylhydrazone (FCCP) injection (FIGS. 9C-E). We next treated hDFs with reprogramming factors (i.e., Y4F) together with miR-200c. Addition of miR-200c OE significantly reduced OXPHOS, compared to Y4F only (FIGS. 9F-K), suggesting that pluripotency-associated miRNAs influence the reprogramming process by facilitating metabolic reprogramming. To test this, we investigated whether other miRNA(s) could, like miR-200c, induce metabolic changes. Based on previous miRNA expression studies (20-23), we identified 8 candidate miRNA clusters (miR-17/92, -106a, -106b, -136s, -200c, -302s, -369s, and -371/373) that are consistently enriched in hPSCs. We tested if OE of these miRNAs in hDFs would lead to metabolic changes. Interestingly, we found that 7 out of these 8 miRNA clusters (excepting miR-17/92) resulted in significant metabolic reprogramming, including decreased OCR and increased ECAR, leading to robust reductions in the OCR/ECAR ratio ranging from $\frac{1}{3}$ to $\frac{1}{20}$ compared to control cells transduced with empty vector (FIGS. 9L-N).

Example 2. Combining Metabolism-Regulating miRNAs with Reprogramming Factors Efficiently Generates High Quality hiPSCs We tested whether adding these metabolism-regulating miRNAs to the usual reprogramming factors (either Y4F or Y3F (OCT4, SOX2, and KLF4)) on lentiviral vectors would facilitate generation of hiPSCs. Among the 7 miRNA clusters identified above, miR-302s exhibited the highest potency in enhancing hiPSC generation when combined with Y3F or Y4F (FIGS. 1, A and B). In addition, miR-106a, -106b, -200c, -369s or -371/373 clusters also modestly but significantly increased hiPSC generation. We next tested if any additional miRNA would further enhance hiPSC generation in combination with Y3F and miR-302s (Y3F+3) or with Y4F and miR-302s (Y4F+3). In the presence of Y3F+3, addition of any of the other miRNA clusters did significantly enhance hiPSC generation (FIG. 1C). When Y4F+3 was used, only miR-200c significantly enhanced hiPSC generation (FIG. 1D), thus identifying the combination of Y4F, miR-302s, and miR-200c (Y4F+3+2) as optimal. We compared the dynamics of metabolic changes during reprogramming induced by Y4F, Y4F+3, and by Y4F+3+2. Notably, Y4F+3+2 induced the most prominent metabolic change (FIGS. 1, E and F), supporting a link between metabolic change and efficient hiPSC generation. We next investigated whether this combination could also influence the overall quality of hiPSCs by staining for alkaline phosphatase (AP) and for a more stringent pluripotency marker, TRA-1-60 (24, 25). Approximately 40% of AP+ colonies generated by Y4F or Y4F+3 were TRA-1-60+. In contrast, over 90% of AP+ colonies generated by Y4F+3+2 were TRA-1-60+ (FIG. 1G and FIG. 10A). Moreover, TRA-1-60+ hiPSC colonies generated by Y4F+3+2 showed typical hESC-like compact colony morphology (FIG. 10A). We also reprogrammed adult hDFs (GM03529, Coriell Institute) and found that over 90% of colonies generated by Y4F+3+2 on lentiviral vectors were AP+/TRA-1-60+ (FIG. 10B).

We next tested whether this combination (Y4F+3+2) could generate high quality hiPSCs using non-viral vectors. We developed two episomal vectors harboring Y4F on one vector (pY4F; FIG. 10C) and miR-302s and miR-200c clusters on the other (p3+2; FIG. 10D). Because of the known transformation activity of c-Myc (26), we replaced it with L-MYC on pY4F. We thus established a novel episomal reprogramming protocol using single transfection with these two vectors (FIG. 10E), that efficiently reprogrammed hDFs to hiPSC colonies that were >90% AP+/TRA-1-60+ (FIG. 1H). We selected hiPSC lines with hESC-like morphology generated by Y4F, Y4F+3, and Y4F+3+2, passaged them >20 times, and characterized their properties. As shown in FIGS. 2, A and B, their morphologies and expression levels of pluripotency markers closely resembled those of H9 hESC. Interestingly, H9 and hiPSCs generated by Y4F+3+2 differentiated equally well to all three germ layer lineages, while differentiation of those generated by Y4F or Y4F+3 were skewed toward mesodermal lineage, as evidenced by (1) staining with antibodies against the three germ layer markers and (2) gene expression of lineage-specific markers (FIGS. 2, C and D). These results suggest that the Y4F+3+2 combination enables the generation of higher quality hiPSCs from both newborn and adult human fibroblasts with less biased differentiation potential, regardless of the delivery vector, compared to conventional methods (Y4F or Y4F+3) (Table 1).

TABLE 1

| | The ratio of TRA-1-60⁺/AP⁺ | | | Metabolic change | Pluripotency marker gene | Differentiation |
|---|---|---|---|---|---|---|
| Combination | Lentiviral vector | | Episomal vector | evidence | expression | potential |
| of factors | BJ | GM03529 | BJ | BJ | BJ | BJ |
| Y4F | 42.4 ± 17.4% | 53.2 ± 23.2% | 49.9 ± 10.8% | ~8 days post-infection | Similar to H9 hESC | Skewed differentiation |
| Y4F + 3 | 44.2 ± 8.8% | 35.4 ± 3.8% | 50.4 ± 15.6% | ~8 days post-infection | Similar to H9 hESC | Skewed differentiation |
| Y4F + 3 + 2 | 94.8 ± 1.8% | 93.9 ± 4.7% | 91.7 ± 9.8% | ~4 days post-infection | Similar to H9 hESC | Unskewed differentiation |

Comparison of hiPSC lines derived from newborn (BJ) or adult fibroblasts (GM03529) by different combinations of factors on lentiviral or episomal vectors

Example 3. Genomic Integrity and Somatic Mutations in hiPSCs

To test whether our reprogramming method can reliably generate clinical grade hiPSCs, we attempted to generate hiPSC lines using adult hDFs from multiple sources, including 9 fibroblast lines from the Coriell Institute (3 familial PD, 3 sporadic PD, and 3 healthy subjects) and 4 samples from new skin biopsies (3 healthy subjects and 1 sporadic PD patient). As shown in Tables B and C and FIGS. 11A and B, our method generated multiple hiPSC lines from all of these fibroblasts using a one-time transfection with pY4F and p3+2 (FIG. 10E), all displaying hESC-like morphology and prominent expression of pluripotent markers, including OCT4, TRA-1-60, NANOG, and SSEA-4.

Figure 12A:
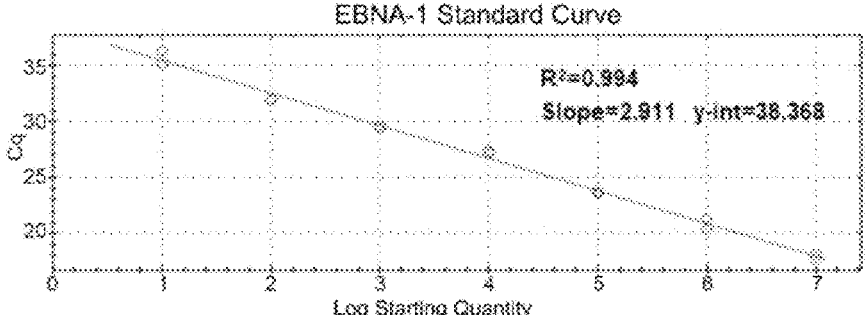
Figure 12F:
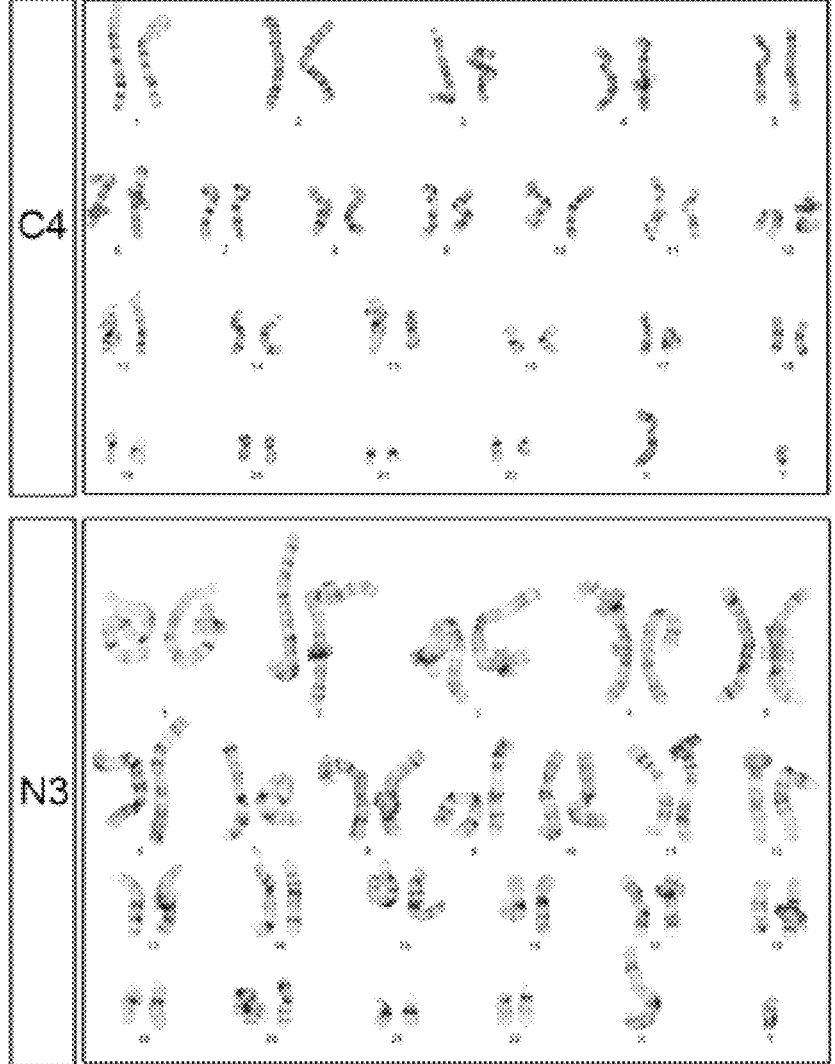
Figure 12G:
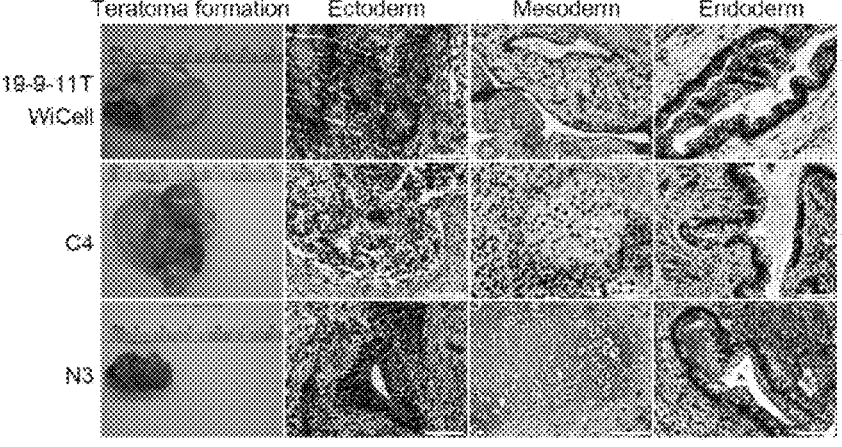

Focusing on personalized cell therapy, we further characterized hiPSC clones made from skin biopsy of a sporadic PD patient (MCL540 in Table B) under an IRB approved protocol (Partners IRB #2010P001100). A fundamental criterion for clinical grade hiPSCs is maintenance of genomic integrity and absence of harmful (e.g., reported cancer-causing) mutation(s) (7, 17). As an example, we tested 5 independent hiPSC clones that were passaged approximately 20 times since the original isolation from MCL540 (N17, C4, N3, C11, and C5) as well as control cells (parental fibroblasts and H9) for potential integration of vector DNAs into the host genome (Table 2). To detect plasmid-derived sequences, we designed 8 sets of EBNA-1 specific primers and identified two sets (EB-01 and EB-02) that specifically detect plasmid DNAs (FIG. 12A). While plasmid DNAs were undetectable in cytoplasmic fractions (FIG. 12B), one (N17) of five clones showed an integrated plasmid sequence (FIG. 12C). qRT-PCR analysis showed that N17 contained $1.3$-$1.7 \times 10^4$ copies of integrated plasmid sequences per 100 nanograms of genomic DNA (FIG. 12D). Since the amount of DNA in a diploid cell is about 6 picograms (bionumbers.hms.harvard.edu/bionumber.aspx?id=111206), 100 nanograms of genomic DNA used in qRT-PCR represents about $1.76 \times 10^4$ cells. Thus, clone N17 appears to contain approximately 1 copy of plasmid sequences per cell. In contrast, four other clones and negative controls (original fibroblasts and H9) were free of integrated plasmid DNAs (FIG. 12D). We thus excluded N17 and further analyzed the remaining 4 hiPSC clones (C4, N3, C11, and C5) by DNA fingerprinting, karyotyping, and in vivo pluripotent differentiation (FIG. 12, E-G).

TABLE 2

Summary of MCL540-derived hiPSC lines.

| iPSC lines | Pluripotency markers expression | Chromosome integration | In vitro 3-germ differentiation | Karyotype | Teratoma formation | Whole exome sequencing |
|---|---|---|---|---|---|---|
| N17 | Passed | Failed | N/A | N/A | N/A | N/A |
| C4 | Passed | Passed | Passed | 46, XY | Passed | Enrolled |
| N3 | Passed | Passed | Passed | 46, XY | Passed | Enrolled |
| C11 | Passed | Passed | Passed | 46, XY | N/A | Enrolled |
| C5 | Passed | Passed | Passed | 46, XY | N/A | Enrolled |

Figure 3A:
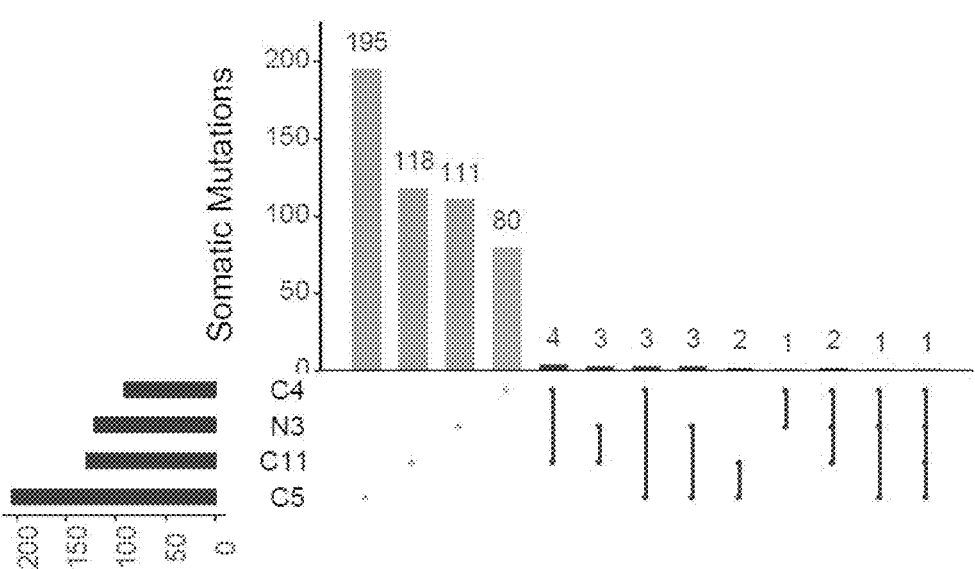
FIGS. 3A-C. Genomic integrity of hiPSC lines generated from skin biopsy of a sporadic PD patient. (A) Somatic mutations found in four hiPSC lines. Columns show the number of singleton mutations in each hiPSC line (different color per hiPSC line) and number of unique mutations found in two or more hiPSC lines (black columns). Below black columns, hiPSC lines sharing the mutations are indicated by dots connected with edges. Bottom left bars represent total numbers of mutations including both singleton and the ones found in two of more hiPSC lines. C4 had the smallest number of somatic mutations (n=92) of which 80 were singleton and 12 were found in C4 and the other hiPSC lines. (B) Mutational burden on coding regions and cancer-associated genes were compared to publicly available datasets. The number of nonsynonymous mutations in our hiPSC lines was significantly lower than for hESC lines. On average, the number of nonsynonymous mutations in the iPSC lines from HipSci project is similar to that of our hiPSC lines. Overall, C4 shows the lowest mutation burden (red). For the somatic mutations in cancer-associated genes, no somatic mutation was found in two widely used hESC lines (H1 and H9, blue) and C4 hiPSC line (red) (right panel). (C) The distribution of minor allelic fractions (MAFs) of all somatic mutations in the four hiPSC lines. The peaks around MAF of 0.5 denote clonal somatic mutations. The second peaks with lower MAFs of 0.1 sub-clonal mutations. For each plot, the density curve with two peaks shows the distribution of somatic mutation MAFs and the color of curve matches with (A) for each hiPSC line and the curves with different colors (peaked around MAF of 0.0) are for somatic mutations detected by the other hiPSC lines.
Figure 3B:
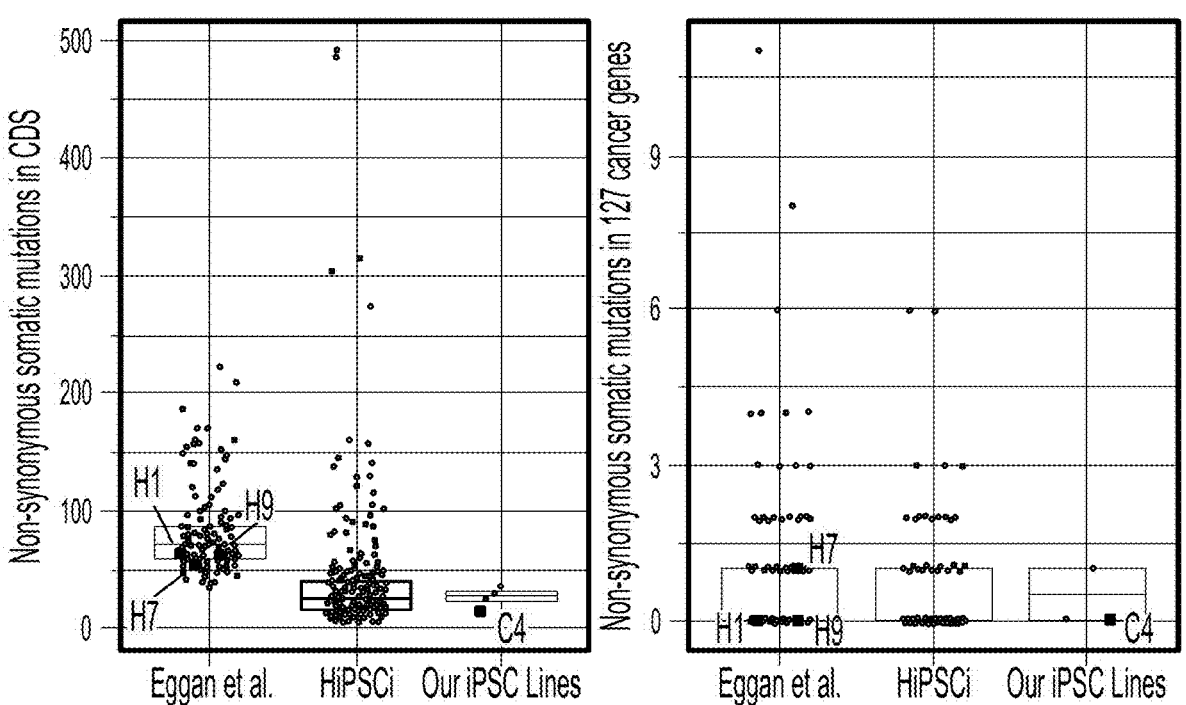
Figure 3C:
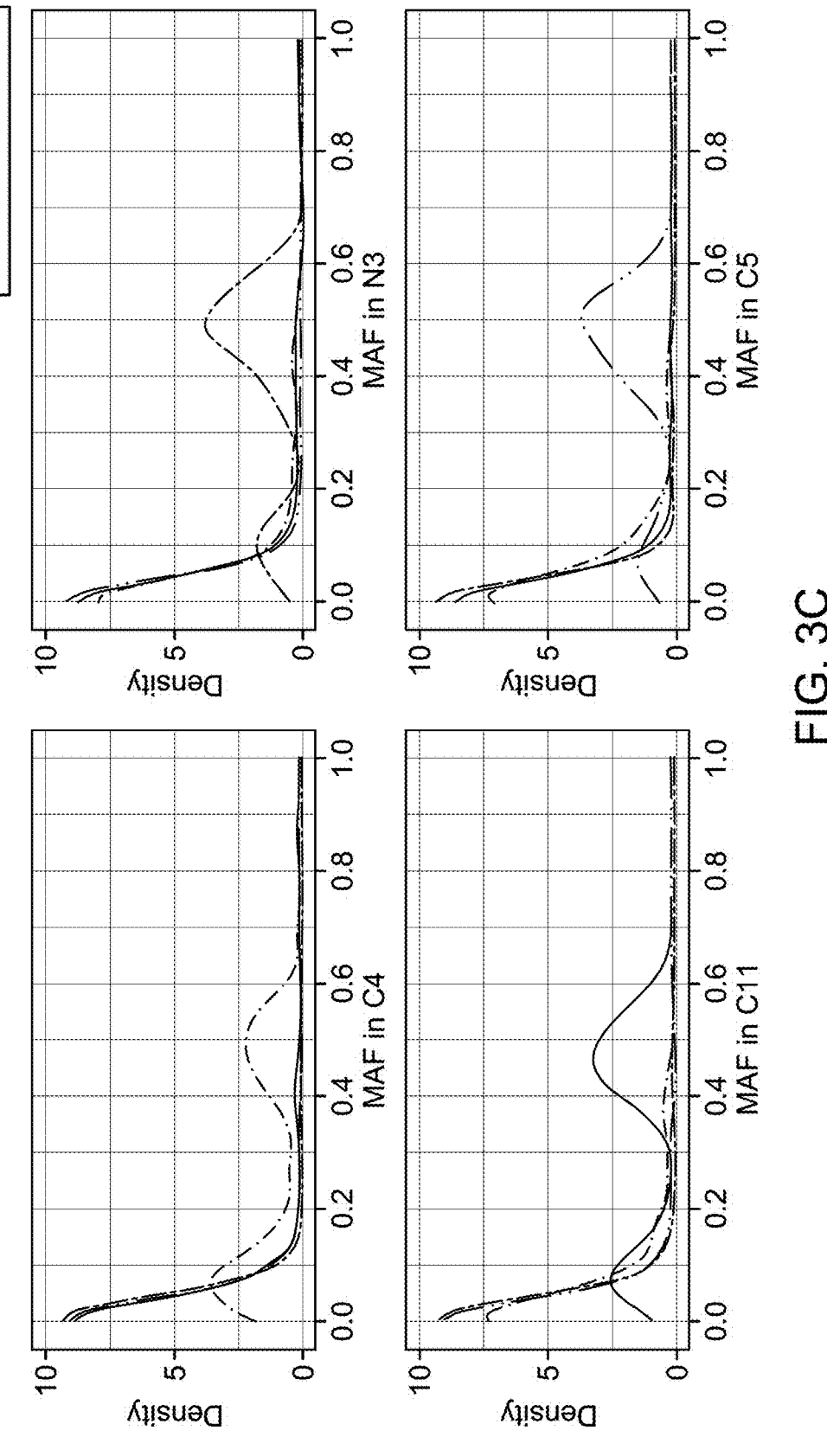

We performed whole-exome sequencing (WES) on these four hiPSC clones and found a total of 524 somatic mutations compared to the parent fibroblast DNA sequence, including 137 mutations in coding exons or in ±2 bps splicing acceptor and donor sites. Each hiPSC line carried a median of 126 somatic mutations (range 92-205) including a median of 114.5 singleton mutations (range 80-195). There were a few shared mutations (n=1-4) between hiPSC lines (FIG. 3A). C5 had the largest number of somatic mutations (n=205) and C4 had the fewest (n=92) including 80 singletons. Of somatic mutations in protein coding regions, hiPSC lines carried a median of 36.5 (range 17-50), including 27 (median, range 14-35) nonsynonymous mutations. Again, C4 had the fewest mutations. We investigated mutations in 127 genes reported as frequently mutated across multiple cancer types (27). Our hiPSC lines carried at most one mutation (synonymous or nonsynonymous) in these genes, and no nonsynonymous mutation was found from C4 or N3. In summary, of somatic mutations discovered in all four hiPSC lines, there were none that have been causally implicated in cancer. Finally, we compared somatic mutation burden in our hiPSC lines with publicly available data sets (FIG. 3B). We collected high-confidence somatic mutations from WES based on 140 hESC lines (28) and somatic coding mutations from WGS data for 299 hiPSC lines (generated by Sendai virus method) in the Human Induced Pluripotent Stem Cells Initiative (HipSci) (29). Our hiPSC lines showed overall mutational burdens similar to HipSci hiPSC lines (median 25, range 5-492) and significantly less than hESC lines (median 70, range 34-223) (Wilcoxon rank sum test, p-value 0.00071) (FIG. 3B; left). Also, our hiPSC lines carried smaller numbers of mutations in genes frequently mutated in cancer (FIG. 3B; right).

We also checked for somatic mutations that might be present in a subpopulation in each hiPSC line. We estimated the distribution of allelic fractions in observed somatic mutations and performed binomial tests with a null model of 45% as the center for SNVs and 35% as the center for indels (28, 30). For each hiPSC line, a median of 16 (9-18 in range) variants, with a Bonferroni corrected p-value <0.01, were considered as potential candidates for somatic mutations originating from a fraction of cells. The distribution of minor allele fractions of all somatic mutations found across all hiPSC lines (FIG. 3C) showed that both clonal and sub-clonal mutations are observed in each hiPSC line (identified as two peaks in plots), but sub-clonal mutations were unique to individual hiPSC lines. We observed 20 mutations conserved across two or more hiPSC lines, but visual inspection of aligned short-reads from WES revealed one or two short-reads with mutant alleles in the parent fibroblast for 14 somatic mutation candidates, suggesting potential germline origin of these sub-clonal mutation candidates. Notably, there were no clonal or sub-clonal somatic mutations in cancer driver genes such as TP53 in our hiPSC lines (28). C4 and N3 had the lowest somatic mutational burden among the four hiPSC lines and were further characterized.

Figure 4A:
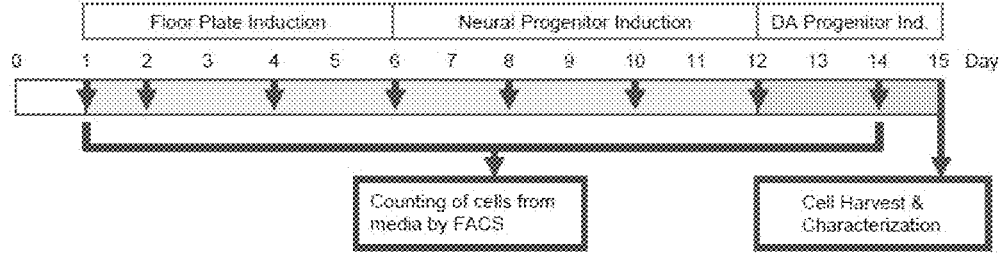
FIGS. 4A-D. Spotting-based in vitro differentiation improves yield and quality of the resulting dopamine cells. (A) Experimental scheme to find optimized physical culture conditions. On days 0 through 15, all cells regardless of viability were quantified by FACS and/or manual cell counting as marked with arrows. At D15, cells were re-plated on cover glass for immunocytochemical analysis or harvested for quantitative real-time PCR. (B-C) Comparison between conventional monolayer-based and spotting-based methods for degree of cell loss (due to detachment) from day 1 to day 14 and cell harvest on D15 (B) and for the percentage of dead cells at D15 (C) for both hESC (H9 and H7) and hiPSC (C4 and N3). Cell densities of 11,000/cm² and 10,000/spot were used for conventional and spotting-based methods, respectively. Data presented reflect experiments with measurable outcomes (see the legend of FIG. 13A). Mean±s.d., n=4, one-way ANOVA. (D) Quantification of dying cells from final cell harvest on D15 using immunocytochemical analysis. Antibody against cleaved caspase-3 was used to detect apoptotic cells. Nuclear condensation was visualized by Hoechst 33342 staining to detect dead or dying cells. Cells plated with spotting technique showed significantly reduced numbers of cleaved caspase-3 positive cells. Scale bar: 100 μm.

Example 4. A "Spotting" Culture Method Reliably Generates High Yield and High Quality mDA Cells Numerous laboratories have investigated the in vitro differentiation of mouse and human PSCs toward the mDA cell fate. Based on the findings that mDANs originate from the neurogenic floor plate and that the Wnt and Sonic Hedgehog signals play critical roles (31-33), recent mDA differentiation protocols utilize activators of these signals (7, 34, 35). Since the embryoid body-derived neurosphere-based method is highly variable between experiments (18, 35, 36), we sought to establish more efficient and reproducible monolayer methods based on "dual-SMAD inhibition" (36, 37). mDA cells used for transplantation studies have generally been differentiated in vitro for 16-32 days (7). Therefore, we sought to optimize the first 15 days, which critically determines floor plate-based mDA progenitor (mDAP) induction, first using the well-studied H9 (passage number of <36) starting with 730,000 cells per 60 mm dish (i.e., 34,000/cm²), according to previously published optimized conditions (37). Surprisingly, we observed severe cell death/loss starting from D8-D10, resulting in highly variable outcomes. Assessing multiple experiments (n=76 for hESCs and n=48 for hiPSCs) performed by 4 independent researchers in our laboratory, >50% failed to provide meaningful data for both hESCs and hiPSCs, due to severe cell loss (FIG. 13A). Thus, we carefully monitored cell loss during the differentiation process by determining the number of detached cells using fluorescence activated cell sorting (FACS) during media change (FIG. 4A). On day15 (D15), we counted the total harvested cell number, then further characterized these cells. Remarkably, the total number of detached/lost cells from D1 to D14 was much higher than that of harvested cells (FIG. 4B and Table 3) when tested for two hESC lines (H9 and H7) and two hiPSC lines (C4 and N3). Thus, we attempted to start the monolayer culture with smaller numbers of H9 and C4 cells (240,000 (11,000 cells/cm²) and 60,000 (3,500 cells/cm²)). Using 11,000 cells/cm², we found a similar pattern of significant cell loss (Table 3). At still lower densities of 3,500 cells/cm², both H9 and C4 cells showed poor viability and were similarly lost to detachment, so that the final cell harvest was unacceptably low. This pattern of severe cell loss regardless of initial cell concentration suggests that evenly distributed monolayer conditions are not ideal for in vitro differentiation of hiPSCs and hESCs. Thus, we hypothesized that dividing the monolayer into smaller isolated portions (here called "spotting") might improve in vitro differentiation. To test this, we limited initial cell attachment to designated areas by pre-coating circular areas ("spots") of ~5 mm diameter using 10 μl of Matrigel on cross points of a 2×2 cm grid (FIGS. 13B and C).

Figure 4B:
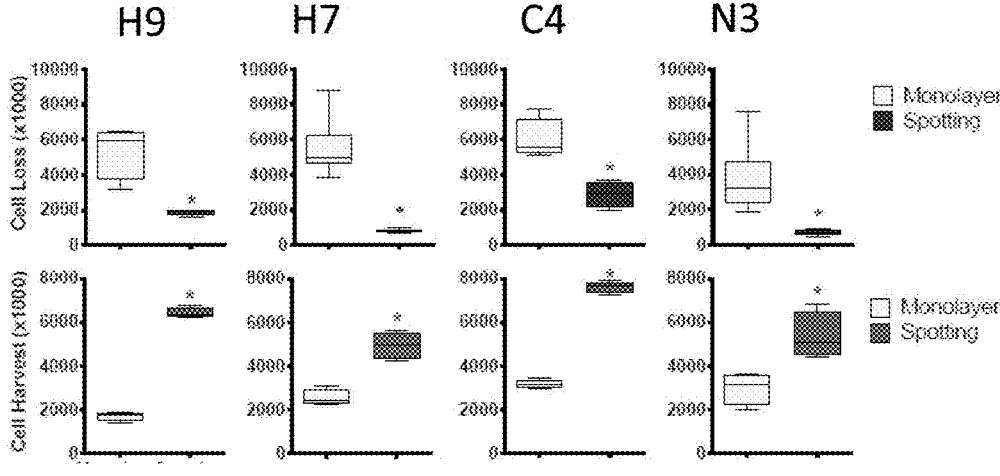
Figure 4C:
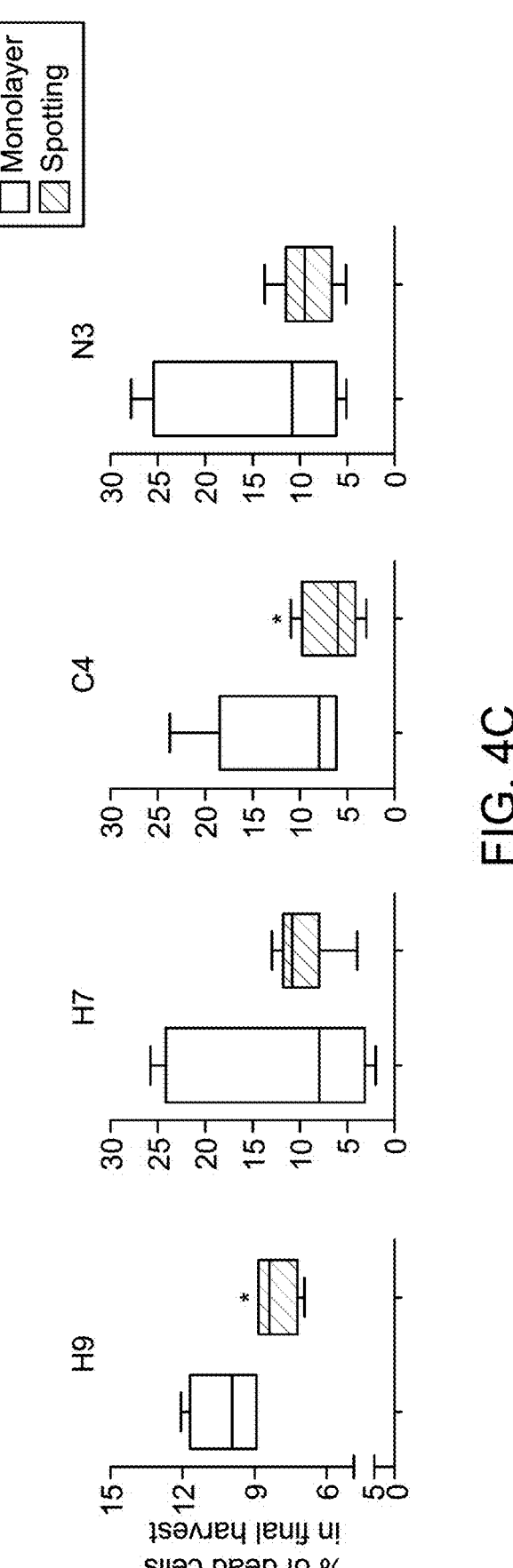
Figure 4D:
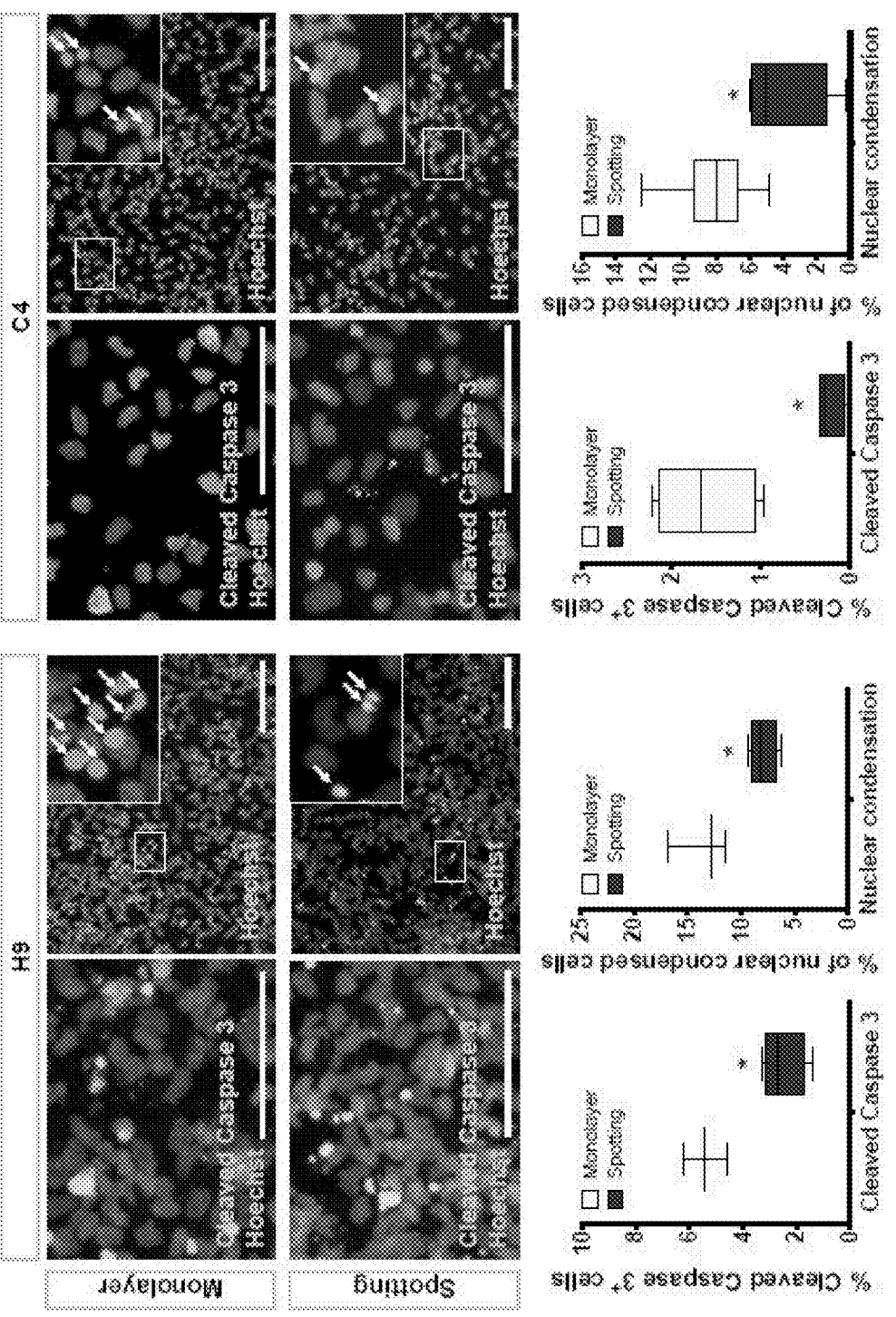
Figure 14A:
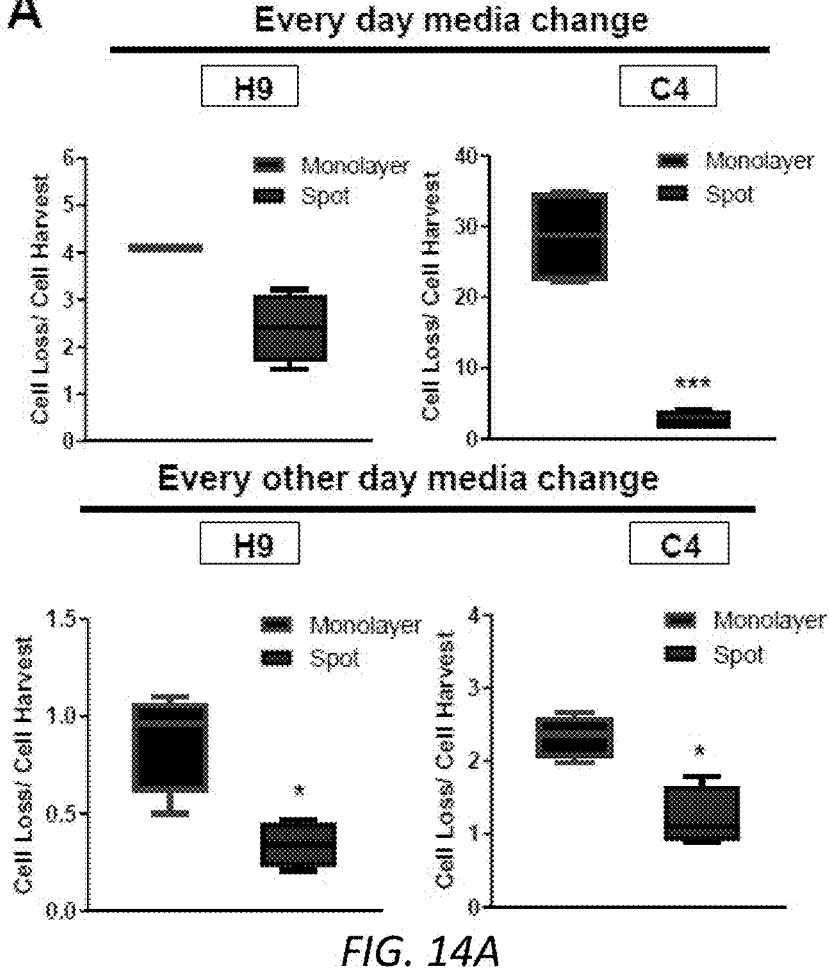
FIGS. 14A-C. Comparison of spotting-based and monolayer-based in vitro differentiation. Using in vitro differentiation in monolayer- and spotting-based methods, comparison of (A) the ratio of cell loss and cell harvest at differentiation D15 on both C4 and H9 (n=4). The cell numbers of loss and harvest were obtained by FACS; (B) the pH value of supernatant harvested at different time points on both C4 and H9 (n=4); (C) morphological features at D4, D8, D12 and D15 on C4. The scale bars present 20 μm. Data are presented as mean±SEM, * $p<0.05$; *** $p<0.005$. Two-tailed paired t test (A), one way ANOVA with Tukey's multiple comparisons test (B) were used to determine statistical significance.
Figure 14B:
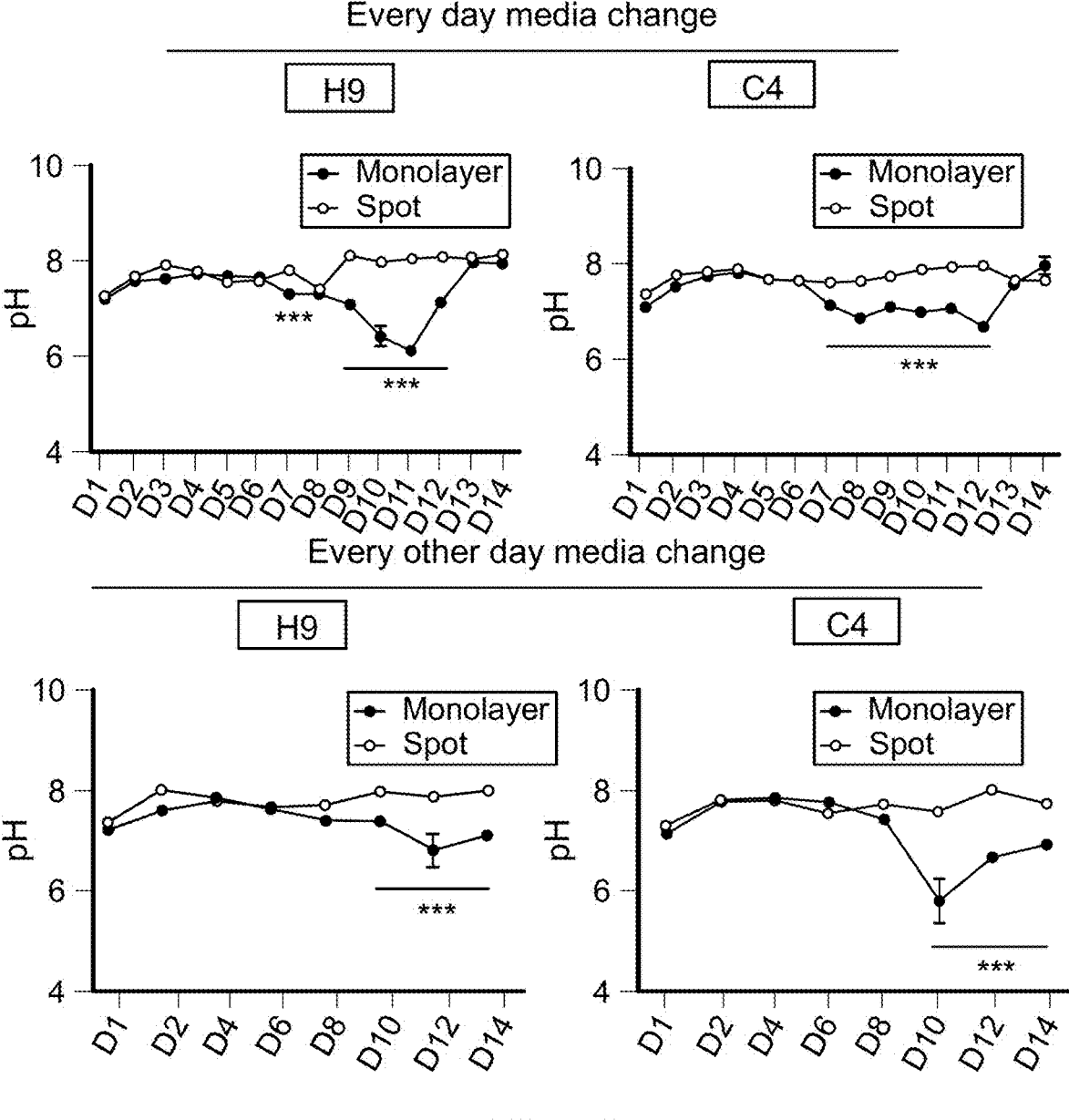

To find the optimal cell density, we plated three different numbers of cells (40,000, 10,000, and 2,500) using H9 or C4 cells on each spot. Remarkably, this spotting method significantly reduced cell loss and improved yield at D15, compared to monolayer methods. In particular, we found that 10,000 cells per spot (total of 60,000 cells per 60 mm dish) resulted in almost 100% successful in vitro differentiation (FIG. 13A) and in a final harvest of 6-8 million mDA cells at D15 while total cell loss was under 3 million cells (FIG. 4B, Table 3). We confirmed a similar pattern for H7 hESC and N3 hiPSC lines (FIG. 4B), suggesting that this spotting method is broadly applicable to mDA differentiation of hPSC lines. More importantly, cells harvested at D15 included fewer dead cells (FIG. 4C) and significantly fewer cleaved caspase-3-positive cells as well as decreased nuclear condensation (FIG. 4D), well-known markers for programmed cell death (38, 39). We speculated that the difference in outcomes between the spotting and monolayer methods was due to insufficient oxygen and nutrition for cells in monolayer conditions, and thus attempted to correct this with more frequent media changes. However, daily media changes neither reduced cell loss nor enhanced cell harvest. On the contrary, this actually increased cell loss (FIG. 14A). In the spotting method, daily media changes did not affect cell loss or harvest, again confirming that differentiation is more stable with spotting than with the monolayer method. Notably, we observed that the culture media became significantly acidic only in the monolayer culture regardless of frequency of media change (FIG. 14B), at least in part explaining the poor cell health. Taken together, this novel spotting-based method reduced cell loss, increased final cell yield, and produced healthier mDA cells, compared to conventional monolayer methods.

Table 3 shows the results of a comparison between monolayer-based methods with 3 different cell densities (34,000/cm2, 11,000/cm2, 3,500/cm2) and spotting-based methods with 3 different cell densities (40,000/spot, 10,000/spot, 2,500/spot) for level of cell loss during in vitro differentiation of H9 and C4. Detached cells present in the supernatants following medium changes were counted using FACS.

TABLE 3

| | | Density | D0 | D1 | D2 | D4 | D6 | D8 | D10 | D12 | D14 | Cell loss | Cell yield |
|---|---|---|---|---|---|---|---|---|---|---|---|---|---|
| H9 | monolayer | 34K/cm² | 730K | 70K ± 11 | 39K ± 5 | 154K ± 35 | 816K ± 170 | 511K ± 57 | 313K ± 71 | 1,071K ± 348 | 2,373K ± 376 | 5,358K ± 340 | 1,726K ± 104 |
| | | 11K/cm² | 240K | 17K ± 3 | 28K ± 8 | 57K ± 14 | 351K ± 46 | 1,282K ± 574 | 720K ± 104 | 793K ± 170 | 1,923K ± 394 | 5,172K ± 468 | 3,582K ± 186 |
| | | 3.5K/cm² | 60K | 11K ± 1 | 14K ± 3 | 51K ± 43 | 873K ± 209 | 337K ± 119 | 102K ± 6 | 115K ± 32 | 1,433K ± 415 | 2,937K ± 325 | 358K ± 20 |
| | spotting | 40K/spot | 240K | 52K ± 31 | 6K ± 1 | 186K ± 48 | 317K ± 45 | 135K ± 16 | 231K ± 22 | 2,098K ± 520 | 2,498K ± 289 | 5,522K ± 452 | 6,124K ± 194 |
| | | 10K/spot | 60K | 16K ± 4 | 11K ± 5 | 109K ± 43 | 345K ± 65 | 151K ± 15 | 172K ± 20 | 131K ± 7 | 936K ± 63 | 1,871K ± 125 | 6,434K ± 124 |
| | | 2.5K/spot | 15K | 6K ± 0 | 2K ± 0 | 10K ± 2 | 122K ± 29 | 11K ± 14 | 5K ± 2 | 7K ± 2 | 5K ± 2 | 167K ± 16 | 1,600K ± 182 |
| C4 | monolayer | 34K/cm² | 730K | 73K ± 8 | 190K ± 56 | 164K ± 25 | 994K ± 177 | 1,544K ± 166 | 351K ± 57 | 1,298K ± 283 | 1,373K ± 215 | 5,988K ± 584 | 3,200K ± 98 |
| | | 11K/cm² | 240K | 26K ± 1 | 27K ± 3 | 50K ± 13 | 1,136K ± 173 | 692K ± 55 | 124K ± 23 | 926K ± 214 | 256K ± 74 | 3,236K ± 288 | 4,251K ± 99 |
| | | 3.5K/cm² | 60K | 12K ± 1 | 9K ± 1 | 14K ± 1 | 562K ± 109 | 833K ± 59 | 677K ± 272 | 1,173K ± 118 | 566K ± 124 | 3,845K ± 432 | 1,165K ± 83 |
| | spotting | 40K/spot | 240K | 5K ± 0 | 17K ± 2 | 71K ± 14 | 223K ± 33 | 210K ± 17 | 85K ± 14 | 1,259K ± 314 | 1,012K ± 216 | 2,882K ± 345 | 6,191K ± 268 |
| | | 10K/spot | 60K | 2K ± 1 | 7K ± 1 | 27K ± 3 | 159K ± 13 | 167K ± 21 | 53K ± 11 | 1,498K ± 289 | 979K ± 132 | 2,891K ± 257 | 7,622K ± 141 |
| | | 2.5K/spot | 15K | 2K ± 1 | 3K ± 0 | 4K ± 0 | 45K ± 11 | 83K ± 13 | 30K ± 2 | 60K ± 3 | 153K ± 20 | 381K ± 42 | 3,493K ± 213 |

Cell loss and yield by monolayer and spotting-based methods

Example 5. Quercetin Treatment Eliminates Undifferentiated Cells During In Vitro Differentiation The most critical issue for hPSC-based cell therapy is to establish safety by removing residual undifferentiated cells with neoplastic potential. Based on the previous finding that BIRC5 (encoding survivin) is highly expressed in hPSCs compared to somatic cells (40), we hypothesized that chemical inhibition of survivin would selectively eliminate remaining undifferentiated hiPSCs. However, since survivin is known to be important for neuronal precursors (41, 42), it is important to test whether this strategy interferes with mDAP generation. Among survivin inhibitors (40), we chose the flavonoid quercetin (3,3',4',5,7-pentahydroxyflavone) because this natural compound is present at high concentration in commonly consumed vegetables and fruits (43). We first treated 100,000 undifferentiated C4 cells with 5, 10, 20, 40, and 100 μM quercetin for 2, 6, 16, and 24 hours. After washing with fresh media, cells were further cultured for a total of 48 hours. As shown in FIG. 5A, viable cells were undetectable when treated with >20 μM quercetin for >16 hours, indicating that undifferentiated hiPSCs can be eliminated with an efficiency of >99.99%. To test whether quercetin affects survival of mDAPs, we treated D9 C4 cells (mostly neuronal precursors) with different concentrations of quercetin for 16 hours and examined outcome on D11. Neither cell viability nor number was affected at D11 (FIGS. 5, B and C), suggesting that quercetin does not affect hiPSC-derived mDAPs.

Figure 5D:
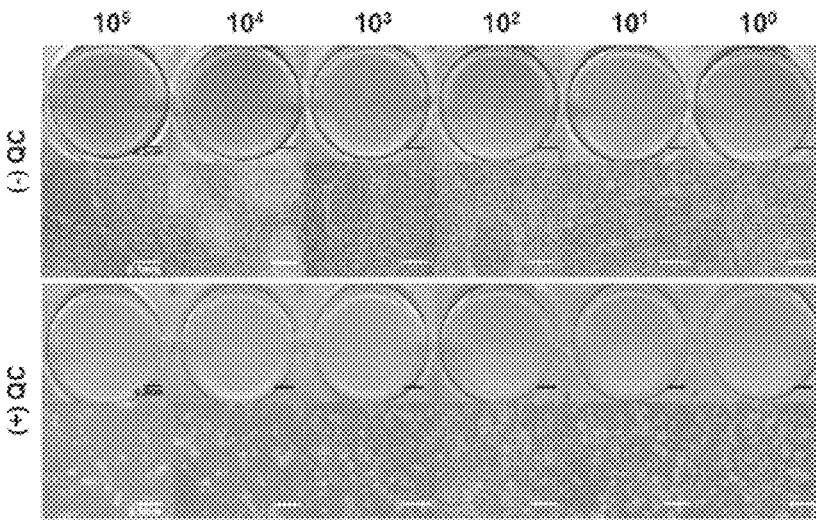
Figure 5E:
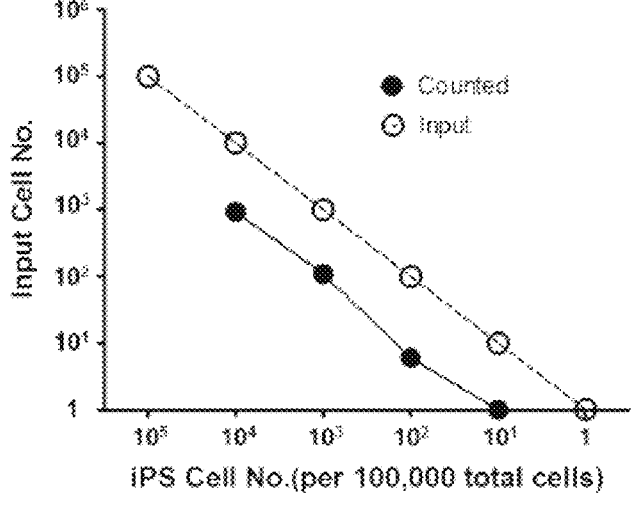
Figure 5F:
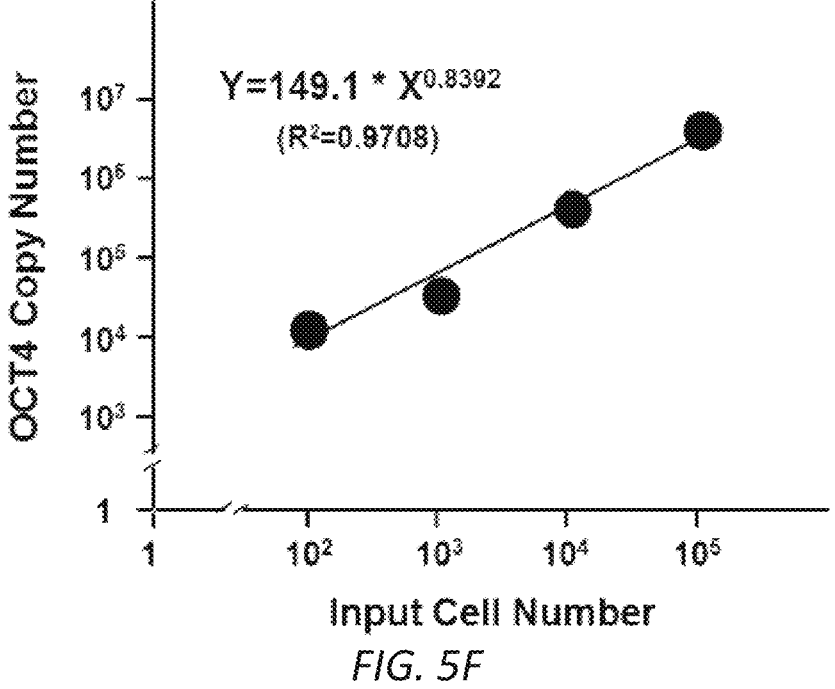
Figure 5G:
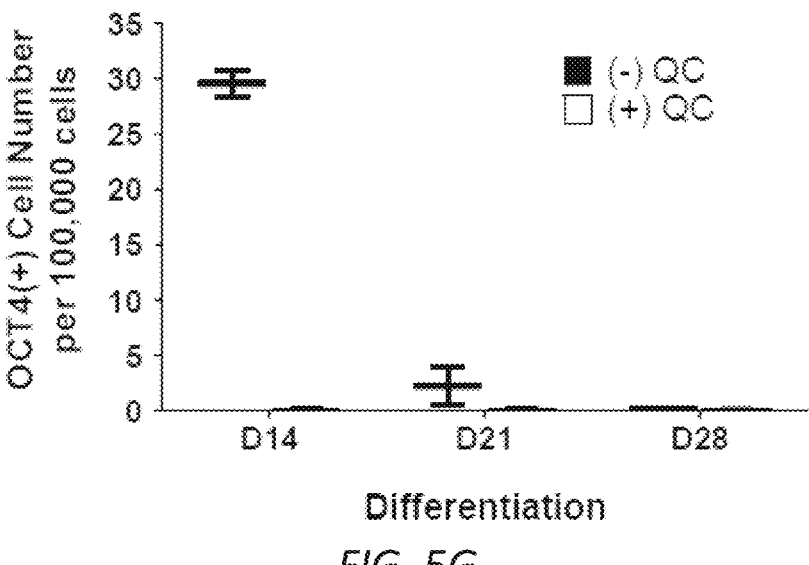
Figure 15A:
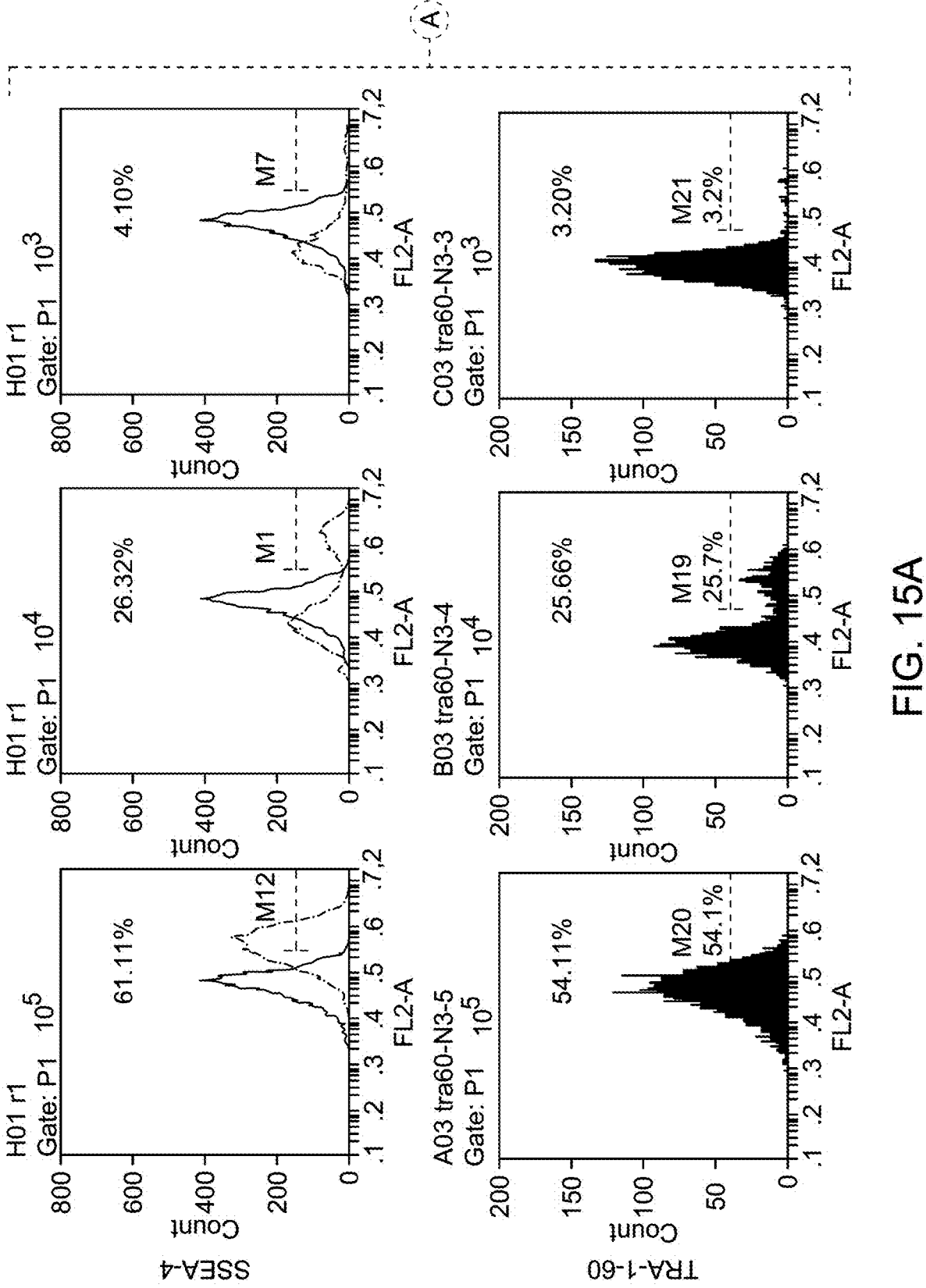
FIGS. 15A-C. Removal of undifferentiated hiPSC by quercetin treatment. (A) Anti-SSEA-4 and TRA-1-60 FACS analyses of undifferentiated hiPSCs serially diluted with fibroblasts by factors of 10 among 100K total cells. (B) Plot of input hiPSC number vs resulting percentage of SSEA-4+ and TRA-1-60+ cells. (C) Immunostaining for NANOG in D14 cells with or without quercetin treatment. Scale bar: 100 μm.
Figure 15A:
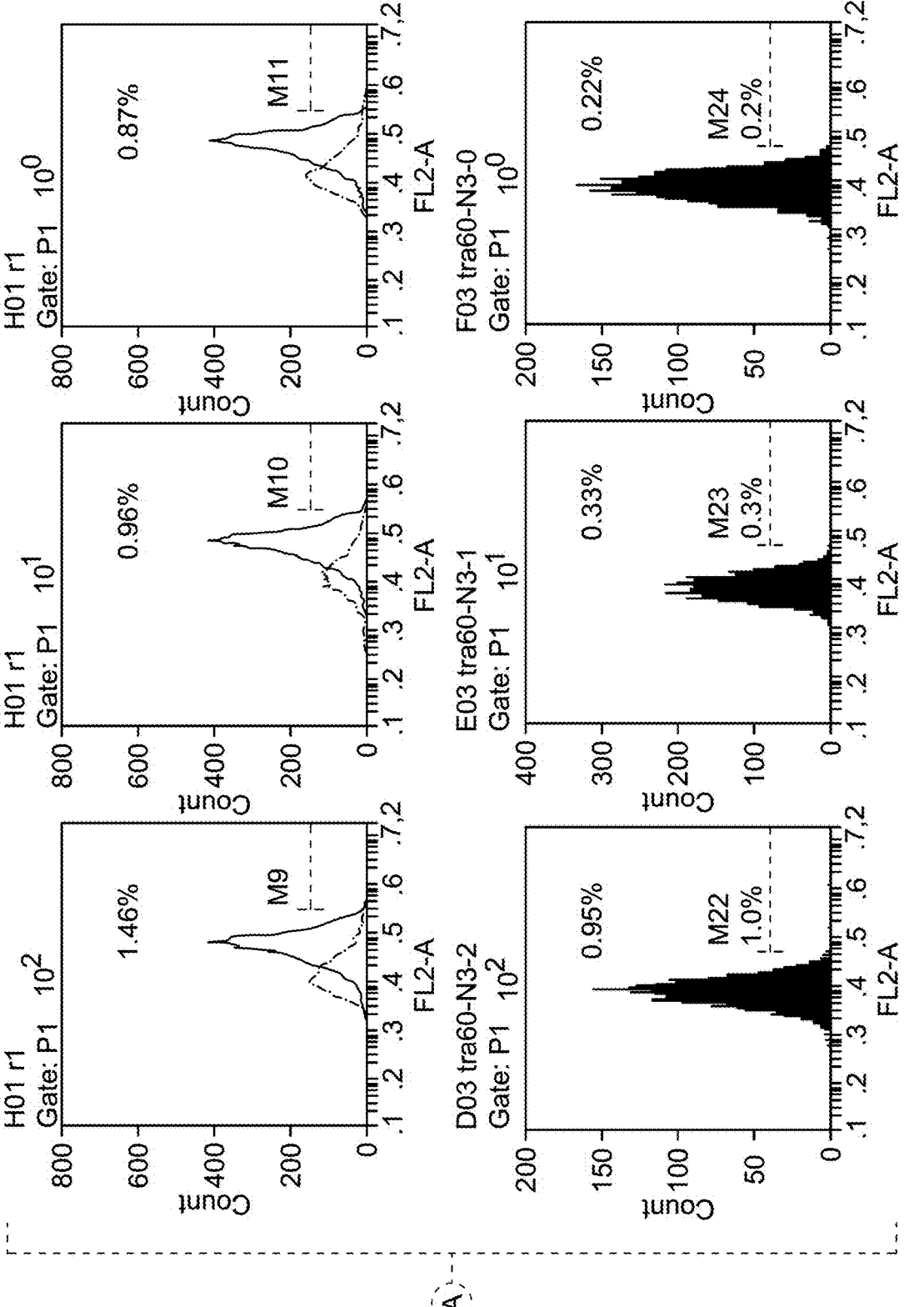
Figure 15B:
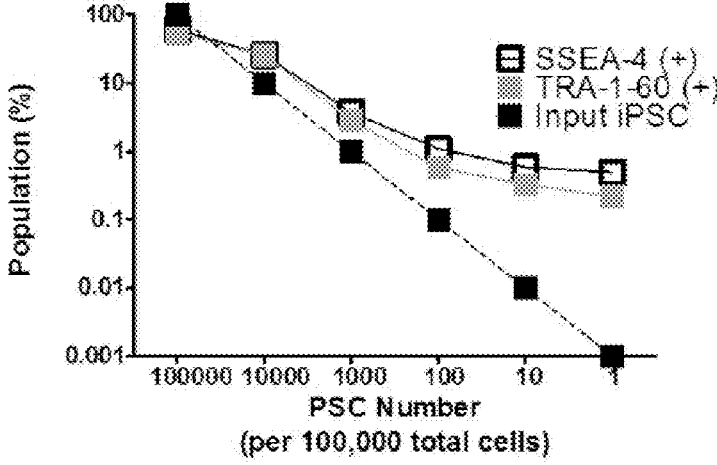
Figure 15C:
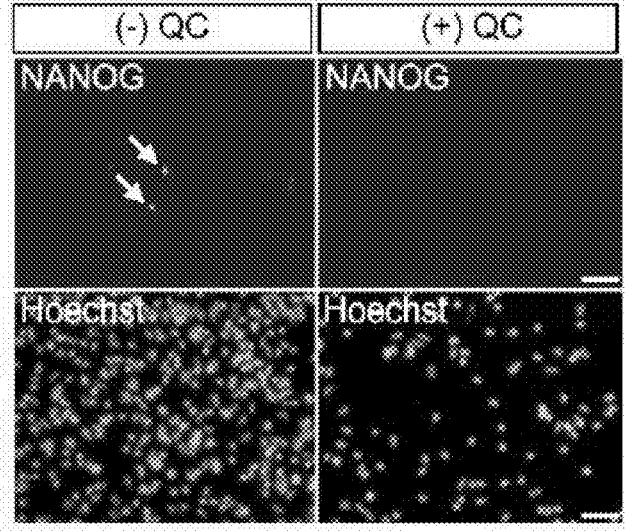

To establish a sensitive and specific assay, we created test mixtures of undifferentiated C4 cells among hDFs in a total of 100,000 cells and performed three different assays. First, we used FACS with monoclonal antibodies against SSEA-4 and TRA-1-60 (FIG. 15A) and found a significant discrepancy between the input and the detected cell number, in particular below 100 cells (FIG. 15B), indicating that this method was insensitive to small numbers of undifferentiated cells. Second, we cultured samples of diluted cells for 6 days and counted AP' colonies as a surrogate marker for undifferentiated cells (FIG. 5D). Although there was a linear relationship, the number of AP' colonies was about one tenth that expected given the input cell numbers (FIG. 5E). This discrepancy may be due to limited survival and growth of individual hiPSCs and/or to their tendency to aggregate during colony formation. Despite this limitation, since there were no AP' colonies detected after treatment with quercetin even when $10^5$ hiPSCs were plated, this result confirmed that the efficacy of quercetin treatment is >99.99%. Nonetheless, since this method cannot detect numbers fewer than 10 undifferentiated cells per 100,000, we next used a qRT-PCR method using OCT4 expression as a surrogate marker. A standard curve of OCT4 copy number was generated using qRT-PCR analysis of mRNAs prepared from $10^2$ to $10^5$ undifferentiated C4 cells (FIG. 5F), allowing us to predict the number of undifferentiated cells. Using this assay, the calculated number of undifferentiated C4 cells at D14, 21, and 28 without quercetin treatment was 30, 2, and 0.17 per 100,000 cells, respectively (FIG. 5G). Thus, if 10 million cells at D14, D21, or D28 of differentiation were transplanted into a PD patient, grafts would contain approximately 3,000, 200, and 17 undifferentiated cells, respectively. Since quercetin treatment can eliminate undifferentiated cells with >99.99% efficiency, following quercetin treatment, the expected number of undifferentiated cells would be at most 17×0.01%=0.0017 cells per 10 million D28 cells. In agreement with this, the calculated number of undifferentiated cells using the qRT-PCR curve at D14, D21, and D28 after quercetin treatment (40 μM at D9 for 16 hours) was far less than 1 cell per 100,000 cells (FIG. 5G). Consistent with these results, a few NANOG' cells were observed at D14 without quercetin treatment, but none were detected with treatment (FIG. 15C). Taken together, our results indicate that quercetin treatment reduces the number of undifferentiated cells to levels undetectable using sensitive techniques, thus greatly reducing the risk of tumor formation even when many millions of differentiated cells are transplantated.

Example 6. Functional Characterization of mDAP and mDAN

Figure 6A:
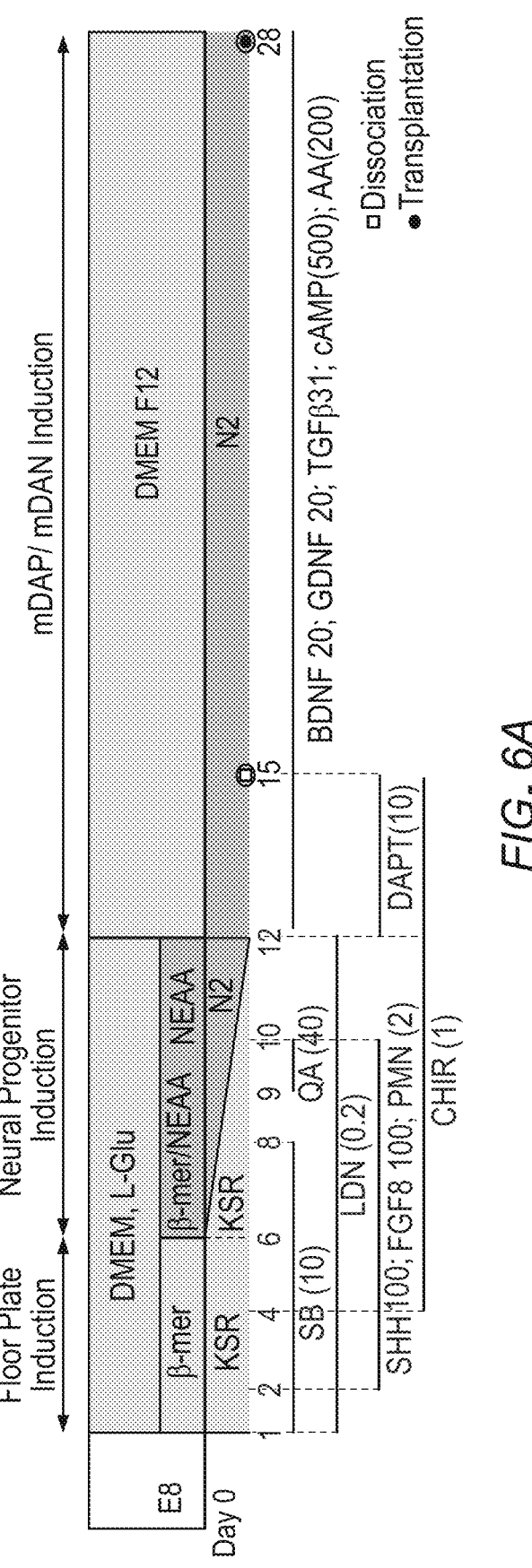
Figure 6B:
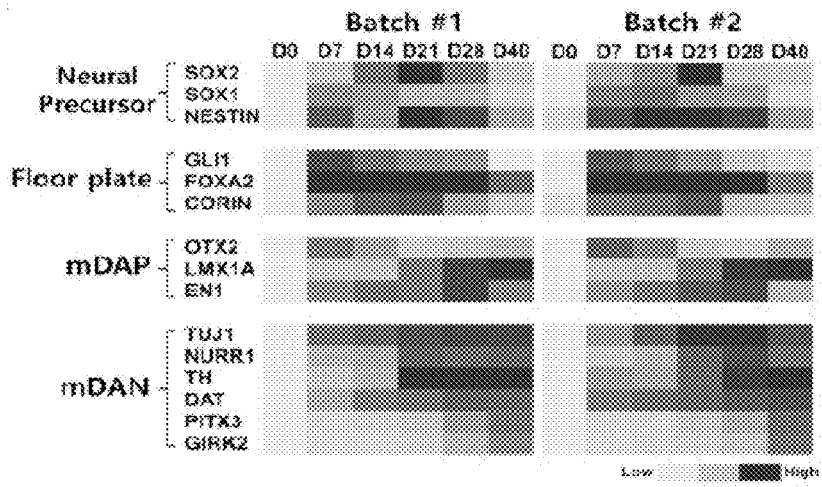
Figure 6C:
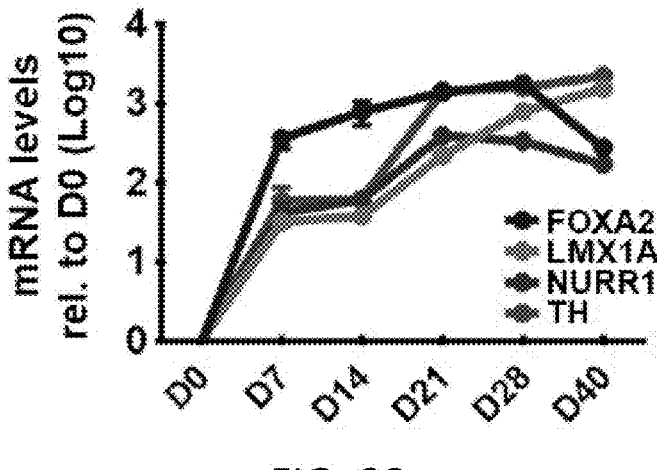
Figure 6D:
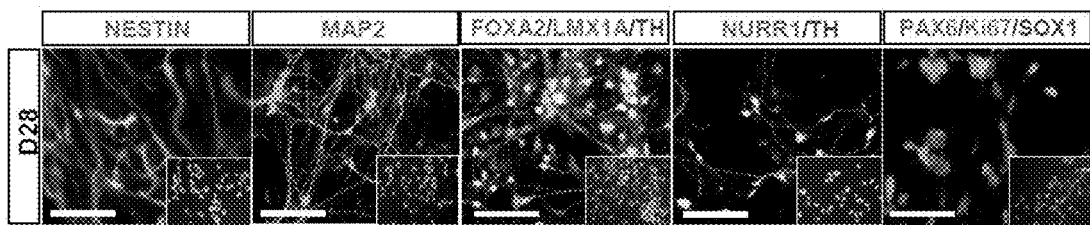
Figure 14C:
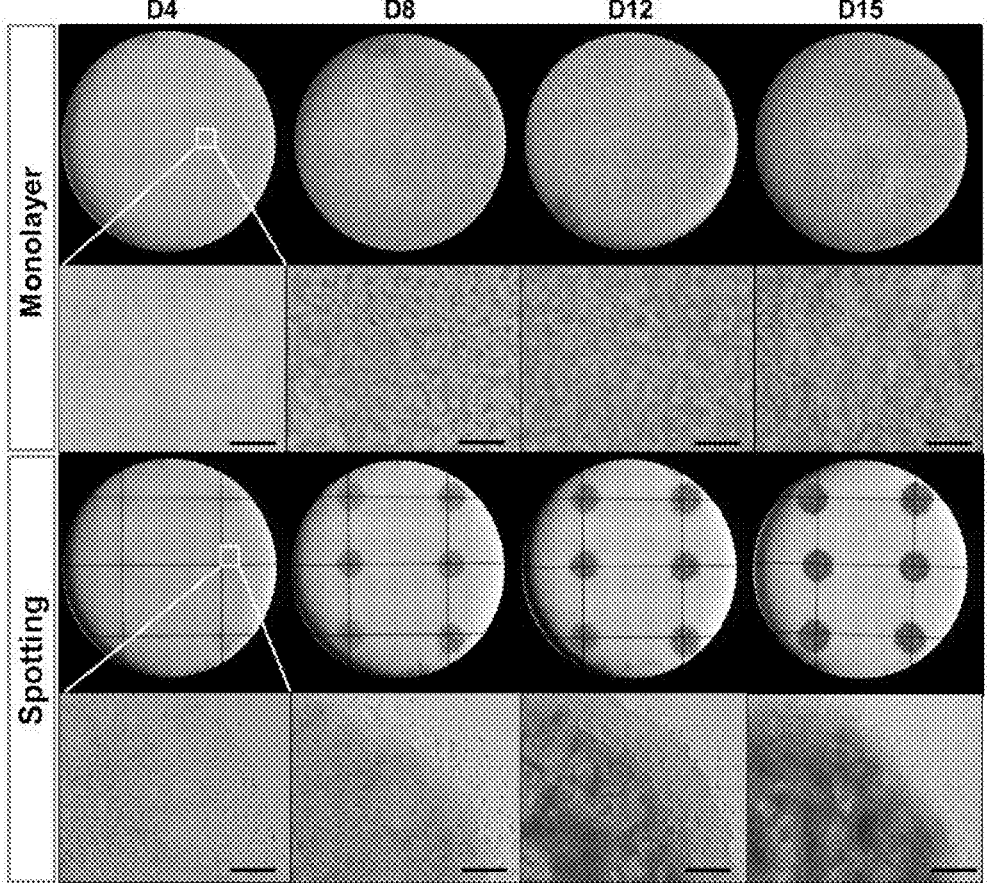
Figure 16A:
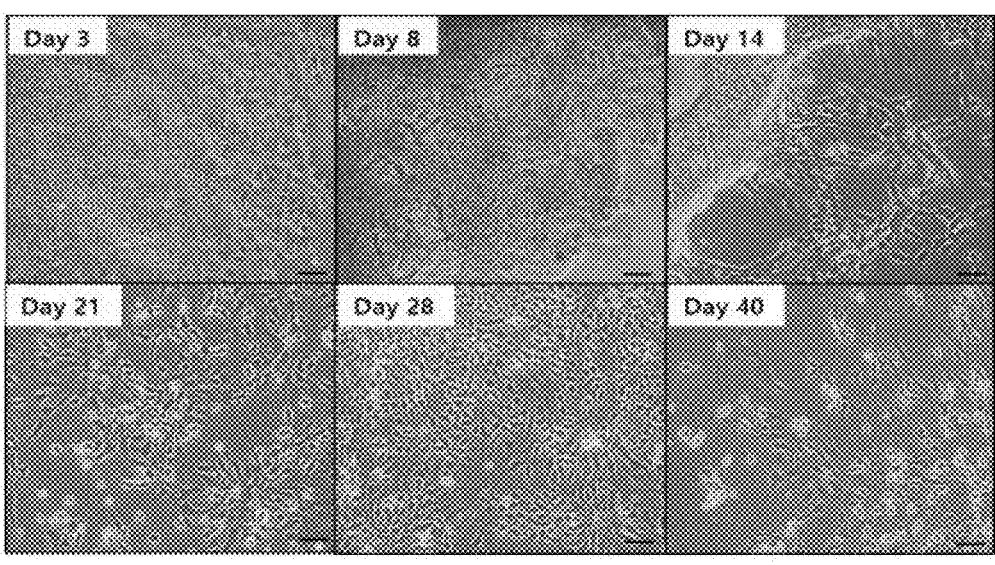
FIGS. 16A-B. Characterization of in vitro differentiated C4 hiPSC. (A) Bright-field images of differentiated cells from D3 to D40. (B) Immunofluorescence staining and percentage of neural precursor (NESTIN), mDAP (FOXA2/LMX1A), mDAN (MAP2 and TH), GABAergic neurons (GABA) and serotonergic neurons (5-HT) positive cells and during mDA differentiation D14, D21, D28 and D50. Scale bar: 100 μm. Data are presented as mean±SEM, n=6.
Figure 16B:
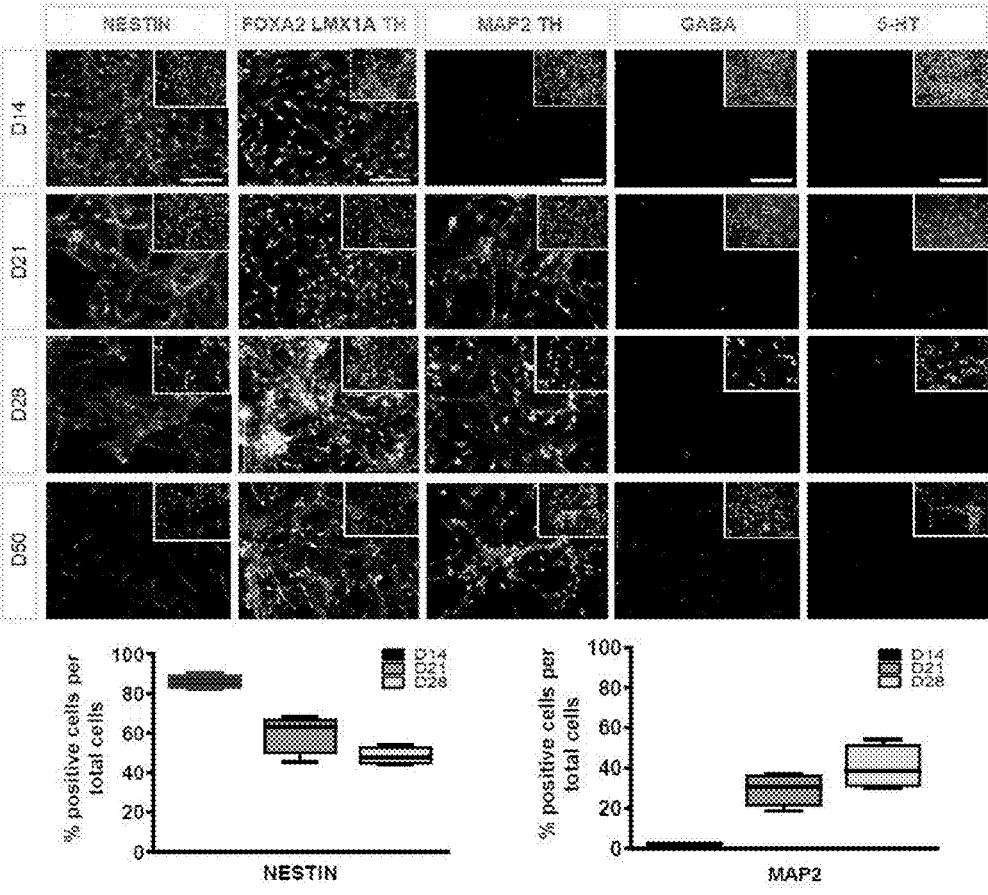

Based on the spotting method and quercetin treatment described above, we established a modified in vitro protocol for differentiation of hiPSCs into mDAP/mDAN (FIG. 6A). C4 cells differentiated using these methods showed progressively more compact morphology, minimal detachment (FIG. 14C), and bipolar outgrowth of neurites from the edge (FIG. 16A). At D15, cells were dissociated into single cell suspensions, replated, and further differentiated. As shown in FIGS. 6, B and C, expression of neural precursor markers (e.g., SOX2, SOX1, and NESTIN) and floor/basal plate markers (e.g., GLI1, FOXA2, and CORIN) started at D7 and continued at high levels through D28, finally decreasing at D40. The expression of mDAP markers (e.g., OTX2, LMX1A, and EN1) was elevated at D21 and 28, whereas mDAN markers (e.g., TH, DAT, and PITX3) increased later. These data were corroborated by stage-specific immunocytochemistry analyses showing a gradual decrease of NESTIN and increases of mDAN markers (FIG. 16B). Since D28 cells exhibited more mature phenotypes than D14 cells (FIG. 16B), we expected that D28 cells might be more suitable than earlier cells and thus analyzed D28 cells using immunocytochemistry for typical mDAP and mDAN markers (FIG. 6, D-H). Approximately 40% and 15% of the total cells expressed MAP2 and TH, respectively, and 38% of the cells expressed NURR1 (FIGS. 6, D and E). More than 80% of the total cells co-expressed FOXA2 and LMX1A (FIGS. 6, D and F) and the majority of TH$^+$ cells co-expressed FOXA2, LMX1A and NURR1 (FIGS. 6, D and G), a feature characteristic of mDA phenotypes. We observed that approximately 30% and 20% of D28 cells expressed the dorsal patterning marker PAX6 and the proliferation marker KI67, respectively (FIGS. 6, D and H). Importantly, cells that co-express PAX6, SOX1, and KI67, known to form abnormal outgrowth upon transplantation (44, 45), were undetectable (FIGS. 6, D and H). GABA$^+$ or 5-HT$^+$ cells were barely detected at any stage of differentiation (FIG. 16B).

Figure 17A:
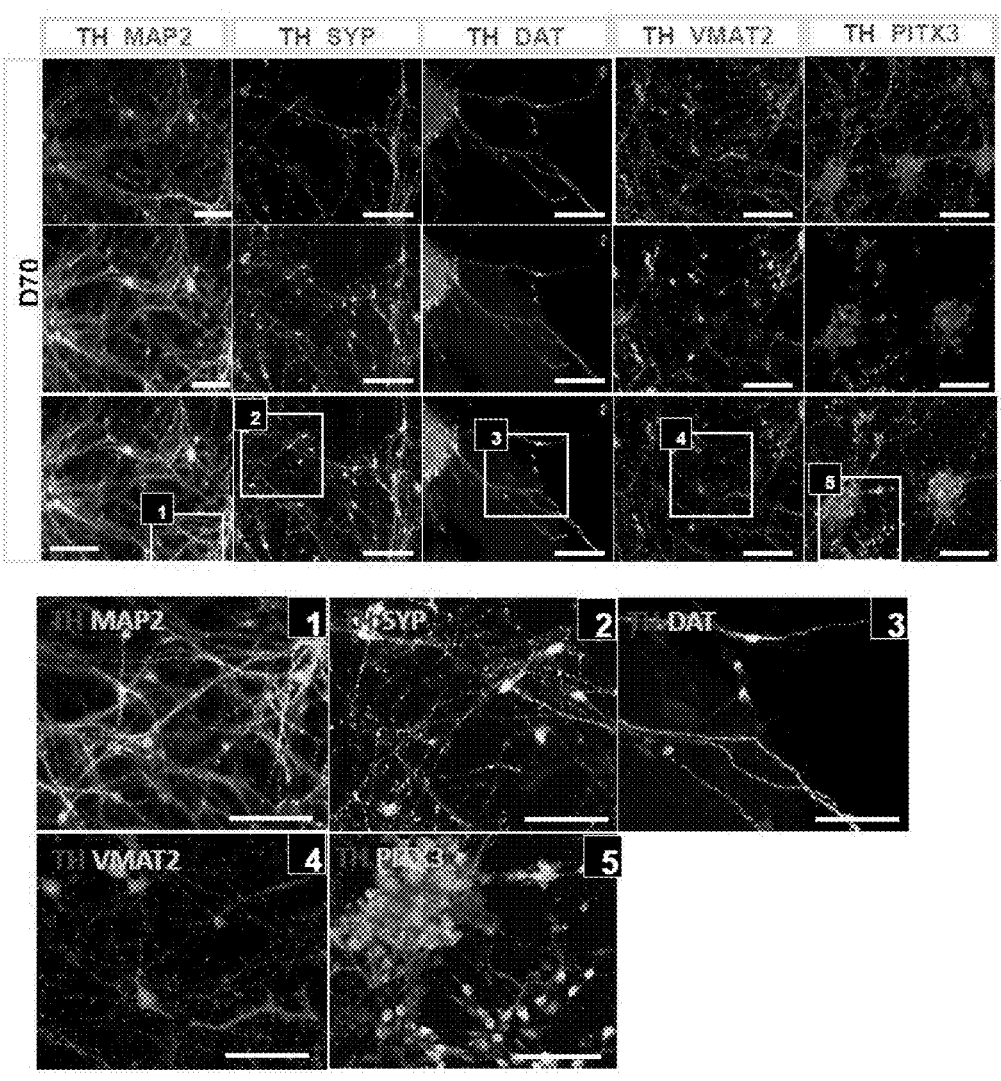
FIGS. 17A-B. Cell fate analysis of in vitro differentiated C4 hiPSC. (A) Immunofluorescence staining of D70 cells recorded electrophysiologically, co-expressing TH, MAP2, SYP (Synaptophysin), DAT (Dopamine transporter), VMAT2 (Vesicular monoamine transporter 2) and PITX3. Scale bar: 100 μm. (B) Immunofluorescence staining of ALDH1A1, GIRK2 and Calbindin with TH positive cells. Scale bar: 100 μm.
Figure 17B:
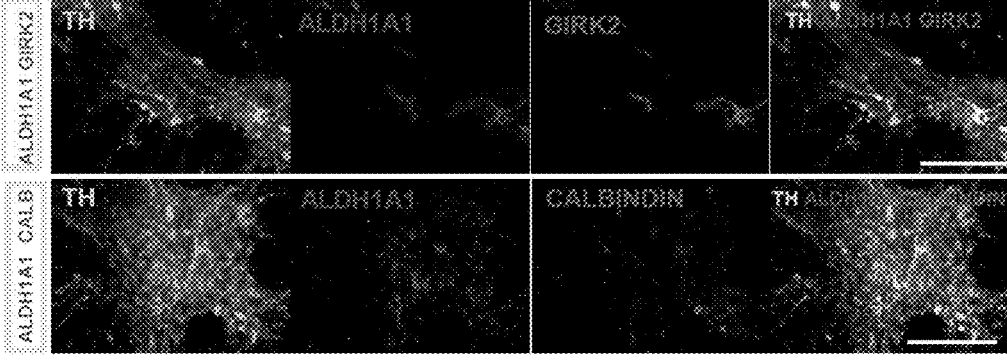
Figure 18A:
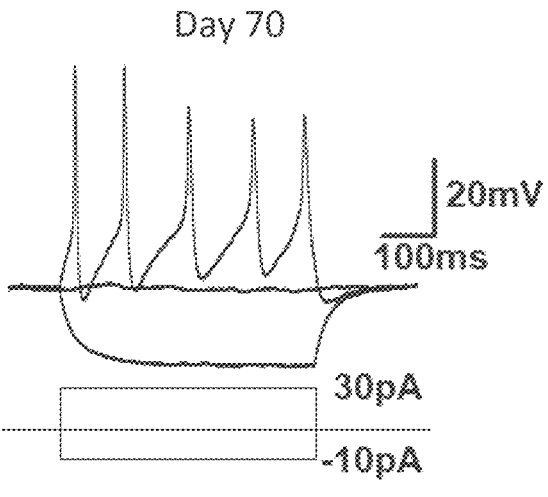
Figure 18B:
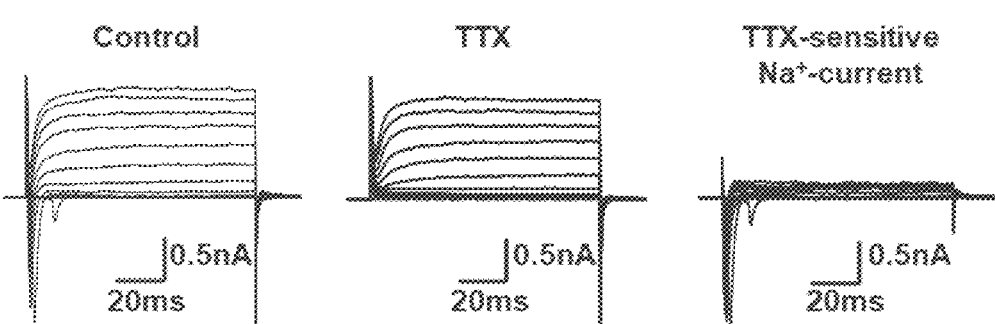
Figure 18C:
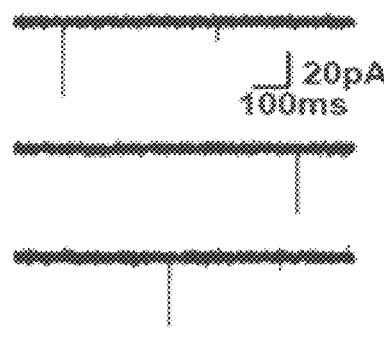
Figure 18D:
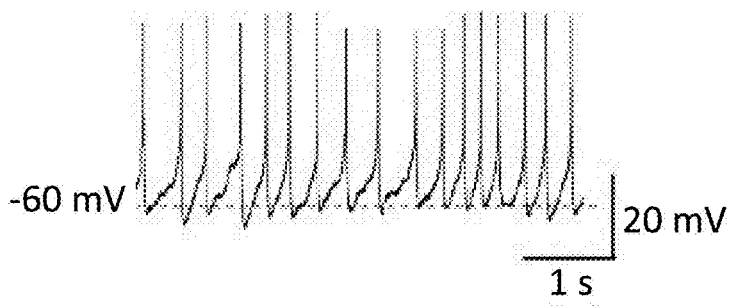
Figure 18E:
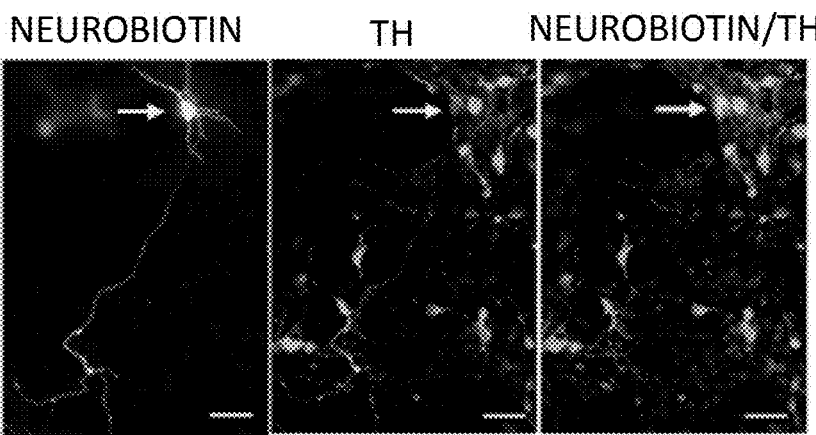
Figure 18F:
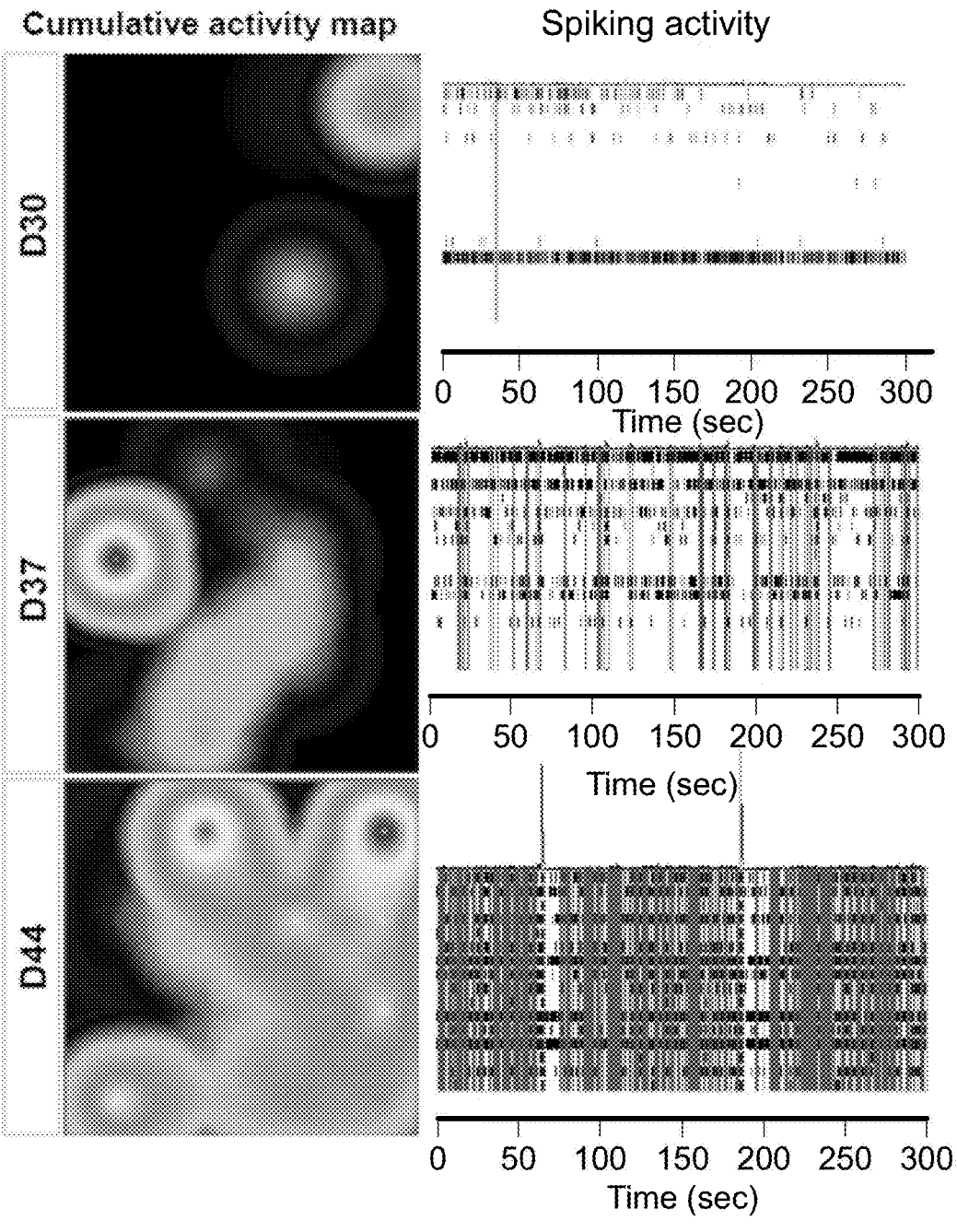

To determine whether these cells become physiologically functional neurons, we performed whole-cell patch-clamp recordings from D70 cultures which contain many TH$^+$ neurons co-expressing MAP2, dopamine transporter (DAT) and synaptophysin (SYP) (FIG. 17A). These D70 TH$^+$ neurons co-expressed additional mature mDA markers including PITX3 and VMAT2 (FIG. 17A). Also, TH$^+$ ALDH1A1$^+$ neurons co-expressed GIRK2 or sometimes CALBINDIN (FIG. 17B), characterizing A9- and A10-type mDANs, respectively. In current-clamp recoding mode, we assessed the intrinsic membrane properties of these cells (resting membrane potential, −55.93±2.43 mV; input resistance, 1.52±0.44 GΩ; n=7 neurons), and observed action potentials (APs) in response to depolarizing current injections (FIG. 18A; average amplitude of APs 54.96±4.66 mV; half-width: 6.04±0.82 ms; amplitude of afterhyperpolarization (AHP): 3.55±1.46 mV; n=7 cells). In voltage-clamp recording mode, voltage pulses from −70 mV to +40 mV evoked transient inward currents, which were completely blocked by tetrodotoxin (TTX; a voltage-gated Na$^+$ channel blocker) indicating expression of voltage-gated Na$^+$ channels, as well as sustained outward currents (FIG. 18B), representing potassium currents. Moreover, during whole-cell voltage-clamp recordings, we observed spontaneous postsynaptic currents (sPSC) indicating presence of functional synapses (at a holding potential of −70 mV, the frequency of sPSCs was 0.11±0.03 Hz; peak amplitude, 14.71±3.05 pA; rise time, 0.73±0.14 ms; decay time, 1.72±0.19 ms; n=5 cells) (FIG. 18C). Consistent with pacemaker activity at the resting membrane potential (46), spontaneous firing was observed in the absence of an injected current. The recorded cells fired spontaneously with an average frequency of 4.4±0.8 Hz (n=4), as typically observed in A9 mDANs (FIG. 18D). Individual recorded neurons (loaded with neuro-biotin through the recording patch pipette, red) co-localized with TH positivity, confirming the identity of these cells as dopaminergic neurons (FIG. 18E). In addition to single-cell patch clamp recordings, we measured population-level electrical activity using multielectrode array (MEAs). Differentiated cells developed robust synchronous bursting patterns indicative of maturing neuronal networks (FIG. 18F). Cumulative activity maps showed an increase in the spike density and the area of spikes within mDA between D30 and D44 (FIG. 18F). In order to isolate spontaneous activity from mDANs, the cultures were treated with a combination of glutamate receptor antagonists, NBQX+AP5, and a GABAA receptor antagonist, picrotoxin. When this cocktail was administered, overall spiking and the number of active electrodes were only modestly diminished (FIGS. 18G and H), suggesting that there are abundant mDANs in these cultures. Finally, HPLC analysis of culture medium further showed that D47 cells release dopamine (3.1±0.1 ng/ml) and DOPAC (0.2±0.0 ng/ml) (FIG. 61).

Example 7. In Vivo Safety Tests Following Transplantation

Figure 7A:
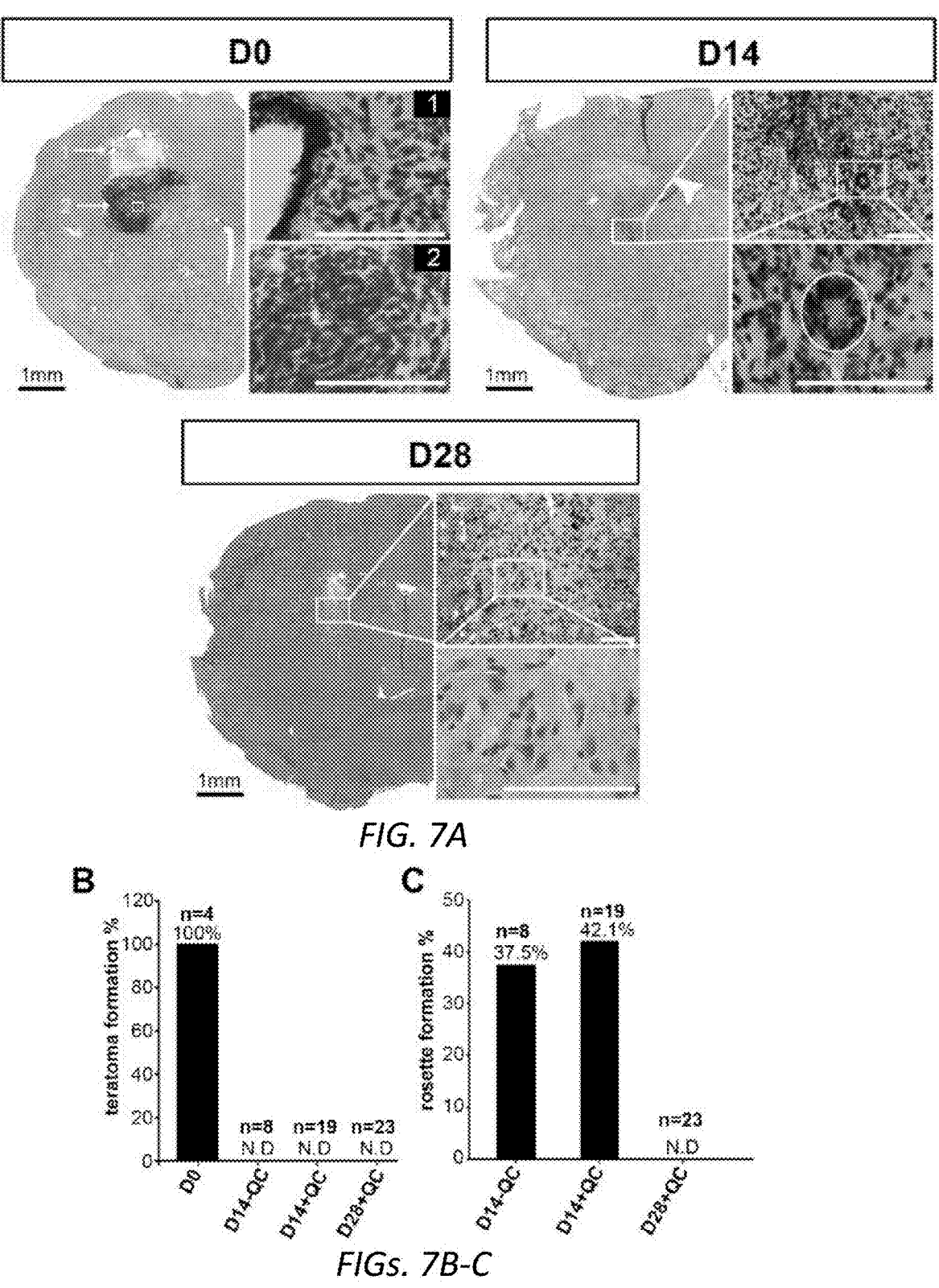
Figure 7D:
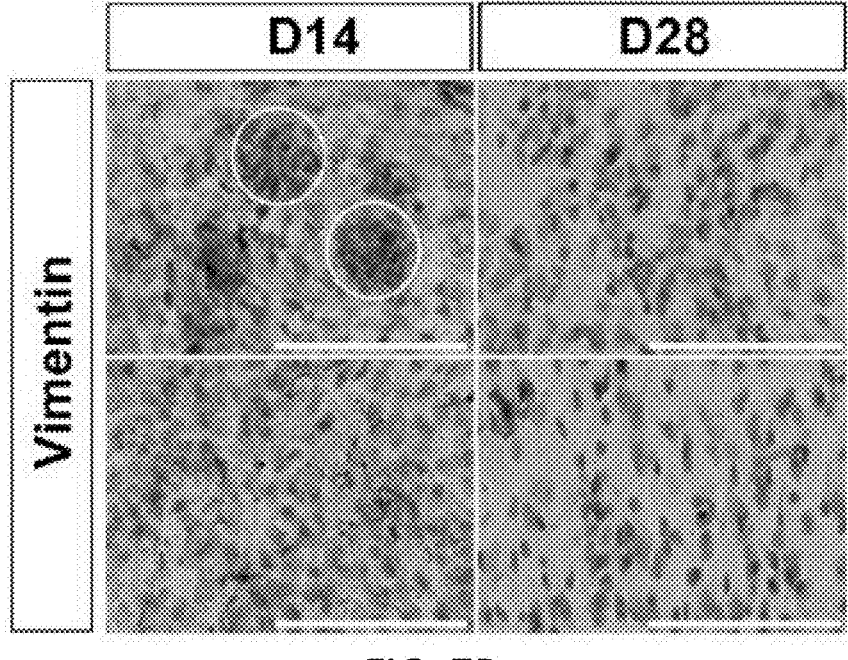
Figure 7E:
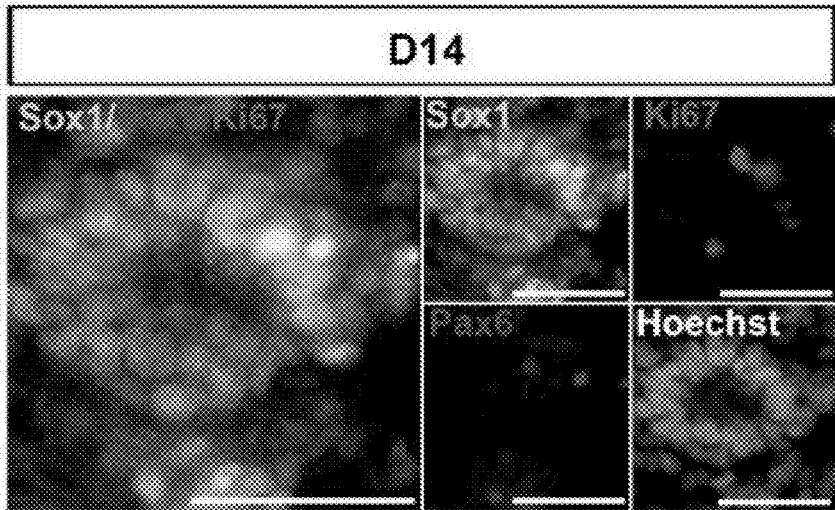
Figure 7F:
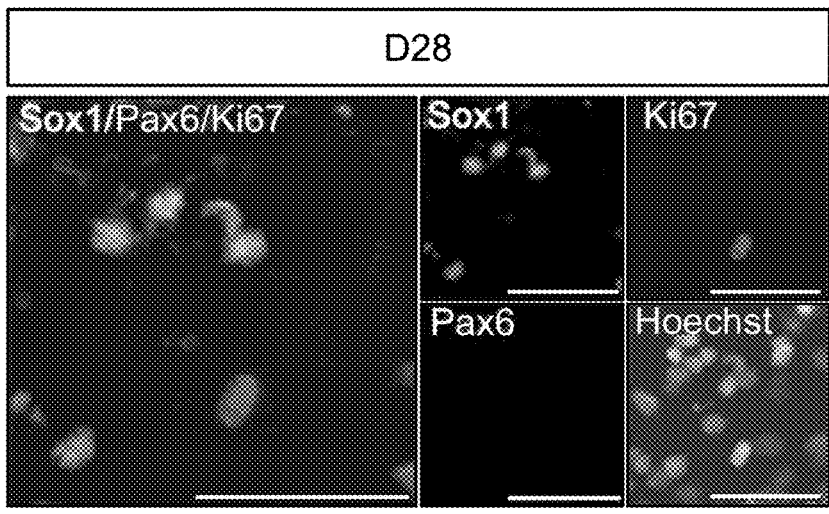
Figure 7G:
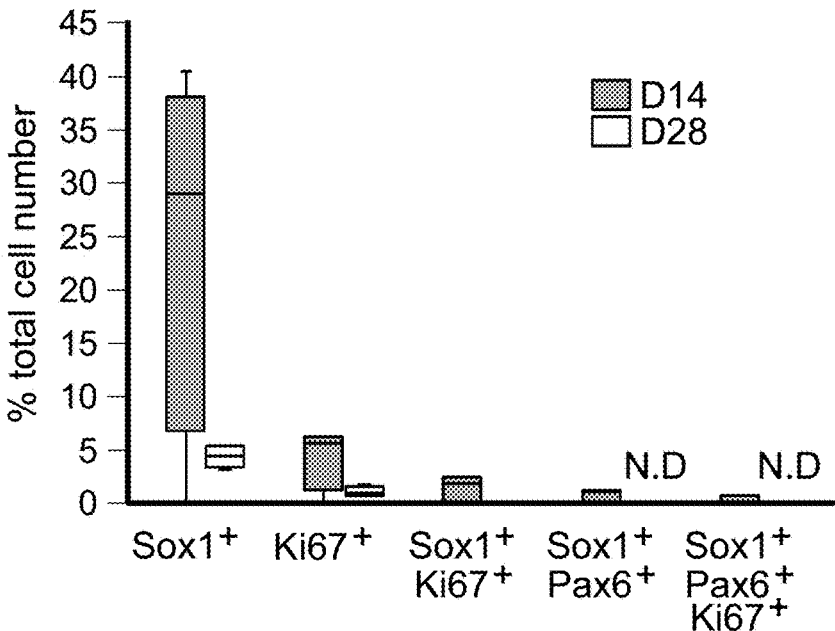
Figure 7H:
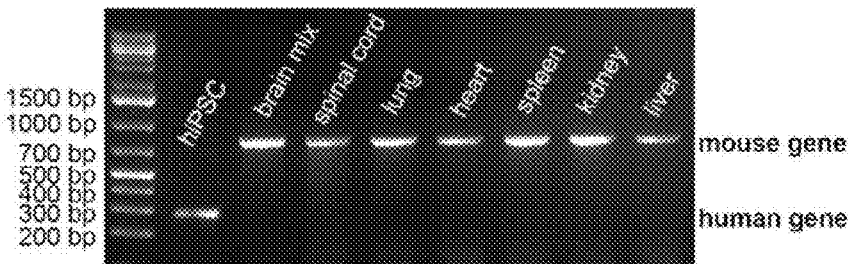

Our in vitro characterization showed that the majority of cells from D14 to D28 represent mDAPs, suitable as transplantable cell sources. To test their safety, we transplanted D14 or D28 C4 cells (without or with quercetin treatment; 100,000 cells per animal) into the striatum of immunodeficient NOD SCID mice. As expected, transplantation of undifferentiated C4 cells (D0) induced formation of teratomas containing the characteristic three germ layers in all 4 mice tested (FIG. 7A, left column), a defining characteristic of PSCs. By comparison, no teratoma formation was observed when D14 without (n=8) or with quercetin (n=19, FIG. 7A, middle column) and D28 with quercetin (n=23; FIG. 7A, right column) treatment were transplanted (FIG. 7B). Interestingly, we observed rosette-like structures in about 40% of the host brains grafted with D14 cells (3 of 8 in D14 without quercetin group; 8 of 19 in D14 with quercetin group; white circle in the middle lane of FIG. 7A). In contrast, there were no rosette-like structure when D28 cells were transplanted (0 of 23 mice; FIGS. 7, A and C). Immunohistochemistry showed that compared to D28 grafts, D14 grafts contained more Vimentin-positive immature cells (FIG. 7D). In addition, SOX1 positive, KI67 positive, SOX1/KI67 double positive, SOX1/PAX6 double positive, and SOX1/PAX6/KI67 triple positive cells were also fewer in grafts from D28 cells than in those from D14 cells (33% vs 4.5%; 5.9% vs 1.2%; 2.1% vs 0.15%; 1.2% vs N.D; 0.75% vs N.D, FIG. 7, E-G), indicating that D28 grafts contain fewer cells with proliferative potential than D14 grafts. These results suggest that although fully undifferentiated cells had been removed and teratomas were not formed, D14 grafts still contain immature progenitor cells capable of forming rosette-like structures. Additionally, since SOX1/PAX6/KI67 triple positive cells were undetectable in D28 grafts, we conclude that D28 cells represent a safer cell source for transplantation than D14 cells. We further tested the safety of D28 cells by assessing their bio-distribution. At 6 months following transplantation of D28 cells into the striatum, we harvested central nervous system regions (mixtures of olfactory bulb and cerebellum, and spinal cord) and five peripheral organs (lung, heart, liver, kidney, and spleen) to search for migration of human-origin cells from the striatal grafts. Genomic qPCR detected no human DNA sequences in any of these regions, while hiPSC positive controls showed prominent expression (FIG. 7H), demonstrating no detectable redistribution of grafted cells within the brain or to peripheral organs.

Example 8. In Vivo Efficacy Tests and Graft Analyses in Animal Models of PD

Figure 19B:
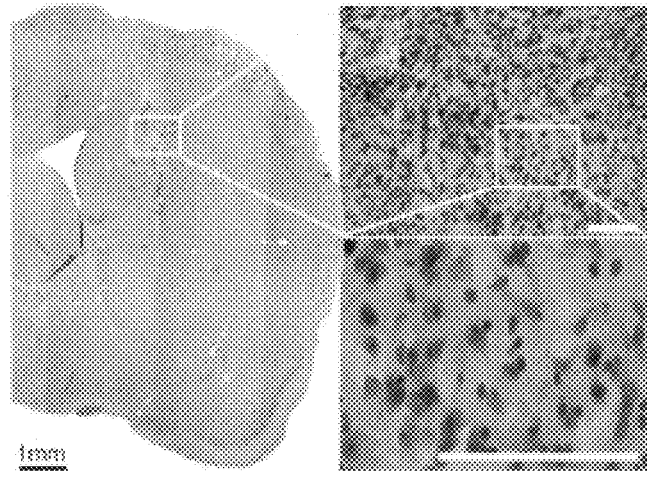
Figure 19C:
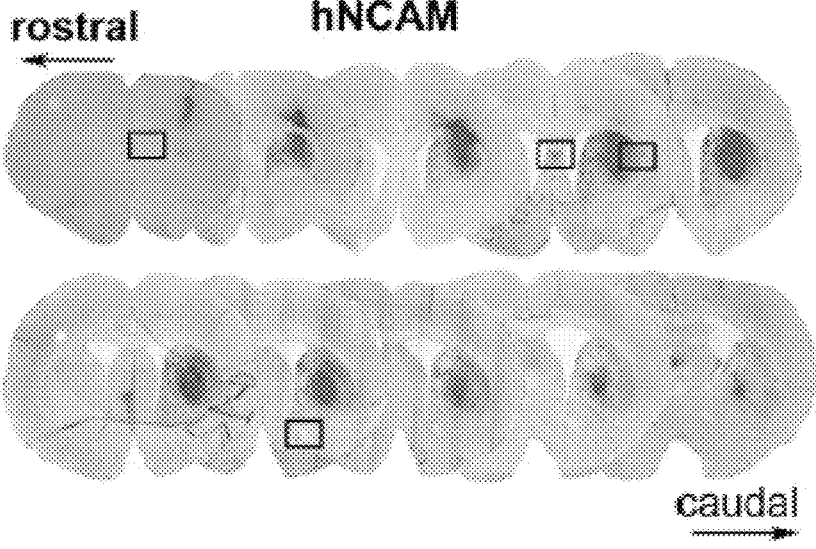

The 6-OHDA lesioned rat model was historically the first PD animal model developed (47) and remains a popular models (48, 49). It is especially useful for quantitative assessment of motor effects of cell transplantation. Its use in athymic rats is emerging as the preferred model because immunosuppression is unnecessary. Two different sources of athymic rats (Taconic Biosciences (Hudson, N.Y.) and Charles River (Wilmington Mass.)) were used. We first transplanted 100,000 and 300,000 C4 D28 cells to the striatum of unilaterally 6-OHDA-lesioned athymic Taconic rats and monitored their amphetamine-induced rotation behavior monthly post-transplantation. At 12 weeks, both the 100,000- and the 300,000-cell groups showed significant reduction of ipsilateral rotation behavior (FIG. 19A). At 16 weeks, rotation behavior was completely rescued in all implanted rats, and some even showed contralateral rotation. In contrast, rats receiving vehicle showed no recovery. Hematoxylin and eosin (HE) staining showed that grafts contained neither teratoma nor rosettes (FIG. 19B). Immunohistochemistry for human neural cell adhesion molecule (hNCAM) showed dense hNCAM$^+$ innervation in the striatum (STR) (FIG. 19C), prefrontal cortex (PFC; FIG. 19D), septal nuclei (FIG. 19E), nucleus accumbens (NAc;

FIG. 19F), and corpus callosum (CC; FIG. 19G). Immunohistochemistry revealed abundant TH$^+$ neurons in the graft (FIG. 19H). Stereological quantification showed that the average number of surviving TH$^+$ neurons was 5,621±1029 per 100,000 grafted cells (n=4), containing a mixture of neuronal morphologies including large, angular cell somata typical of A9 neurons (FIG. 19I) and smaller spherical neurons typical of A10 identity (FIG. 19J).

Figure 8A:
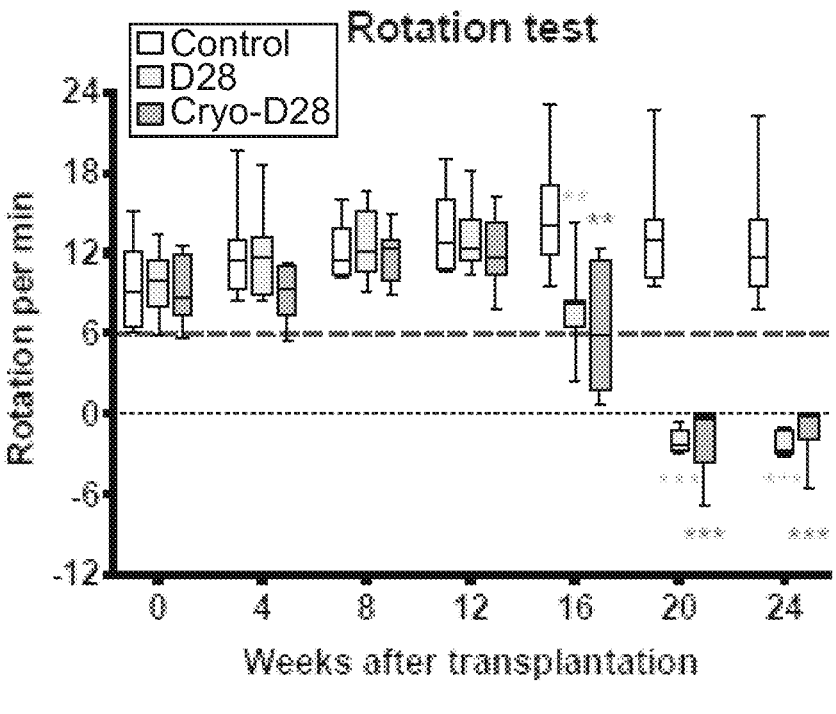
FIGS. 8A-N. In vivo survival and function of C4 hiPSC-derived mDA cells. (A-D) Behavioral assessments using the drug-induced rotation test (A), corridor test (B), cylinder test (C) and stepping test (D) in D28 and cryopreserved ("Cryo")-D28 groups (n=9). (E-F) Overview of graft-derived hNCAM⁺ innervation and TH⁺ innervation of the host brain. (G-L) Innervation by graft-derived hNCAM⁺ neurons (G-I) or TH⁺ neurons (J-L) into host STR, NAc and PFC of intact side, grafted side and lesioned ungrafted side. (M) High magnification image showing graft-derived innervation. (N) Immunofluorescence staining of the human-specific synaptic marker synaptophysin, of TH, and of DARPP32 in grafted neurons. All graft analysis data (E-M) were obtained 26 weeks after transplantation. AC, anterior commissure; cc, corpus callosum; dSTR, dorsal striatum; LV, lateral ventricle; NAc, nucleus accumbens; PFC, prefrontal cortex; T, transplant. Data are presented as mean±SEM. *$p<0.05$, $p<0.01$, *$p<0.001$, Student's t-test. Scale bars: 500 μm (G-L); 100 μm (M-N).
Figure 8B:
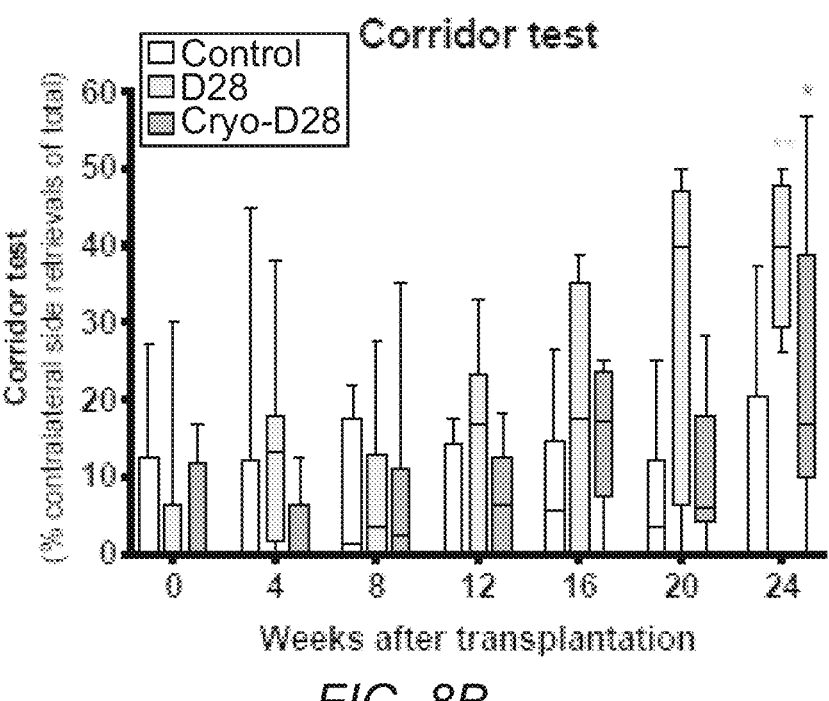
Figure 8D:
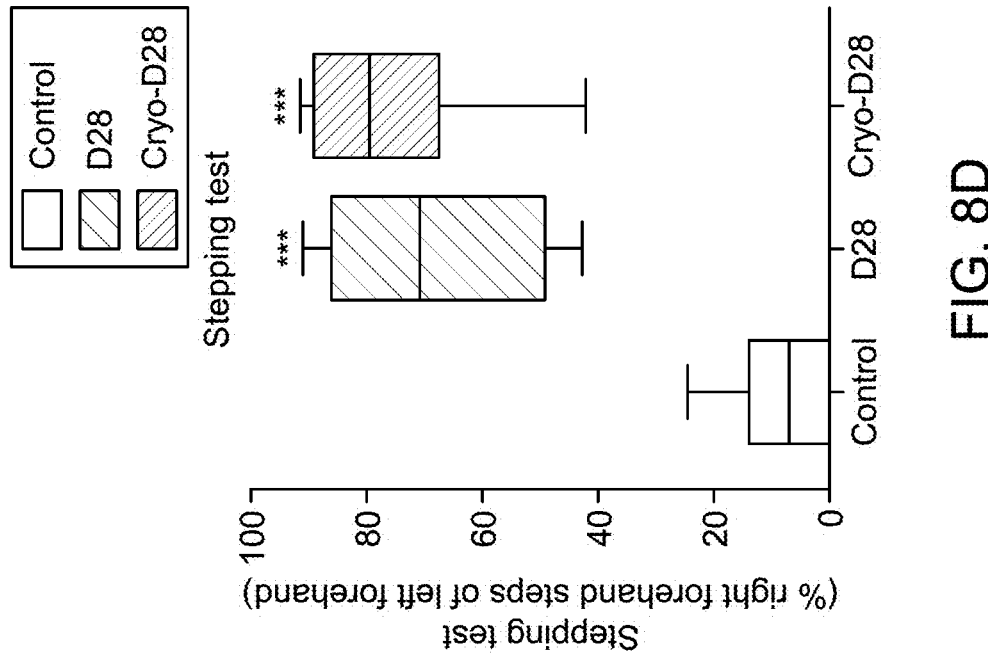
Figure 8C:
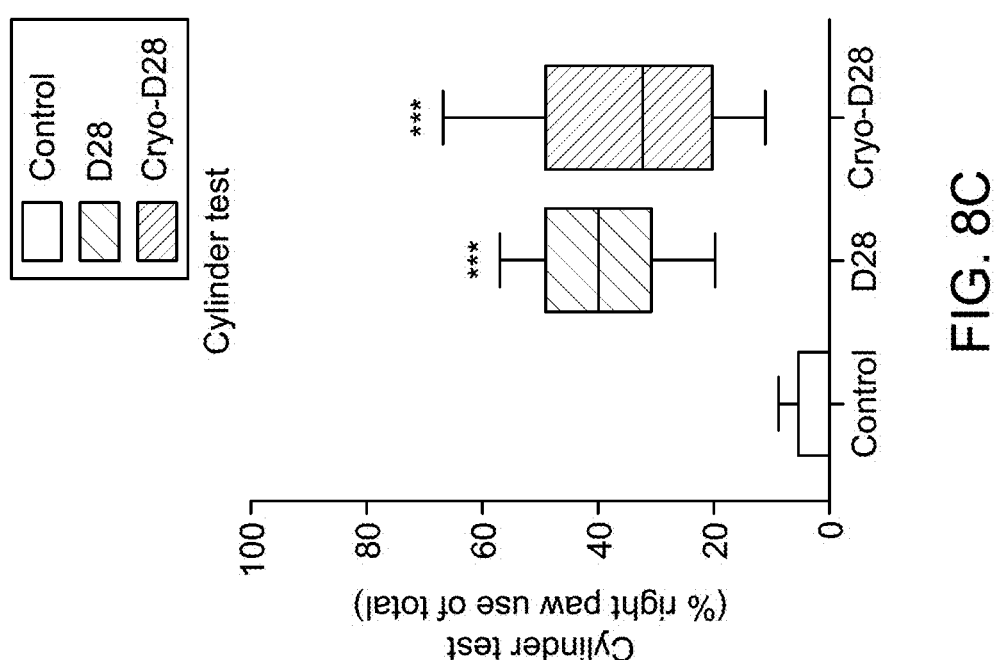
Figure 19L:
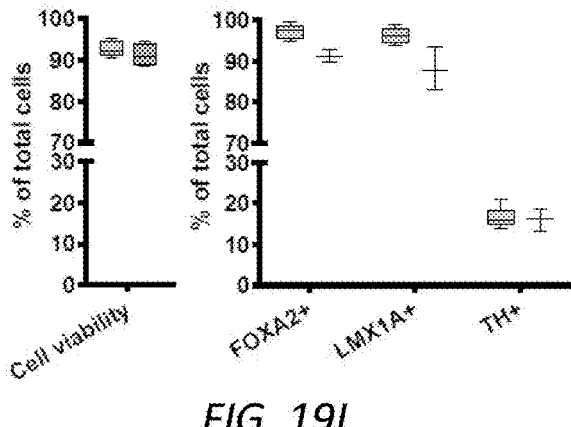
Figure 19M:
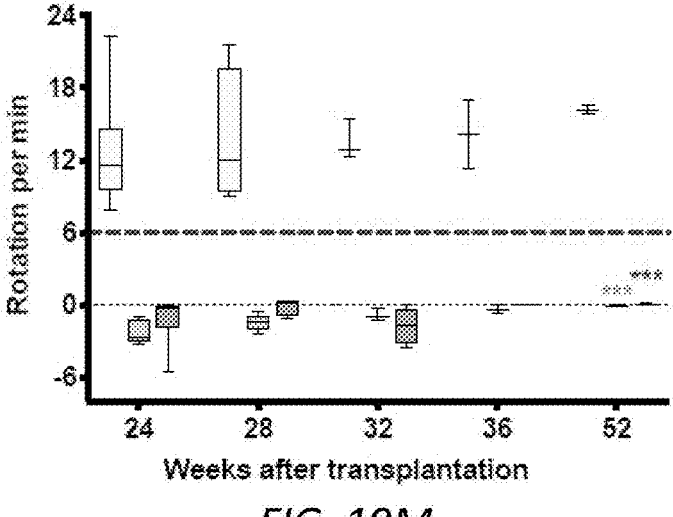

With these data suggesting safety and efficacy of D28 C4 cells, we further extensively tested them in athymic rats from Charles River, which were more physically robust and facilitated longer-term analyses than the Taconic strain. We selected a single dose (100,000) of D28 C4 cells for transplantation (FIG. 19K) and compared the efficacy and safety of cryopreserved to freshly prepared cells. Cryopreserved D28 C4 cells (Cryo-D28) retained a level of viability similar to freshly prepared equivalents (approximately 90%) and displayed the same mDA cell phenotypes (FIG. 19L) following storage for 1 week in liquid nitrogen. Amphetamine-induced rotation was significantly reduced at 16 weeks and completely rescued at 20 and 24 weeks post transplantation of either fresh or Cryo-D28 C4 cells (FIG. 8A). As noted for the Taconic rats (FIG. 19A), some animals exhibited contralateral rotation at 20 and 24 weeks. We also evaluated the functional efficacy of these grafts in several tests not involving exogenous pharmacological stimulation, thus providing a measure of motor deficits more analogous to those of human PD. In the corridor test, a sensitive test of lateralized sensorimotor response selection (50), either fresh or Cryo-D28 C4 cells significantly reduced the lesion-induced ipsilateral bias at 24 weeks post transplantation (FIG. 8B). Notably, no significant reduction had been observed yet at 16 or 20 weeks, suggesting that improvement in this task takes more time than rotation behavior. In the cylinder and stepping tests, which measure forelimb akinesia (51, 52), impaired forelimb function produced by 6-OHDA lesion was also significantly improved by transplantation of fresh or Cryo-D28 C4 cells at 24 weeks post-transplantation (FIGS. 8, C and D). Taken together, in all 4 behavioral tests both fresh and Cryo-D28 C4 cells significantly and similarly improved motor dysfunction. Further, additional grafted animals at later timepoints demonstrated that recovery of rotation behavior was sustained up to 52 weeks (FIG. 19M), the latest time tested, suggesting that functional improvements due to transplantation are well maintained.

Since H9-derived mDA cells have been extensively validated and explicitly shown to be equally functional to human fetal ventral mesencephalic (VM) cells (53), we directly compared outcomes following transplantation of H9 hESC- and C4 hiPSC-derived D28 cells. Transplantation of $1\times10^5$ and $4\times10^5$ cells showed that both lines resulted in identical recovery of rotational behavior both in degree and in time course (FIG. 20A).

Figure 20B:
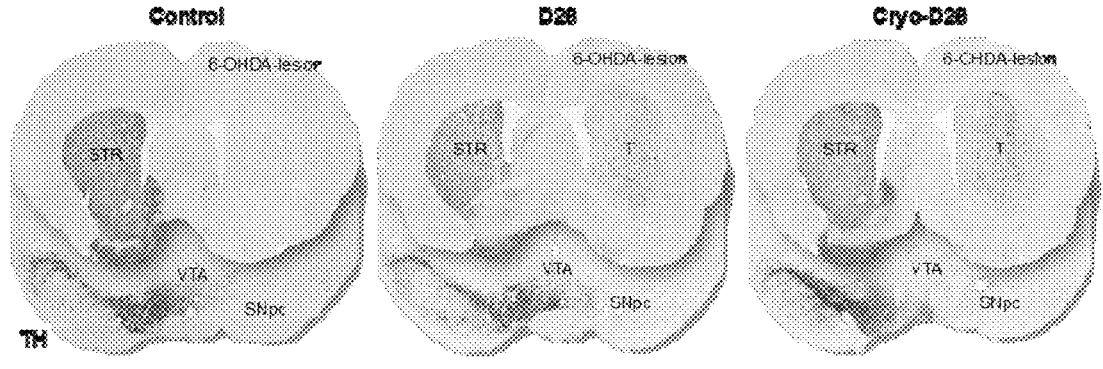
Figure 20C:
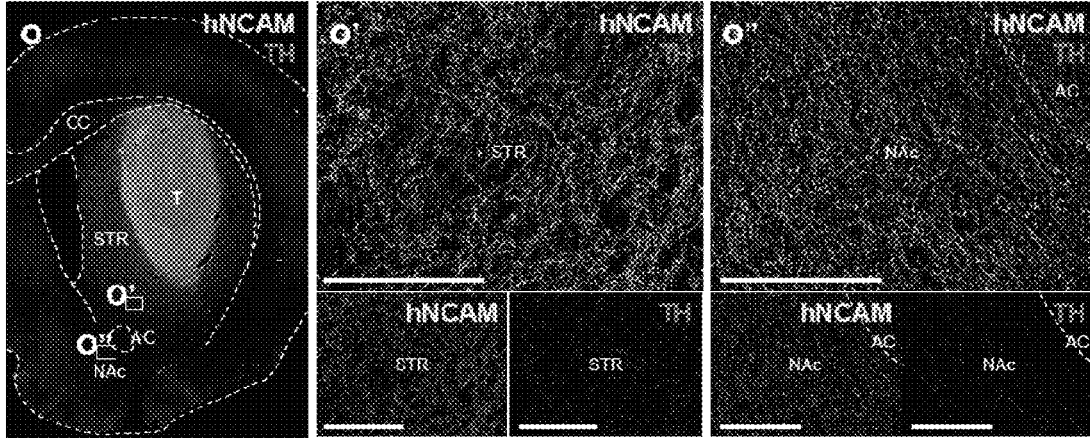
Figure 22A:
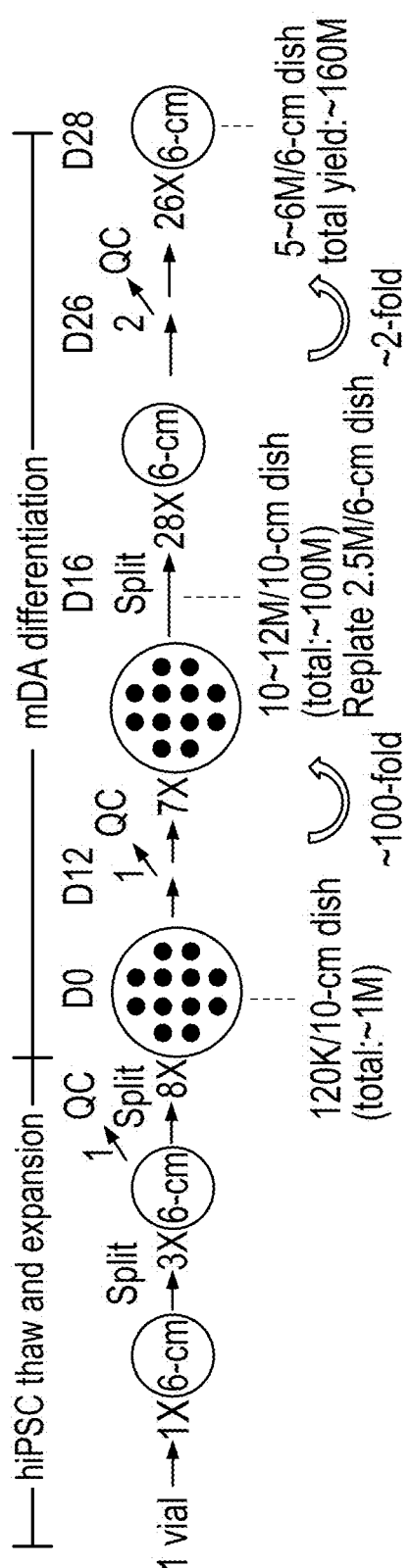
FIGS. 22A-I. GMP differentiation protocol schematic overview and quality control results. (A) Schematic overview of GMP differentiation protocol with cell yield at each stage shown in red. QC indicates quality control. (B) D0 immunocytochemistry QC staining for OCT4 and SSEA-4. (C) D0 QC for Oct4 and Nanog mRNA expression levels using qRT-PCR. (D) C4 D26 DNA fingerprinting QC showing the same patterns as the original fibroblasts, while the negative controls are different, confirming that the C4 iPS cells from the working cell bank originate from the patient's fibroblasts. Fib: fibroblast. M: DNA markers. (E) D26 QC for FOXA2, LMX1A and TH mRNA expression level using qRT-PCR. (F) D26 immunocytochemistry QC staining for FOXA2, LMX1A and Nurr1 using D0 undifferentiated cells as negative control. (G) Quantification of FOXA2, LMX1A and Nurr1 expression from (F). (H) D26 immunocytochemistry quality control staining for TH, 5-HT, TPH, OCT4 and SSEA-4 staining Do undifferentiated cells for OCT4 and SSEA-4 as negative control. (I) Quantification of TH, 5-HT, TPH, OCT4 and SSEA-4 expression from (H). Some cells were harvested at D26 for immunocytochemistry QC to allow cells to adhere to cover slips and complete the staining and analysis process before the final harvest at D28. Scale bar: 100 μm. n=3 for each experiment.
Figure 22B:
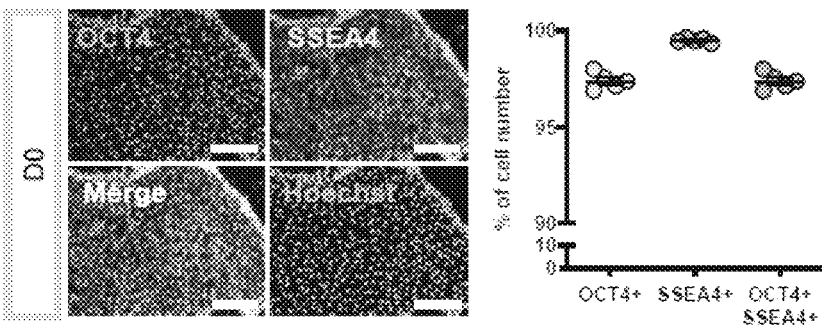
Figure 22C:
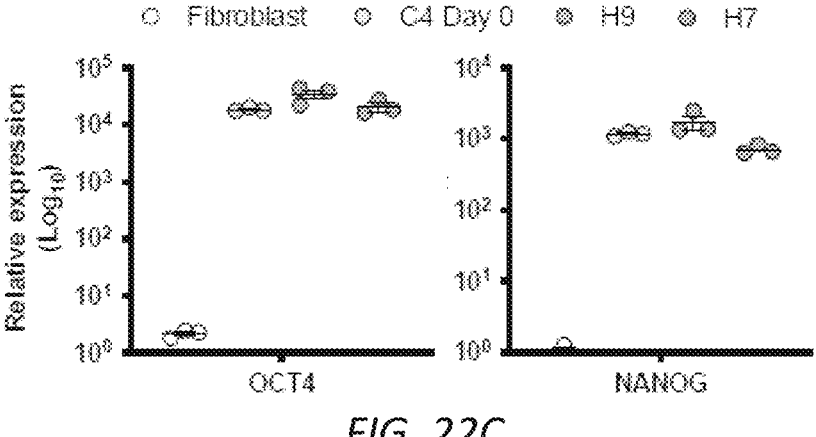
Figure 22D:
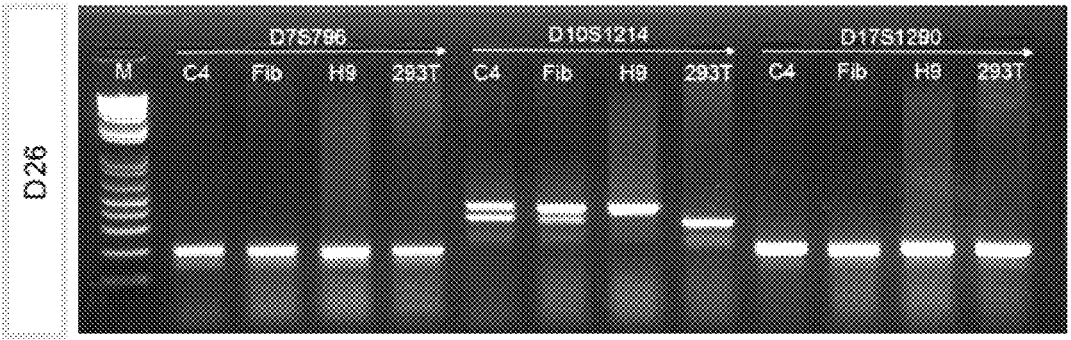
Figure 22E:
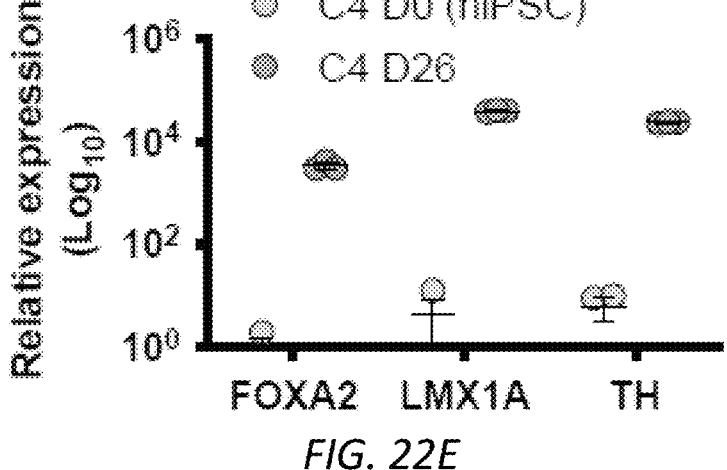
Figure 22F:
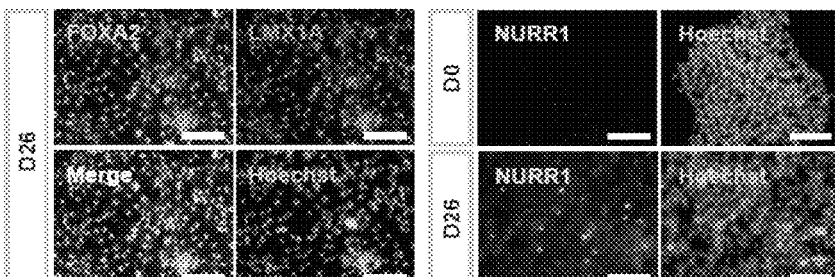
Figure 22G:
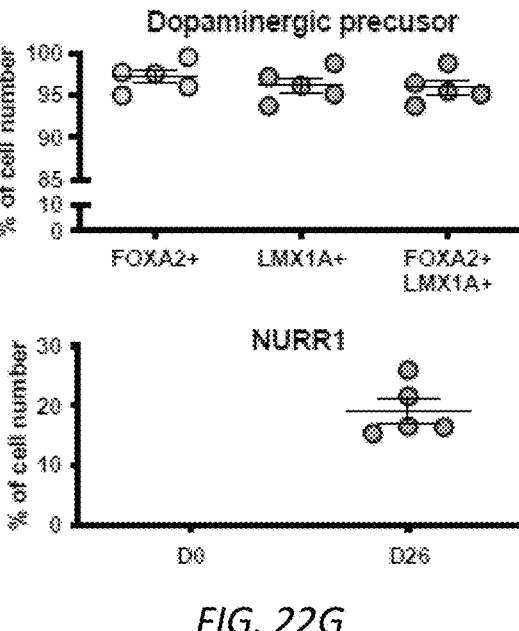
Figure 22H:
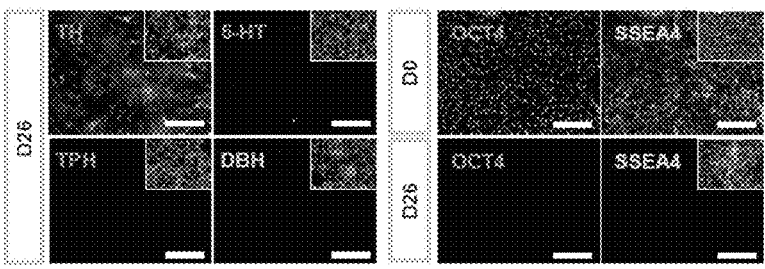
Figure 22I:
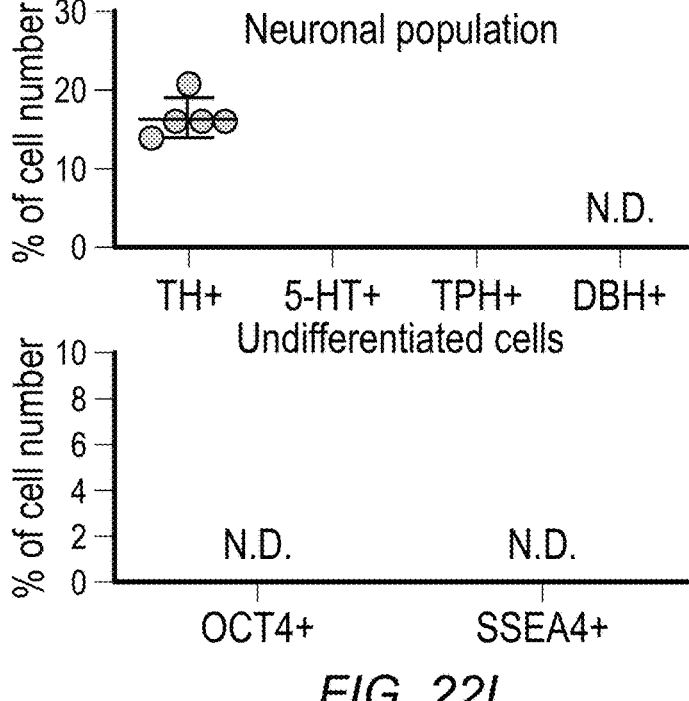

We next analyzed grafts at 26 weeks post transplantation and found that both hNCAM$^+$ and TH$^+$ cells display extensive innervation of the entire STR with copious extension to dopaminergic target areas such as dorso lateral STR (dl-STR), PFC, and NAc (FIGS. 8, E-L and FIG. 20B). Robust innervation of the host brain by these graft-derived mDANs was further validated by extensive co-expression of hNCAM in dopaminergic fibers in the dl-STR (FIG. 8M). In addition, triple immunofluorescence staining was performed using antibodies against TH, a human presynaptic protein (synaptophysin; hSyn), and a striatal medium spiny neuron marker (DARPP32). We observed TH$^+$/hSyn$^+$ neuronal terminals on their preferential targets and the host dendritic spines (DARPP32$^+$ neurons) at the border of the grafts, indicating that grafted DANs had formed synaptic connections with the host striatal neurons (FIG. 8N). Cryo-D28 and fresh D28 grafts showed similar hNCAM$^+$/TH$^+$ reinnervation and synaptic formation patterns (FIG. 20C). Grafts of both fresh and Cryo-D28 C4 cells contained similarly high numbers of DA neurons with A9- or A10-like morphologies (D28, 34,560±3,200; Cryo-D28, 46,094±8,967; FIGS. 21, A and B). The graft volume was also similar between D28 and Cryo-D28 (D28, 12.2±1.1 mm$^3$; Cryo-D28, 13.0±1.7 mm$^3$; FIG. 21C). The total number of hNCAM$^+$ cells was approximately $3.0\times10^6$ and $2.45\times10^6$, and the average percentage of TH$^+$ cells was 1.48±0.55% and 2.08±0.65% in the grafts of D28 and Cryo-D28, respectively. Most (70-80%) of these TH$^+$ neurons co-expressed FOXA2 and LMX1A and more than 90% co-expressed NURR1 (FIG. 21, D-F). A mature DA marker, DAT, was abundantly expressed in TH$^+$ neurons (FIG. 21G), while a marker associated with proliferative potential, KI67$^+$, was expressed in <1% of cells (D28, 0.86±0.09%; Cryo-D28, 0.54±0.21%; FIGS. 21, H and I). Rosettes or teratomas were not observed and proliferative cells co-expressing SOX1, PAX6, and KI67 were scant or undetected (SOX1$^+$PAX6$^+$, D28, 0.37±0.10%; Cryo-D28, 0.15±0.11%; SOX1$^+$PAX6$^+$KI67$^+$, D28, 0.02±0.02%; Cryo-D28, N/D; FIGS. 21, H and I). GIRK2 or CALBINDIN was expressed in TH$^+$ neurons (FIGS. 21J and K), with the majority co-expressing GIRK2 (D28, 79.29±4.88%; Cryo- D28, 81.28±3.50%; FIG. 21L). These TH$^+$ neurons in grafts co-express additional A9 markers such as ALDH1A1. TH$^+$ ALDH1A1$^+$ neurons often co-expressed SOX6 and GIRK2, representing A9-type mDANs (FIGS. 21, M and N); while some TH$^+$ ALDH1A1$^+$ neurons co-expressed CALBINDIN, representing A10-type mDANs (FIG. 21O). In sum, these data show that the great majority of TH$^+$ neurons in grafts of both fresh- and Cryo-D28 C4 cells have the characteristics of A9-type mDANs, consistent with the extensive and long-term recovery of motor dysfunction in behavioral tests.

When these data were compared with recently published transplantation studies of hiPSC-derived DA cells in 6-OHDA lesioned rat models (44, 45, 57-64), the DA yield (the ratio of surviving DA neurons to the number of transplanted cells) in this study was higher than in any of these other studies (Table 4).

facility in the Dana Farber Institute. We successfully produced >160 million D28 cells starting from about 1 million D0 C4 iPS cells (FIGS. 22A-F). Quality control data (e.g., genomic footprint, ICC of marker proteins, qRT-PCR) demonstrated that these clinically relevant quantities were free of pathogens and of high quality, as evidenced by the high percentage of FOXA2$^+$ LMX1A$^+$ cells (>85%) and absence of inappropriate markers (e.g., 5-HT, DBH, OCT4, and SSEA-4; representing serotonergic, noradrenergic, and pluripotent markers, respectively).

Example 10. In Vivo Efficacy Test in a Human Subject

A human patient with PD was treated by implantation of autologous mDA progenitors created by methods described

TABLE 4

Survival and Function of hiPSC-derived dopamine cells in rat brain (Related to FIG. 7)

| References | Cell stage | Rat host strain | Grafted cell number | Avg. DA yield (TH$^+$/100,000) (period) | D-Amp rotation recovery % (period) |
|---|---|---|---|---|---|
| This study | D28 | Athymic (CR) | 1 × 10$^5$ | 34,560 ± 3,200 (24 w) | ~130% (16-52 w) |
| | D28 (cryo) | Athymic (CR) | 1 × 10$^5$ | 46,094 ± 8,967 (24 w) | ~130% (16-52 w) |
| | D28 | Athymic (Taconic) | 1 × 10$^5$ | 5,621 ± 1029 (16 w) | ~125% (8-16 w) |
| 58 | D20 | SD | N/A | 2,106 ± 313/mm$^3$ (12 w)* | ~40% (12 w) |
| 59 | D42 | SD | 4 × 10$^5$ | 1,222 ± 160 (16 w) | ~80% (12-16 w) |
| 60 | NPC | SD | 3 × 10$^5$ | 8,960 ± 3,029 (8 w) | 52.46% ± 6.28% (4-8 w) |
| 44 | D28 (Corin sorted at D12) | SD | 4 × 10$^5$ | 1687 ± 585 (16 w) | ~75% (12-16 w) |
| 61 | D21 | SD | 1 × 10$^5$ | 1,800 ± 1,506 (3 w) | N/A |
| 64 | D16 (Corin sorted at D12) | X-SCID | N/A | N/A | ~90% (16 w) |
| 45 | D28 (LRTM1 sorted at D14) | SD | 1.3 × 10$^5$ | 9002 ± 1,974 (16 w) | ~80% (12-16 w) |
| 65 | D28 (Corin sorted at D12) | SD | 4 × 10$^5$ | 56.8-65.5 (16 w) | ~65-90% (8-16 w) |
| 62 | D16 (IAP sorted) | SD | 1.5 × 10$^5$ | ~300 (6 w) | N/A |
| 63 | D33 (cryo) | SD | 4.5 × 10$^5$ | 5,796 ± 446 (24 w) | ~100% (8-24 w) |

| References | Corridor test recovery % (period) | Cylinder test recovery % (period) | Stepping test recovery % (period) |
|---|---|---|---|
| This study | ~40% (16-24 w) | ~40% (24 w) | ~60% (24 w) |
| | ~30% (16-24 w) | ~30% (24 w) | ~70% (24 w) |
| | N/A | N/A | N/A |
| 58 | N/A | N/A | N/A |
| 59 | N/A | N/A | N/A |
| 60 | N/A | N/A | N/A |
| 44 | N/A | N/A | N/A |
| 61 | N/A | N/A | N/A |
| 64 | N/A | N/A | N/A |
| 45 | N/A | N/A | N/A |
| 65 | N/A | N/A | N/A |
| 62 | N/A | N/A | N/A |
| 63 | N/A | N/A | N/A |

Abbreviations: CR, Charles River;
cryo, cryopreserved cells;
N/A, not available;
NPC, neuronal precursor cells;
SD, Sprague Dawley;
X-SCID, X-linked severe combined immunodeficiency
*2,106 ± 313/mm$^3$ indicated DA density and DA yield result was not available in this study.

Example 9. GMP Production of Differentiated Cells

Finally, we tested the scalability and clinical applicability of our platform by production and characterization of differentiated C4 cells in vitro under this protocol at the GMP herein. The patient was a 69-year-old right-handed male physician with a 10-year history of progressive idiopathic PD. His PD medications were Rytary (carbidopa/levodopa extended release) 23.75/95, 3 capsules four times daily, rotigotine 4 mg daily, and rasagiline 1 mg daily (904 mg levodopa equivalent dose). Despite best medical therapy, he reported suboptimal control of his symptoms, with 3 hours of off time per day on average, characterized by worsening tremor, posture, and fine motor control. He had no dyskinesia. Informed consent included a thorough discussion of the risks associated with first-in-human use of this technology in PD and a review of currently available medical and surgical therapeutic options, including deep brain stimulation. Fibroblasts harvested from a skin biopsy were used to generate multiple iPSC lines that were extensively tested for pluripotent differentiation potential in vitro and in vivo and screened for somatic mutations using whole exome sequencing. Based on these data, a single clone (designated C4) devoid of known cancer-related mutations and with the lowest overall mutational burden was selected for production of transplantable mDAP cells. Strict GMP and quality control standards were met, and testing performed for gene expression of A9 mDA-specific and other neural markers, as well as for genomic integrity by whole genome sequencing (WGS), before release of the mDAP cells for clinical use.

The patient underwent two MRI-guided stereotactic surgical procedures for implantation in the putamen, left hemisphere followed by right hemisphere, separated by 6 months, conforming to regulatory guidance from the FDA. At each operation, three trajectories were made in the putamen posterior to the level of the anterior commissure, each spanning the superior-inferior extent of the nucleus (Schweitzer et al., Oper Neurosurg (Hagerstown) 2019; 18:321-328). A total of 4 million cells were delivered at each operative procedure, divided equally among the three tracks. Intravenous cefazolin was administered perioperatively. No immunosuppressants, glucocorticoids, or anticonvulsants were used at any time. After each surgery, the patient was monitored overnight and discharged the following day.

Materials and Methods

The following materials and methods were used in this example.

Oversight

Informed consent included a discussion of the risks associated with first-in-human use of this method in Parkinson's disease, with a review of currently available medical and surgical therapeutic options, including deep-brain stimulation. The study was conducted under regulatory guidance from the Food and Drug Administration (FDA). Approval was obtained from institutional review boards at Weill Cornell Medical Center and at Massachusetts General Hospital. All procedures in animals were conducted with approval from the McLean Hospital Animal Care and Use Committee.

iPSC Production, Differentiation, and Preclinical Safety and Efficacy Testing.

iPSCs were produced using a protocol combining the conventional Yamanaka factors with two microRNA clusters as described above. Fibroblasts that were harvested from a skin biopsy were used to generate multiple iPSC lines that were tested for pluripotent differentiation potential in vitro and in vivo and screened by whole-exome sequencing for the presence of protein-coding mutations. A single iPSC clone (designated C4) that showed normal karyotype was selected for further characterization and for production of mDAPs under Good Manufacturing Practice conditions. The C4 iPSCs were differentiated in vitro for 28 days into mDA cells using a "spotting"-based method under GMP conditions as described above. This protocol included overnight treatment with quercetin at day 9 to eliminate remaining undifferentiated iPSCs (i.e., cells expressing pluripotent markers such as OCT4, SSEA1, and NANOG) by inhibiting the PSC-specific anti-apoptotic gene, BIRC5, encoding survivin. See above and Lee et al., Proc Natl Acad Sci USA 2013; 110:E3281-90.

Characterization of In Vitro Differentiated mDAPs

The C4 iPSC-derived cells showed normal karyotype and were characterized as mDAPs with dopamine neuron-specific and other neural markers, in two validation experiments as described above. Whole-genome sequencing of both the C4 iPSCs and C4-derived progenitors was performed, and the progenitors were compared with the original source fibroblasts; the results confirmed the absence in the progenitors of known cancer-associated and neurodegeneration-associated mutations.

We found 23 somatic mutations that included missense and splice site disrupting variants in C4 iPSCs and mDAPs compared to the parent fibroblasts; however, no known cancer-related genes (i.e., according to the CENSUS database), disease genes reported for neurodegenerative disorders (i.e., according to the HGMD and ClinVar) and the genes involved in tyrosine metabolism and dopaminergic synapse pathways (i.e., according to the KEGG database) were affected by these variants. Notably, a missense variant in FLG2 (ENSP00000373370.4:p.Val672Gly) was present in C4 iPSCs sample with low fraction, which was called as a heterozygous variant in C4 iPSCs. Therefore, we suspect that this missense variant was present in both C4 iPSCs and mDAPs as subclonal somatic mutations. During differentiation from C4 iPSCs to mDAPs, no new somatic mutation was introduced. The majority of mutations that were found in either C4 iPSCs or mDAPs appeared as subclonal in the other sample (the two left-most peaks in each box). Next, we performed read-depth based CNV analysis using the allele-specific copy number analysis of tumors (ASCAT) (Van Loo et al. Proceedings of the National Academy of Sciences of the United States of America 2010; 107:16910-5). We found a heterozygous deletion in PODXL gene covering intron and a single exon in C4 iPSCs and mDAPs but did not find any additional CNVs introduced to mDAPs compared to C4 iPSCs. This copy number variant was not detected using WES. PODXL has not been reported as a cancer driver gene.

Before clinical use, neurons that were derived from these progenitor cells showed dopamine secretion and electrophysiological properties in vitro characteristic of substantia nigra pars compacta dopaminergic neurons, showed functional efficacy in animal models similar to that of fetal midbrain-derived tissue as described above, and passed FDA-mandated release criteria. After treatment with quercetin, the final cell products (at day 28) had no detectable remaining undifferentiated iPSCs (with an upper boundary of the 95% confidence interval of <1 undifferentiated cell per 1 billion day-28 differentiated cells), on the basis of immunostaining and real-time polymerase chain reaction-based assays. Serotonergic neurons, a potential cause of graft-induced dyskinesia (Olanow et al. Ann Neurol 2003; 54:403-14), were not detected in the final product.

Graft Survival Under Autologous Vs. Allogeneic Conditions in Humanized Mice.

Patient-derived iPSCs (C4) and allogeneic human embryonic stem cells (H9) were differentiated to day-28 mDAPs (C4-mDAPs and H9-mDAPs), and $1\times10^5$ cells of each line were grafted into the striatum of nonobese diabetic mice with severe combined immunodeficiency (NOD SCID) and depletion of the interleukin-2 receptor γ (NOD SCID gamma mice), patient-humanized NOD SCID gamma mice (C4-hu; using patient's peripheral-blood mononuclear cells obtained 24 months [left hemisphere] and 18 months [right hemisphere] after surgery), and allogeneic humanized mice (Kl-hu). Animals were killed at 2 weeks and examined histologically for graft survival by labeling for human neural-cell adhesion molecule (hNCAM+) cells, for the presence within the graft of neurons expressing markers for dopaminergic neurons (tyrosine hydroxylase [TH+] neurons), and for cellular immune response (CD4+ cells).

Patient Surgical Procedure.

Figure 24A:
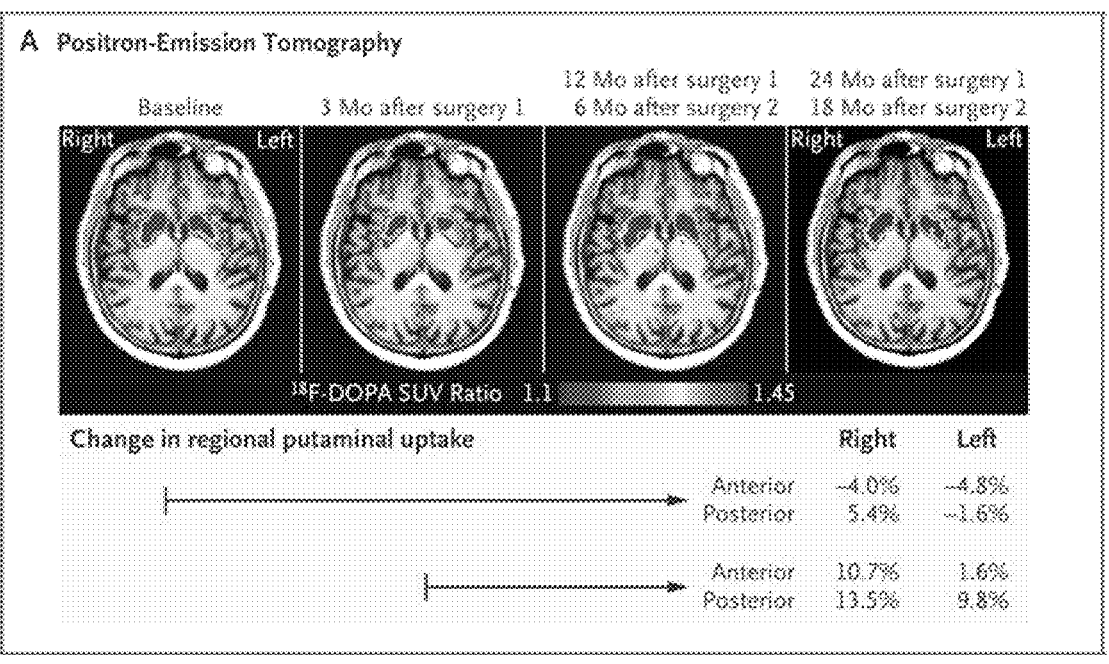
FIGS. 24A-B. Imaging. (A), axial 18F-DOPA PET images at the level of the basal ganglia at time points indicated: baseline (4 months before first surgery), 3 months after left implant, 6 months after right implant and 12 months after left implant, and 24 months after left implant and 18 months after right implant. Transient decrease of 18F-DOPA uptake 3 months after the initial left implant followed by progressive modest increase of dopamine uptake bilaterally (right greater than left), mainly in the posterior putamen near the graft sites. (B), a T2 blade MR image at 18 months following the left and 12 months following the right side implantation. Arrows indicate location of the implants.
Figure 24B:
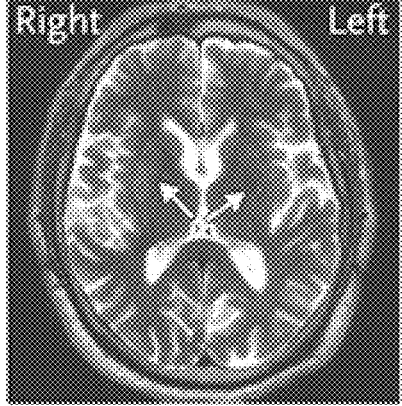

The patient underwent two surgical procedures for cell implantation, left hemisphere followed by right, separated by six months (per regulatory guidance from the FDA). An MRI-based Leksell stereotactic technique was used. At each operation, three trajectories were created starting from a single high frontal parasagittal cortical entry point. Cells were prepared at the DF/HCC GMP Cell Manipulation Core and harvested the day of surgery. Cells were injected into each tract using a specially designed device (Schweitzer et al. 2019) to create columns spanning the sagittal extent of the putamen. Intraoperative CT was used to image the cannula and to fuse this image back onto the preoperative surgical plan to confirm localization accuracy, and to rule out hemorrhage (FIGS. 24A-B). A total dose of 4 million viable cells was delivered at each operative procedure, divided equally among the three tracks. Antibiotics (cefazolin, 2 g intravenous every 8 hours for 3 doses perioperatively) were administered, but no immunosuppressants, steroids, or anticonvulsants were used. Following surgery the patient was monitored overnight in the intensive care unit prior to discharge the following day.

Clinical Measures

Neurologic examinations were performed and Parkinson's disease-specific measures assessed at baseline and at 1, 3, 6, 9, and 12 months after each implantation and at 6-month intervals thereafter. At each examination, the neurologist recorded the "off" time, when medication did not adequately control motor symptoms, as reported by the patient. Prespecified assessments included the Movement Disorder Society Unified Parkinson's Disease Rating Scale (MDS-UPDRS), part III (scores range from 0 to 132, with higher scores indicating worse parkinsonian motor signs) (Cha et al., Nat Cell Biol 2017; 19:445-56), and the 39-item Parkinson's Disease Questionnaire (PDQ-39; scores range from 0 to 156, with higher scores indicating worse quality of life) (Lee et al., 2013).

Brain Imaging

Computed tomographic (CT) scans were performed intraoperatively to confirm accurate placement of the cell injection in the putamen and immediately postoperatively for hemorrhage screening at or near the site of implantation. Serial magnetic resonance imaging (MRI) scans and magnetic resonance spectroscopic findings were reviewed for any evidence of tumor, stroke, or hemorrhage. Serial fluorine-18-L-dihydroxyphenylalanine ($^{18}$F-DOPA) positron-emission tomography (PET)-CT was performed to assess for the presence of presynaptic dopamine terminal activity in the engrafted putaminal regions. Changes in radioisotope uptake were judged semiquantitatively by $^{18}$F-DOPA standardized uptake value ratios.

Safety Monitoring

Serial clinical neurologic examination to detect adverse neurologic events, along with imaging reviews, was performed by two study neurologists and a study radiologist. The patient continued to be treated independently by his community neurologist.

Results

Immunogenicity of Grafts after Implantation in Humanized Mice

As shown in FIG. 23A and above both patient-derived mDAPs (C4-mDAPs) and allogeneic mDAPs (H9-mDAPs) survived in NOD SCID gamma mice, and both graft types were rejected when transplanted to allogeneic humanized mice (K1-hu). Patient-humanized mice (C4-hu) permitted the survival of autologous C4-mDAPs, with grafts staining positively for hNCAM+ cells and containing TH+ neurons at 2 weeks after implantation, whereas C4-hu mice rejected allogeneic H9-mDAPs, with prominent CD4+ lymphocytic infiltrates (FIGS. 23B-C).

Imaging at 0 to 24 Months after Implantation in the Patient

At 3 months after the first implantation, $^{18}$F-DOPA PET-CT imaging showed an initial decline in $^{18}$F-DOPA uptake from baseline in the putamina, followed by small increases in $^{18}$F-DOPA uptake at subsequent times up to 18 months and 24 months after implantations on the right side and left side, respectively. Increased activity was greater on the right (second implant) than on the left and was most prominent in the posterior putamen near the graft sites, as seen on the color intensity scale and on quantitative comparisons of selected subregions (FIGS. 24A-B). Semiquantitative changes from baseline in uptake of the radioisotope are shown in FIGS. 24A-B and varied from −4.0% to 13.5% on the right and from −4.8% to 9.8% on the left.

MRI at 6 months after the first implantation and subsequent time points showed areas of increased T2-weighted signal intensity approximating the locations of the graft sites in the putamina, as well as along parts of the surgical tracts within the white matter, more pronounced on the right (FIGS. 24A-B). No contrast enhancement was seen at the six putaminal implantation sites. At 6 months after the second surgery, a 4-mm region of enhancement was observed 3 cm above the target in one tract; CT and MRI including arterial spin labeling magnetic resonance perfusion imaging and magnetic resonance spectroscopy showed changes consistent with postsurgical gliosis.

Clinical Assessments

At 24 months after the first (left) implantation and 18 months after the second (right) implantation, the patient reported no adverse events or decline in function. Scores on the MDS-UPDRS, part III (assessing parkinsonian motor signs), after overnight withdrawal of dopamine replacement therapy ("off") were not measured before the first implantation because the patient declined to cease medications owing to worsened symptoms. Scores in the off period were 43 at 4 weeks after the first implantation, 33 to 41 at subsequent follow-up times, and 33 at 24 months. Scores on the MDS-UPDRS, part III, at the peak dose of dopamine replacement therapy ("on") were 38 at the time of implantation, 19 to 35 during follow-up, and 29 at 24 months. PDQ-39 scores (assessing Parkinson's disease-related quality of life, with lower scores indicating better quality) were 62 at the time of implantation, 2 to 34 during follow-up, and 2 at 24 months (FIGS. 25A-B and Table 5).

TABLE 5

Clinical Assessments

Months post implant / Right hemisphere: (B/L, 1, 4, 6, 9, 12, 18) — aligned under Left hemisphere columns 6, 7, 10, 12, 15, 18, 24

| MDS-UPDRS | Screen | B/L | 1 | 3 | 6 | 7 | 10 | 12 | 15 | 18 | 24 |
|---|---|---|---|---|---|---|---|---|---|---|---|
| Part I | 13 | 12 | 6 | 3 | 9 | 5 | 1 | 0 | | 2 | 1 |
| Part II | 21 | 24 | 13 | 12 | 18 | 14 | 5 | 10 | | 11 | 10 |
| Part III off | | | 43 | 36 | | | | 41 | | 39 | 33 |
| Part III on | 39 | 36 | 35 | 19 | 29 | 29 | 35 | 33 | 27 | 25 | 29 |
| Part IV | 2 | 4 | 3 | 3 | 1 | 0 | 2 | 4 | | 0 | 1 |
| Hoehn & Yahr | 2.5 | 2 | 2 | 2 | 2 | 2 | 2 | 2 | | 2 | 2 |
| MoCA | | 29 | 30 | 30 | 29 | | | 28 | | 29 | 27 |
| BAI | | 14 | 1 | 2 | 3 | | | 1 | | 1 | 1 |
| BDI | | 20 | 1 | 1 | 1 | | | 0 | | 1 | 3 |
| QUIP-RS | | 0 | 0 | 0 | 0 | | | 0 | | 0 | 0 |
| NMSS | | 61 | 35 | 35 | 35 | | | 12 | | 22 | 5 |
| PDQ-39 | | 62 | 13 | 31 | 34 | | | 4 | | 8 | 2 |

B/L=baseline pre-implantation; MDS-UPDRS: Movement Disorders Society Unified Parkinson's Disease Rating Scale (Goetz et al., Mov Disord 2008; 23:2129-70); MoCA: Montreal Cognitive Assessment (Nasreddine et al. J Am Geriatr Soc 2005; 53:695-9); BAI: Beck Anxiety Inventory (Beck et al., J Consult Clin Psychol 1988; 56:893-7); BDI: Beck Depression Inventory (Beck A T, Steer R A, Brown G K. BDI-II, Beck depression inventory: manual. San Antonio, Tex.; Boston: Psychological Corp.; Harcourt Brace; 1996); QUIP-RS: Questionnaire for Impulsive-Compulsive Disorders in Parkinson's Disease-Rating Scale (Weintraub et al., Mov Disord 2012; 27:242-7); NMS: Non-Motor Symptoms Scale (Chaudhuri et al. Mov Disord 2007; 22:1901-11); PDQ-39: Parkinson's Disease Questionnaire—39 (Peto et al. Qual Life Res 1995; 4:241-8).

At 24 months, the patient's Parkinson's disease medications were extended-release carbidopa-levodopa (in capsules containing 23.75 mg and 95 mg, respectively, at a dose of three, three, two, and three capsules four times daily), rotigotine (4 mg daily), rasagiline (1 mg daily), and droxidopa (100 mg daily) (total daily dose, 847 mg of levodopa equivalents); this represented a 6% decrease in levodopa equivalents as compared with before the implantations. He reported less than 1 hour of "off" time per day. Dyskinesias were not reported by the patient or observed during clinical examination—similar to their absence preoperatively.

In addition to improvements in motor scores and motor ADLs, the subject reported improvements in sleep quality including reduced REM sleep behavior disorder symptoms, reductions in sialorrhea and dysphagia, and reductions in anxiety and depression. There was no decline in subjective cognitive function, and MoCA scores remained between 27 and 30.

This study, which reports the production and implantation of iPSC-derived autologous dopaminergic progenitor cells in a patient with Parkinson's disease, with clinical and imaging results, providing evidence of therapeutic benefit.

REFERENCES 1. de Lau, L. M., and Breteler, M. M. 2006. Epidemiology of Parkinson's disease. Lancet Neurol 5:525-535.
2. Kang, U. J., and Fahn, S. 1988. Management of tardive dyskinesia. Ration Drug Ther 22:1-7.
3. Bjorklund, A., and Kordower, J. H. 2013. Cell therapy for Parkinson's disease: what next? Mov Disord 28:110-115.
4. Kefalopoulou, Z., Politis, M., Piccini, P., Mencacci, N., Bhatia, K., Jahanshahi, M., Widner, H., Rehncrona, S., Brundin, P., Bjorklund, A., et al. 2014. Long-term clinical outcome of fetal cell transplantation for Parkinson disease: two case reports. JAMA Neurol 71:83-87.
5. Barker, R.A., Drouin-Ouellet, J., and Parmar, M. 2015. Cell-based therapies for Parkinson disease-past insights and future potential. Nat Rev Neurol 11:492-503.
6. Lindvall, O. 2016. Clinical translation of stem cell transplantation in Parkinson's disease. J Intern Med 279:30-40.
7. Sonntag, K. C., Song, B., Lee, N., Jung, J. H., Cha, Y., Leblanc, P., Neff, C., Kong, S.W., Carter, B.S., Schweitzer, J., et al. 2018. Pluripotent stem cell-based therapy for Parkinson's disease: Current status and future prospects. Prog Neurobiol 168:1-20.
8. Takahashi, K., and Yamanaka, S. 2006. Induction of pluripotent stem cells from mouse embryonic and adult fibroblast cultures by defined factors. Cell 126:663-676.
9. Takahashi, K., Tanabe, K., Ohnuki, M., Narita, M., Ichisaka, T., Tomoda, K., and Yamanaka, S. 2007. Induction of pluripotent stem cells from adult human fibroblasts by defined factors. Cell 131:861-872.
10. Yu, J., Vodyanik, M.A., Smuga-Otto, K., Antosiewicz-Bourget, J., Frane, J. L., Tian, S., Nie, J., Jonsdottir, G. A., Ruotti, V., Stewart, R., et al. 2007. Induced pluripotent stem cell lines derived from human somatic cells. Science 318:1917-1920.
11. Park, I. H., Zhao, R., West, J. A., Yabuuchi, A., Huo, H., Ince, T. A., Lerou, P. H., Lensch, M. W., and Daley, G. Q. 2008. Reprogramming of human somatic cells to pluripotency with defined factors. Nature 451:141-146.
12. Scudellari, M. 2016. How iPS cells changed the world. Nature 534:310-312.
13. Takahashi, K., and Yamanaka, S. 2016. A decade of transcription factor-mediated reprogramming to pluripotency. Nat Rev Mol Cell Biol 17:183-193.
14. Tapia, N., and Scholer, H. R. 2016. Molecular Obstacles to Clinical Translation of iPSCs. Cell Stem Cell 19:298-309.
15. Miura, K., Okada, Y., Aoi, T., Okada, A., Takahashi, K., Okita, K., Nakagawa, M., Koyanagi, M., Tanabe, K., Ohnuki, M., et al. 2009. Variation in the safety of induced pluripotent stem cell lines. Nat Biotechnol 27:743-745.

16. Ohnishi, K., Semi, K., Yamamoto, T., Shimizu, M., Tanaka, A., Mitsunaga, K., Okita, K., Osafune, K., Arioka, Y., Maeda, T., et al. 2014. Premature termination of reprogramming in vivo leads to cancer development through altered epigenetic regulation. Cell 156:663-677.

17. Mandai, M., Kurimoto, Y., and Takahashi, M. 2017. Autologous Induced Stem-Cell-Derived Retinal Cells for Macular Degeneration. N Engl J Med 377:792-793.

18. Kirkeby, A., Nolbrant, S., Tiklova, K., Heuer, A., Kee, N., Cardoso, T., Ottosson, D. R., Lelos, M. J., Rifes, P., Dunnett, S. B., et al. 2017. Predictive Markers Guide Differentiation to Improve Graft Outcome in Clinical Translation of hESC-Based Therapy for Parkinson's Disease. Cell Stem Cell 20:135-148.

19. Cha, Y., Han, M. J., Cha, H. J., Zoldan, J., Burkart, A., Jung, J. H., Jang, Y., Kim, C. H., Jeong, H.C., Kim, B. G., et al. 2017. Metabolic control of primed human pluripotent stem cell fate and function by the miR-200c-SIRT2 axis. Nat Cell Biol 19:445-456.

20. Korpal, M., Lee, E. S., Hu, G., and Kang, Y. 2008. The miR-200 family inhibits epithelial-mesenchymal transition and cancer cell migration by direct targeting of E-cadherin transcriptional repressors ZEB1 and ZEB2. J Biol Chem 283:14910-14914.

21. Valastyan, S., and Weinberg, R. A. 2011. Roles for microRNAs in the regulation of cell adhesion molecules. J Cell Sci 124:999-1006.

22. Banyard, J., Chung, I., Wilson, A.M., Vetter, G., Le Bechec, A., Bielenberg, D. R., and Zetter, B. R. 2013. Regulation of epithelial plasticity by miR-424 and miR-200 in a new prostate cancer metastasis model. Sci Rep 3:3151.

23. Pieters, T., and van Roy, F. 2014. Role of cell-cell adhesion complexes in embryonic stem cell biology. J Cell Sci 127:2603-2613.

24. Chan, E. M., Ratanasirintrawoot, S., Park, I. H., Manos, P. D., Loh, Y. H., Huo, H., Miller, J.D., Hartung, O., Rho, J., Ince, T. A., et al. 2009. Live cell imaging distinguishes bona fide human iPS cells from partially reprogrammed cells. Nat Biotechnol 27:1033-1037.

25. Tanabe, K., Nakamura, M., Narita, M., Takahashi, K., and Yamanaka, S. 2013. Maturation, not initiation, is the major roadblock during reprogramming toward pluripotency from human fibroblasts. Proc Natl Acad Sci USA 110:12172-12179.

26. Nakagawa, M., Takizawa, N., Narita, M., Ichisaka, T., and Yamanaka, S. 2010. Promotion of direct reprogramming by transformation-deficient Myc. Proc Natl Acad Sci USA 107:14152-14157.

27. Kandoth, C., McLellan, M. D., Vandin, F., Ye, K., Niu, B., Lu, C., Xie, M., Zhang, Q., McMichael, J. F., Wyczalkowski, M. A., et al. 2013. Mutational landscape and significance across 12 major cancer types. Nature 502:333-339.

28. Merkle, F. T., Ghosh, S., Kamitaki, N., Mitchell, J., Avior, Y., Mello, C., Kashin, S., Mekhoubad, S., Ilic, D., Charlton, M., et al. 2017. Human pluripotent stem cells recurrently acquire and expand dominant negative P53 mutations. Nature 545:229-233.

29. Kilpinen, H., Goncalves, A., Leha, A., Afzal, V., Alasoo, K., Ashford, S., Bala, S., Bensaddek, D., Casale, F. P., Culley, O. J., et al. 2017. Common genetic variation drives molecular heterogeneity in human iPSCs. Nature 546:370-375.

30. Martincorena, I., and Campbell, P. J. 2015. Somatic mutation in cancer and normal cells. Science 349:1483-1489.

31. Chung, S., Leung, A., Han, B.S., Chang, M. Y., Moon, J. I., Kim, C. H., Hong, S., Pruszak, J., Isacson, O., and Kim, K. S. 2009. Wnt1-lmx1a forms a novel autoregulatory loop and controls midbrain dopaminergic differentiation synergistically with the SHH-FoxA2 pathway. Cell Stem Cell 5:646-658.

32. Joksimovic, M., Anderegg, A., Roy, A., Campochiaro, L., Yun, B., Kittappa, R., McKay, R., and Awatramani, R. 2009. Spatiotemporally separable Shh domains in the midbrain define distinct dopaminergic progenitor pools. Proc Natl Acad Sci USA 106:19185-19190.

33. Joksimovic, M., Yun, B.A., Kittappa, R., Anderegg, A.M., Chang, W.W., Taketo, M.M., McKay, R. D., and Awatramani, R. B. 2009. Wnt antagonism of Shh facilitates midbrain floor plate neurogenesis. Nat Neurosci 12:125-131.

34. Arenas, E., Denham, M., and Villaescusa, J. C. 2015. How to make a midbrain dopaminergic neuron. Development 142:1918-1936.

35. Tao, Y., and Zhang, S.C. 2016. Neural Subtype Specification from Human Pluripotent Stem Cells. Cell Stem Cell 19:573-586.

36. Chambers, S. M., Fasano, C. A., Papapetrou, E. P., Tomishima, M., Sadelain, M., and Studer, L. 2009. Highly efficient neural conversion of human ES and iPS cells by dual inhibition of SMAD signaling. Nat Biotechnol 27:275-280.

37. Kriks, S., Shim, J. W., Piao, J., Ganat, Y. M., Wakeman, D. R., Xie, Z., Carrillo-Reid, L., Auyeung, G., Antonacci, C., Buch, A., et al. 2011. Dopamine neurons derived from human ES cells efficiently engraft in animal models of Parkinson's disease. Nature 480:547-551.

38. Porter, A. G., and Janicke, R. U. 1999. Emerging roles of caspase-3 in apoptosis. Cell Death Differ 6:99-104.

39. Cummings, B. S., and Schnellmann, R. G. 2004. Measurement of cell death in mammalian cells. Curr Protoc Pharmacol Chapter 12:Unit 12 18.

40. Lee, M. O., Moon, S. H., Jeong, H. C., Yi, J. Y., Lee, T. H., Shim, S. H., Rhee, Y. H., Lee, S. H., Oh, S. J., Lee, M. Y., et al. 2013. Inhibition of pluripotent stem cell-derived teratoma formation by small molecules. Proc Natl Acad Sci USA 110:E3281-3290.

41. Pennartz, S., Belvindrah, R., Tomiuk, S., Zimmer, C., Hofmann, K., Conradt, M., Bosio, A., and Cremer, H. 2004. Purification of neuronal precursors from the adult mouse brain: comprehensive gene expression analysis provides new insights into the control of cell migration, differentiation, and homeostasis. Mol Cell Neurosci 25:692-706.

42. Jiang, Y., de Bruin, A., Caldas, H., Fangusaro, J., Hayes, J., Conway, E. M., Robinson, M. L., and Altura, R. A. 2005. Essential role for survivin in early brain development. J Neurosci 25:6962-6970.

43. Darband, S. G., Kaviani, M., Yousefi, B., Sadighparvar, S., Pakdel, F. G., Attari, J. A., Mohebbi, I., Naderi, S., and Majidinia, M. 2018. Quercetin: A functional dietary flavonoid with potential chemo-preventive properties in colorectal cancer. J Cell Physiol 233:6544-6560.

44. Doi, D., Samata, B., Katsukawa, M., Kikuchi, T., Morizane, A., Ono, Y., Sekiguchi, K., Nakagawa, M., Parmar, M., and Takahashi, J. 2014. Isolation of human induced pluripotent stem cell-derived dopaminergic progenitors by cell sorting for successful transplantation. Stem Cell Reports 2:337-350.

45. Samata, B., Doi, D., Nishimura, K., Kikuchi, T., Watanabe, A., Sakamoto, Y., Kakuta, J., Ono, Y., and Takahashi, J. 2016. Purification of functional human ES and iPSC-derived midbrain dopaminergic progenitors using LRTM1. Nat Commun 7:13097.

46. Guzman, J. N., Sanchez-Padilla, J., Chan, C. S., and Surmeier, D. J. 2009. Robust pacemaking in substantia nigra dopaminergic neurons. J Neurosci 29: 11011-11019.

47. Ungerstedt, U., and Arbuthnott, G. W. 1970. Quantitative recording of rotational behavior in rats after 6-hydroxy-dopamine lesions of the nigrostriatal dopamine system. Brain Res 24:485-493.

48. Tieu, K. 2011. A guide to neurotoxic animal models of Parkinson's disease. Cold Spring Harb Perspect Med 1:a009316.

49. Blandini, F., and Armentero, M. T. 2012. Animal models of Parkinson's disease. FEBS J 279:1156-1166.

50. Dowd, E., Monville, C., Torres, E. M., and Dunnett, S. B. 2005. The Corridor Task: a simple test of lateralised response selection sensitive to unilateral dopamine deafferentation and graft-derived dopamine replacement in the striatum. Brain Res Bull 68:24-30.

51. Olsson, M., Nikkhah, G., Bentlage, C., and Bjorklund, A. 1995. Forelimb akinesia in the rat Parkinson model: differential effects of dopamine agonists and nigral transplants as assessed by a new stepping test. J Neurosci 15:3863-3875.

52. Lundblad, M., Andersson, M., Winkler, C., Kink, D., Wierup, N., and Cenci, M. A. 2002. Pharmacological validation of behavioural measures of akinesia and dyskinesia in a rat model of Parkinson's disease. Eur J Neurosci 15:120-132.

53. Grealish, S., Diguet, E., Kirkeby, A., Mattsson, B., Heuer, A., Bramoulle, Y., Van Camp, N., Perrier, A. L., Hantraye, P., Bjorklund, A., et al. 2014. Human ESC-derived dopamine neurons show similar preclinical efficacy and potency to fetal neurons when grafted in a rat model of Parkinson's disease. Cell Stem Cell 15:653-665.

54. Barker, R.A., Parmar, M., Studer, L., and Takahashi, J. 2017. Human Trials of Stem Cell-Derived Dopamine Neurons for Parkinson's Disease: Dawn of a New Era. Cell Stem Cell 21:569-573.

55. Ostrom, Q. T., Bauchet, L., Davis, F. G., Deltour, I., Fisher, J. L., Langer, C. E., Pekmezci, M., Schwartzbaum, J.A., Turner, M.C., Walsh, K. M., et al. 2014. The epidemiology of glioma in adults: a "state of the science" review. Neuro Oncol 16:896-913.

56. Katsukawa, M., Nakajima, Y., Fukumoto, A., Doi, D., and Takahashi, J. 2016. Fail-Safe Therapy by Gamma-Ray Irradiation Against Tumor Formation by Human-Induced Pluripotent Stem Cell-Derived Neural Progenitors. Stem Cells Dev 25:815-825.

57. Hargus, G., Cooper, O., Deleidi, M., Levy, A., Lee, K., Marlow, E., Yow, A., Soldner, F., Hockemeyer, D., Hallett, P. J., et al. 2010. Differentiated Parkinson patient-derived induced pluripotent stem cells grow in the adult rodent brain and reduce motor asymmetry in Parkinsonian rats. Proc Natl Acad Sci USA 107:15921-15926.

58. Rhee, Y. H., Ko, J. Y., Chang, M. Y., Yi, S. H., Kim, D., Kim, C. H., Shim, J. W., Jo, A. Y., Kim, B. W., Lee, H., et al. 2011. Protein-based human iPS cells efficiently generate functional dopamine neurons and can treat a rat model of Parkinson disease. J Clin Invest 121:2326-2335.

59. Effenberg, A., Stanslowsky, N., Klein, A., Wesemann, M., Haase, A., Martin, U., Dengler, R., Grothe, C., Ratzka, A., and Wegner, F. 2015. Striatal Transplantation of Human Dopaminergic Neurons Differentiated From Induced Pluripotent Stem Cells Derived From Umbilical Cord Blood Using Lentiviral Reprogramming. Cell Transplant 24:2099-2112.

60. Samata, B., Kikuchi, T., Miyawaki, Y., Morizane, A., Mashimo, T., Nakagawa, M., Okita, K., and Takahashi, J. 2015. X-linked severe combined immunodeficiency (X-SCID) rats for xeno-transplantation and behavioral evaluation. J Neurosci Methods 243:68-77.

61. Kikuchi, T., Morizane, A., Doi, D., Okita, K., Nakagawa, M., Yamakado, H., Inoue, H., Takahashi, R., and Takahashi, J. 2017. Idiopathic Parkinson's disease patient-derived induced pluripotent stem cells function as midbrain dopaminergic neurons in rodent brains. J Neurosci Res 95:1829-1837.

62. Lehnen, D., Banal, S., Cardoso, T., Grealish, S., Heuer, A., Smiyakin, A., Kirkeby, A., Kollet, J., Cremer, H., Parmar, M., et al. 2017. IAP-Based Cell Sorting Results in Homogeneous Transplantable Dopaminergic Precursor Cells Derived from Human Pluripotent Stem Cells. Stem Cell Reports 9:1207-1220.

63. Wakeman, D. R., Hiller, B. M., Marmion, D. J., McMahon, C. W., Corbett, G. T., Mangan, K. P., Ma, J., Little, L. E., Xie, Z., Perez-Rosello, T., et al. 2017. Cryopreservation Maintains Functionality of Human iPSC Dopamine Neurons and Rescues Parkinsonian Phenotypes In Vivo. Stem Cell Reports 9:149-161.

64. Swistowski, A., Peng, J., Liu, Q., Mali, P., Rao, M.S., Cheng, L., and Zeng, X. 2010. Efficient generation of functional dopaminergic neurons from human induced pluripotent stem cells under defined conditions. Stem Cells 28:1893-1904.

65. Kikuchi, T., Morizane, A., Doi, D., Magotani, H., Onoe, H., Hayashi, T., Mizuma, H., Takara, S., Takahashi, R., Inoue, H., et al. 2017. Human iPS cell-derived dopaminergic neurons function in a primate Parkinson's disease model. Nature 548:592-596.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of generating a population of midbrain dopaminergic progenitor cells (mDAPs), the method comprising:

providing a population of induced pluripotent stem cells (iPSCs);

plating the population of cells in discrete, individual areas with sufficient distance between the areas to maintain isolation between the areas, in a biomatrix hydrogel support, with a density of about 5,000-20,000, preferably about 10,000, cells per area; and maintaining the cells in the isolated areas under conditions sufficient for the iPSCs to differentiate into mDAPs.

2. The method of claim 1, wherein the biomatrix hydrogel support is a basement membrane extract or synthetic matrix.

3. The method of claim 1, wherein the cells are suspended in the biomatrix hydrogel support before plating.

4. The method of claim 1, wherein the areas are about 2-10 mm in diameter.

5. The method of claim 1, wherein the distance between the areas is 1-3 cm.

6. The method of claim 1, wherein the iPSC express alkaline phosphatase (AP) and TRA-1-60.

7. The method of claim 1, wherein the mDAPs express one, two, or more markers comprising FOXA2, OTX2, LMX1A, and/or EN1, preferably at least FOXA2 and LMX1A; optionally wherein the mDAPS are TH+ cells that co-express FOXA2, LMX1A and NURR1.

8. The method of claim 1, wherein the iPSC are generated by a method comprising:

obtaining a population of primary cells from a subject;

inducing expression of OCT4, KLF4, SOX2, and L-MYC in the cells; and maintaining the cells under conditions sufficient for the primary cells to become iPSCs.

9. The method of claim 8, wherein inducing expression of OCT4, KLF4, SOX2, and L-MYC comprises transfecting the primary cells with polycistronic episomal vector that comprises human Oct4 linked with 2A sequence of foot-and-mouth disease virus (OCT4-F2A), KLF4, SOX2 linked with 2A sequence of porcine teschovirus (SOX2-P2A), and L-MYC coding sequences.

10. The method of claim 1, wherein the iPSCs are generated by a method comprising expressing in the cells one or more exogenous microRNAs (miRNAs) selected from the group consisting of miR-106a, -106b, -136s, -200c, -302s, -369s, and -371/373.

11. The method of claim 10, wherein the miRNAs comprise one or both of a miR-302s and miR-200c.

12. The method of claim 11, comprising introducing into the cells an episomal vector that comprises sequences coding for a miR-302s and miR-200c.

13. The method of claim 1, wherein the iPSCs are generated by a method comprising expressing in the primary cells all of OCT4, KLF4, SOX2, miR-302s and miR-200c.

14. The method of claim 13, comprising introducing into the cells (i) a vector that comprises human Oct4 linked with 2A sequence of foot-and-mouth disease virus (OCT4-F2A), KLF4, SOX2 linked with 2A sequence of porcine teschovirus (SOX2-P2A), and L-MYC coding sequences, or mature RNAs of Oct4, KLF4, SOX2, and L-MYC, or corresponding proteins, and (ii) a vector that comprises sequences coding for miR-302s and miR-200c, or mature miR-302s and miR-200c.

15. The method of claim 1, wherein the cells are human cells.

16. The method of claim 8, further comprising reduction of undifferentiated iPSCs, preferably by inhibiting the BIRC5 gene.

17. The method of claim 1, wherein the iPSCs are human iPSCs.

18. The method of claim 1, wherein the method comprises plating the population of cells with a density of about 10,000 cells per area.

19. The method of claim 8, wherein the primary cells are fibroblasts, hair keratinocytes, blood cells, or bone marrow mesenchymal stem cells (MSCs).

20. The method of claim 14, wherein the vector is a viral vector or episomal vector.

\* \* \* \* \*